(12) United States Patent
Elledge et al.

(10) Patent No.: US 7,101,985 B2
(45) Date of Patent: Sep. 5, 2006

(54) METHODS AND COMPOSITIONS IN CHECKPOINT SIGNALING

(75) Inventors: Stephen J. Elledge, Houston, TX (US); David K. Cortez, Houston, TX (US); Lee Zou, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 558 days.

(21) Appl. No.: 10/300,453

(22) Filed: Nov. 20, 2002

(65) Prior Publication Data

US 2003/0165934 A1 Sep. 4, 2003

Related U.S. Application Data

(60) Provisional application No. 60/331,821, filed on Nov. 20, 2001.

(51) Int. Cl.
*C07H 21/02* (2006.01)
*C12N 15/00* (2006.01)

(52) U.S. Cl. .................................. 536/23.1; 435/320.1
(58) Field of Classification Search ............... 536/23.1; 435/320.1
See application file for complete search history.

(56) References Cited

U.S. PATENT DOCUMENTS

| | | |
|---|---|---|
| 6,211,164 B1 | 4/2001 | Luo et al. |
| 6,218,109 B1 | 4/2001 | Elledge et al. |
| 6,307,015 B1 | 10/2001 | Elledge et al. |

OTHER PUBLICATIONS

Zou, Lee, et a;.; Sensing DNA Damage Through ATRIP Recognition of RPA-ssDNA Complexes; Science (Jun. 6, 2003); vol. 300; pp. 1542-1548.
Rouse, John, et al.; LCD1: an essential gene involved in checkpoint control and regulation of the MEC1 signalling pathway in *Saccharomyces cerevisiae*; The EMBO Journal 19(21):5801-5812, 2000.
Zou, Lee, et al.; Regulation of ATR substrate selection by Rad17-dependent loading of Rad9 complexes onto chromatin; Genes & Development 16:198-208, 2000.
Brown, Eric J., et al.; ATR disruption leads to chromosomal fragmentation and early embryonic lethality; Genes & Development 14:397-402, 2000.
Tibbetts, Randal S., et al.; A role for ATR in the DNA damage-induced phosphorylation of p. 53; Research Communication in Genes & Development, 13(2):152-157, Jan. 15, 1999.
Tibbetts, Randal S., et al.; Functional interactions between BRCA1 and the checkpoint kinase ATR during genotoxic stress; Genes & Development, 14(23):2090-3002, Dec. 1, 2000.
Edwards, Rhian J., et al.; A Rad3-Rad26 complex responds to DNA damage independently of other checkpoint proteins; Nature Cell Biology 1:393-398, Nov. 1999.

Wakayama, Tatsushi, et al.; Pie1, a Protein Interacting with Mec1, Controls Cell Growth and Checkpoint Responses in *Saccharomyces cerevisiae*, Molecular and Cellular Biology 21(3):755-764, Feb. 2001.
Paciotti, Vera, et al.; The checkpoint protein Ddc2, functionally related to S. pombe Rad26, interacts with Mec1 and is regulated by Mec1-dependent phosphorylation in budding yeast; Genes & Development 14:2046-2059, 2000.
Cliby, William A., et al.; Overexpression of a kinasae-inactive ATR protein causes sensitivity to DNA-damaging agents and defects in cell cycle checkpoints; The EMBO Journal 17(1):159-169, 1998.
Wright, Jocyndra A., et al.; Protein kinase mutants of human ATR increase sensitivity to UV and ionizing radiation and abrogate cell cycle checkpoint control; Proc. Natl. Acad. Sci. USA (Cell Biology) 95:7445-7450, Jun. 1998.
Brodsky, Michael H., et al.; mus304 encodes a novel DNA damage checkpoint protein required during Drosophila development; Genes & Development 14:666-678, 2000.
Liu, Qinghua, et al.; Chk1 is an essential kinase that is regulated by Atr and required for the G2/M DNA damage checkpoint; Genes & Development 14:1448-1459, 2000.
Cortez, David, et al.; ATR and ATRIP: Partners in Checkpoint Signaling; Science 294:1713-1716, Nov. 23, 2001.
GenBank Submission of NM_033628. *Homo sapiens* Thre . . . .
GenBank Submission of AAH14153. hypothetical prot . . . .
GenBank Submission of XP_051515.hypothetical prot . . . .
GenBank Submission of XM_051516.
GenBank Submission of NM_130384. *Homo sapiens* thre . . . .
GenBank Submission of AL832917. *Homo sapiens* mRNA . . . .
GenBank Submission of NP_569055. three prime repai . . . .
GenBank Submission of AF451323. *Homo sapiens* ATR . . . .
GenBank Submission of NP_115542. three prime repai . . . .
GenBank Submission of BC030597. *Homo sapiens*, thr . . . .
GenBank Submission of AB046054. Macaca fascicular . . . .
GenBank Submission of AK022405. *Homo sapiens* cDNA . . . .
GenBank Submission of BC014153. *Homo sapiens*, hyp . . . .
GenBank Submission of NM_032166. *Homo sapiens* hypo . . . .
GenBank Submission of AF319567. *Homo sapiens* clon . . . .
GenBank Submission of XP_054821. hypothetical prot . . . .
GenBank Submission of NP_115542. hypothetical prot . . . .
GenBank Submission of XM_051514. *Homo sapiens* hypo . . . .
GenBank Submission of AF319566. *Homo sapiens* clon . . . .
GenBank Submission of XM_051513. *Homo sapiens* hypo . . . .
GenBank Submission of XM_051515. *Homo sapiens* hypo . . . .
GenBank Submission of XM_054821. *Homo sapiens* hypo . . . .

*Primary Examiner*—Gary B. Nickol
(74) *Attorney, Agent, or Firm*—Fulbright & Jaworski, LLP

(57) ABSTRACT

The present invention is directed to compositions and methods regarding the signaling for the presence of DNA damage or replication stress and activating cell cycle checkpoints. Specifically, ATRIP was identified as an interactor with ATR, a member of the phosphatidylinositol kinase-related protein family that includes ATM and DNA-PK. In some embodiments, the present invention is directed to ATRIP and ATR acting as mutually dependent partners in cell cycle checkpoint signaling pathways.

5 Claims, 10 Drawing Sheets

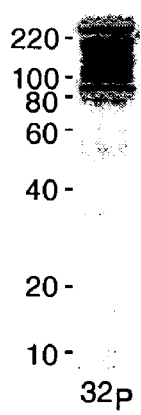

FIG. 1A

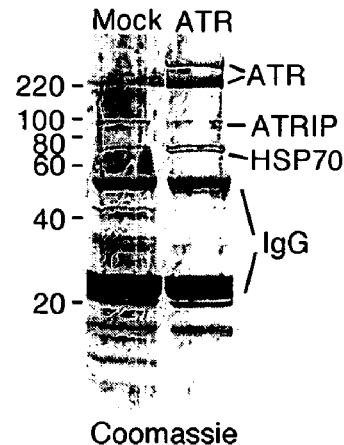

FIG. 1B

```
RAD26   ------------------------------------------
ATRIP   1 -----------------MAGTSAPGSKRRSEPPAPRPGPPP
MUS304  61 KGGTEVDIGNSEVTFSEPAPTPQGSTSTQQMFP-----PPP

RAD26   1 -----------------MMADESFDLESLGSDEIFEGVNL
ATRIP   25 GTGHPPSKRARGFSAAAAPDPDDPF-----GAHGDFTADDL
MUS304  97 ----PPQKKPTSLDMDAIFADDDDF---------DFLAVTL

RAD26   24 DELEQQAQTQV-QAQSSQVVVPSEKQKQNLNLPNSYTNSSQ
ATRIP   62 EELDTLASQALSQCPAAARDVSSDRKVH-RLLDGMSKNPSG
MUS304  125 --MDSEPQKMPEPKTSTSRLTTSSISVQQKTTTTTTINATQ

RAD26   64 KVRES--------------TVNSQASLSSNDLRTELLIKSG
ATRIP   101 KNRETVPIKDNFE-LEVLQAQYKELKEKMKVMEEEVLIKNG
MUS304  164 SRQQEHQLKPLMDRISALKRENAQLEKNLGDSKERNEIKSG

RAD26   91 ENAILRANL------LKQSEANNAALES-LNNSIKQKQDEY
ATRIP   141 EIKILRDSLHQTESVLEEQRRSEFLLEQEKTQALSDKEKEP
MUS304  205 EVSELRDELKHLRQQLQASKMEKLALADETNRDCNKKVAEA

RAD26   125 QRKLEEIKKELEYA-------KTKSLFHEREAQD- (SEQ ID NO:48)
ATRIP   182 SKKLQSLQSELQFKDAEMNELRTKLQTSER----- (SEQ ID NO:49)
MUS304  246 AKQIAAKDIELKIKNAEFSKLKTQQKAHERSMNSS
                                               (SEQ ID NO:50)
```

FIG. 1C

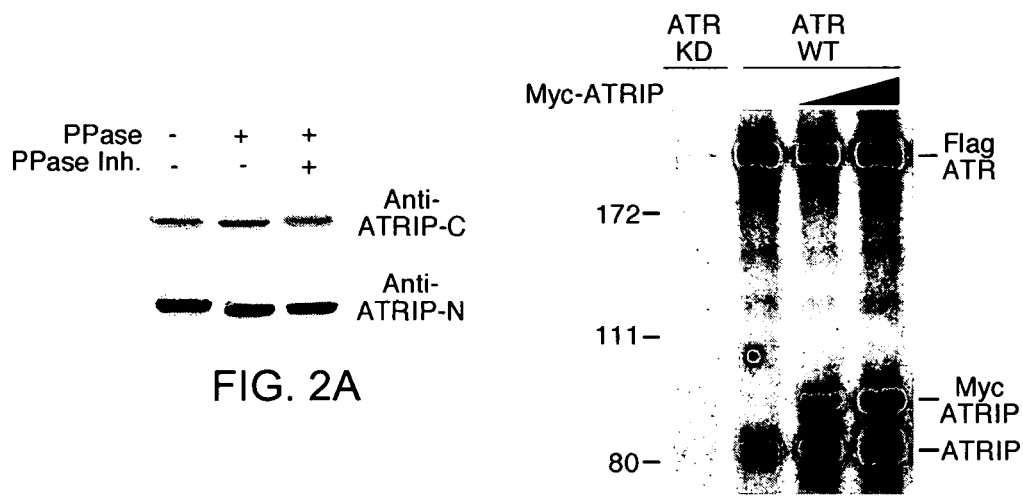
FIG. 2A
FIG. 2B
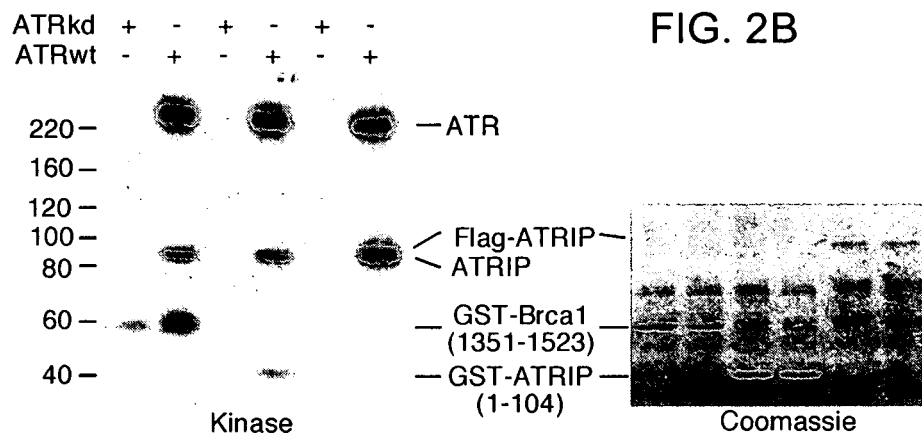
FIG. 2C
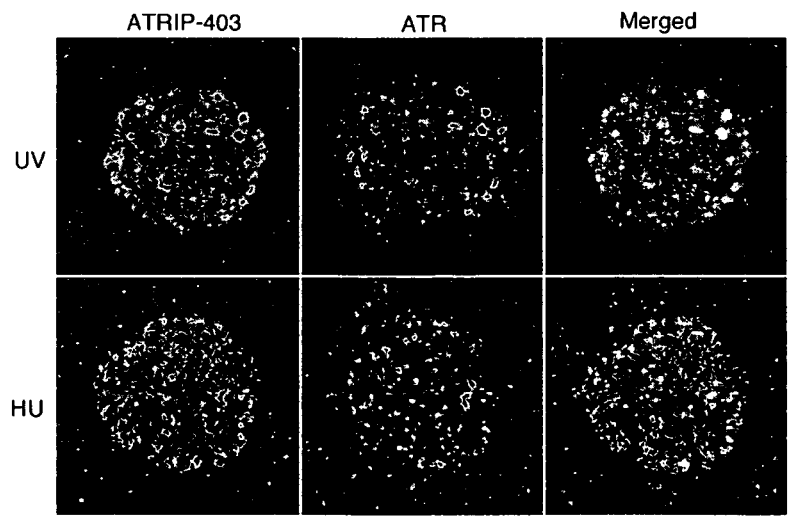
FIG. 2D

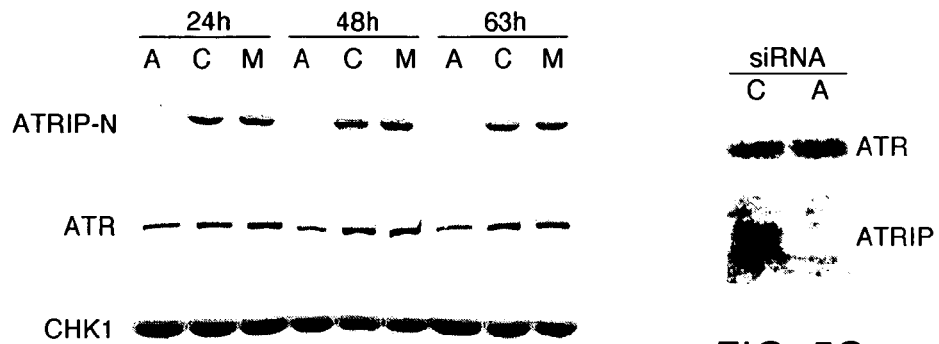
FIG. 5A
FIG. 5C
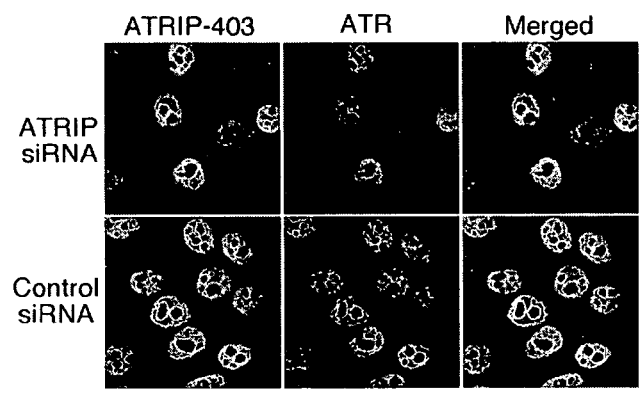
FIG. 5B
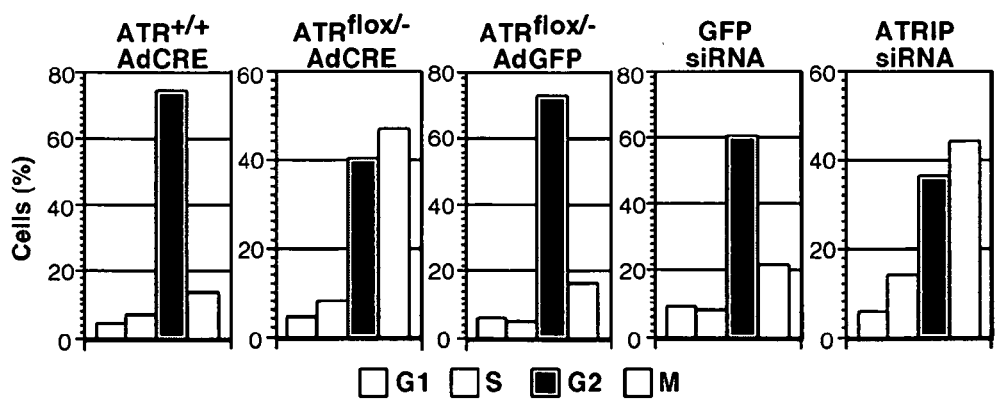
FIG. 5D

METHODS AND COMPOSITIONS IN CHECKPOINT SIGNALING

This application claims the benefit of Provisional Application No. 60/331,821, filed Nov. 20, 2001.

FIELD OF THE INVENTION

The present invention is directed to the fields of cellular biology, molecular biology, and cancer. Specifically, the present invention is directed to methods and compositions in checkpoint signaling. More specifically, the present invention regards an ATR-interacting protein essential in a DNA damage checkpoint pathway.

BACKGROUND OF THE INVENTION

Ataxia telangiectasia and Rad-3-related (ATR) is a member of the phosphatidylinositol kinase-related protein family that includes ATM and DNA-PK. These kinases are essential for signaling the presence of DNA damage or replication blocks and activating cell cycle checkpoints (Durocher and Jackson, 2001; Shiloh, 2001). ATR is the sequence and functional homologue of the Rad3 and Mec1 checkpoint proteins from S. pombe and S. cerevisiae respectively (Bentley et al., 1996; Cimprich et al., 1996).

The function of ATM has been extensively studied in cell lines derived from A-T patients that lack expression of the ATM protein. The lack of comparable cell lines for ATR has impaired analysis of its specific activities. Overexpression of catalytically-inactive versions of ATR indicates that it is required for checkpoint responses following treatment of cells with agents that cause various forms of DNA damage or block replication (Wright et al., 1998; Cliby et al., 1998; Tibbetts et al., 1999; Tibbetts et al., 2000). Furthermore, homozygous deletion of ATR in mice causes early embryonic lethality, suggesting that ATR has essential functions during development (Brown and Baltimore, 2000; de Klein et al., 2000).

Rad3 and Mec1 function in cooperation with the Rad26 and DDC2 (also called LCD1 or PIE1) proteins respectively (Edwards et al., 1999; Paciotti et al., 2000; Rouse and Jackson, 2000; Wakayama et al., 2001). Rad26 binds to and is phosphorylated by Rad3, whereas DDC2 binds to and is phosphorylated by Mec1. Mutations in either Rad3 or Rad26 yield almost identical phenotypes, as do mutations in either Mec1 or DDC2. As yet, the functional roles of Rad26 and DDC2 are unclear. However, Rad3 and DDC2 are essential for transducing checkpoint signals to downstream proteins such as the Chk1 protein kinase (Edwards et al., 1999; Paciotti et al., 2000; Rouse and Jackson, 2000; Wakayama et al., 2001).

The present invention is directed to an ATR-interaction gene product defined as ATRIP, and compositions and methods related thereto are described herein.

SUMMARY OF THE INVENTION

The present invention is directed to the following embodiments In one embodiment of the present invention, there is as a composition of matter an isolated nucleic acid sequence comprising SEQ ID NO:1. In another embodiment there is as a composition of matter a purified polypeptide sequence comprising SEQ ID NO:2. In an additional specific embodiment, there is as a composition of matter an isolated genomic DNA sequence encoding the polypeptide comprising SEQ ID NO:2.

In another embodiment of the present invention, there is a vector comprising the nucleic acid sequence of SEQ ID NO:1, wherein the expression of the nucleic acid sequence is regulated by nucleic acid sequences operatively linked to the nucleic acid sequence comprising SEQ ID NO:1. In a specific embodiment, the vector is a plasmid, a viral vector, or a lipid composition. In a specific embodiment, the viral vector is an adenoviral vector, an adeno-associated viral vector, or a retroviral vector.

In an additional embodiment of the present invention, there is as a composition of matter a fusion polypeptide comprising at least a portion of an ATRIP polypeptide and a non-ATRIP polypeptide. In a specific embodiment, ATRIP polypeptide comprises SEQ ID NO:2. In another specific embodiment, the non-ATRIP polypeptide is an epitope tag. In a further specific embodiment, the epitope tag is myc, FLAG, or HA.

In an additional embodiment of the present invention, there is a method of preventing or delaying a cell from entering into mitosis following damage to DNA in the cell, comprising contacting a cell with an ATRIP polypeptide in an amount effective to prevent or delay entry of the cell into mitosis. In a specific embodiment, the cell is further defined as having a defective endogenous ATRIP polynucleotide or ATRIP polypeptide. In a further specific embodiment, the ATRIP polypeptide is introduced into the cell by the direct introduction of the ATRIP polypeptide. In an additional specific embodiment, the ATRIP polypeptide comprises a sequence of SEQ ID NO:2. In another specific embodiment, the ATRIP polypeptide comprises a sequence of SEQ ID NO:2, SEQ ID NO:14, SEQ ID NO:15, SEQ ID NO:16, SEQ ID NO:17, or SEQ ID NO:18. In a specific embodiment, the ATRIP polypeptide is introduced into the cell through the introduction of an ATRIP-encoding polynucleotide. In a specific embodiment, the polynucleotide encodes a polypeptide comprising SEQ ID NO:2. In another specific embodiment, the polynucleotide encodes a polypeptide comprising SEQ ID NO:2, SEQ ID NO:14, SEQ ID NO:15, SEQ ID NO:16, SEQ ID NO:17, or SEQ ID NO:18. In a further specific embodiment, the ATRIP polynucleotide has a sequence comprising SEQ ID NO:1. In an additional specific embodiment, the ATRIP polynucleotide has a sequence comprising SEQ ID NO:1, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, or SEQ ID NO:13. In an additional specific embodiment, the polynucleotide is a deoxyribonucleic acid molecule. In a further specific embodiment, the ATRIP-encoding polynucleotide further comprises at least one regulatory sequence. In a specific embodiment, the regulatory sequence is a promoter. In another specific embodiment, the promoter is a CMV (cytomegalovirus) promoter, a RSV (rous sarcoma virus) promoter, a LTR (long terminal repeat of retroviruses) promoter, or a MMTV (mouse mammary tumor virus) promoter. In an additional specific embodiment, the ATRIP-encoding polynucleotide is comprised in a vector, such as a plasmid or a viral vector. In a specific embodiment, the viral vector is a retroviral vector, adenoviral vector, herpesviral vector, vaccinia viral vector, or adeno-associated viral vector. In another specific embodiment, the ATRIP-encoding polynucleotide is comprised with a non-viral gene delivery system, wherein the system comprises lipids, peptides, proteins, polymers, micelles, emulsion, or a combination thereof. In a specific embodiment, the polynucleotide is complexed with the lipid. In another specific embodiment, the polynucleotide is comprised in a liposome.

In another embodiment of the present invention, there is a method of preventing or delaying proliferation of a cell, the cell comprising a defective ATRIP polynucleotide or polypeptide, comprising contacting the cell with ATRIP in an amount effective to prevent or delay the cell proliferation. In a specific embodiment, the cell is further defined as being a neoplastic cell. In another specific embodiment, the ATRIP is a polypeptide. In a further specific embodiment, the ATRIP polypeptide comprises SEQ ID NO:2, SEQ ID NO:14, SEQ ID NO:15, SEQ ID NO:16, SEQ ID NO:17, or SEQ ID NO:18. In a further specific embodiment, the ATRIP is a polynucleotide, such as one comprising SEQ ID NO:1, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, or SEQ ID NO:13

In an additional embodiment of the present invention, there is a method for identifying an agent that interacts with an ATRIP polypeptide, comprising the steps of providing the ATRIP polypeptide; providing a candidate agent to the ATRIP polypeptide; and assaying for an interaction between the candidate agent and the ATRIP polypeptide. In a specific embodiment, the assaying is by two hybrid, immunoprecipitation, affinity purification, phage display, or a combination thereof. In another specific embodiment, the candidate agent inhibits a function of an ATR/ATRIP complex. In a specific embodiment, the candidate agent inhibits binding of ATRIP to ATR.

In another embodiment of the present invention, there is a method for identifying a modulator of ATRIP activity comprising (a) providing a candidate modulator;

(b) admixing the candidate modulator with an isolated compound, cell, or suitable experimental animal comprising ATRIP; (c) measuring one or more characteristics of the compound, cell or animal in step (b); and (d) comparing the characteristic measured in step (c) with the characteristic of the compound, cell or animal in the absence of the candidate modulator, wherein a difference between the measured characteristics indicates that the candidate modulator is a modulator of the compound, cell or animal comprising ATRIP. In a specific embodiment, the candidate modulator inhibits a function of an ATR/ATRIP complex. In another embodiment of the present invention, there is as a composition of matter the candidate modulator identified in the method.

In another embodiment of the present invention, there is a method of screening for an agent that interacts with ATR, comprising the steps of introducing into a cell a first nucleic acid expressing a fused test peptide/DNA binding domain; and a second nucleic acid expressing a fused ATR polypeptide/DNA activation domain; and assaying for an interaction between the test peptide and the ATR polypeptide by measuring binding between the DNA binding domain and the DNA activation domain, wherein the interaction between the test peptide and the ATR polypeptide indicates the test peptide is the agent.

In an additional embodiment of the present invention, there is a method of screening for an agent that interacts with ATRIP, comprising the steps of introducing into a cell a first nucleic acid expressing a fused test peptide/DNA binding domain; and a second nucleic acid expressing a fused ATRIP polypeptide/DNA activation domain; and assaying for an interaction between the test peptide and said ATRIP polypeptide by measuring binding between said DNA binding domain and the DNA activation domain, wherein the interaction between the test peptide and the ATRIP polypeptide indicates the test peptide is the agent. In an additional specific embodiment, there is as a composition of matter, the agent identified by the method.

In an additional embodiment of the present invention, there is a method of screening in vitro for an active compound for the treatment of cancer, comprising the steps of obtaining a cell, wherein the cell comprises a nucleic acid sequence having a reporter sequence and wherein the expression of said reporter sequence is controlled by an ATRIP regulatory nucleic acid sequence; exposing a test agent to the cell; and measuring a change in the expression, wherein said change indicates the test agent is the active compound. In a specific embodiment, the reporter sequence is selected from the group consisting of β-galactosidase, β-glucuronidase, green fluorescent protein, blue fluorescent protein, and chloramphenicol acetyltransferase. In a further specific embodiment, there is as a composition of matter the agent identified by the method.

In another embodiment of the present invention, there is a method of screening in vitro for an active compound for the treatment of cancer, comprising the steps of obtaining a cell, wherein the cell includes a nucleic acid sequence comprising a reporter sequence and wherein the expression of the reporter sequence is controlled by an ATR regulatory nucleic acid sequence; exposing a test agent to the cell; and measuring a change in said expression, wherein the change indicates the test agent is the active compound. In a specific embodiment, there is a reporter sequence is selected from the group consisting of β-galactosidase, β-glucuronidase, green fluorescent protein, blue fluorescent protein, and chloramphenicol acetyltransferase. In a specific embodiment, there is as a composition of matter the agent identified by the method.

In an additional embodiment of the present invention, there is a method for detecting an ATRIP polypeptide in a sample, comprising obtaining the sample suspected of containing the ATRIP polypeptide; providing an antibody that recognizes an ATRIP polypeptide; mixing the sample and the antibody under conditions wherein the antibody can bind to the ATRIP protein; and detecting the binding.

In an additional embodiment of the present invention, there is a method for detecting a cancer cell, comprising obtaining a sample comprising a cell having an ATRIP polynucleotide; and identifying a defect in the ATRIP polynucleotide.

In another embodiment of the present invention, there is a method for detecting a cancer cell, comprising obtaining a sample comprising a cell having an ATRIP polypeptide; and identifying a defect in the ATRIP polypeptide.

In an additional embodiment of the present invention, there is a method for treating a cancer cell having a defective ATRIP polynucleotide or polypeptide, comprising administering to the cell a non-defective ATRIP polynucleotide or polypeptide.

In a further embodiment of the present invention, there is a monoclonal antibody that binds immunologically to a polypeptide comprising SEQ ID NO:2, or an antigenic fragment thereof.

In an additional embodiment of the present invention, there is a polyclonal antisera, antibodies of which bind immunologically to a polypeptide comprising SEQ ID NO:2, or an antigenic fragment thereof.

In another embodiment of the present invention, there is a method of identifying an agent that interacts with ATR, comprising providing a cell that is reduced for ATR function; providing to the cell an ATR polypeptide; providing to the cell a candidate agent; and assaying for an interaction between the ATR polypeptide and the candidate agent. In a specific embodiment, the cell has a conditional ATR-null allele. In another embodiment, the agent that interacts with ATR inhibits activity of ATR. In a specific embodiment, the agent that interacts with ATR enhances activity of ATR. In an additional embodiment, there is as a composition of matter the agent identified by the method.

In an additional embodiment of the present invention, there is a method of treating cancer in an individual, comprising the step of administering to the individual in a pharmaceutically acceptable formulation a therapeutically effective amount of an agent identified by a method described herein.

In an additional embodiment of the present invention, there is a method of treating cancer in an individual, comprising the step of administering to the individual in a pharmaceutically acceptable formulation a therapeutically effective amount of an agent identified by a method described herein.

In another embodiment of the present invention, there is a method for identifying an agent that interacts with an ATRIP polypeptide, comprising the steps of providing the ATRIP polypeptide; providing a candidate agent to the ATRIP polypeptide; and assaying for an interaction between the candidate agent and the ATRIP polypeptide. In an additional embodiment of the present invention, there is as a composition of matter, the agent that interacts with an ATR polypeptide identified by a method described herein. In a specific embodiment, the agent that interacts with an ATR polypeptide inhibits activity of the ATR polypeptide.

In another embodiment of the present invention, there is a method of treating cancer in an individual, comprising the step of administering to the individual in a pharmaceutically acceptable formulation a therapeutically effective amount of an agent identified by a method described herein In another embodiment of the present invention, there is a method of identifying an agent that inhibits binding of ATRIP to a ssDNA molecule, comprising the steps of providing a ssDNA molecule; providing an ATRIP polypeptide; introducing to the ssDNA molecule a test agent; and assaying for an interaction between the ATRIP polypeptide and the ssDNA molecule, wherein when the interaction does not occur, the test agent is the agent that inhibits binding. In a specific embodiment, the ssDNA molecule is comprised in a ssDNA/RPA complex. In another specific embodiment, the ATRIP polypeptide is comprised in an ATR/ATRIP complex. In a specific embodiment, the cell comprises at least one mutation that renders the cell a neoplastic cell. In another specific embodiment, the method further comprises the step of administering a pharmaceutical composition comprising the agent that promotes cell death to an individual with a cell proliferation disorder, an example of which is cancer.

In an additional embodiment of the present invention, there is a method of identifying an agent that inhibits a function of an ATR/ATRIP complex, comprising the steps of providing a ssDNA molecule; providing a replication protein A (RPA) polypeptide, wherein the ssDNA molecule and the RPA polypeptide form a ssDNA/RPA complex; providing an ATR/ATRIP-phosphorylatable protein, wherein the ATR/ATRIP-phosphorylatable protein binds to said ssDNA or said ssDNA/RPA complex; providing an ATRIP polypeptide; providing an ATR polypeptide, wherein the ATRIP polypeptide and said ATR polypeptide form an ATR/ATRIP complex; providing a test agent; and assaying phosphorylation status of the ATR/ATRIP-phosphorylatable protein, wherein when the ATR/ATRIP-phosphorylatable protein is not phosphorylated following said providing of the ATRIP polypeptide, said test agent is identified as said agent that inhibits function of the ATR/ATRIP complex. In a specific embodiment, the function of an ATR/ATRIP complex is further defined as binding a ssDNA molecule, binding a ssDNA/RPA complex, binding a RPA polypeptide, phosphorylating a polypeptide, or a combination thereof. In another specific embodiment, the cell comprises at least one mutation that renders the cell a neoplastic cell. In an additional specific embodiment, the method further comprises the step of administering a pharmaceutical composition comprising the agent that promotes cell death to an individual with a cell proliferation disorder, an example of which is cancer.

In an additional embodiment of the present invention, there is a method of identifying an agent that promotes cell death, comprising the steps of providing a ssDNA/replication protein A (RPA) complex; providing an ATRIP polypeptide; introducing to the ssDNA/RPA complex a test agent; and assaying for an interaction between the ATRIP polypeptide and the ssDNA/RPA complex, wherein when the interaction does not occur, said test agent is the agent that promotes cell death.

In one embodiment of the present invention, there is a method of identifying an agent that promotes cell death, comprising the steps of providing a ssDNA molecule; providing a replication protein A (RPA) polypeptide, wherein the ssDNA molecule and the RPA polypeptide form a ssDNA/RPA complex; providing an ATR/ATRIP-phosphorylatable protein, wherein the ATR/ATRIP-phosphorylatable protein binds to the ssDNA or the ssDNA/RPA complex; providing an ATRIP polypeptide; providing an ATR polypeptide, wherein the ATRIP polypeptide and the ATR polypeptide form an ATR/ATRIP complex; providing a test agent; and assaying phosphorylation status of the ATR/ATRIP-phosphorylatable protein, wherein when the ATR/ATRIP-phosphorylatable protein is not phosphorylated following the providing of the ATRIP polypeptide, the test agent is identified as the agent that promotes cell death.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A through 1F illustrate cloning of ATRIP as an ATR-interacting protein. FIG. 1A demonstrates that Flag-ATR produced by overexpression in 293 cells was immunoprecipitated, incubated in kinase buffer with $\gamma$-$^{32}$P-ATP, then resolved on a 4–20% SDS-PAGE gel prior to autoradiography. Kinase assays were performed as described (Wang et al., 2000). FIG. 1B shows anti-Flag immunoprecipitates from equal amounts of 293 cell lysate from either mock or Flag-ATR transfected cells were resolved by SDS-PAGE and stained with coomassie blue. Protein bands were trypsinized and the recovered peptides were identified by mass spectrometry. FIG. 1C shows alignment of ATRIP with *S. pombe* Rad26 protein and *D. melanogaster* Mus304 protein. FIG. 1D illustrates schematic representation of Rad26 family members. Shaded boxes indicate predicted coiled-coil domains. Asterisks represent S/TQ locations which are potential phosphorylation sites for ATR or ATM. FIG. 1E demonstrates western blot analysis performed with three rabbit polyclonal antibodies to ATRIP on cell lysates from 293, HCT116, or 293 cells transfected with a CMV-Myc(3X)-ATRIP expression plasmid. FIG. 1F demonstrates 293 cell lysates that were immunoprecipitated with the indicated antibodies to either ATRIP or ATR and immunoblotted with anti-ATR antibodies.

FIGS. 2A through 2D show that ATRIP is an ATR substrate and co-localizes with ATR to intra-nuclear foci following DNA damage or replication blocks. FIG. 2A demonstrates mock treated, phosphatase treated, or phosphatase+phosphatase inhibitor treated 293 cell lysates that were immunoblotted with ATRIP-N or ATRIP-C antibodies. FIG. 2B shows 293 cells transfected with either Flag-tagged catalytically-inactive ATR or wild-type ATR expression vectors as well as various amounts of Myc-ATRIP expression vector where indicated. Flag immunoprecipitates were incubated in kinase buffer with [$\gamma$-$^{32}$P]-ATP, and then resolved on a 4 to 20% SDS-PAGE gel prior to autoradiography. FIG. 2C shows that recombinant Brca1 or ATRIP fragments that were purified from *E. coli* or full length Flag-ATRIP protein purified from insect cells following baculovirus infection were incubated in kinase buffer containing $\gamma$-$^{32}$P-ATP and either wild-type or catalytically-inactive Flag-ATR immunoprecipitates. The kinase reaction was resolved by SDS-PAGE prior to staining with coomassie blue and autoradiography. FIG. 2D demonstrates Hela cells exposed to 40 J/m$^2$ ultraviolet light or 2 mM hydroxyurea for five hours were fixed using paraformaldehyde, permeabilized with triton X-100, and then immunostained with goat polyclonal anti-ATR antibody and rabbit polyclonal ATRIP-403 antibody. Following incubation with appropriate Cy3 and FITC conjugated secondary antibodies, fluorescent images were captured on a confocal microscope. Each image represents a single section of the cell nucleus.

FIG. 3 shows requirement of ATR for cell viability and ATRIP expression.

FIGS. 4A through 4C show that ATR is essential for cell viability. In FIG. 4A, two days after infection the cells were counted and plated at low dilutions. Colonies were scored two weeks after plating. In FIG. 4B, surviving colonies of Ad-Cre-infected ATR$^{flox/-}$ cells or ATR$^{flox/-}$ cells complemented with the Flag-ATR cDNA were genotyped using PCR as performed in FIG. 6C. The control column indicates ATR$^{flox/-}$ cells that were genotyped two days after infection with Ad-Cre virus. A representative sample of the 60 clones tested is shown.

FIGS. 5A through 5D show requirement of ATRIP for ATR expression and the G2-M DNA damage checkpoint. Hela cells were transfected with 21 nucleotide siRNAs targeting ATRIP (A) or GFP (C) or mock transfected (M) (Elbashir et al., 2001). FIG. 5A shows immunoblots of cell lysates prepared at the indicated times after transfection were performed using antibodies directed against ATRIP, ATR, or CHK1. FIG. 5B shows the transfected cells were fixed and stained with antibodies against ATRIP and ATR and the appropriate FITC and Cy3 conjugated secondary antibodies. FIG. 5C demonstrates total RNA from transfected cells was separated by electrophoresis, blotted onto nitrocellulose, and probed with portions of either the ATR or ATRIP cDNA. FIG. 5D shows ATR$^{flox/-}$ or ATR$^{+/+}$ cells were infected with Ad-GFP or Ad-Cre viruses, or ATR$^{flox/-}$ cells were transfected with siRNAs targeting ATRIP or GFP three times over a three-day period.

In FIG. 6A, there is a schematic diagram of a strategy to produce a conditional ATR allele. In FIG. 6B, southern blot analysis of genomic DNA isolated from the indicated cell lines after digestion with ApaL1 and SacI is shown. ATR$^{flox*/+}$ indicates cells after the first targeting event with the flox targeting construct and prior to removal of the neomycin-disrupted exon. The probe location is shown in (A). Band 1 is the product from the wild-type allele. Band 2 is produced from the flox allele. Band 3 is produced from the second knockout allele. Band 4 is produced from the flox allele after Cre-medicated excision of exon 2. FIG. 6C shows PCR analysis of wild-type and ATR$^{flox/-}$ cells before and 48 hours after infection with increasing concentrations of adenovirus encoding the Cre recombinase. Primer binding sites are indicated in (A), and band numbers are the same as in panel (B).

FIG. 7A shows flag and nuclear localization signal (NLS)-tagged ATRIP fragments that were co-expressed in 293 cells with ATR. Expression constructs were created using PCR and transferred to the Flag-NLS expression vector using the univector plasmid fusion system. Lysates were immunoprecipitated with anti-ATR antibody and immunoblotted with anti-Flag antibody. FIG. 7B demonstrates Flag-NLS-tagged ATRIP fragments that were expressed in 293 cells and immunoprecipitated with anti-Flag antibodies. The immunoprecipitates were immunoblotted with anti-ATR antibodies.

DETAILED DESCRIPTION OF THE INVENTION

I. Definitions

Figure 1D:
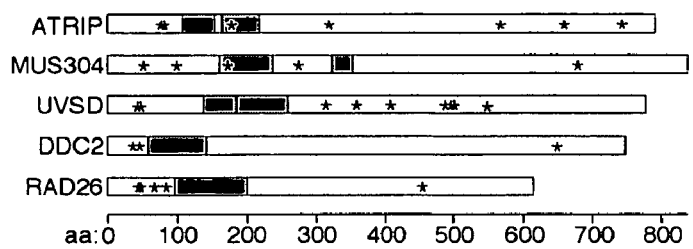

The term "a" or "an" as used herein in the specification may mean one or more. As used herein in the claim(s), when used in conjunction with the word "comprising", the words "a" or "an" may mean one or more than one. As used herein "another" may mean at least a second or more.

The term "ATR/ATRIP complex" as used herein is defined as at least one ATR polypeptide associating with at least one ATRIP polypeptide. In a specific embodiment, the association is a direct interaction. In a further specific embodiment, the association is direct binding of ATR to ATRIP. In an alternative embodiment, at least another compound bridges interaction between ATR and ATRIP. In a specific embodiment, non-limiting examples of the function of ATR/ATRIP complex include providing a DNA damage checkpoint for a cell; delay of mitosis; localization to a nucleus (such as following DNA damage or inhibition of replication); binding of ssDNA (either alone or, for example, through a third party compound such as replication protein A); associating with ssDNA; sensing DNA damage (such as a ssDNA, a nick, or a break); facilitating (either directly or indirectly) expression of ATR, ATRIP, or both; and/or detection of an altered DNA structure (compared to a wild type, non-damaged DNA-comprising cell).

The term "ATR/ATRIP-phosphorylatable" refers to a polypeptide that is capable of being phosphorylated by an ATR/ATRIP complex, or a component thereof.

The term "neoplastic" as used herein is defined as abnormal growth of tissue that may be benign or cancerous. In a specific embodiment, the neoplastic cell or tissue is cancerous. In a specific embodiment, a neoplastic and/or cancerous cell comprises a defect in a gene that renders the cell neoplastic and/or cancerous. In a further specific embodiment, that defect is in a tumor suppressor gene. Examples of tumor suppressor genes are well known in the art, such as p53, BRCA1, and BRCA2.

The term "ssDNA/replication protein A (RPA) complex" as used herein is defined as at least one RPA polypeptide bound to at least one ssDNA molecule. In a specific embodiment, the ssDNA molecule comprises a plurality of RPA molecules bound to it. In a further specific embodiment, the complex comprises a plurality of ssDNA molecules, at least the majority of which comprise multiple RPA polypeptides bound to it. In a further specific embodiment, the RPA polypeptide and/or the ssDNA is labeled, such as with a chromophore, a fluorophore, or radioactivity. In specific embodiments, the ssDNA comprises a biotin label.

II. The Present Invention

The checkpoint kinases ATM (ataxia telangiectasia mutated) and ATR (ATM and Rad3 related) transduce genomic stress signals to halt cell cycle progression and promote DNA repair. The identification of an ATR-interacting protein (ATRIP) is described herein. ATRIP is phosphorylated by ATR, regulates ATR expression, and is an essential component of the DNA damage checkpoint pathway. ATR and ATRIP both localize to intra-nuclear foci following DNA damage or inhibition of replication. Deletion of ATR mediated by the Cre recombinase caused the loss of ATR and ATRIP expression, loss of DNA damage checkpoint responses, and cell death. Therefore, ATR is essential for the viability of human somatic cells. Small interfering RNA (siRNA) directed against ATRIP caused the loss of both ATRIP and ATR expression and the loss of checkpoint responses to DNA damage. Thus, ATRIP an ATR are mutually dependent partners in cell cycle checkpoint signaling pathways.

A skilled artisan recognizes that the present invention is directed to methods and compositions regarding ATRIP and ATR. Specifically, loss of functional ATR and ATRIP results in loss of important cell cycle checkpoints, resulting in the entrance of the cell into mitosis. In some embodiments, the cell harbors potentially harmful mutations that would result in the cell proliferating into a neoplasm. In some specific embodiments, the neoplasm is malignant, and therapeutic intervention is necessary. Thus, a skilled artisan recognizes, based on the teachings herein that the ATR and ATRIP genes and gene products are useful for identifying and screening for cancer drug targets and as targets themselves for drug therapy. In addition, defective alleles of ATR and/or ATRIP genes may be utilized for diagnosis of a cell capable of proliferating into a neoplasm.

In another embodiment, ATR and/or ATRIP are targeted to be inhibited. Although ATR and ATRIP are required for checkpoint signaling, in some embodiments the inhibition of one or both genes and/or gene products may not affect a normal cell but facilitate the death or delayed proliferation of a mutated cancer cell. That is, in some embodiments inhibition of ATR and/or ATRIP in a particular background (such as having at least one defective member in the ATR pathway) results in death of the cell, such as by causing destruction of an ATR and/or ATRIP pathway in the cell.

In other embodiments, the present invention provides screens for a therapeutic agent(s) useful for promoting death of a cell, and preferably useful for cancer treatment. In a specific embodiment, a screen is performed to identify an agent that impairs or inhibits ATR/ATRIP complex function, or a component thereof. In further specific embodiments, a screen identifies an agent that inhibits the ability of ATR to bind ATRIP, or ATRIP to bind ssDNA (or RPA, or a ssDNA/RPA complex), or both.

In a specific embodiment, overproduction of ATR is provided for a therapeutic purpose, preferably in the presence of overproduction of ATRIP, because stability of ATR is then enhanced.

III. Definitions and Techniques Affecting Gene Products and Genes

A. ATRIP Gene Products and Genes

In this patent, the terms "ATRIP gene product" and "ATRIP" refer to proteins and polypeptides having amino acid sequences which are substantially identical to the native ATRIP amino acid sequences or that are biologically active in that they are capable of performing functional activities similar to an endogenous ATRIP and/or cross-reacting with anti-ATRIP antibody raised against ATRIP. In a specific embodiment, an ATRIP polypeptide of SEQ ID NO:2, or a functionally similar fragment thereof, is utilized. Examples of other ATRIP amino acid sequences, followed by their National Center for Biotechnology Information's GenBank Accession No., include: SEQ ID NO:14 (XP_054821); SEQ ID NO:15 (AAH14153); SEQ ID NO:16 (XP_051515); SEQ ID NO:17 (BAB01636); SEQ ID NO:18 (NP_115542), SEQ ID NO:29 (NP_569055); SEQ ID NO:30 (AAH30597); SEQ ID NO:31 (AAH14153); and/or SEQ ID NO:32 (BAB14029). The term "ATRIP gene product" also includes analogs of ATRIP molecules that exhibit at least some biological activity in common with native ATRIP. Such analogs include, but are not limited to, truncated ATRIP polypeptides and ATRIP polypeptides having fewer amino acids than native ATRIP. Furthermore, those skilled in the art of mutagenesis will appreciate that homologs to the mouse ATRIP gene, including human homologs, which homologs are as yet undisclosed or undiscovered, may be used in the methods and compositions disclosed herein.

A skilled artisan recognizes, based on the sequences and Examples provided herein, that there is an alternatively spliced exon encoding amino acids 658–684 near the C-terminus. Given that RT-PCR from two human cell lines suggests that both forms are expressed in each cell type, both forms are within the scope of the invention as described herein.

The term "ATRIP gene," "ATRIP polynucleotide," or "ATRIP nucleic acid" refers to any DNA sequence that is substantially identical to a DNA sequence encoding an ATRIP gene product as defined above. The term also refers to RNA or antisense sequences compatible with such DNA sequences. An "ATRIP gene" may also comprise any combination of associated control sequences. In a specific embodiment of the present invention, a polynucleotide of SEQ ID NO:1 or a functionally similar fragment thereof, is utilized. Examples of other ATRIP nucleic acid sequences, followed by their GenBank Accession No. include: SEQ ID NO:1, SEQ ID NO:3 (XM_051513); SEQ ID NO:4 (AF319567); SEQ ID NO:5 (BC014153); SEQ ID NO:6 (AB046054); SEQ ID NO:7 (NM_032166); SEQ ID NO:8

(AK022405); SEQ ID NO:9 (XM_054821); SEQ ID NO:10 (XM_051515); SEQ ID NO:11 (AF319566); SEQ ID NO:12 (XM_051514); SEQ ID NO:13 (XM_051516); SEQ ID NO:33 (NM_130384); SEQ ID NO:34 (AF451323); SEQ ID NO:35 (BC030597); SEQ ID NO:36 (AL832917); and/or SEQ ID NO:37 (NM_033628).

Thus, nucleic acid compositions encoding ATRIP are herein provided and are also available to a skilled artisan at accessible databases, including the National Center for Biotechnology Information's GenBank database and/or commercially available databases, such as from Celera Genomics, Inc. (Rockville, Md.). Also included are splice variants that encode different forms of the protein. The ATRIP nucleic acid sequences may be naturally occurring or synthetic.

As used herein, the terms "ATRIP nucleic acid sequence," "ATRIP polynucleotide," and "ATRIP gene" refer to nucleic acids provided herein, homologs thereof, and sequences having substantial similarity and function. A skilled artisan recognizes that the sequences are within the scope of the present invention if they encode a product that has prevents or delays entry into mitosis following DNA damage, and furthermore knows how to obtain such sequences as is standard in the art.

The term "substantially identical", when used to define either an ATRIP amino acid sequence or ATRIP polynucleotide sequence, means that a particular subject sequence, for example, a mutant sequence, varies from the sequence of natural ATRIP by one or more substitutions, deletions, or additions, the net effect of which is to retain at least some biological activity of the ATRIP protein. Alternatively, DNA analog sequences are "substantially identical" to specific DNA sequences disclosed herein if: (a) the DNA analog sequence is derived from coding regions of the natural ATRIP gene; or (b) the DNA analog sequence is capable of hybridization of DNA sequences of (a) under moderately stringent conditions and that encode biologically active ATRIP; or (c) DNA sequences that are degenerative as a result of the genetic code to the DNA analog sequences defined in (a) or (b). Substantially identical analog proteins will be greater than about 80% similar to the corresponding sequence of the native protein. Sequences having lesser degrees of similarity but comparable biological activity are considered to be equivalents. In determining polynucleotide sequences, all subject polynucleotide sequences capable of encoding substantially similar amino acid sequences are considered to be substantially similar to a reference polynucleotide sequence, regardless of differences in codon sequence.

1. Percent Similarity

Percent similarity may be determined, for example, by comparing sequence information using the GAP computer program, available from the University of Wisconsin Geneticist Computer Group. The GAP program utilizes the alignment method of Needleman et al., 1970, as revised by Smith et al., 1981. Briefly, the GAP program defines similarity as the number of aligned symbols (i.e. nucleotides or amino acids) that are similar, divided by the total number of symbols in the shorter of the two sequences. The preferred default parameters for the GAP program include (1) a unitary comparison matrix (containing a value of 1 for identities and 0 for non-identities) of nucleotides and the weighted comparison matrix of Gribskov et al., 1986, (2) a penalty of 3.0 for each gap and an additional 0.01 penalty for each symbol and each gap; and (3) no penalty for end gaps.

2. Polynucleotide Sequences

In certain embodiments, the invention concerns the use of ATRIP genes and gene products, such as the ATRIP that includes a sequence that is essentially that of the known ATRIP polynucleotide, or the corresponding protein. The term "a sequence essentially as ATRIP" means that the sequence substantially corresponds to a portion of the ATRIP polynucleotide and has relatively few bases or amino acids (whether DNA or protein) which are not identical to those of ATRIP (or a biologically functional equivalent thereof, when referring to proteins). The term "biologically functional equivalent" is well understood in the art and is further defined in detail herein. Accordingly, sequences that have between about 70% and about 80%; or more preferably, between about 81% and about 90%; or even more preferably, between about 91% and about 99%; of amino acids that are identical or functionally equivalent to the amino acids of ATRIP will be sequences that are "essentially the same".

In specific embodiments, an ATRIP mutant is utilized in methods and compositions of the present invention. A skilled artisan recognizes there are a variety of well-known methods to generate mutations in an ATRIP polynucleotide. In a specific example, a particular motif in ATRIP is mutated, and the subsequent mutant is utilized for an application, such as to interfere with an ATR/ATRIP binding, to alter the function of an ATR/ATRIP complex, to promote cell death, and/or to treat cancer, to name a few examples. In a specific embodiment, a particular domain or motif is mutated in ATRIP. A skilled artisan recognizes that there are a variety of means to identify structural and/or functional motifs, such as through commercially available and well-known software.

In a particular embodiment, a coiled coil domain of ATRIP is mutated. In some embodiments, the coiled-coil structure stabilizes alpha helices in proteins through a very efficient burial of hydrophobic side chains so that they are primarily inaccessible to water. Many structural proteins both inside and outside of cells (keratins, tropomyosin, laminin, etc.) that have to bear considerable stress have a coilel-coil domain. Basic features that are common to coiled-coil peptides include overall secondary structure as being alpha helical and arrangement of hydrophobic residues on one side of the helices. The typical positioning of the hydrophobic residues in coiled-coils, the coiled-coil motif, can be often recognized from primary structure of the protein. The coiled coil in specific embodiments is utilized for protein-protein interactions.

Thus, ATRIP polynucleotides that have functionally equivalent codons are also covered by the invention. The term "functionally equivalent codon" is used herein to refer to codons that encode the same amino acid, such as the six codons for arginine or serine, and also refers to codons that encode biologically equivalent amino acids (Table 1).

TABLE 1

| FUNCTIONALLY EQUIVALENT CODONS. | | | |
|---|---|---|---|
| Amino Acids | | | Codons |
| Alanine | Ala | A | GCA GCC GCG GCU |
| Cysteine | Cys | C | UGC UGU |
| Aspartic Acid | Asp | D | GAC GAU |
| Glutamic Acid | Glu | E | GAA GAG |

TABLE 1-continued

FUNCTIONALLY EQUIVALENT CODONS.

| Amino Acids | | | Codons |
|---|---|---|---|
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

It will also be understood that amino acid and polynucleotide sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to polynucleotide sequences that may, for example, include various non-coding sequences flanking either of the 5' or 3' portions of the coding region or may include various internal sequences, i.e., introns, which are known to occur within genes.

In certain embodiments, the invention concerns the use of truncated ATRIP genes or polynucleotide sequences that encode an ATRIP polypeptide with less amino acids than native ATRIP. The present invention also encompasses the use of DNA segments that are complementary, or essentially complementary, to the sequences set forth in the specification. Polynucleotide sequences that are "complementary" are those that are capable of base-pairing according to the standard Watson-Crick complementarily rules. As used herein, the term "complementary sequences" means polynucleotide sequences which are substantially complementary, as may be assessed by the same nucleotide comparison set forth above, or as defined as being capable of hybridizing to the polynucleotide segment in question under relatively stringent conditions such as those described herein.

3. Biologically Functional Equivalents

As mentioned above, modification and changes may be made in the structure of ATRIP and still obtain a molecule having like or otherwise desirable characteristics. For example, certain amino acids may be substituted for other amino acids in a protein structure without appreciable loss of the ability to bind to ATR, the loss of the ability to facilitate ATR kinase function, the loss of the ability to bind as an ATR/ATRIP complex with ssDNA and/or RPA, the loss of antitumor activity, or a combination thereof. Since it is the interactive capacity and nature of a protein that defines that protein's biological functional activity, certain amino acid sequence substitutions and/or deletions can be made in a protein sequence (or, of course, its underlying DNA coding sequence) and nevertheless obtain a protein with like or even countervailing properties (e.g., antagonistic v. agonistic). It is thus contemplated by the inventors that various changes may be made in the sequence of the ATRIP proteins or peptides (or underlying DNA) without appreciable loss of their biological utility or activity. Included in such changes are truncated ATRIP polypeptides and ATRIP polypeptides having less amino acid residues than native ATRIP.

It is also well understood by the skilled artisan that, inherent in the definition of a biologically functional equivalent protein or peptide, is the concept that there is a limit to the number of changes that may be made within a defined portion of the molecule and still result in a molecule with an acceptable level of equivalent biological activity. Biologically functional equivalent peptides are thus defined herein as those peptides in which certain, not most or all, of the amino acids may be substituted. Of course, a plurality of distinct proteins/peptides with different substitutions may easily be made and used in accordance with the invention.

It is also well understood that where certain residues are shown to be particularly important to the biological or structural properties of a protein or peptide, e.g., residues in active sites, such residues may not generally be exchanged. This is the case in the present invention, where any changes in ATRIP that render the polypeptide incapable of preventing or delaying entry into mitosis following DNA damage would result in a loss of utility of the resulting peptide for the present invention.

Amino acid substitutions, such as those that might be employed in modifying ATRIP are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

In making such changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte and Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those that are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein. It is understood that an amino acid can be substituted for another having a similar hydrophilicity value and still obtain a biologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (□0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 is preferred, those that are within ±1 are particularly preferred, and those within ±0.5 are even more particularly preferred.

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid.

4. Sequence Modification Techniques

Modifications to the ATRIP peptides may be carried out using techniques such as site directed mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art as exemplified by publications (Adelman et al., 1983). As will be appreciated, the technique typically employs a phage vector that exists in both a single stranded and double stranded form. Typical vectors useful in site-directed mutagenesis include vectors such as the M13 phage (Messing et al., 1981). These phage are readily commercially available and their use is generally well known to those skilled in the art. Double stranded plasmids are also routinely employed in site directed mutagenesis that eliminates the step of transferring the gene of interest from a plasmid to a phage.

In general, site-directed mutagenesis in accordance herewith is performed by first obtaining a single-stranded vector (or melting apart the two strands of a double stranded vector) that includes within its sequence a DNA sequence that encodes the ATRIP polynucleotide. An oligonucleotide primer bearing the desired mutated sequence is prepared, generally synthetically, for example by the method of Crea et al. (1978). This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

The preparation of sequence variants of the selected gene using site-directed mutagenesis is provided as a means of producing potentially useful ATRIP and is not meant to be limiting as there are other ways in which sequence variants of these peptides may be obtained. For example, recombinant vectors encoding the desired genes may be treated with mutagenic agents to obtain sequence variants (see, e.g., a method described by Eichenlaub, 1979) for the mutagenesis of plasmid DNA using hydroxylamine.

5. Antisense Constructs

In some cases, a gene is essential to the life of the cell, wherein its removal, such as by homologous replacement, results in the death of the cell. In other cases, a gene may have aberrant functions that cannot be overcome by replacement gene therapy, even where the "wild-type" molecule is expressed in amounts in excess of the mutant polypeptide. Antisense treatments are one way of addressing these situations. Antisense technology also may be used to "knockout" function of ATRIP in the development of cell lines or transgenic mice for research, diagnostic and screening purposes.

Antisense methodology takes advantage of the fact that nucleic acids tend to pair with "complementary" sequences. By complementary, it is meant that polynucleotides are those which are capable of base-pairing according to the standard Watson-Crick complementarily rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases, such as inosine, 5-methylcytosine, 6-methyladenine, hypoxanthine and others, in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the mRNA or preprocessed transcript. This would include control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50–200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences that are completely complementary will be sequences that are entirely complementary throughout their entire length and have no base mismatches. Other sequences with lower degrees of homology also are contemplated. For example, an antisense construct that has limited regions of high homology, but also contains a non-homologous region (e.g., ribozyme) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

6. RNA Interference

RNA interference (RNAi) is the process of sequence-specific, post-transcriptional gene silencing in animals and plants, initiated by double-stranded RNA (dsRNA) that is homologous in sequence to the silenced gene. Elbashir et al. (2001a) demonstrated that 21- and 22-nt RNA fragments are the sequence-specific mediators of RNAi. In a specific embodiment, the short interfering RNAs (siRNAs) are generated by an RNase III-like processing reaction from long dsRNA. Chemically synthesized siRNA duplexes with overhanging 3' ends mediate efficient target RNA cleavage in the lysate, and the cleavage site is located near the center of the region spanned by the guiding siRNA. Furthermore, the direction of dsRNA processing determines whether sense or antisense target RNA can be cleaved by the siRNA-protein complex. Also, Elbashir et al. (2001b) showed that 21-nucleotide siRNA duplexes specifically suppress expression of endogenous and heterologous genes in different mammalian cell lines, including human embryonic kidney (293) and HeLa cells.

Therefore, a skilled artisan recognizes that 21-nucleotide siRNA duplexes provide an effective tool for studying gene function in mammalian cells and are useful as gene-specific therapeutics.

7. Synthetic Polypeptides

The present invention also describes ATRIP proteins and related peptides for use in various embodiments of the present invention. The ATRIP polypeptide may have fewer amino acids than native ATRIP. Relatively small peptides can be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference. Short peptide sequences, or libraries of overlapping peptides, usually from about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids, which correspond to the selected regions described herein, can be readily synthesized and then screened in screening assays designed to identify reactive peptides. Alternatively, recombinant DNA technology may be employed wherein a nucleotide sequence which encodes a peptide of the invention is inserted into an expression vector, transformed or transfected into an appropriate host cell and cultivated under conditions suitable for expression.

8. Other Structural Equivalents

In addition to the ATRIP peptidyl compounds described herein, the inventors also contemplate that other sterically similar compounds may be formulated to mimic the key portions of the peptide structure. Such compounds may be used in the same manner as the peptides of the invention and hence are also functional equivalents. The generation of a structural functional equivalent may be achieved by the techniques of modeling and chemical design known to those of skill in the art. It will be understood that all such sterically similar constructs fall within the scope of the present invention.

B. Expression Vectors

In certain aspects of the present invention it may be necessary to express the ATRIP proteins and/or polypeptides. Throughout this application, the term "expression construct" is meant to include any type of genetic construct containing a polynucleotide coding for a gene product in which part or all of the polynucleotide encoding sequence is capable of being transcribed. The transcript may be translated into a protein, but it need not be. Thus, in certain embodiments, expression includes both transcription of an ATRIP gene and translation of an ATRIP mRNA into an ATRIP protein or polypeptide product. In other embodiments, expression only includes transcription of the polynucleotide encoding an ATRIP or its complement.

In order for the construct to effect expression of at least an ATRIP transcript, the polynucleotide encoding the ATRIP polynucleotide will be under the transcriptional control of a promoter. A "promoter" refers to a DNA sequence recognized by the synthetic machinery of the host cell, or introduced synthetic machinery, that is required to initiate the specific transcription of a gene. The phrase "under transcriptional control" means that the promoter is in the correct location in relation to the polynucleotide to control RNA polymerase initiation and expression of the polynucleotide.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best-known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter that is employed to control the expression of an ATRIP polynucleotide is not believed to be critical, so long as it is capable of expressing the polynucleotide in the targeted cell at sufficient levels. Thus, where a human cell is targeted, it is preferable to position the polynucleotide coding region adjacent to and under the control of a promoter that is capable of being expressed in a human cell. Generally speaking, such a promoter might include either a human or viral promoter. Examples of specific promoters include CMV (cytomegalovirus), RSV (rous sarcoma virus), LTR (long terminal repeat of retroviruses), and/or also regulated promoters specific for different tissues, such as the MMTV (mouse mammary tumor virus).

In various embodiments, the human cytomegalovirus (CMV) immediate early gene promoter, the SV40 early promoter and the Rous sarcoma virus long terminal repeat can be used to obtain high-level expression of the ATRIP polynucleotide. The use of other viral or mammalian cellular or bacterial phage promoters which are well-known in the art to achieve expression of polynucleotides is contemplated as well, provided that the levels of expression are sufficient to produce a growth inhibitory effect.

By employing a promoter with well-known properties, the level and pattern of expression of a polynucleotide following transfection can be optimized. For example, selection of a promoter which is active in specific cells, such as tyrosinase (melanoma), alpha-fetoprotein and albumin (liver tumors), CC10 (lung tumor) and prostate-specific antigen (prostate tumor) will permit tissue-specific expression of ATRIP polynucleotides. Table 2 lists several elements/promoters that may be employed, in the context of the present invention, to regulate the expression of ATRIP constructs. This list is not intended to be exhaustive of all the possible elements involved in the promotion of ATRIP expression but, merely, to be exemplary thereof.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Additionally any promoter/enhancer combination (as per the Eukaryotic Promoter Data Base EPDB) could also be used to drive expression of an ATRIP construct. Use of a T3, T7 or SP6 cytoplasmic expression system is another possible embodiment. Eukaryotic cells can support cytoplasmic transcription from certain bacteriophage promoters if the appropriate bacteriophage polymerase is provided, either as part of the delivery complex or as an additional genetic expression vector.

TABLE 2

| ENHANCER |
|---|
| Immunoglobulin Heavy Chain |
| Immunoglobulin Light Chain |
| T-Cell Receptor |
| HLA DQ α and DQ β |
| β-Interferon |
| Interleukin-2 |
| Interleukin-2 Receptor |
| MHC Class II 5 |
| MHC Class II HLA-DRα |
| β-Actin |
| Muscle Creatine Kinase |
| Prealbumin (Transthyretin) |
| Elastase I |
| Metallothionein |
| Collagenase |
| Albumin Gene |
| α-Fetoprotein |
| τ-Globin |
| β-Globin |
| c-fos |
| c-HA-ras |
| Insulin |
| Neural Cell Adhesion Molecule (NCAM) |
| ENHANCER |
| $α_1$-Antitrypsin |
| H2B (TH2B) Histone |
| Mouse or Type I Collagen |
| Glucose-Regulated Proteins (GRP94 and GRP78) |
| Rat Growth Hormone |
| Human Serum Amyloid A (SAA) |
| Troponin I (TN I) |
| Platelet-Derived Growth Factor |
| Duchenne Muscular Dystrophy |
| SV40 |
| Polyoma |
| Retroviruses |
| Papilloma Virus |
| Hepatitis B Virus |
| Human Immunodeficiency Virus |
| Cytomegalovirus |
| Gibbon Ape Leukemia Virus |

Further, selection of a promoter that is regulated in response to specific physiologic signals can permit inducible expression of the ATRIP construct. For example, with the polynucleotide under the control of the human PAI-1 promoter, expression is inducible by tumor necrosis factor. Table 3 illustrates several promoter/inducer combinations:

TABLE 3

| Element | Inducer |
|---|---|
| MT II Phorbol Ester (TFA) | Heavy metals |
| MMTV (mouse mammary tumor virus) | Glucocorticoids |
| β-Interferon | Poly(rI)XPoly(rc) |
| Adenovirus 5 E2 | Ela |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease |
| GRP78 Gene | A23187 |
| α-2-Macroglobulin | IL-6 |

TABLE 3-continued

| Element | Inducer |
| --- | --- |
| Vimentin | Serum |
| MHC Class I Gene H-2kB | Interferon |
| HSP70 Ela, SV40 Large T Antigen | |
| Proliferin | Phorbol Ester-TPA |
| Tumor Necrosis Factor | FMA |
| Thyroid Stimulating Hormone α Gene | Thyroid Hormone |

In certain embodiments of the invention, the delivery of an expression vector in a cell may be identified in vitro or in vivo by including a marker in the expression vector. The marker would result in an identifiable change to the transfected cell permitting easy identification of expression. Usually the inclusion of a drug selection marker aids in cloning and in the selection of transformants. Alternatively, enzymes such as herpes simplex virus thymidine kinase (tk) (eukaryotic) or chloramphenicol acetyltransferase (CAT) (prokaryotic) may be employed. Immunologic markers also can be employed. The selectable marker employed is not believed to be important, so long as it is capable of being expressed along with the polynucleotide encoding ATRIP. Further examples of selectable markers are well known to one of skill in the art.

One typically will include a polyadenylation signal to effect proper polyadenylation of the transcript. The nature of the polyadenylation signal is not believed to be crucial to the successful practice of the invention, and any such sequence may be employed. The inventor has employed the SV40 polyadenylation signal in that it was convenient and known to function well in the target cells employed. Also contemplated as an element of the expression construct is a terminator. These elements can serve to enhance message levels and to minimize read through from the construct into other sequences.

The expression construct may comprise a virus or engineered construct derived from a viral genome. The ability of certain viruses to enter cells via receptor-mediated endocytosis and, in some cases, integrate into the host cell chromosomes, have made them attractive candidates for gene transfer in to mammalian cells. However, because it has been demonstrated that direct uptake of naked DNA, as well as receptor-mediated uptake of DNA complexes, expression vectors need not be viral but, instead, may be any plasmid, cosmid or phage construct that is capable of supporting expression of encoded genes in mammalian cells, such as pUC or Bluescript™ plasmid series.

C. Rational Drug Design

The goal of rational drug design is to produce structural analogs of biologically active polypeptides or compounds with which they interact (agonists, antagonists, inhibitors, binding partners, etc.). By creating such analogs, it is possible to fashion drugs that are more active or stable than the natural molecules, which have different susceptibility to alteration, or which may affect the function of various other molecules. In one approach, one would generate a three-dimensional structure for ATRIP or a fragment thereof. This could be accomplished by x-ray crystallography, computer modeling or by a combination of both approaches. An alternative approach, "alanine scan," involves the random replacement of residues throughout molecule with alanine, and the resulting affect on function determined.

It also is possible to isolate an ATRIP specific antibody, selected by a functional assay, and then solve its crystal structure. In principle, this approach yields a pharmacore upon which subsequent drug design can be based. It is possible to bypass protein crystallograph altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

Thus, one may design drugs which have improved ATRIP activity or which act as stimulators, inhibitors, agonists, antagonists or ATRIP or molecules affected by ATRIP function. By use of cloned ATRIP sequences, sufficient amounts of ATRIP can be produced to perform crystallographic studies. In addition, knowledge of the polypeptide sequences permits computer-employed predictions of structure-function relationships.

The present invention also contemplates the use of ATRIP and active fragments, and nucleic acids coding therefor, in the screening of compounds for activity in either stimulating ATRIP activity, overcoming the lack of ATRIP or blocking the effect of a mutant ATRIP molecule.

The present invention also encompasses the use of various animal models. By developing or isolating mutant cells lines that fail to express normal ATRIP, one can, in some embodiments, generate cancer models in mice that will be highly predictive of cancers in humans and other mammals. These models may employ the orthotopic or systemic administration of tumor cells to mimic primary and/or metastatic cancers. Transgenic animals (discussed below) that lack a wild-type ATRIP may be utilized as models for cancer development and treatment.

Treatment of animals with test compounds will involve the administration of the compound, in an appropriate form, to the animal. Administration will be by any route the could be utilized for clinical or non-clinical purposes, including but not limited to oral, nasal, buccal, rectal, vaginal or topical. Alternatively, administration may be by intratracheal instillation, bronchial instillation, intradermal, subcutaneous, intramuscular, intraperitoneal or intravenous injection. Specifically contemplated are systemic intravenous injection, regional administration via blood or lymph supply, and intratumoral injection.

Determining the effectiveness of a compound in vivo may involve a variety of different criteria. Such criteria include, but are not limited to, survival, reduction of tumor burden or mass, arrest or slowing of tumor progression, elimination of tumors, inhibition or prevention of metastasis, increased activity level, improvement in immune effector function and improved food intake.

D. In vivo Delivery and Treatment Protocols

Where the gene itself is employed to introduce the gene products, a convenient method of introduction will be through the use of a recombinant vector that incorporates the desired gene, together with its associated control sequences. The preparation of recombinant vectors is well known to those of skill in the art and described in many references, such as, for example, Sambrook et al. (1989), specifically incorporated herein by reference.

In vectors, it is understood that the DNA coding sequences to be expressed, in this case those encoding the ATRIP gene products, are positioned adjacent to and under the control of a promoter. It is understood in the art that to bring a coding sequence under the control of such a promoter, one generally positions the 5' end of the transcription initiation site of the transcriptional reading frame of the gene product to be expressed between about 1 and about 50 nucleotides "downstream" of (i.e., 3' of) the chosen promoter. One may also desire to incorporate into the transcriptional unit of the vector an appropriate polyadenylation site (e.g., 5'-AATAAA-3'; SEQ ID NO:28), if one was not contained within the original inserted DNA. Typically, these poly A addition sites are placed about 30 to 2000 nucleotides "downstream" of the coding sequence at a position prior to transcription termination.

While use of the control sequences of the ATRIP will be preferred, there is no reason why other control sequences could not be employed, so long as they are compatible with the genotype of the cell being treated. Thus, one may mention other useful promoters by way of example, including, e.g., an SV40 early promoter, a long terminal repeat promoter from retrovirus, an actin promoter, a heat shock promoter, a metallothionein promoter, and the like.

For introduction of the ATRIP gene, it is proposed that one will desire to preferably employ a vector construct that will deliver the desired gene to the affected cells. This will, of course, generally require that the construct be delivered to the targeted tumor cells, for example, breast, genital, or lung tumor cells. It is proposed that this may be achieved most preferably by introduction of the desired gene through the use of a viral or non-viral vector to carry the ATRIP sequences to efficiently transfect the tumor, or pretumorous tissue. This infection may be achieved preferably by liposomal delivery but may also be via adenoviral, a retroviral, a vaccinia virus, herpesvirus or adeno-associated virus vector. These vectors have been successfully used to deliver desired sequences to cells and tend to have a high infection efficiency.

Commonly used viral promoters for expression vectors are derived from polyoma, cytomegalovirus, Adenovirus 2, and Simian Virus 40 (SV40). The early and late promoters of SV40 virus are particularly useful because both are obtained easily from the virus as a fragment that also contains the SV40 viral origin of replication. Smaller or larger SV40 fragments may also be used, provided there is included the approximately 250 bp sequence extending from the HindIII site toward the Bgl I site located in the viral origin of replication. Further, it is also possible, and often desirable, to utilize promoter or control sequences normally associated with the desired gene sequence, provided such control sequences are compatible with the host cell systems.

The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

1. Liposomal Transfection

The expression construct may be entrapped in a liposome. Liposomes are structures created by mixing phospholipids with water, or hydration of phospholipid. The resultant bilayer structures tend to fold back upon themselves. Liposomes are frequently multilamellar, composed of concentric bilayer membranes separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

The present invention also provides particularly useful methods for introducing ATRIP gene products into cells. One method of in vivo gene transfer that can lead to expression of genes transfected into cells involves the use of liposomes. Liposomes can be used for both in vitro and in vivo transfection. Liposome-mediated gene transfer seems to have great potential for certain in vivo applications in animals (Nicolau et al., 1987). Studies have shown that intravenously injected liposomes are taken up essentially in the liver and the spleen, by the macrophages of the reticuloendothelial system. The specific cellular sites of uptake of injected liposomes appear to be mainly spleen macrophages and liver Kupffer cells. Intravenous injection of liposomes/DNA complexes can lead to the uptake of DNA by these cellular sites, and result in the expression of a gene product encoded in the DNA (Nicolau, 1982).

The inventors contemplate that ATRIP gene products can be introduced into cells using liposome-mediated gene transfer. It is proposed that such constructs can be coupled with liposomes and directly introduced via a catheter, as described by Nabel et al. (1990). By employing these methods, ATRIP gene products can be expressed efficiently at a specific site in vivo, not just the liver and spleen cells which are accessible via intravenous injection. Therefore, this invention also encompasses compositions of DNA constructs encoding an ATRIP gene product formulated as a DNA/liposome complex and methods of using such constructs.

Liposomal transfection can be via liposomes composed of, for example, phosphatidylcholine (PC), phosphatidylserine (PS), cholesterol (Chol), N-[1-(2,3-dioleyloxy)propyl]-N,N-trimethylammonium chloride (DOTMA), dioleoylphosphatidylethanolamine (DOPE), and/or 3b[N-(N'N'-dimethylaminoethane)-carbarmoyl cholesterol (DC-Chol), as well as other lipids known to those of skill in the art. Those of skill in the art will recognize that there are a variety of liposomal transfection techniques that will be useful in the present invention. Among these techniques are those described in Nicolau et al., 1987, Nabel et al., 1990, and Gao et al., 1991. In one embodiment of the present invention, liposomes comprising DC-Chol and DOPE that have been prepared following the teaching of Gao et al., 1991, are used. The inventors also anticipate utility for liposomes comprised of DOTMA, such as those that are available commercially under the trademark Lipofectin™, from Vical, Inc., in San Diego, Calif.

Liposomes may be introduced into contact with cells to be transfected by a variety of methods. In cell culture, the liposome-DNA complex can simply be dispersed in the cell culture solution. For application in vivo, liposome-DNA complex are typically injected. Intravenous injection allows liposome-mediated transfer of DNA complex, for example, the liver and the spleen. In order to allow transfection of DNA into cells that are not accessible through intravenous injection, it is possible to directly inject the liposome-DNA complexes into a specific location in an animal's body. For example, Nabel et al. teach injection via a catheter into the arterial wall. In another example, the inventors have used intraperitoneal injection to allow for gene transfer into mice.

The present invention also contemplates compositions comprising a liposomal complex. This liposomal complex will comprise a lipid component and a DNA segment encoding an ATRIP gene.

The lipid employed to make the liposomal complex can be any of the above-discussed lipids. In particular, DOTMA, DOPE, and/or DC-Chol may form all or part of the liposomal complex. The inventors have had particular success with complexes comprising DC-Chol. In a preferred embodiment, the lipid will comprise DC-Chol and DOPE. While any ratio of DC-Chol to DOPE is expected to have utility, it is expected that those comprising a ratio of DC-Chol:DOPE between 1:20 and 20:1 will be particularly advantageous. The inventors have found that liposomes prepared from a ratio of DC-Chol:DOPE of about 1:10 to about 1:5 have been useful.

It is proposed that it will ultimately be preferable to employ the smallest region needed to suppress the ATRIP gene so that one is not introducing unnecessary DNA into cells which receive an ATRIP gene construct. Techniques well known to those of skill in the art, such as the use of restriction enzymes, will allow for the generation of small regions of ATRIP. The ability of these regions to inhibit tumor cell proliferation, tumorigenicity and transformation phenotype can easily be determined by the assays reported in the Examples.

In certain embodiments of the invention, the liposome may be complexed with a hemagglutinatin virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of polynucleotide in vitro and in vivo, then they are applicable for the present invention. Where a bacterial promoter is employed in the DNA construct, it also will be desirable to include within the liposome an appropriate bacterial polymerase.

2. Adenovirus

Another method for in vivo delivery involves the use of an adenovirus vector. "Adenovirus expression vector" is meant to include those constructs containing adenovirus sequences sufficient to (a) support packaging of the construct and (b) to express an antisense polynucleotide that has been cloned therein. In this context, expression does not require that the gene product be synthesized.

Adenovirus is a particularly suitable gene transfer vector because of its midsized genome, ease of manipulation, high titer, wide target-cell range and high infectivity. Both ends of the viral genome contain 100–200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, located at 16.8 mm is particularly efficient during the late phase of infection, and all the mRNA's issued from this promoter possess a 5'-tripartite leader (TL) sequence which makes them preferred mRNA's for translation.

In some cases, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure. Use of the YAC system is an alternative approach for the production of recombinant adenovirus.

A particular method of introducing the ATRIP to an animal is to introduce a replication-deficient adenovirus containing the ATRIP gene. The replication-deficient construct made by E1B and E3 deletion also avoids the viral reproduction inside the cell and transfer to other cells and infection of other people, which means the viral infection activity is shut down after it infects the target cell. The ATRIP gene is still expressed inside the cells. Also, unlike retrovirus, which can only infect proliferating cells, adenovirus is able to transfer the ATRIP gene into both proliferating and non-proliferating cells. Further, the extrachromosomal location of adenovirus in the infected cells decreases the chance of cellular oncogene activation within the treated animal.

Introduction of the adenovirus containing the ATRIP gene product gene into a suitable host is typically done by injecting the virus contained in a buffer.

The nature of the adenovirus vector is not believed to be crucial to the successful practice of the invention. Of course, as discussed above, it is advantageous if the adenovirus vector is replication defective, or at least conditionally defective, The adenovirus may be of any of the 42 different known serotypes or subgroups A–F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

Adenovirus is easy to grow and manipulate and exhibits broad host range in vitro and in vivo. This group of viruses can be obtained in high titers, e.g., 109–1011 plaque-forming units per ml, and they are highly infective. The life cycle of adenovirus does not require integration in to the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus have been used in eukaryotic gene expression (Levrero et al., 1991; Gomez-Foix et al., 1992) and vaccine development (Grunhaus and Horwitz, 1992; Graham and Prevec, 1992). Animal studies have suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotatic inoculation into the brain (Le Gal La Salle et al., 1993).

3. Retroviruses

The retroviruses are a group of single-stranded RNA viruses characterized by an ability to convert their RNA to double-stranded DNA to infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene, termed y components is constructed (Mann et al., 1983). When a recombinant plasmid containing a human cDNA, together with the retroviral LTR and y sequences is introduced into this cell line (by calcium phosphate precipitation for example), the y sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. One limitation to the use of retrovirus vectors in vivo is the limited ability to produce retroviral vector titers greater than 106 infections U/mL. Titers 10- to 1,000-fold higher are necessary for many in vivo applications.

Several properties of the retrovirus have limited its use in lung cancer treatment (Stratford-Perricaudet and Perricaudet, 1991; (i) Infection by retrovirus depends on host cell division. In human cancer, very few mitotic cells can be found in tumor lesions. (ii) The integration of retrovirus into the host genome may cause adverse effects on target cells, because malignant cells are high in genetic instability. (iii) Retrovirus infection is often limited by a certain host range. (iv) Retrovirus has been associated with many malignancies in both mammals and vertebrates. (v) The titer of retrovirus, in general, is 100- to 1,000-fold lower than that of adenovirus.

4. Other Viral Vectors as Expression Constructs

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpes viruses may be employed. They offer several attractive features for various mammalian cells (Friedmann, 1989; Ridgeway, 1988; Baichwal and Sugden, 1986; Coupar et al., 1988; Howrich et al., 1990).

With the recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al. introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Cultures media containing high titers of the recombinant virus were used to infect primary duckling hepatocytes. Stable CAT gene expression was detected for at least 24 days after transfection (Chang et al., 1991).

5. Other Non-viral Vectors

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. As described above, delivery may be via viral infection where the expression construct is encapsidated in an infectious viral particle.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the polynucleotide encoding the gene of interest may be positioned and expressed at different sites. In certain embodiments, the polynucleotide encoding the gene may be stably maintained in the cell as a separate, episomal segment of DNA. Such polynucleotide segments or "episomes" encode sequences sufficient to permit maintenance and replication independent of or in synchronization with the host cell cycle. How the expression construct is delivered to a cell and where in the cell the polynucleotide remains is dependent on the type of expression construct employed.

In one embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of $CaPO_4$ precipitates into liver and spleen of adult and newborn mice demonstrating active viral replication and acute infection. Benvenisty and Reshef (1986) also demonstrated that direct intraperitoneal injection of $CaPO_4$ precipitated plasmids results in expression of the transfected genes. It is envisioned that DNA encoding a gene of interest may also be transferred in a similar manner in vivo and express the gene product.

Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present invention.

Other expression constructs that can be employed to deliver a polynucleotide encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific.

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). A synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that a polynucleotide encoding a particular gene also may be specifically delivered into a cell type such as lung, epithelial or tumor cells, by any number of receptor-ligand systems with or without liposomes. For example, epidermal growth factor (EGF) may be used as the receptor for mediated delivery of a polynucleotide encoding a gene in many tumor cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a polynucleotide into the cells, in vitro, and then the return of the modified cells back into an animal. This may involve the surgical removal of tissue/organs from an animal or the primary culture of cells and tissues. Anderson et al., U.S. Pat. No. 5,399,346, and incorporated herein in its entirety, disclose ex vivo therapeutic methods.

6. Protein Therapy

Another therapy approach is the provision, to a subject, of ATRIP polypeptide, active fragments, synthetic peptides, mimetics or other analogs thereof. The protein may be produced by recombinant expression means or, if small enough, generated by an automated peptide synthesizer. Formulations would be selected based on the route of administration and purpose including, but not limited to, liposomal formulations and classic pharmaceutical preparations.

7. Lipid Compositions

In certain embodiments, the present invention concerns a novel composition comprising one or more lipids associated with at least one ATRIP polynucleotide or ATRIP polypeptide, protein, or peptide. A lipid is a substance that is characteristically insoluble in water and extractable with an organic solvent. Lipids include, for example, the substances comprising the fatty droplets that naturally occur in the cytoplasm as well as the class of compounds which are well known to those of skill in the art which contain long-chain aliphatic hydrocarbons and their derivatives, such as fatty acids, alcohols, amines, amino alcohols, and aldehydes. Of course, compounds other than those specifically described herein that are understood by one of skill in the art as lipids are also encompassed by the compositions and methods of the present invention.

A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof.

a. Lipid Types

A neutral fat may comprise a glycerol and a fatty acid. A typical glycerol is a three carbon alcohol. A fatty acid generally is a molecule comprising a carbon chain with an acidic moeity (e.g., carboxylic acid) at an end of the chain. The carbon chain may of a fatty acid may be of any length, however, it is preferred that the length of the carbon chain be of from about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, to about 30 or more carbon atoms, and any range derivable therein. However, a preferred range is from about 14 to about 24 carbon atoms in the chain portion of the fatty acid, with about 16 to about 18 carbon atoms being particularly preferred in certain embodiments. In certain embodiments the fatty acid carbon chain may comprise an odd number of carbon atoms, however, an even number of carbon atoms in the chain may be preferred in certain embodiments. A fatty acid comprising only single bonds in its carbon chain is called saturated, while a fatty acid comprising at least one double bond in its chain is called unsaturated.

Specific fatty acids include, but are not limited to, linoleic acid, oleic acid, palmitic acid, linolenic acid, stearic acid, lauric acid, myristic acid, arachidic acid, palmitoleic acid, arachidonic acid, ricinoleic acid, tuberculosteric acid, lactobacillic acid. An acidic group of one or more fatty acids is covalently bonded to one or more hydroxyl groups of a glycerol. Thus, a monoglyceride comprises a glycerol and one fatty acid, a diglyceride comprises a glycerol and two fatty acids, and a triglyceride comprises a glycerol and three fatty acids.

A phospholipid generally comprises either glycerol or an sphingosine moiety, an ionic phosphate group to produce an amphipathic compound, and one or more fatty acids. Types of phospholipids include, for example, phosphoglycerides, wherein a phosphate group is linked to the first carbon of glycerol of a diglyceride, and sphingophospholipids (e.g., sphingomyelin), wherein a phosphate group is esterified to a sphingosine amino alcohol. Another example of a sphingophospholipid is a sulfatide, which comprises an ionic sulfate group that makes the molecule amphipathic. A phospholipid may, of course, comprise further chemical groups, such as for example, an alcohol attached to the phosphate group. Examples of such alcohol groups include serine, ethanolamine, choline, glycerol and inositol. Thus, specific phosphoglycerides include a phosphatidyl serine, a phosphatidyl ethanolamine, a phosphatidyl choline, a phosphatidyl glycerol or a phosphotidyl inositol. Other phospholipids include a phosphatidic acid or a diacetyl phosphate. In one aspect, a phosphatidylcholine comprises a dioleoylphosphatidylcholine (a.k.a. cardiolipin), an egg phosphatidylcholine, a dipalmitoyl phosphalidycholine, a monomyristoyl phosphatidylcholine, a monopalmitoyl phosphatidylcholine, a monostearoyl phosphatidylcholine, a monooleoyl phosphatidylcholine, a dibutroyl phosphatidylcholine, a divaleroyl phosphatidylcholine, a dicaproyl phosphatidylcholine, a diheptanoyl phosphatidylcholine, a dicapryloyl phosphatidylcholine or a distearoyl phosphatidylcholine.

A glycolipid is related to a sphinogophospholipid, but comprises a carbohydrate group rather than a phosphate group attached to a primary hydroxyl group of the sphingosine. A type of glycolipid called a cerebroside comprises one sugar group (e.g., a glucose or galactose) attached to the primary hydroxyl group. Another example of a glycolipid is a ganglioside (e.g., a monosialoganglioside, a GM1), which comprises about 2, about 3, about 4, about 5, about 6, to about 7 or so sugar groups, that may be in a branched chain, attached to the primary hydroxyl group. In other embodiments, the glycolipid is a ceramide (e.g., lactosylceramide).

A steroid is a four-membered ring system derivative of a phenanthrene. Steroids often possess regulatory functions in cells, tissues and organisms, and include, for example, hormones and related compounds in the progestagen (e.g., progesterone), glucocoricoid (e.g., cortisol), mineralocorticoid (e.g., aldosterone), androgen (e.g., testosterone) and estrogen (e.g., estrone) families. Cholesterol is another example of a steroid, and generally serves structural rather than regulatory functions. Vitamin D is another example of a sterol, and is involved in calcium absorption from the intestine.

A terpene is a lipid comprising one or more five carbon isoprene groups. Terpenes have various biological functions, and include, for example, vitamin A, coenyzme Q and carotenoids (e.g., lycopene and β-carotene).

b. Charged and Neutral Lipid Compositions

In certain embodiments, a lipid component of a composition is uncharged or primarily uncharged. In one embodiment, a lipid component of a composition comprises one or more neutral lipids. In another aspect, a lipid component of a composition may be substantially free of anionic and cationic lipids, such as certain phospholipids (e.g., phosphatidyl choline) and cholesterol. In certain aspects, a lipid component of an uncharged or primarily uncharged lipid composition comprises about 95%, about 96%, about 97%, about 98%, about 99% or 100% lipids without a charge, substantially uncharged lipid(s), and/or a lipid mixture with equal numbers of positive and negative charges.

In other aspects, a lipid composition may be charged. For example, charged phospholipids may be used for preparing a lipid composition according to the present invention and can carry a net positive charge or a net negative charge. In a non-limiting example, diacetyl phosphate can be employed to confer a negative charge on the lipid composition, and stearylamine can be used to confer a positive charge on the lipid composition.

c. Making Lipids

Lipids can be obtained from natural sources, commercial sources or chemically synthesized, as would be known to one of ordinary skill in the art. For example, phospholipids can be from natural sources, such as egg or soybean phosphatidylcholine, brain phosphatidic acid, brain or plant phosphatidylinositol, heart cardiolipin and plant or bacterial phosphatidylethanolamine. In another example, lipids suitable for use according to the present invention can be obtained from commercial sources. For example, dimyristyl phosphatidylcholine ("DMPC") can be obtained from Sigma Chemical Co., dicetyl phosphate ("DCP") is obtained from K & K Laboratories (Plainview, N.Y.); cholesterol ("Chol") is obtained from Calbiochem-Behring; dimyristyl phosphatidylglycerol ("DMPG") and other lipids may be obtained from Avanti Polar Lipids, Inc. (Birmingham, Ala.). In certain embodiments, stock solutions of lipids in chloroform or chloroform/methanol can be stored at about −20° C. Preferably, chloroform is used as the only solvent since it is more readily evaporated than methanol.

d. Lipid Composition Structures

In a preferred embodiment of the invention, the ATRIP composition may be associated with a lipid. An ATRIP composition associated with a lipid may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure. A lipid or lipid/ATRIP composition associated composition of the present invention is not limited to any particular structure. For example, they may also simply be interspersed in a solution, possibly forming aggregates that are not uniform in either size or shape. In another example, they may be present in a bilayer structure, as micelles, or with a "collapsed" structure. In another non-limiting example, a lipofectamine (Gibco BRL)-ATRIP composition or Superfect (Qiagen)-ATRIP composition complex is also contemplated.

In certain embodiments, a lipid composition may comprise about 1%, about 2%, about 3%, about 4% about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, or any range derivable therein, of a particular lipid, lipid type or non-lipid component such as a drug, protein, sugar, nucleic acids or other material disclosed herein or as would be known to one of skill in the art. In a non-limiting example, a lipid composition may comprise about 10% to about 20% neutral lipids, and about 33% to about 34% of a cerebroside, and about 1% cholesterol. In another non-limiting example, a liposome may comprise about 4% to about 12% terpenes, wherein about 1% of the micelle is specifically lycopene, leaving about 3% to about 11% of the liposome as comprising other terpenes; and about 10% to about 35% phosphatidyl choline, and about 1% of a drug. Thus, it is contemplated that lipid compositions of the present invention may comprise any of the lipids, lipid types or other components in any combination or percentage range.

e. Emulsions

A lipid may be comprised in an emulsion. A lipid emulsion is a substantially permanent heterogenous liquid mixture of two or more liquids that do not normally dissolve in each other, by mechanical agitation or by small amounts of additional substances known as emulsifiers. Methods for preparing lipid emulsions and adding additional components are well known in the art (e.g., Modern Pharmaceutics, 1990, incorporated herein by reference).

For example, one or more lipids are added to ethanol or chloroform or any other suitable organic solvent and agitated by hand or mechanical techniques. The solvent is then evaporated from the mixture leaving a dried glaze of lipid. The lipids are resuspended in aqueous media, such as phosphate buffered saline, resulting in an emulsion. To achieve a more homogeneous size distribution of the emulsified lipids, the mixture may be sonicated using conventional sonication techniques, further emulsified using microfluidization (using, for example, a Microfluidizer, Newton, Mass.), and/or extruded under high pressure (such as, for example, 600 psi) using an Extruder Device (Lipex Biomembranes, Vancouver, Canada).

f. Micelles

A lipid may be comprised in a micelle. A micelle is a cluster or aggregate of lipid compounds, generally in the form of a lipid monolayer, and may be prepared using any micelle producing protocol known to those of skill in the art (e.g., Canfield et al., 1990; El-Gorab et al, 1973; Colloidal Surfactant, 1963; and Catalysis in Micellar and Macromolecular Systems, 1975, each incorporated herein by reference). For example, one or more lipids are typically made into a suspension in an organic solvent, the solvent is evaporated, the lipid is resuspended in an aqueous medium, sonicated and then centrifuged.

g. Liposomes

In particular embodiments, a lipid comprises a liposome. A "liposome" is a generic term encompassing a variety of single and multilamellar lipid vehicles formed by the generation of enclosed lipid bilayers or aggregates. Liposomes may be characterized as having vesicular structures with a bilayer membrane, generally comprising a phospholipid, and an inner medium that generally comprises an aqueous composition.

A multilamellar liposome has multiple lipid layers separated by aqueous medium. They form spontaneously when lipids comprising phospholipids are suspended in an excess of aqueous solution. The lipid components undergo self-rearrangement before the formation of closed structures and entrap water and dissolved solutes between the lipid bilayers (Ghosh and Bachhawat, 1991). Lipophilic molecules or molecules with lipophilic regions may also dissolve in or associate with the lipid bilayer.

In certain less preferred embodiments, phospholipids from natural sources, such as egg or soybean phosphatidylcholine, brain phosphatidic acid, brain or plant phosphatidylinositol, heart cardiolipin and plant or bacterial phosphatidylethanolamine are preferably not used as the primary phosphatide, i.e., constituting 50% or more of the total phosphatide composition or a liposome, because of the instability and leakiness of the resulting liposomes.

In particular embodiments, an ATRIP composition may be, for example, encapsulated in the aqueous interior of a liposome, interspersed within the lipid bilayer of a liposome, attached to a liposome via a linking molecule that is associated with both the liposome and the ATRIP composition, entrapped in a liposome, complexed with a liposome, etc.

h. Making Liposomes

A liposome used according to the present invention can be made by different methods, as would be known to one of ordinary skill in the art. Phospholipids can form a variety of structures other than liposomes when dispersed in water, depending on the molar ratio of lipid to water. At low ratios the liposome is the preferred structure.

For example, a phospholipid (Avanti Polar Lipids, Alabaster, Ala.), such as for example the neutral phospholipid dioleoylphosphatidylcholine (DOPC), is dissolved in tert-butanol. The lipid(s) is then mixed with the ATRIP composition, and/or other component(s). Tween 20 is added to the lipid mixture such that Tween 20 is about 5% of the composition's weight. Excess tert-butanol is added to this mixture such that the volume of tert-butanol is at least 95%. The mixture is vortexed, frozen in a dry ice/acetone bath and lyophilized overnight. The lyophilized preparation is stored at −20° C. and can be used up to three months. When required the lyophilized liposomes are reconstituted in 0.9% saline. The average diameter of the particles obtained using Tween 20 for encapsulating the ATRIP composition is about 0.7 to about 1.0 µm in diameter.

Alternatively, a liposome can be prepared by mixing lipids in a solvent in a container, e.g., a glass, pear-shaped flask. The container should have a volume ten-times greater than the volume of the expected suspension of liposomes. Using a rotary evaporator, the solvent is removed at approximately 40° C. under negative pressure. The solvent normally is removed within about 5 min. to 2 hours, depending on the desired volume of the liposomes. The composition can be dried further in a desiccator under vacuum. The dried lipids generally are discarded after about 1 week because of a tendency to deteriorate with time.

Dried lipids can be hydrated at approximately 25–50 mM phospholipid in sterile, pyrogen-free water by shaking until all the lipid film is resuspended. The aqueous liposomes can be then separated into aliquots, each placed in a vial, lyophilized and sealed under vacuum.

In other alternative methods, liposomes can be prepared in accordance with other known laboratory procedures (e.g., see Bangham et al., 1965; Gregoriadis, 1979; Deamer and Uster 1983, Szoka and Papahadjopoulos, 1978, each incorporated herein by reference in relevant part). These methods differ in their respective abilities to entrap aqueous material and their respective aqueous space-to-lipid ratios.

The dried lipids or lyophilized liposomes prepared as described above may be dehydrated and reconstituted in a solution of inhibitory peptide and diluted to an appropriate concentration with an suitable solvent, e.g., DPBS. The mixture is then vigorously shaken in a vortex mixer. Unencapsulated additional materials, such as agents including but not limited to hormones, drugs, nucleic acid constructs and the like, are removed by centrifugation at 29,000×g and the liposomal pellets washed. The washed liposomes are resuspended at an appropriate total phospholipid concentration, e.g., about 50–200 mM. The amount of additional material or active agent encapsulated can be determined in accordance with standard methods. After determination of the amount of additional material or active agent encapsulated in the liposome preparation, the liposomes may be diluted to appropriate concentrations and stored at 4° C. until use. A pharmaceutical composition comprising the liposomes will usually include a sterile, pharmaceutically acceptable carrier or diluent, such as water or saline solution.

The size of a liposome varies depending on the method of synthesis. Liposomes in the present invention can be a variety of sizes. In certain embodiments, the liposomes are small, e.g., less than about 100 nm, about 90 nm, about 80 nm, about 70 nm, about 60 nm, or less than about 50 nm in external diameter. In preparing such liposomes, any protocol described herein, or as would be known to one of ordinary skill in the art may be used. Additional non-limiting examples of preparing liposomes are described in U.S. Pat. Nos. 4,728,578, 4,728,575, 4,737,323, 4,533,254, 4,162,282, 4,310,505, and 4,921,706; International Applications PCT/US85/01161 and PCT/US89/05040; U.K. Patent Application GB 2193095 A; Mayer et al., 1986; Hope et al., 1985; Mayhew et al. 1987; Mayhew et al., 1984; Cheng et al., 1987; and Liposome Technology, 1984, each incorporated herein by reference).

A liposome suspended in an aqueous solution is generally in the shape of a spherical vesicle, having one or more concentric layers of lipid bilayer molecules. Each layer consists of a parallel array of molecules represented by the formula XY, wherein X is a hydrophilic moiety and Y is a hydrophobic moiety. In aqueous suspension, the concentric layers are arranged such that the hydrophilic moieties tend to remain in contact with an aqueous phase and the hydrophobic regions tend to self-associate. For example, when aqueous phases are present both within and without the liposome, the lipid molecules may form a bilayer, known as a lamella, of the arrangement XY-YX. Aggregates of lipids may form when the hydrophilic and hydrophobic parts of more than one lipid molecule become associated with each other. The size and shape of these aggregates will depend upon many different variables, such as the nature of the solvent and the presence of other compounds in the solution.

The production of lipid formulations often is accomplished by sonication or serial extrusion of liposomal mixtures after (I) reverse phase evaporation (II) dehydration-rehydration (III) detergent dialysis and (IV) thin film hydration. In one aspect, a contemplated method for preparing liposomes in certain embodiments is heating sonicating, and sequential extrusion of the lipids through filters or membranes of decreasing pore size, thereby resulting in the formation of small, stable liposome structures. This preparation produces liposomal/ATRIP composition or liposomes only of appropriate and uniform size, which are structurally stable and produce maximal activity. Such techniques are well-known to those of skill in the art (see, for example Martin, 1990).

Once manufactured, lipid structures can be used to encapsulate compounds that are toxic (e.g., chemotherapeutics) or labile (e.g., nucleic acids) when in circulation. The physical characteristics of liposomes depend on pH, ionic strength and/or the presence of divalent cations. Liposomes can show low permeability to ionic and/or polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and/or results in an increase in permeability to ions, sugars and/or drugs. Liposomal encapsulation has resulted in a lower toxicity and a longer serum half-life for such compounds (Gabizon et al., 1990).

Liposomes interact with cells to deliver agents via four different mechanisms: Endocytosis by phagocytic cells of the reticuloendothelial system such as macrophages and/or neutrophils; adsorption to the cell surface, either by non-specific weak hydrophobic and/or electrostatic forces, and/or by specific interactions with cell-surface components; fusion with the plasma cell membrane by insertion of the lipid bilayer of the liposome into the plasma membrane, with simultaneous release of liposomal contents into the cytoplasm; and/or by transfer of liposomal lipids to cellular and/or subcellular membranes, and/or vice versa, without any association of the liposome contents. Varying the liposome formulation can alter which mechanism is operative, although more than one may operate at the same time.

Numerous disease treatments are using lipid based gene transfer strategies to enhance conventional or establish novel therapies, in particular therapies for treating hyperproliferative diseases. Advances in liposome formulations have improved the efficiency of gene transfer in vivo (Templeton et al., 1997) and it is contemplated that liposomes are prepared by these methods. Alternate methods of preparing lipid-based formulations for nucleic acid delivery are described (WO 99/18933).

In another liposome formulation, an amphipathic vehicle called a solvent dilution microcarrier (SDMC) enables integration of particular molecules into the bi-layer of the lipid vehicle (U.S. Pat. No. 5,879,703). The SDMCs can be used to deliver lipopolysaccharides, polypeptides, nucleic acids and the like. Of course, any other methods of liposome preparation can be used by the skilled artisan to obtain a desired liposome formulation in the present invention.

i. Liposome Targeting

Association of the ATRIP composition with a liposome may improve biodistribution and other properties of the ATRIP composition. For example, liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong et al., 1980). Successful liposome-mediated gene transfer in rats after intravenous injection has also been accomplished (Nicolau et al., 1987).

It is contemplated that a liposome/ATRIP composition may comprise additional materials for delivery to a tissue. For example, in certain embodiments of the invention, the lipid or liposome may be associated with a hemagglutinating virus (HVJ). This has been shown to facilitate fusion with the cell membrane and promote cell entry of liposome-encapsulated DNA (Kaneda et al., 1989). In another example, the lipid or liposome may be complexed or employed in conjunction with nuclear non-histone chromosomal proteins (HMG-1) (Kato et al., 1991). In yet further embodiments, the lipid may be complexed or employed in conjunction with both HVJ and HMG-1.

Targeted delivery is achieved by the addition of ligands without compromising the ability of these liposomes deliver large amounts of ATRIP composition. It is contemplated that this will enable delivery to specific cells, tissues and organs. The targeting specificity of the ligand-based delivery systems are based on the distribution of the ligand receptors on different cell types. The targeting ligand may either be non-covalently or covalently associated with the lipid complex, and can be conjugated to the liposomes by a variety of methods.

j. Cross-linkers

Bifunctional cross-linking reagents have been extensively used for a variety of purposes including preparation of affinity matrices, modification and stabilization of diverse structures, identification of ligand and receptor binding sites, and structural studies. Homobifunctional reagents that carry two identical functional groups proved to be highly efficient in inducing cross-linking between identical and different macromolecules or subunits of a macromolecule, and linking of polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino, sulfhydryl, guanidino, indole, carboxyl specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiol-reactive group.

Exemplary methods for cross-linking ligands to liposomes are described in U.S. Pat. Nos. 5,603,872 and 5,401,511, each specifically incorporated herein by reference in its entirety). Various ligands can be covalently bound to liposomal surfaces through the cross-linking of amine residues. Liposomes, in particular, multilamellar vesicles (MLV) or unilamellar vesicles such as microemulsified liposomes (MEL) and large unilamellar liposomes (LUVET), each containing phosphatidylethanolamine (PE), have been prepared by established procedures. The inclusion of PE in the liposome provides an active functional residue, a primary amine, on the liposomal surface for cross-linking purposes. Ligands such as epidermal growth factor (EGF) have been successfully linked with PE-liposomes. Ligands are bound covalently to discrete sites on the liposome surfaces. The number and surface density of these sites will be dictated by the liposome formulation and the liposome type. The liposomal surfaces may also have sites for non-covalent association. To form covalent conjugates of ligands and liposomes, cross-linking reagents have been studied for effectiveness and biocompatibility. Cross-linking reagents include glutaraldehyde (GAD), bifunctional oxirane (OXR), ethylene glycol diglycidyl ether (EGDE), and a water soluble carbodiimide, preferably 1-ethyl-3-(3-dimethylaminopropyl) carbodiimide (EDC). Through the complex chemistry of cross-linking, linkage of the amine residues of the recognizing substance and liposomes is established.

In another example, heterobifunctional cross-linking reagents and methods of using the cross-linking reagents are described (U.S. Pat. No. 5,889,155, specifically incorporated herein by reference in its entirety). The cross-linking reagents combine a nucleophilic hydrazide residue with an electrophilic maleimide residue, allowing coupling in one example, of aldehydes to free thiols. The cross-linking reagent can be modified to cross-link various functional groups and is thus useful for cross-linking polypeptides and sugars. Table 4 details certain hetero-bifunctional cross-linkers considered useful in the present invention.

TABLE 4

HETERO-BIFUNCTIONAL CROSS-LINKERS

| Linker | Reactive Toward | Advantages and Applications | Space Arm Length/after cross-linking |
|---|---|---|---|
| SMPT | Primary amines Sulfhydryls | Greater stability | 11.2 A |
| SPDP | Primary amines Sulfhydryls | Thiolation Cleavable cross-linking | 6.8 A |
| LC-SPDP | Primary amines Sulfhydryls | Extended spacer arm | 15.6 A |
| Sulfo-LC-SPDP | Primary amines Sulfhydryls | Extended spacer arm Water-soluble | 15.6 A |
| SMCC | Primary amines Sulfhydryls | Stable maleimide reactive group Enzyme-antibody conjugation Hapten-carrier protein conjugation | 11.6 A |
| Sulfo-SMCC | Primary amines Sulfhydryls | Stable maleimide reactive group Water-soluble Enzyme-antibody conjugation | 11.6 A |
| MBS | Primary amines Sulfhydryls | Enzyme-antibody conjugation Hapten-carrier protein conjugation | 9.9 A |
| Sulfo-MBS | Primary amines Sulfhydryls | Water-soluble | 9.9 A |
| SIAB | Primary amines Sulfhydryls | Enzyme-antibody conjugation | 10.6 A |
| Sulfo-SIAB | Primary amines Sulfhydryls | Water-soluble | 10.6 A |
| SMPB | Primary amines Sulfhydryls | Extended spacer arm Enzyme-antibody conjugation | 14.5 A |
| Sulfo-SMPB | Primary amines Sulfhydryls | Extended spacer arm Water-soluble | 14.5 A |
| EDC/Sulfo-NHS | Primary amines Carboxyl groups | Hapten-Carrier conjugation | 0 |
| ABH | Carbohydrates Nonselective | Reacts with sugar groups | 11.9 A |

In instances where a particular polypeptide does not contain a residue amenable for a given cross-linking reagent in its native sequence, conservative genetic or synthetic amino acid changes in the primary sequence can be utilized.

k. Targeting Ligands

The targeting ligand can be either anchored in the hydrophobic portion of the complex or attached to reactive terminal groups of the hydrophilic portion of the complex. The targeting ligand can be attached to the liposome via a linkage to a reactive group, e.g., on the distal end of the hydrophilic polymer. Preferred reactive groups include amino groups, carboxylic groups, hydrazide groups, and thiol groups. The coupling of the targeting ligand to the hydrophilic polymer can be performed by standard methods of organic chemistry that are known to those skilled in the art. In certain embodiments, the total concentration of the targeting ligand can be from about 0.01 to about 10% mol.

Targeting ligands are any ligand specific for a characteristic component of the targeted region. Preferred targeting ligands include proteins such as polyclonal or monoclonal antibodies, antibody fragments, or chimeric antibodies, enzymes, or hormones, or sugars such as mono-, oligo- and poly-saccharides (see, Heath et al., Chem. Phys. Lipids 40:347 (1986)). For example, disialoganglioside GD2 is a tumor antigen that has been identified neuroectodermal origin tumors, such as neuroblastoma, melanoma, small-cell lung carcenoma, glioma and certain sarcomas (Mujoo et al., 1986, Schulz et al., 1984). Liposomes containing anti-disialoganglioside GD2 monoclonal antibodies have been used to aid the targeting of the liposomes to cells expressing the tumor antigen (Montaldo et al., 1999; Pagan et al., 1999). In another non-limiting example, breast and gynecological cancer antigen specific antibodies are described in U.S. Pat. No. 5,939,277, incorporated herein by reference. In a further non-limiting example, prostate cancer specific antibodies are disclosed in U.S. Pat. No. 6,107,090, incorporated herein by reference. Thus, it is contemplated that the antibodies described herein or as would be known to one of ordinary skill in the art may be used to target specific tissues and cell types in combination with the compositions and methods of the present invention. In certain embodiments of the invention, contemplated targeting ligands interact with integrins, proteoglycans, glycoproteins, receptors or transporters. Suitable ligands include any that are specific for cells of the target organ, or for structures of the target organ exposed to the circulation as a result of local pathology, such as tumors.

In certain embodiments of the present invention, in order to enhance the transduction of cells, to increase transduction of target cells, or to limit transduction of undesired cells, antibody or cyclic peptide targeting moieties (ligands) are associated with the lipid complex. Such methods are known in the art. For example, liposomes have been described further that specifically target cells of the mammalian central nervous system (U.S. Pat. No. 5,786,214, incorporated herein by reference). The liposomes are composed essentially of N-glutarylphosphatidylethanolamine, cholesterol and oleic acid, wherein a monoclonal antibody specific for neuroglia is conjugated to the liposomes. It is contemplated that a monoclonal antibody or antibody fragment may be used to target delivery to specific cells, tissues, or organs in the animal, such as for example, brain, heart, lung, liver, etc.

Still further, an ATRIP composition may be delivered to a target cell via receptor-mediated delivery and/or targeting vehicles comprising a lipid or liposome. These take advantage of the selective uptake of macromolecules by receptor-mediated endocytosis that will be occurring in a target cell. In view of the cell type-specific distribution of various receptors, this delivery method adds another degree of specificity to the present invention.

Thus, in certain aspects of the present invention, a ligand will be chosen to correspond to a receptor specifically expressed on the target cell population. A cell-specific ATRIP composition delivery and/or targeting vehicle may comprise a specific binding ligand in combination with a liposome. The ATRIP composition to be delivered is housed within a liposome and the specific binding ligand is functionally incorporated into a liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a nucleic acid to cells that exhibit upregulation of the EGF receptor.

In certain embodiments, a receptor-mediated delivery and/or targeting vehicles comprise a cell receptor-specific ligand and an ATRIP composition-binding agent. Others comprise a cell receptor-specific ligand to which ATRIP composition to be delivered has been operatively attached. For example, several ligands have been used for receptor-mediated gene transfer (Wu and Wu, 1987; Wagner et al., 1990; Perales et al., 1994; Myers, EPO 0273085), which establishes the operability of the technique. In another example, specific delivery in the context of another mammalian cell type has been described (Wu and Wu, 1993; incorporated herein by reference).

In still further embodiments, the specific binding ligand may comprise one or more lipids or glycoproteins that direct cell-specific binding. For example, lactosyl-ceramide, a galactose-terminal asialganglioside, have been incorporated into liposomes and observed an increase in the uptake of the insulin gene by hepatocytes (Nicolau et al., 1987). The asialoglycoprotein, asialofetuin, which contains terminal galactosyl residues, also has been demonstrated to target liposomes to the liver (Spanjer and Scherphof, 1983; Hara et al., 1996). The sugars mannosyl, fucosyl or N-acetyl glucosamine, when coupled to the backbone of a polypeptide, bind the high affinity manose receptor (U.S. Pat. No. 5,432,260, specifically incorporated herein by reference in its entirety). It is contemplated that the cell or tissue-specific transforming constructs of the present invention can be specifically delivered into a target cell or tissue in a similar manner.

In another example, lactosyl ceramide, and peptides that target the LDL receptor related proteins, such as apolipoprotein E3 ("Apo E") have been useful in targeting liposomes to the liver (Spanjer and Scherphof, 1983; WO 98/0748).

Folate and the folate receptor have also been described as useful for cellular targeting (U.S. Pat. No. 5,871,727). In this example, the vitamin folate is coupled to the complex. The folate receptor has high affinity for its ligand and is over-expressed on the surface of several malignant cell lines, including lung, breast and brain tumors. Anti-folate such as methotrexate may also be used as targeting ligands. Transferrin mediated delivery systems target a wide range of replicating cells that express the transferrin receptor (Gilliland et al., 1980).

1. Liposome/Nucleic Acid Combinations

In certain embodiments, a liposome/ATRIP composition may comprise a nucleic acid, such as, for example, an oligonucleotide, a polynucleotide or a nucleic acid construct (e.g., an expression vector). Where a bacterial promoter is employed in the DNA construct that is to be transfected into eukaryotic cells, it also will be desirable to include within the liposome an appropriate bacterial polymerase.

It is contemplated that when the liposome/ATRIP composition comprises a cell or tissue specific nucleic acid, this technique may have applicability in the present invention. In certain embodiments, lipid-based non-viral formulations provide an alternative to viral gene therapies. Although many cell culture studies have documented lipid-based non-viral gene transfer, systemic gene delivery via lipid-based formulations has been limited. A major limitation of non-viral lipid-based gene delivery is the toxicity of the cationic lipids that comprise the non-viral delivery vehicle. The in vivo toxicity of liposomes partially explains the discrepancy between in vitro and in vivo gene transfer results. Another factor contributing to this contradictory data is the difference in liposome stability in the presence and absence of serum proteins. The interaction between liposomes and serum proteins has a dramatic impact on the stability characteristics of liposomes (Yang and Huang, 1997). Cationic liposomes attract and bind negatively charged serum proteins. Liposomes coated by serum proteins are either dissolved or taken up by macrophages leading to their removal from circulation. Current in vivo liposomal delivery methods use aerosolization, subcutaneous, intradermal, intratumoral, or intracranial injection to avoid the toxicity and stability problems associated with cationic lipids in the circulation. The interaction of liposomes and plasma proteins is largely responsible for the disparity between the efficiency of in vitro (Felgner et al., 1987) and in vivo gene transfer (Zhu et al., 1993; Philip et al., 1993; Solodin et al., 1995; Liu et al., 1995; Thierry et al., 1995; Tsukamoto et al., 1995; Aksentijevich et al., 1996).

An exemplary method for targeting viral particles to cells that lack a single cell-specific marker has been described (U.S. Pat. No. 5,849,718). In this method, for example, antibody A may have specificity for tumor, but also for normal heart and lung tissue, while antibody B has specificity for tumor but also normal liver cells. The use of antibody A or antibody B alone to deliver an anti-proliferative nucleic acid to the tumor would possibly result in unwanted damage to heart and lung or liver cells. However, antibody A and antibody B can be used together for improved cell targeting. Thus, antibody A is coupled to a gene encoding an anti-proliferative nucleic acid and is delivered, via a receptor mediated uptake system, to tumor as well as heart and lung tissue. However, the gene is not transcribed in these cells as they lack a necessary transcription factor. Antibody B is coupled to a universally active gene encoding the transcription factor necessary for the transcription of the anti-proliferative nucleic acid and is delivered to tumor and liver cells. Therefore, in heart and lung cells only the inactive anti-proliferative nucleic acid is delivered, where it is not transcribed, leading to no adverse effects. In liver cells, the gene encoding the transcription factor is delivered and transcribed, but has no effect because no an anti-proliferative nucleic acid gene is present. In tumor cells, however, both genes are delivered and the transcription factor can activate transcription of the anti-proliferative nucleic acid, leading to tumor-specific toxic effects.

The addition of targeting ligands for gene delivery for the treatment of hyperproliferative diseases permits the delivery of genes whose gene products are more toxic than do non-targeted systems. Examples of the more toxic genes that can be delivered includes pro-apoptotic genes such as Bax and Bak plus genes derived from viruses and other pathogens such as the adenoviral E4 or f4 and the *E. coli* purine nucleoside phosphorylase, a so-called "suicide gene" which converts the prodrug 6-methylpurine deoxyriboside to toxic purine 6-methylpurine. Other examples of suicide genes used with prodrug therapy are the *E. coli* cytosine deaminase gene and the HSV thymidine kinase gene.

It is also possible to utilize untargeted or targeted lipid complexes to generate recombinant or modified viruses in vivo. For example, two or more plasmids could be used to introduce retroviral sequences plus a therapeutic gene into a hyperproliferative cell. Retroviral proteins provided in trans from one of the plasmids would permit packaging of the second, therapeutic gene-carrying plasmid. Transduced cells, therefore, would become a site for production of non-replicative retroviruses carrying the therapeutic gene. These retroviruses would then be capable of infecting nearby cells. The promoter for the therapeutic gene may or may not be inducible or tissue specific.

Similarly, the transferred nucleic acid may represent the DNA for a replication competent or conditionally replicating viral genome, such as an adenoviral genome that lacks all or part of the adenoviral E1a or E2b region or that has one or more tissue-specific or inducible promoters driving transcription from the E1a and/or E1b regions. This replicating or conditional replicating nucleic acid may or may not contain an additional therapeutic gene such as a tumor suppressor gene or anti-oncogene.

m. Lipid Administration

The actual dosage amount of a lipid composition (e.g., a liposome-ATRIP composition) administered to a patient can be determined by physical and physiological factors such as body weight, severity of condition, idiopathy of the patient and on the route of administration. With these considerations in mind, the dosage of a lipid composition for a particular subject and/or course of treatment can readily be determined.

The present invention can be administered intravenously, intradermally, intraarterially, intraperitoneally, intralesionally, intracranially, intraarticularly, intraprostaticaly, intrapleurally, intratracheally, intranasally, intravitreally, intravaginally, rectally, topically, intratumorally, intramuscularly, subcutaneously, intravesicularlly, mucosally, intrapericardially, orally, topically, locally and/or using aerosol, injection, infusion, continuous infusion, localized perfusion bathing target cells directly or via a catheter and/or lavage.

E. Combined Therapy Protocols

Tumor cell resistance to anti-cancer agents represents a major problem in clinical oncology. The present invention may also be used in combination with conventional therapies to improve the efficacy of chemotherapy, radiotherapy, and/or surgery. For example, the herpes simplex-thymidine kinase (HS-tK) gene, when delivered to brain tumors by a retroviral vector system, successfully induced susceptibility to the antiviral agent ganciclovir (Culver, et al., 1992). In the context of the present invention, it is contemplated that ATRIP therapy could be used similarly in conjunction with chemotherapeutic, radiotherapeutic, or surgical intervention.

To kill cells, such as malignant or metastatic cells, using the methods and compositions of the present invention, one would generally contact a "target" cell with an ATRIP composition and at least one anti-cancer agent. These compositions would be provided in a combined amount effective to kill or inhibit proliferation of the cell. This process may involve contacting the cells with the ATRIP composition and the anti-cancer agent(s) or factor(s) at the same time. This may be achieved by contacting the cell with a single composition or pharmacological formulation that includes both agents, or by contacting the cell with two distinct compositions or formulations, at the same time, wherein one composition includes the ATRIP composition and the other includes the anti-cancer agent.

Alternatively, the ATRIP treatment may precede or follow the anti-cancer agent treatment by intervals ranging from min to weeks. In embodiments where the anti-cancer agent and ATRIP are applied separately to the cell, one would generally ensure that a significant period of time did not expire between the time of each delivery, such that the anti-cancer agent and ATRIP composition would still be able to exert an advantageously combined effect on the cell. In such instances, it is contemplated that one would contact the cell with both agents within about 6 h to one wk of each other and, more preferably, within about 24–72 h of each other, with a delay time of only about 48 h being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either the ATRIP or the anti-cancer agent will be desired. Various combinations may be employed, where ATRIP is "A" and the anti-cancer agent is "B":

| A/B/A | B/A/B | B/B/A | A/A/B | B/B/B/A | B/B/A/B |
|-------|-------|-------|-------|---------|---------|
| A/A/B/B | A/B/A/B | A/B/B/A | B/B/A/A | B/A/B/A | B/A/A/B |
| A/A/A/B | B/A/A/A | A/B/A/A | A/A/B/A | A/B/B/B | B/A/B/B |

To achieve cell killing, both agents are delivered to a cell in a combined amount effective to kill the cell.

In one representative embodiment of the present invention, the anti-cancer agent is taxol (paclitaxel). This agent has proved has proved to be effective for the treatment of patients with metastatic breast or ovarian cancer, and has potential for patients with cervical or endometrial cancer. The regimen of paclitaxel administration has varied in clinical trials, the most common including a dosage of between 135 and 250 mg/m2 administered over an infusion period of 3 or 24 h once every 3 weeks (Wiseman and Spencer, 1998). Promising results have been achieved in phase I/II trials of a weekly regimen of paclitaxel (60 to 175 mg/m2). The objective response rate in patients with metastatic breast cancer (either pretreated or chemotherapy-naive) is generally between 20 and 35% with paclitaxel monotherapy, which compares well with that of other current treatment options including the anthracycline doxorubicin. Combination therapy with paclitaxel plus doxorubicin appears superior to treatment with either agent alone in terms of objective response rate and median duration of response (Wiseman and Spencer, 1998). The present invention contemplates the use of ATRIP combined with taxol and the use of ATRIP combined with taxol plus other anti-cancer agents such as doxorubicin.

Many anti-cancer agents are DNA damaging agents. DNA damaging agents or factors are defined herein as any chemical compound or treatment method that induces DNA damage when applied to a cell. Such agents and factors include radiation and waves that induce DNA damage such as, γ-irradiation, X-rays, UV-irradiation, microwaves, electronic emissions, and the like. A variety chemotherapeutic agents function to induce DNA damage, all of which are intended to be of use in the combined treatment methods disclosed herein. Chemotherapeutic agents contemplated to be of use, include, e.g., adriamycin, 5-fluorouracil (5FU), etoposide (VP-16), camptothecin, actinomycin-D, mitomycin C, cisplatin (CDDP) and even hydrogen peroxide. The invention also encompasses the use of a combination of one or more DNA damaging agents, whether radiation-based or actual compounds, such as the use of X-rays with cisplatin or the use of cisplatin with etoposide. Many DNA damaging agents induce apoptosis. One aspect of the present invention is the use of ATRIP to sensitize tumor cells to apoptotic agents.

In treating cancer according to the invention, one would contact the tumor cells with a DNA damaging agent in addition to the ATRIP composition. This may be achieved by irradiating the localized tumor site with DNA damaging radiation such as X-rays, UV-light, γ-rays or even microwaves. Alternatively, the tumor cells may be contacted with the DNA damaging agent by administering to the subject a therapeutically effective amount of a pharmaceutical composition comprising a DNA damaging compound such as, adriamycin, 5-fluorouracil, etoposide, camptothecin, actinomycin-D, mitomycin C, or more preferably, cisplatin. The DNA damaging agent may be prepared and used as a combined therapeutic composition, or kit, by combining it with an ATRIP composition, as described above.

Agents that directly cross-link polynucleotides, specifically DNA, are envisaged and are shown herein, to eventuate DNA damage leading to a synergistic antineoplastic combination. Agents such as cisplatin, and other DNA alkylating may be used. Cisplatin has been widely used to treat cancer, with efficacious doses used in clinical applications of 20 mg/m2 for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25–75 mg/m2 at 21 day intervals for adriamycin, to 35–50 mg/m2 for etoposide intravenously or double the intravenous dose orally.

Agents that disrupt the synthesis and fidelity of polynucleotide precursors and subunits also lead to DNA damage. As such a number of polynucleotide precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of DNA damage, or the precursors of DNA, the replication and repair of DNA, and the assembly and maintenance of chromosomes. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

The skilled artisan is directed to "Remington's Pharmaceutical Sciences" 15th Edition, chapter 33, in particular pages 624–652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The inventor proposes that the regional delivery of ATRIP compositions to patients with tumors will be a very efficient method for delivering a therapeutically effective gene to counteract the clinical disease. Similarly, the chemotherapy, radiotherapy, or surgery may be directed to a particular, affected region of the subject's body. Alternatively, systemic delivery of the ATRIP or the DNA damaging agent may be appropriate in certain circumstances, for example, where extensive metastasis has occurred.

Cytokine therapy also has proven to be an effective partner for combined therapeutic regimens. Various cytokines may be employed in such combined approaches. Examples of cytokines include IL-1a IL-1β, IL-2, IL-3, IL-4, IL-5, IL-6, IL-7, IL-8, IL-9, IL-10, IL-11, IL-12, IL-13, TGF-β, GM-CSF, M-CSF, G-CSF, TNFa, TNFβ, LAF, TCGF, BCGF, TRF, BAF, BDG, MP, LIF, OSM, TMF, PDGF, IFN-a, IFN-β, IFN-γ. Cytokines are administered according to standard regimens, as described below, consistent with clinical indications such as the condition of the patient and relative toxicity of the cytokine.

A number of polypeptides are known to induce apoptosis and may be used in the combination therapies of the present invention. In one embodiment, the combination therapy is the use of ATRIP with a polypeptide form the tumor necrosis factor ("TNF") family. In a preferred embodiment, the TNF polypeptide is TNFα. Other polypeptide inducers of apoptosis that may be used in the present invention include, but are not limited to, p53, Bax, Bak, Bcl-x, Bad, Bim, Bik, Bid, Harakiri, Ad E1B, Bad and ICE-CED3 proteases.

F. Pharmaceutical Compositions and Routes of Administration

Compositions of the present invention may have an effective amount of a gene for therapeutic administration and, in some embodiments, in combination with an effective amount of a compound (second agent) that is an anti-cancer agent. Such compositions will generally be dissolved or dispersed in a pharmaceutically acceptable carrier or aqueous medium.

The phrases "pharmaceutically or pharmacologically acceptable" refer to molecular entities and compositions that do not produce an adverse, allergic or other untoward reaction when administered to an animal, or human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredients, its use in the therapeutic compositions is contemplated. Supplementary active ingredients, such as other anti-cancer agents, can also be incorporated into the compositions.

In addition to the compounds formulated for parenteral administration, such as intravenous or intramuscular injection, other pharmaceutically acceptable forms include, e.g., tablets or other solids for oral administration; time release capsules; and any other form currently used, including cremes, lotions, mouthwashes, inhalants and the like.

The expression vectors and delivery vehicles of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, described supra.

The vectors of the present invention are advantageously administered in the form of injectable compositions either as liquid solutions or suspensions; solid forms suitable for solution in, or suspension in, liquid prior to injection also may be prepared. These preparations also may be emulsified. A typical compositions for such purposes comprises a 50 mg or up to about 100 mg of human serum albumin per milliliter of phosphate buffered saline. Other pharmaceutically acceptable carriers include aqueous solutions, non-toxic excipients, including salts, preservatives, buffers and the like. Examples of non-aqueous solvents are propylene glycol, polyethylene glycol, vegetable oil and injectable organic esters, such as theyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components in the pharmaceutical are adjusted according to well known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

An effective amount of the therapeutic agent is determined based on the intended goal. The term "unit dose" refers to a physically discrete unit suitable for use in a subject, each unit containing a predetermined quantity of the therapeutic composition calculated to produce the desired response in association with its administration, i.e., the appropriate route and treatment regimen. The quantity to be administered, both according to number of treatments and unit dose, depends on the subject to be treated, the state of the subject and the protection desired. Precise amounts of the therapeutic composition also depend on the judgment of the practitioner and are peculiar to each individual.

All the essential materials and reagents required for inhibiting tumor cell proliferation may be assembled together in a kit. When the components of the kit are provided in one or more liquid solutions, the liquid solution preferably is an aqueous solution, with a sterile aqueous solution being particularly preferred.

For in vivo use, a chemotherapeutic agent may be formulated into a single or separate pharmaceutically acceptable syringeable composition. In this case, the container means may itself be an inhalant, syringe, pipette, eye dropper, or other such like apparatus, from which the formulation may be applied to an infected area of the body, such as the lungs, injected into an animal, or even applied to and mixed with the other components of the kit.

The components of the kit may also be provided in dried or lyophilized forms. When reagents or components are provided as a dried form, reconstitution generally is by the addition of a suitable solvent. It is envisioned that the solvent also may be provided in another container means. The kits of the invention may also include an instruction sheet defining administration of the gene therapy and/or the chemotherapeutic drug.

The kits of the present invention also will typically include a means for containing the vials in close confinement for commercial sale such as, e.g., injection or blow-molded plastic containers into which the desired vials are retained. Irrespective of the number or type of containers, the kits of the invention also may comprise, or be packaged with, an instrument for assisting with the injection/administration or placement of the ultimate complex composition within the body of an animal. Such an instrument may be an inhalant, syringe, pipette, forceps, measured spoon, eye dropper or any such medically approved delivery vehicle.

The active compounds of the present invention will often be formulated for parenteral administration, e.g., formulated for injection via the intravenous, intramuscular, subcutaneous, or even intraperitoneal routes. The preparation of an aqueous composition that contains a second agent(s) as active ingredients will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

The active compounds may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In certain cases, the therapeutic formulations of the invention could also be prepared in forms suitable for topical administration, such as in cremes and lotions. These forms may be used for treating skin-associated diseases, such as various sarcomas.

Upon formulation, solutions will be administered in a manner compatible with the dosage formulation and in such amount as is therapeutically effective. The formulations are easily administered in a variety of dosage forms, such as the type of injectable solutions described above, with even drug release capsules and the like being employable.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject.

Targeting of cancerous tissues may be accomplished in any one of a variety of ways. Plasmid vectors and retroviral vectors, adenovirus vectors, and other viral vectors all present means by which to target human cancers. The inventors anticipate particular success for the use of liposomes to target ATRIP genes to cancer cells. For example, DNA encoding ATRIP may be complexed with liposomes in the manner described above, and this DNA/liposome complex injected into patients with certain forms of cancer, such as breast cancer, intravenous injection can be used to direct the gene to all cell. Directly injecting the liposome complex into the proximity of a cancer can also provide for targeting of the complex with some forms of cancer. For example, cancers of the ovary can be targeted by injecting the liposome mixture directly into the peritoneal cavity of patients with ovarian cancer. Of course, the potential for liposomes that are selectively taken up by a population of cancerous cells exists, and such liposomes will also be useful for targeting the gene.

Those of skill in the art will recognize that the best treatment regimens for using ATRIP to suppress tumors can be straightforwardly determined. This is not a question of experimentation, but rather one of optimization, which is routinely conducted in the medical arts. The in vivo studies in nude mice provide a starting point from which to begin to optimize the dosage and delivery regimes. The frequency of injection will initially be once a wk, as was done some mice studies. However, this frequency might be optimally adjusted from one day to every two weeks to monthly, depending upon the results obtained from the initial clinical trials and the needs of a particular patient. Human dosage amounts can initially be determined by extrapolating from the amount of ATRIP used in mice. In certain embodiments it is envisioned that the dosage may vary from between about 1 mg ATRIP DNA/Kg body weight to about 5000 mg ATRIP DNA/Kg body weight; or from about 5 mg/Kg body weight to about 4000 mg/Kg body weight or from about 10 mg/Kg body weight to about 3000 mg/Kg body weight; or from about 50 mg/Kg body weight to about 2000 mg/Kg body weight; or from about 100 mg/Kg body weight to about 1000 mg/Kg body weight; or from about 150 mg/Kg body weight to about 500 mg/Kg body weight. In other embodiments this dose may be about 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, 5000 mg/Kg body weight. In other embodiments, it is envisaged that higher does may be used, such doses may be in the range of about 5 mg ATRIP DNA/Kg body to about 20 mg ATRIP DNA/Kg body. In other embodiments the doses may be about 8, 10, 12, 14, 16 or 18 mg/Kg body weight. Of course, this dosage amount may be adjusted upward or downward, as is routinely done in such treatment protocols, depending on the results of the initial clinical trials and the needs of a particular patient.

G. Transgenic Animals/Knockout Animals

In one embodiment of the invention, transgenic animals are produced which contain a functional transgene encoding a functional ATRIP polypeptide or variants thereof. Transgenic animals expressing ATRIP transgenes, recombinant cell lines derived from such animals and transgenic embryos may be useful in methods for screening for and identifying agents that induce or repress function of ATRIP. Transgenic animals of the present invention also can be used as models for studying indications such as cancers.

In one embodiment of the invention, an ATRIP transgene is introduced into a non-human host to produce a transgenic animal expressing a human or murine ATRIP gene. The transgenic animal is produced by the integration of the transgene into the genome in a manner that permits the expression of the transgene. Methods for producing transgenic animals are generally described by Wagner and Hoppe (U.S. Pat. No. 4,873,191; which is incorporated herein by reference), Brinster et al. 1985; which is incorporated herein by reference in its entirety) and in "Manipulating the Mouse Embryo; A Laboratory Manual" 2nd edition (eds., Hogan, Beddington, Costantimi and Long, Cold Spring Harbor Laboratory Press, 1994; which is incorporated herein by reference in its entirety).

It may be desirable to replace the endogenous ATRIP by homologous recombination between the transgene and the endogenous gene; or the endogenous gene may be eliminated by deletion as in the preparation of "knock-out" animals. Typically, an ATRIP gene flanked by genomic sequences is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish. Within a particularly preferred embodiment, transgenic mice are generated which overexpress ATRIP or express a mutant form of the polypeptide. Alternatively, the absence of an ATRIP in "knock-out" mice permits the study of the effects that loss of ATRIP protein has on a cell in vivo. Knock-out mice also provide a model for the development of ATRIP-related cancers.

As noted above, transgenic animals and cell lines derived from such animals may find use in certain testing experiments. In this regard, transgenic animals and cell lines capable of expressing wild-type or mutant ATRIP may be exposed to test substances. These test substances can be screened for the ability to enhance wild-type ATRIP expression and or function or impair the expression or function of mutant ATRIP.

IV. Screening for Modulators of the Protein Function

The present invention further comprises methods for identifying modulators of the function of ATRIP and/or ATR. These assays may comprise random screening of large libraries of candidate substances; alternatively, the assays may be used to focus on particular classes of compounds selected with an eye towards structural attributes that are believed to make them more likely to modulate the function of ATRIP and/or ATR. By function, it is meant that one may assay for checkpoint signaling activity.

To identify an ATRIP and/or ATR modulator, one generally will determine the function of ATRIP and/or ATR in the presence and absence of the candidate substance, a modulator defined as any substance that alters function. For example, a method generally comprises:

(a) providing a candidate modulator;
(b) admixing the candidate modulator with an isolated compound or cell, or a suitable experimental animal;
(c) measuring one or more characteristics of the compound, cell or animal in step (c); and
(d) comparing the characteristic measured in step (c) with the characteristic of the compound, cell or animal in the absence of said candidate modulator, wherein a difference between the measured characteristics indicates that said candidate modulator is, indeed, a modulator of the compound, cell or animal.

Assays may be conducted in cell free systems, in isolated cells, or in organisms including transgenic animals.

It will, of course, be understood that all the screening methods of the present invention are useful in themselves notwithstanding the fact that effective candidates may not be found. The invention provides methods for screening for such candidates, not solely methods of finding them.

A. Modulators

As used herein the term "candidate substance" or "test agent" and the like refers to any molecule that may potentially inhibit or enhance ATRIP and/or ATR activity. The candidate substance may be a protein or fragment thereof, a small molecule, or even a nucleic acid molecule. It may prove to be the case that the most useful pharmacological compounds will be compounds that are structurally related to fit active sites of ATRIP and/or ATR. Using lead compounds to help develop improved compounds is know as "rational drug design" and includes not only comparisons with know inhibitors and activators, but predictions relating to the structure of target molecules.

The goal of rational drug design is to produce structural analogs of biologically active polypeptides or target compounds. By creating such analogs, it is possible to fashion drugs, which are more active or stable than the natural molecules, which have different susceptibility to alteration or which may affect the function of various other molecules. In one approach, one would generate a three-dimensional structure for a target molecule, or a fragment thereof. This could be accomplished by x-ray crystallography, computer modeling or by a combination of both approaches.

It also is possible to use antibodies to ascertain the structure of a target compound activator or inhibitor. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

On the other hand, one may simply acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate compounds may include fragments or parts of naturally-occurring compounds, or may be found as active combinations of known compounds, which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be peptide, polypeptide, polynucleotide, small molecule inhibitors or any other compounds that may be designed through rational drug design starting from known inhibitors or stimulators.

Other suitable modulators include antisense molecules, ribozymes, and antibodies (including single chain antibodies), each of which would be specific for the target molecule. Such compounds are described in greater detail elsewhere in this document. For example, an antisense molecule that bound to a translational or transcriptional start site, or splice junctions, would be ideal candidate inhibitors.

In addition to the modulating compounds initially identified, the inventors also contemplate that other sterically similar compounds may be formulated to mimic the key portions of the structure of the modulators. Such compounds, which may include peptidomimetics of peptide modulators, may be used in the same manner as the initial modulators.

An inhibitor according to the present invention may be one which exerts its inhibitory or activating effect upstream, downstream or directly on ATRIP and/or ATR. Regardless of the type of inhibitor or activator identified by the present screening methods, the effect of the inhibition or activator by such a compound results in a change in function or activity of ATRIP and/or ATR, as compared to that observed in the absence of the added candidate substance.

B. In vitro Assays

A quick, inexpensive and easy assay to run is an in vitro assay. Such assays generally use isolated molecules, can be run quickly and in large numbers, thereby increasing the amount of information obtainable in a short period of time. A variety of vessels may be used to run the assays, including test tubes, plates, dishes and other surfaces such as dipsticks or beads.

One example of a cell free assay is a binding assay. While not directly addressing function, the ability of a modulator to bind to a target molecule in a specific fashion is strong evidence of a related biological effect. For example, binding of a molecule to a target may, in and of itself, be inhibitory, due to steric, allosteric or charge-charge interactions. The target may be either free in solution, fixed to a support, expressed in or on the surface of a cell. Either the target or the compound may be labeled, thereby permitting determining of binding. Usually, the target will be the labeled species, decreasing the chance that the labeling will interfere with or enhance binding. Competitive binding formats can be performed in which one of the agents is labeled, and one may measure the amount of free label versus bound label to determine the effect on binding.

A technique for high throughput screening of compounds is described in WO 84/03564. Large numbers of small peptide test compounds are synthesized on a solid substrate, such as plastic pins or some other surface. Bound polypeptide is detected by various methods.

C. In cyto Assays

The present invention also contemplates the screening of compounds for their ability to modulate ATRIP and/or ATR in cells. Various cell lines can be utilized for such screening assays, including cells specifically engineered for this purpose. Depending on the assay, culture may be required. The cell is examined using any of a number of different physiologic assays. Alternatively, molecular analysis may be performed, for example, looking at protein expression, mRNA expression (including differential display of whole cell or polyA RNA) and others.

D. In vivo Assays

In vivo assays involve the use of various animal models, including transgenic animals that have been engineered to have specific defects, or carry markers that can be used to measure the ability of a candidate substance to reach and effect different cells within the organism. Due to their size, ease of handling, and information on their physiology and genetic make-up, mice are a preferred embodiment, especially for transgenics. However, other animals are suitable as well, including rats, rabbits, hamsters, guinea pigs, gerbils, woodchucks, cats, dogs, sheep, goats, pigs, cows, horses and monkeys (including chimps, gibbons and baboons). Assays for modulators may be conducted using an animal model derived from any of these species.

In such assays, one or more candidate substances are administered to an animal, and the ability of the candidate substance(s) to alter one or more characteristics, as compared to a similar animal not treated with the candidate substance(s), identifies a modulator. The characteristics may be any of those discussed above with regard to the function of a particular compound (e.g., enzyme, receptor, hormone) or cell (e.g., growth, tumorigenicity, survival), or instead a broader indication such as behavior, anemia, immune response, etc.

The present invention provides methods of screening for a candidate substance that enhances or inhibits ATRIP and/or ATR function or activity. In these embodiments, the present invention is directed to a method for determining the ability of a candidate substance to decrease undesirable cell proliferation, generally including the steps of: administering a candidate substance to the animal; and determining the ability of the candidate substance to reduce one or more characteristics of associated with loss of ATRIP and/or ATR.

Treatment of these animals with test compounds will involve the administration of the compound, in an appropriate form, to the animal. Administration will be by any route that could be utilized for clinical or non-clinical purposes, including but not limited to oral, nasal, buccal, or even topical. Alternatively, administration may be by intratracheal instillation, bronchial instillation, intradermal, subcutaneous, intramuscular, intraperitoneal or intravenous injection. Specifically contemplated routes are systemic intravenous injection, regional administration via blood or lymph supply, or directly to an affected site.

Determining the effectiveness of a compound in vivo may involve a variety of different criteria. Also, measuring toxicity and dose response can be performed in animals in a more meaningful fashion than in in vitro or in cyto assays.

V. Screening Methods

In some embodiments of the, present invention, there is a method of screening in vitro or in vivo for an active compound for the treatment of cancer. In some embodiments, the method comprises the steps of obtaining a cell, wherein the cell includes a nucleic acid sequence having a reporter sequence and wherein the expression of the reporter sequence is controlled by an ATRIP or ATR regulatory nucleic acid sequence; exposing a test agent to the cell; and measuring a change in the expression, wherein the change indicates the test agent is the active compound. In a specific embodiment, the changes is an increase in expression and in another embodiment the change is a decrease in expression.

The term "regulatory nucleic acid sequence" as used herein is defined as any sequence that directs transcription of another sequence and which itself is under regulatory control by an extrinsic factor or state. Examples of extrinsic factors or states include but are not limited to exposure to chemicals, nucleic acids, proteins, peptides, lipids, carbohydrates, sugars, light, sound, hormones, touch, or tissue-specific milieu. Examples of regulatory reporter sequences include the ATR or ATRIP promoter sequence, the GAL promoter sequence or the tetracycline promoter/transactivator sequence. The promoter sequences can be partial or can contain the entire promoter.

The term "reporter sequence" as used herein is defined as any sequence that demonstrates expression by a regulatory sequence. The reporter sequence can be used as a marker in the form of an RNA or in a protein. Examples of reporter sequences include β-galactosidase, green fluorescent protein (GFP), blue fluorescent protein (BFP), neomycin, kanamycin, luciferase, β-glucuronidase and chloramphenicol transferase (CAT). In a specific aspect of the present invention, the presence and quantity of the reporter sequence product, whether it be a nucleic acid or amino acid, reflects the level of transcription by the promoter sequence that regulates it. In an additional embodiment, a transgenic animal of the present invention has a detectable condition wherein the condition reflects, for example, a particular state of checkpoint signaling, such as its partial or full loss, and/or the abnormal proliferation of cells.

In additional specific embodiments, an ATR of ATRIP allele is replaced with an ATR of ATRIP nucleic acid sequence, respectively, under control of a regulatable promoter sequence or a tissue-specific promoter sequence. In additional embodiments, a transgenic animal is a mouse, Drosophila, frog, zebrafish, rat, guinea pig, or hamster.

In specific embodiments, a sequence may be required to perform a method taught by the present invention. A skilled artisan recognizes that DNA, RNA, and protein sequences may be obtained by the publicly available National Center for Biotechnology Information's GenBank database or from commercially available databases such as from Celera Genomics, Inc. (Rockville, Md.). An example of an ATR polynucleotide is SEQ ID NO:38 (NM_001184), and an example of an ATR polypeptide is SEQ ID NO:39 (NP_001175). An example of a replication protein A polynucleotide is SEQ ID NO:40 (NM_002945), and an example of a replication protein A polypeptide is SEQ ID NO:41 (NP_002936). Another example of a human replication protein A polynucleotide is SEQ ID NO:42 (NM_002946), and another example of a replication protein A polypeptide is SEQ ID NO:43 (NP_002937). An additional example of a replication protein A polynucleotide is SEQ ID NO:44 (NM_002947), and an additional example of a replication protein A polypeptide is SEQ ID NO:45 (NP_002938). An example of a Rad17 polynucleotide is SEQ ID NO:46 (AJ004977), and an example of a Rad17 polypeptide is SEQ ID NO:47 (CAA06251).

The present invention can also be used as, or as part of, a method for screening for a compound, wherein the administration of the compound affects a developmental and/or pathological condition wherein said condition is a result of reduction in expression of the ATR and/or ATRIP. As used herein, the screen provides for a compound that by upregulating expression of a heterologous nucleic acid sequence is a positive effector and for a compound that by downregulating expression of a heterologous nucleic acid sequence is a negative effector.

In a specific embodiment, a screen is provided wherein a preferred candidate molecule prevents ATRIP or ATR from binding ssDNA, or both. In one specific embodiment, a ssDNA molecule comprises bound RPA in a ssDNA-RPA complex, and a test molecule is obtained that prevents ATRIP from binding to the ssDNA-RPA complex.

In another embodiment of the present invention, a screen is provided wherein a successful candidate molecule prevents phosphorylation of a target protein that is bound to ssDNA comprising bound RPA. In a specific embodiment, the target protein is Rad17. In other specific embodiments, the target protein is BRCA1 (such as with phosphorylation at Ser 1423; Tibbetts et al., 2000), Chk1, Chk2, or p53.

In an additional specific embodiment, there is a screen for a molecule that prevents ATR from binding to ATRIP. Such a molecule may be obtained from a small molecule library, from a peptide library, from a polypeptide library, from a nucleic acid library, or other analogous sources. In one specific embodiment, a mutated ATR, such as in a dominant negative form, is administered that binds up the available pool of ATRIP but prevents ATR/ATRIP complex activity, such as being recruited to ssDNA by RPA.

In other embodiments, the present invention provides screens for a therapeutic agent(s) useful for promoting death of a cell, and preferably useful for cancer treatment. In a specific embodiment, a screen is performed to identify an agent that impairs or inhibits ATR/ATRIP complex function, or a component thereof. In further specific embodiments, a screen identifies an agent that inhibits the ability of ATR to bind ATRIP, or ATRIP to bind ssDNA (or RPA, or a ssDNA/RPA complex), or both.

In a specific embodiment, there is a method of identifying an agent that inhibits binding of ATRIP to ssDNA or ssDNA/RPA complex, or that promotes cell death, or both, comprising the steps of providing a ssDNA/replication protein A (RPA) complex; providing an ATR/ATRIP-phosphorylatable protein, wherein said ATR/ATRIP-phosphorylatable protein binds to said ssDNA or said ssDNA/RPA complex; providing an ATRIP polypeptide; providing an ATR polypeptide, providing a test agent; and assaying phosphorylation status of said ATR/ATRIP-phosphorylatable protein, wherein when said ATR/ATRIP-phosphorylatable protein is not phosphorylated following said providing of said ATRIP polypeptide, said test agent is identified as said agent that promotes cell death. In specific embodiments, the providing of an ATR or ATRIP polypeptide comprises providing a polynucleotide encoding the respective polypeptide.

In another specific embodiment, there is a method of identifying an agent inhibits binding of ATR to ATRIP and/or that promotes cell death, comprising the steps of providing a ssDNA/replication protein A (RPA) complex; providing an ATRIP polypeptide; introducing to the ssDNA/RPA complex a test agent; and assaying for an interaction between the ATRIP polypeptide and the ssDNA/RPA complex, wherein when the interaction does not occur, the test agent is the agent that promotes cell death.

The screens may utilize a variety of well known methods in the art. For example, co-immunoprecipitation experiments are often utilized wherein binding status of, for example, ATR or ATRIP to another protein or nucleic acid is assayed upon exposure to a test agent. Antibodies to one or more of the components in the complex tracks the co-immunoprecipitation, and the results are analyzed on a solid support such as a western blot.

In a specific embodiment, a component in a screen is labeled for monitoring, such as with a chromophore (for example, biotin), a fluorophore (for example fluorescein), radioactivity (for example, $^{35}$S), or the like. In a specific embodiment, binding of ATRIP to another entity, such as ATR, ssDNA, or RPA, is monitored through fluorescence. That is, for example, ATRIP is labeled with fluorescein and binds to a solid matrix. Upon exposure to a test agent, a decrease in fluorescence is assayed for, wherein a decrease indicates the test agent binds ATRIP. In a specific embodiment, said binding inhibits binding of ATRIP to ATR. In another embodiment of the present invention, ATRIP antibodies are utilized to monitor interference of binding of ATRIP to another entity.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Cloning and Characterization of ATRIP

In a search for substrates of ATM and ATR a protein with an apparent molecular size of 85 to 90 kD immunoprecipitated with ATR and incorporated $^{32}$P when ATR immunoprecipitates were incubated with [γ-$^{32}$P]ATP (FIG. 1A). To identify this phosphoprotein ATR tagged with a Flag epitope was transiently overexpressed in 293T cells, the expressed ATR was immunoprecipitated, and the co-immunoprecipitating proteins were sequenced by mass spectrometry (FIG. 1B). In addition to peptides from heat shock protein 70, two peptides were identified, DSLHQTESVLEEQR (SEQ ID NO:19) and DTVLLLHGLSQK (SEQ ID NO:20), that corresponded to two expressed sequence tags (ESTs) in the National Center for Biotechnology Information Genbank database. By comparison of overlapping cDNAs and genomic sequence, both EST sequences were assigned to the same gene and designed primers to amplify and clone a full length cDNA. Sequencing of the cloned cDNA indicated that it encodes a 791-amino acid protein with a predicted molecular size of 86 kD containing a coiled-coil domain near its NH$_2$-terminus. This protein was named ATRIP for ATR-interacting-protein. Blast searches revealed sequence similarity to the *D. melanogaster* mus304protein—a protein implicated in DNA damage checkpoint signal transduction (Brodsky et al., 2000). ATRIP also has weak sequence similarity to Rad26, DDC2, and to *A. nidulans* UVSD proteins (FIG. 1C). Each of these proteins contains a coiled-coil domain near the NH$_2$-terminus (FIG. 1D). RNA blotting indicated that ATRIP is expressed in all tissues tested, including heart, brain, lung, placenta, liver, pancreas, kidney, and skeletal muscle. An alternatively spliced exon encoding amino acids 658 to 684 was also identified near the COOH-terminus. Reverse transcription polymerase chain reaction from two cell lines indicated that both forms were expressed.

Example 2

Confirmation of ATR and ATRIP Interaction

Figure 1E:
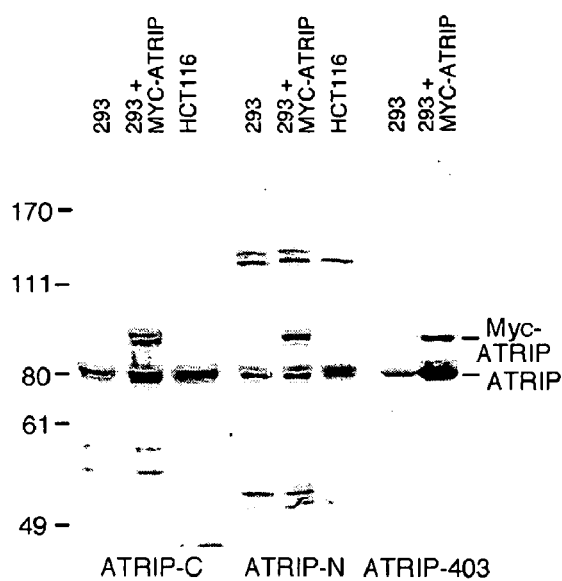
Figure 1F:
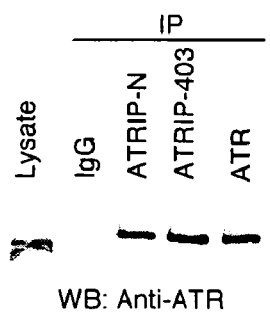

Co-transfection of Myc(3x)-tagged ATRIP cDNA with Flag-tagged ATR followed by reciprocal co-immunoprecipitation confirmed that the overexpressed proteins could associate in vivo. Anti-peptide antibodies to the NH$_2$-terminus (ATRIP-N) and COOH-terminus (ATRIP-C) of ATRIP and polyclonal antiserum to GST-ATRIP (amino acids 1 to 107) purified from bacteria (ATRIP-403) were produced. Each of these antibodies recognized a protein with an apparent size between 80 and 85 kD in lysates of human cells separated by SDS-PAGE and a slightly larger protein in cells transfected with a Myc-ATRIP expression vector (FIG. 1E). The ATRIP-N and ATRIP-403 antibodies both co-immunoprecipitated ATR from 293T cell lysates (FIG. 1F). Under similar conditions an association of ATRIP with ATM has not been detected. Mapping of the ATRIP domain that binds ATR indicated that there may be multiple interaction domains including the coiled-coil domain between amino acids 107 to 214 (Desany et al., 1998).

To confirm that ATRIP is the phosphoprotein originally immunoprecipitated with ATR, ATRIP was further analyzed as an ATR substrate. Western blotting of cell lysates that were treated with phosphatase revealed a change in ATRIP migration on SDS-PAGE gels, suggesting that ATRIP is phosphorylated in vivo (FIG. 2A). The 85 kD protein phosphorylated during incubation with immunoprecipitated ATR co-migrated with ATRIP detected by the ATRIP-N antibody. Furthermore, kinase assays with Flag-ATR immunoprecipitated from cells that also expressed Myc-ATRIP revealed $^{32}$P-labeling of co-immunoprecipitated Myc-ATRIP (FIG. 2B). Finally, recombinant full-length ATRIP isolated from baculovirus-infected insect cells and an NH$_2$-terminal fragment of ATRIP isolated from bacteria could both be phosphorylated when placed in a kinase reaction with ATR isolated from human cells (FIG. 2C). These results suggest that the 85 kD protein that is phosphorylated in ATR kinase reactions is indeed ATRIP.

Example 3

Subcellular Localization of ATRIP

ATR localizes to intra-nuclear foci that may correspond to sites of DNA synthesis and repair after cells have been treated with agents that cause DNA damage or stalling of replication forks (Tibbetts et al., 2000). Immunostaining using the ATRIP-403 antibody revealed that ATRIP is a diffuse nuclear protein that also re-distributes to intra-nuclear foci after treatment of cells with UV radiation, hydroxyurea (HU), or ionizing radiation (FIG. 2D). Co-staining with an antibody to ATR showed strong colocalization of ATRIP and ATR after treatment of cells with UV or HU. Expression of a green-fluorescent protein (GFP)-ATRIP fusion revealed similar intranuclear localization patterns, and siRNA inhibition of ATRIP expression indicated that the ATRIP-403 antibody specifically recognizes ATRIP in stained cells (see FIG. 5B).

Example 4

Conditional ATR-Null Allele

To further elucidate the function of ATR and determine if ATRIP phosphorylation and localization in vivo is dependent on ATR, a conditional ATR-null cell line ($ATR^{flox/-}$; see Example 6) was generated in which one allele of ATR is disrupted by the neomycin resistance gene and the second "flox" allele has lox sites flanking exon 2 (Desany et al., 1998). Prior to Cre expression the amount of ATR protein expressed by the $ATR^{flox/-}$ cells was approximately 20% of that in wild-type cells. This may indicate that insertion of the lox sites partially disrupts proper transcription or splicing of this allele. After infection with adenovirus encoding Cre (Ad-Cre), exon 2 was deleted and the amount of ATR protein rapidly declined (FIG. 3A and (Desany et al., 1998)).

Figure 3A:
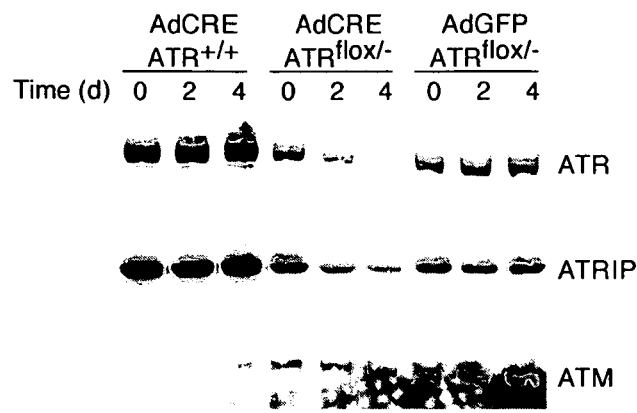
FIG. 3A shows that lysates prepared from the indicated cells following infection with adenovirus encoding either the Cre recombinase or green fluorescent protein (GFP) were separated by SDS-PAGE, blotted, and probed with the indicated antibodies.
Figure 3B:
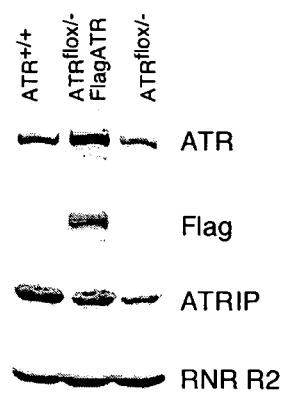
FIG. 3B demonstrates ATR$^{flox/-}$ cells were complemented with Flag-ATR by transfection of CMV-Flag-ATR (in pCDNA3.1Zeo, Invitrogen) and selection of a stable clonal cell line. Lysates from the indicated cell lines were blotted using antibodies for ATR, Flag, ATRIP, and RNR2.

The amounts of ATRIP protein were proportional to those of ATR. ATRIP was expressed at approximately 20% of wild-type amount in $ATR^{flox/-}$ cells. Less ATR and ATRIP was expressed after Ad-Cre infection to delete the flox allele (FIG. 3A). Stable expression of Flag-ATR in the $ATR^{flox/-}$ cell line restored ATR and ATRIP expression to approximately wild-type levels (FIG. 3B). The loss of ATRIP expression after deletion of ATR precluded further analysis of phosphorylation and localization dependencies.

Figure 3C:
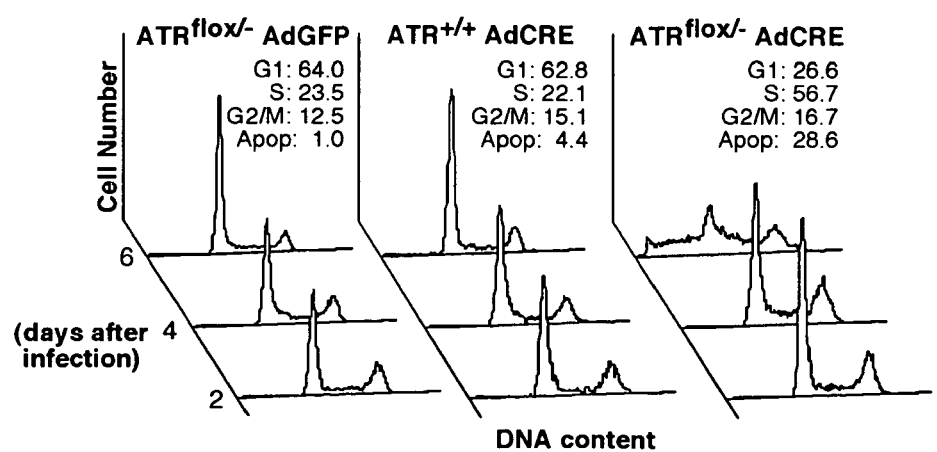
FIG. 3C shows ATR$^{+/+}$ or ATR$^{flox/-}$ cells were infected with Ad-Cre or Ad-GFP virus, and DNA content was measured by flow cytometric analysis of propidium iodine stained cells at the indicated times after infection.
Figure 4A:
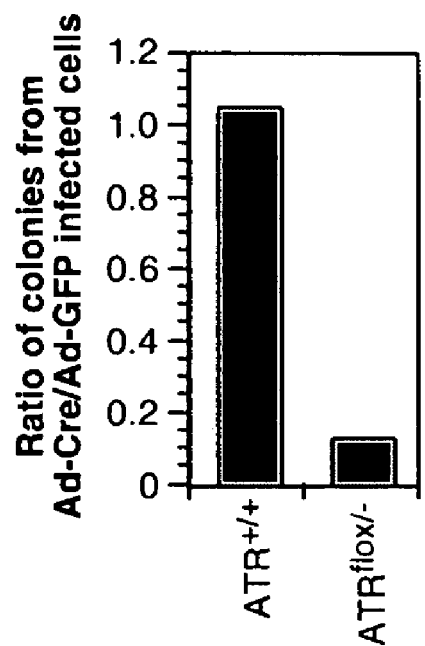
Figure 4B:
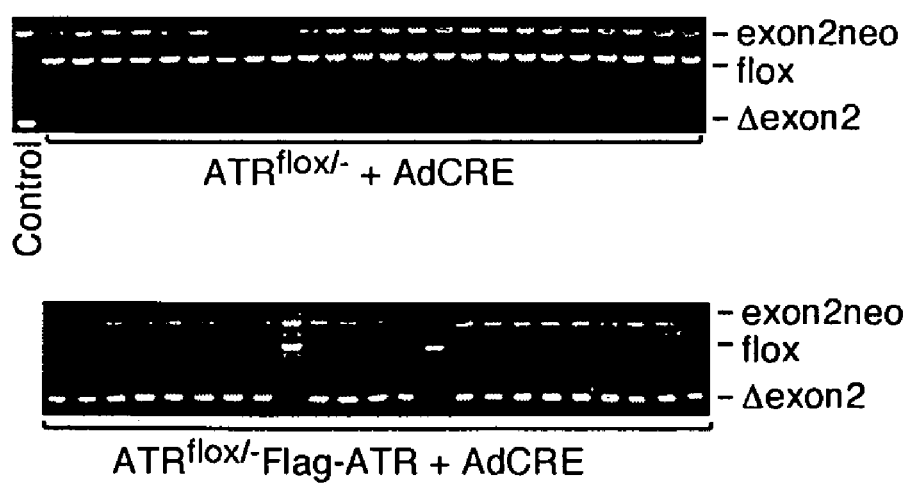

Interestingly, the loss of ATR protein from the $ATR^{flox/-}$ cells was maximal at day 4 after Ad-Cre infection to induce loss of the second ATR allele. By day 6 after infection, ATR levels actually increased and by day 10 had returned to the starting levels. The $ATR^{flox/-}$ cells lost viability starting at day 5 after Cre-infection, whereas $ATR^{+/+}$ cells infected with the same amount of virus showed no signs of toxicity. Therefore, it was suspected that deletion of ATR caused cell death, and that cells that had not been infected by the Ad-Cre virus eventually overtook the culture. On day 6 after infection 28% of the cells underwent apoptosis as indicated by a less than 2n DNA content (FIG. 3C). Plating efficiency of the Ad-Cre-infected $ATR^{flox/-}$ cells was reduced by approximately 85–90% compared to Ad-GFP-infected $ATR^{flox/-}$ cells. Finally, when we analyzed the genotype of the surviving colonies derived from the Ad-Cre infected cells we found 60 out of 60 clones analyzed retained ATR exon 2 indicating that they had not undergone Cre-mediated recombination (FIG. 4). In contrast 90% of the surviving colonies derived from limiting dilution plating of Ad-Cre infected $ATR^{flox/-}$ cells that stably expressed the Flag-ATR cDNA had deleted exon 2. These results indicate that ATR is an essential gene in this human somatic cell line.

Example 5

ATRIP Function

To study the function of ATRIP, siRNA was used to inhibit its expression. Reduction of ATRIP expression also resulted in less ATR expression. Both western blotting and immunolocalization analysis revealed that ATRIP is required for continued expression of the ATR protein (FIGS. 5A and 5B). ATR RNA levels were unaffected by transfection of siRNA targeting ATRIP (FIG. 5C). Three independent, 21 base pair RNA duplexes targeting ATRIP yielded similar results, while two control duplexes had no effect on either ATRIP or ATR expression. Therefore, ATRIP and ATR are mutually dependent on each other for expression.

The amount of ATRIP in Hela cells was unable to be reduced below 15% to 20% of that in wild-type cells. This amount of reduction yielded no-detectable checkpoint defects, which was not unexpected since approximately the same amount of protein is observed in the $ATR^{flox/-}$ cells that also have no detectable checkpoint defects prior to excision of exon 2. Therefore, the siRNA method was employed to interfere with ATRIP expression in the $ATR^{flox/-}$ cells that already had reduced ATRIP expression.

The siRNA duplexes were 21 base pairs including a two base pair deoxynucleotide overhang.

```
The coding strands of the three ATRIP siRNAs were:
5'-GGUCCACAGAUUAUUAGAUTT-3',      (SEQ ID NO:21)
5'-AGAGGAACAGAGAAGAUCACA-3', and  (SEQ ID NO:22)
5'-GAAGAGGCCCAGAAAAGCUTT-3'.      (SEQ ID NO:23)

The two control siRNAs used were
5'-GACCCGCGCCGAGGUGAAGUU-3' and   (SEQ ID NO:24)
5'-UGGCUUUCUGUAGAGGACAUCTT-3'.    (SEQ ID NO:25)

Italics indicate deoxynucleotides.
```

Three days after infection or the initial transfection, the cells were exposed to 8 Gy of γ-irradiation and 1 µg/ml nocodazole was added to the medium. Sixteen hours after irradiation the cells were harvested, stained with propidium iodide for DNA content analysis using flow cytometry or fixed with Carnoy's fixative. The percentage of mitotic cells was determined by counting 600 DAPI stained cells. The percentage of G2 cells was determined by subtracting the percentage of cells in mitosis from the percentage of cells in G2-M as determined by flow cytometry. Alternatively, the percentage of cells that were in M phase was determined by staining with propidium iodide and anti-phospho-histone H3 antibody (Cell Signaling) followed by FITC-conjugated secondary antibody and the percentage of G1, S, G2, and M phase cells was determined by flow cytometry (Xu et al., 2001). Phospho-histone H3 staining and DAPI staining of mitotic figures yielded similar percentages of mitotic cells in multiple experiments.

Transfection of siRNA in HCT116 cells effectively reduced ATRIP expression. Transfection of control siRNAs in $ATR^{flox/-}$ cells, Ad-Cre infection of $ATR^{+/+}$ cells, or Ad-GFP infection of $ATR^{flox/-}$ cells had no effect on the ability of these cells to delay entry into mitosis following ionizing radiation. However, transfection of siRNAs against ATRIP yielded a profound γ-irradiation-induced G2-M checkpoint defect that was similar to that seen in the $ATR^{flox/-}$ cells treated with Ad-Cre (FIG. 5D).

Approximately 40% of Cre-infected or ATRIP siRNA transfected ATR$^{flox/-}$ cells enter mitosis 16 hours after irradiation compared with 20% of control cells. These results are consistent with checkpoint defects of cells overexpressing catalytically-inactive ATR protein (Cliby et al., 1998). Thus, ATR and ATRIP are essential for a normal DNA-damage induced delay of mitosis initiated by ionizing radiation.

These data indicate that ATRIP is the functional human homologue of the Rad26 family of genes. ATRIP associates with ATR, is a substrate of ATR in vitro and a phosphoprotein in vivo, and co-localizes with ATR to sites of DNA synthesis and repair after treatment of cells with DNA damaging agents or replication inhibitors. Furthermore, interference with ATRIP function generates the same G2-M checkpoint defect as observed after deletion of ATR. ATRIP expression is dependent on ATR, and ATR expression is dependent on ATRIP. This mutual dependency for expression suggests that the amount of ATR and ATRIP in cells is tightly coordinated, and may indicate that these proteins form a stable complex with each other at a fixed stoichiometry.

ATR function is required for the viability of undamaged, proliferating cells and in cells exposed to DNA damaging agents. In this respect, ATR is similar to MEC1, which is essential for viability due to difficulties in the proper coordination of DNA replication (Zhao et al., 1998; Canman et al., 1998). An increase in the percentage of S phase cells after Ad-Cre infection of the ATR$^{flox/-}$ cells was observed (see FIG. 3C), perhaps reflecting a requirement for ATR and ATRIP signaling to ensure successful DNA replication.

Example 6

Creation of ATR$^{Flox/-}$ Cells

Figure 6A:
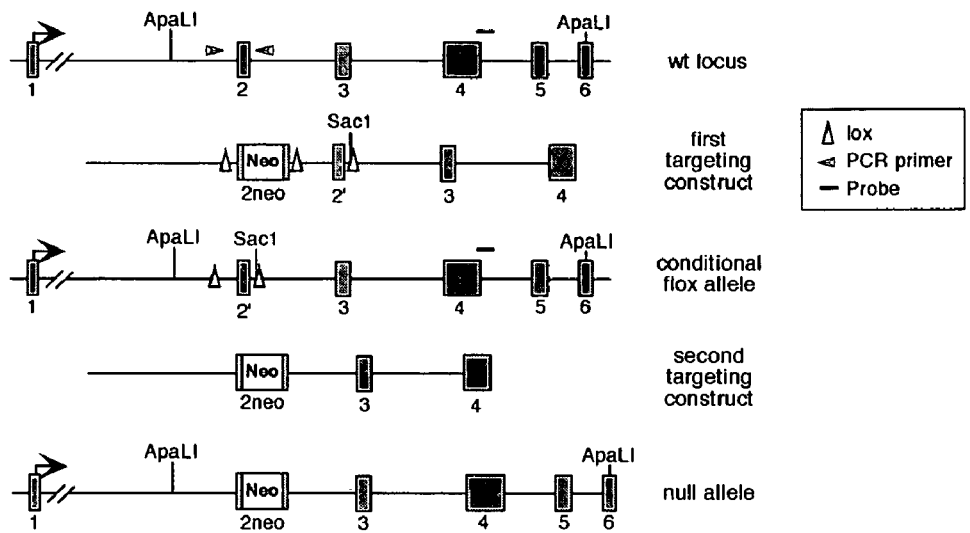
FIGS. 6A through 6C show creation of ATR$^{flox/-}$ cells.
Figure 6B:
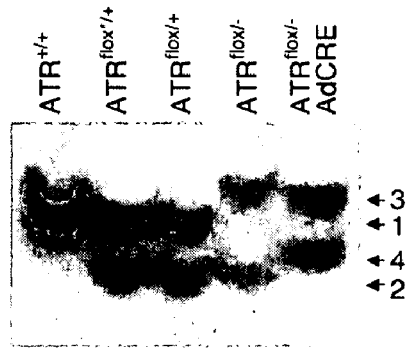
Figure 6C:
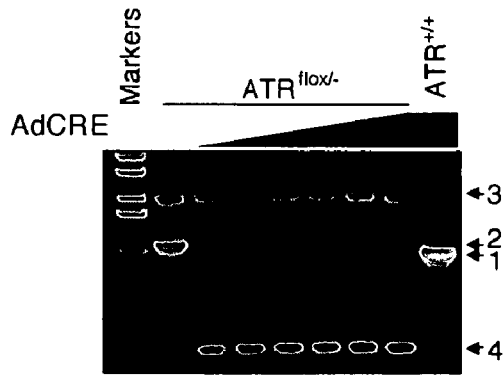

The ATR gene was targeted in human diploid HCT116 cells by homologous recombination. Initially, an ATR "flox" allele was generated by inserting lox sites flanking exon 2 (FIG. 6A). Constructs to generate the allele by standard means in the art include (ATR clone8 genomic sequence; SEQ ID NO:26) and (pDC353 knockout construct; SEQ ID NO:27). An ATR$^{flox}$ targeting construct containing a duplicated exon 2 as well as an exon 2 disrupted in frame with the coding region of the neomycin resistance gene and polyadenylation sequence was created using ATR genomic DNA cloned from a lambda genomic library. Three lox sites were inserted as indicated as well as a SacI site to facilitate genotyping. This targeting construct was linearized and transfected into HCT116 cells. Colonies containing the appropriate homologously-targeted ATR allele were screened by southern blotting using the indicated probe. The neomycin-disrupted exon 2 was excised using the Cre recombinase followed by PCR screening for the appropriate genomic rearrangement. A second targeting construct containing exon 2 disrupted in frame with the coding region of the neomycin resistance gene was then transfected into the ATR$^{flox/+}$ cells to create an ATR$^{flox/-}$ cell line. Southern blotting indicated the proper homologous targeting of both alleles (FIG. 6B). Furthermore, expression of Cre using an adenoviral vector (Ad-Cre) resulted in site-specific recombination between the two lox sites and deletion of exon 2 from the flox allele (FIGS. 6B and C). Deletion of exon 2 is predicted to yield a frame shift mutation at amino acid 20 and a stop codon 9 amino acids later coded by exon 3.

Example 7

Mapping of the ATR Interacting Domain on ATRIP

Figure 7A:
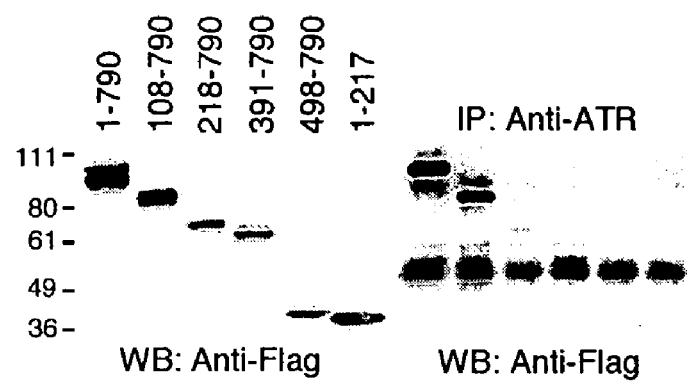
FIGS. 7A through 7B demonstrate mapping of the ATR interacting domain on ATRIP.
Figure 7B:
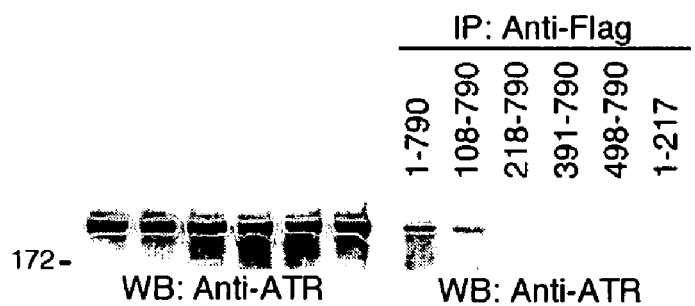

The region of ATRIP that interacts with ATR was determined. FIG. 7A shows flag and nuclear localization signal (NLS)-tagged ATRIP fragments that were co-expressed in 293 cells with ATR. Expression constructs were created using PCR and transferred to the Flag-NLS expression vector using the univector plasmid fusion system. Lysates were immunoprecipitated with anti-ATR antibody and immunoblotted with anti-Flag antibody. FIG. 7B demonstrates Flag-NLS-tagged ATRIP fragments that were expressed in 293 cells and immunoprecipitated with anti-Flag antibodies. The immunoprecipitates were immunoblotted with anti-ATR antibodies.

Example 8

Recruitment of ATR/ATRIP to ssDNA by RPA

As stated, ATR and ATRIP both localize to intranuclear foci after DNA damage or inhibition of replication. In specific non-limiting embodiments, the damaged DNA is sensed by ATR and/or ATRIP, either through direct interaction with the damaged DNA or through indirect interaction with the damaged DNA. In some embodiments ATR, ATRIP, or a complex comprising ATR and ATRIP sense damaged DNA, such as a nick or break. In a specific embodiment, at least one other molecule senses the damaged DNA and recruits either ATR, ATRIP, or a complex comprising ATR and ATRIP to the damaged DNA.

Figure 8:
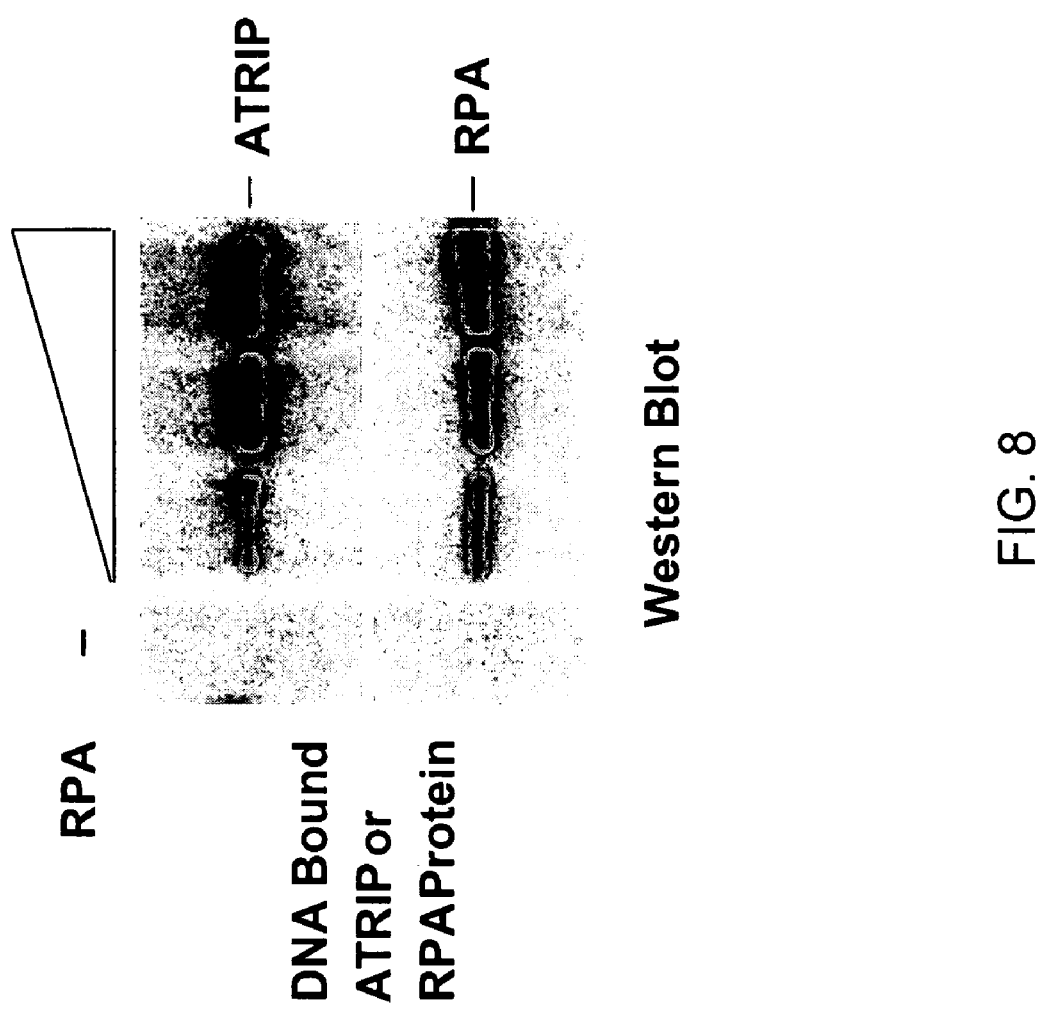
FIG. 8 illustrates that human replication protein A (RPA) stimulates the association of ATRIP with single-stranded DNA.

RPA and Polalpha accumulate on chromatin following DNA damage (Lupardus et al., 2002). In a further specific embodiment, human replication protein A (RPA stimulates the association of ATRIP with single-stranded DNA (FIG. 8). Purified ATRIP was incubated with biotinylated single-stranded DNA in the absence of RPA (−) or in the presence of increasing amounts of RPA shown as a triangle. The ATRIP-RPA-DNA complexes were recovered by streptavidin beads. DNA-bound ATRIP and RPA were detected with antibodies to ATRIP and RPA, respectively. To perform this experiment, recombinant human RPA was a trimeric complex purified from *E. coli*. ssDNA was a biotinylated 75mer oligo by well-known methods. Human ATRIP was purified from baculovirus-infected insect cells by standard methods in the art.

Thus, although ATRIP has a low affinity for ssDNA when alone, it has a high affinity for ssDNA when bound by RPA. Single-stranded DNA is a product formed when DNA is damaged, particularly damage that blocks replication. The ATR/ATRIP complex in specific embodiments is the sensor of DNA damage and therefore detects altered DNA structures. In a preferred non-limiting embodiment of the present invention, ATRIP senses ssDNA in this manner.

In one embodiment of the present invention, this RPA interaction is exploited to screen for drugs that inhibit ATR/ATRIP function. In further specific embodiments, a possible anti-cancer therapy comprises a drug identified by this assay. In an exemplary manner, ssDNA comprises at least one bound RPA molecule. As a control, an introduced ATRIP binds the RPA-ssDNA complex. Test candidates are introduced to the RPA-bound ssDNA, and a preferred candidate prevents ATRIP from binding the complex. In a further specific embodiment, the preferred candidate is comprised in a pharmaceutical composition and administered in an effective amount to an individual stricken with a proliferative disorder, such as cancer.

Example 9

RPA Stimulates Phosphorylation of RAD17 by ATR/ATRIP Complex

ATR/ATM-dependent phosphorylation of hRad17 is a critical early event during checkpoint signalling in DNA-damaged cells (Bao et al., 1999). Rad 17 binds to chromatin prior to damage and is phosphorylated by ATR on chromatin after damage. Phosphorylation of Rad17 serines 635 and 645 is cell cycle regulated. Furthermore, the phosphorylation is required for G(1)/S checkpoint activation in response to DNA damage (Post et al., 2001).

Figure 9:
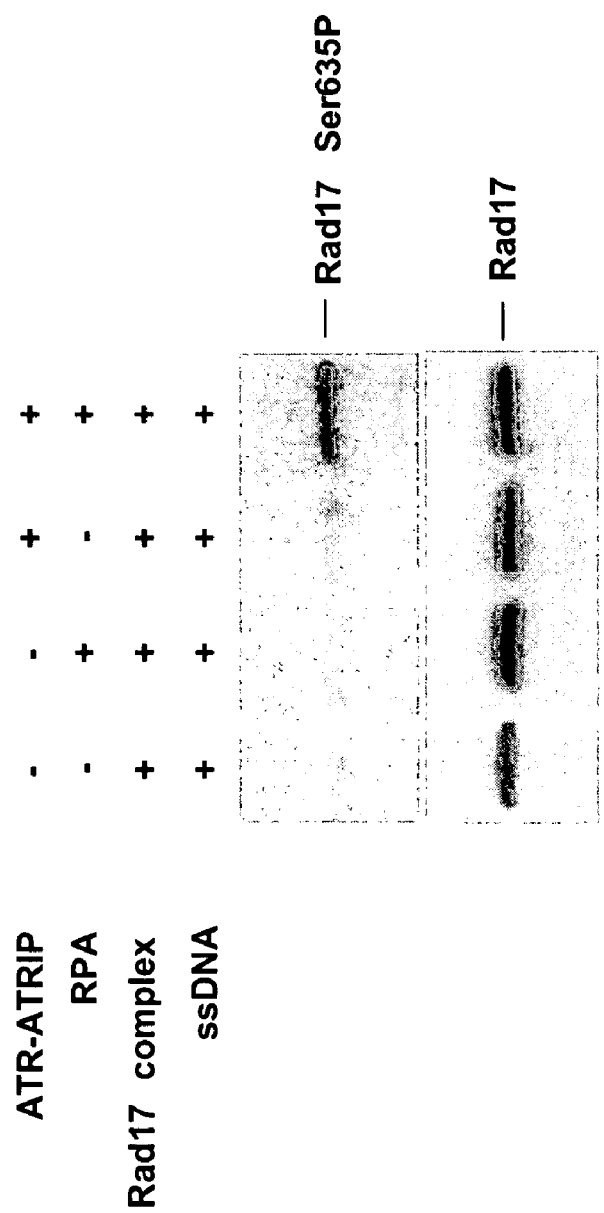
FIG. 9 shows that human replication protein A stimulates the phosphorylation of Rad17 by the ATR-ATRIP complex.

In FIG. 9, human replication protein A (RPA) stimulates the phosphorylation of Rad17 by the ATR-ATRIP complex. Purified Rad17/Rfc2-5 complex was incubated with the ATR-ATRIP complex, RPA, and biotinylated ssDNA as indicated above. The DNA-bound Rad17 complex was retrieved by streptavidin beads. Total Rad17 protein and phosphorylated Rad17 on DNA were detected with antibodies to Rad17 and phospho-Rad17 (Ser635P), respectively. In a specific embodiment, phosphorylation of Ser645 is assayed, and in another specific embodiment, phosphorylation of Ser635 and Ser 645 is assayed.

To perform this experiment, recombinant human Rad17 protein purified from baculoviruse infected insect cells. The human Rad17 protein was tagged with a Flag epitope at its N terminus for purification, and it was purified as a complex with RFC2-5 subunits. ATR was purified from human cells transiently overexpressing ATR. Subsequently, purified ATR and ATRIP were mixed in vitro to reconstitute the ATR/ATRIP complex.

As demonstrated, Rad 17 is phosphorylated upon recruitment to the ssDNA of ATR/ATRIP by RPA. A skilled artisan recognizes that other entities associated with the ATR/ATRIP complex in some embodiments are indirectly or directly involved in DNA damage sensing by the complex. Examples of such entities include Hus1, Rad1, and/or Rad9 (Zou et al., 2002). Modifications of the Hus1, Rad1, and/or Rad9 gene products' activity, function, and/or level in some embodiments result in inhibition of ATR/ATRIP function.

In one embodiment of the present invention, this phosphorylation is exploited to screen for drugs that inhibit ATR/ATRIP function. In a specific embodiment, a possible anti-cancer therapy comprises a drug identified by this assay. In one non-limiting exemplary embodiment, a protein (a "target protein") capable of being phosphorylated by ATR/ATRIP complex is bound to ssDNA. In controls, RPA recruits ATR/ATRIP to the ssDNA, and the target protein is phosphorylated. The assay screens for absence of phosphorylation upon administration of a test candidate, which in specific embodiments inhibits ATR/ATRIP function. In further specific embodiments, the identified test candidate that results in inhibition of ATR/ATRIP function is comprised in a pharmaceutically acceptable composition, and is administered in an effective amount to an individual stricken with a proliferative cell disease, such as cancer.

REFERENCES

The following references, to the extent that they provide exemplary procedural or other details supplementary to those set forth herein, are specifically incorporated herein by reference.

Patents Publications

Bao S, Tibbetts R S, Brumbaugh K M, Fang Y, Richardson D A, Ali A, Chen S M, Abraham R T, Wang X F, Nature 2001 Jun. 21;411(6840):969–74
Bentley, N. J. et al., Embo J 15, 6641–51 (1996).
Brodsky, M., J. J. Sekelsky, G. Tsang, R. S. Hawley, G. M. Rubin, Genes Dev 14, 666–78. (2000).
Brown, E. J. and D. Baltimore, Genes Dev 14, 397–402 (2000).
Canman, C. E. et al., Science 281, 1677–9 (1998).
Cimprich, K. A., T. B. Shin, C. T. Keith, S. L. Schreiber, Proc Natl Acad Sci USA 93, 2850–5 (1996).
Cliby, W. A. et al., Embo J 17, 159–69 (1998).
de Klein, A. et al., Curr Biol 10, 479–82 (2000).
Desany, B. A., A. A. Alcasabas, J. B. Bachant, S. J. Elledge, Genes Dev 12, 2956–70 (1998).
Durocher, D. and S. P. Jackson, Curr Opin Cell Biol 13, 225–31. (2001).
Edwards, R. J., N. J. Bentley, A. M. Carr, Nat Cell Biol 1, 393–398 (1999).
Elbashir, S. M. et al., Nature 411, 494–8. (2001).
Lupardus P J, Byun T, Yee M C, Hekmat-Nejad M, Cimprich K A. A requirement for replication in activation of the ATR-dependent DNA damage checkpoint. Genes Dev 2002 Sep. 15;16(18):2327–32.
Post, S. et al. Phosphorylation of of serines 635 and 645 of human Rad17 is cell cycle regulated and is required for G(1)/S checkpoint activation in response to DNA damage Proc Natl Acad Sci USA 2001 Nov. 6;98(23):13102–7
Paciotti, V., M. Clerici, G. Lucchini, M. P. Longhese, Genes Dev 14, 2046–59 (2000).
Rouse, J., S. P. Jackson, Embo J 19, 5801–12 (2000).
Shiloh, Y. Curr Opin Genet Dev 11, 71–7. (2001).
Tibbetts, R. S. et al., Genes Dev 13, 152–7 (1999).
Tibbetts, R. S. et al., Genes Dev 14, 2989–3002 (2000).
Wakayama, T., T. Kondo, S. Ando, K. Matsumoto, K. Sugimoto, Mol Cell Biol 21, 755–764 (2001).
Wang, Y. et al., Genes Dev 14, 927–39 (2000).
Wright, J. A. et al., Proc Natl Acad Sci USA 95, 7445–50 (1998).
Xu, B., S. Kim, M. B. Kastan, Mol Cell Biol 21, 3445–50. (2001).
Zhao, X., E. G. Muller, R. Rothstein, Mol Cell 2, 329–40 (1998).
Zou, L., Cortez, D., Elledge S J, Genes Dev 16(2): 198–208.

One skilled in the art readily appreciates that the present invention is well adapted to carry out the objectives and obtain the ends and advantages mentioned as well as those inherent therein. Methods, procedures, techniques, and kits described herein are presently representative of the preferred embodiments and are intended to be exemplary and are not intended as limitations of the scope. Changes therein and other uses will occur to those skilled in the art which are encompassed within the spirit of the invention or defined by the scope of the invention.

We claim:

1. An isolated nucleic acid sequence comprising SEQ ID NO:1.

2. An isolated DNA sequence encoding the polypeptide comprising SEQ ID NO:2.

3. A vector comprising the nucleic acid sequence of SEQ ID NO:1, wherein the expression of the nucleic acid sequence is regulated by nucleic acid sequences operatively linked to said nucleic acid sequence comprising SEQ ID NO:1.

4. The vector of claim 3, wherein said vector is a plasmid, a viral vector, or a lipid composition.

5. The vector of claim 4, wherein said viral vector is an adenoviral vector, an adeno-associated viral vector, or a retroviral vector.

* * * * *

SEQUENCE LISTING

<160> NUMBER OF SEQ ID NOS: 47

<210> SEQ ID NO 1
<211> LENGTH: 2509
<212> TYPE: DNA
<213> ORGANISM: Homo sapiens

<400> SEQUENCE: 1

| | | | | | |
|---|---|---|---|---|---|
| gcgctgtcgg | atacttgggg | tgagcggaaa | gcatggcggg | gacctccgcg | ccaggcagca | 60 |
| agaggcggag | cgagcccccg | gcgcctcgcc | ccggcccgcc | gccgggcacc | gggcacccccc | 120 |
| cgagcaagcg | ggcccggggc | ttctccgcag | ccgctgcccc | ggaccctgac | gacccgttcg | 180 |
| gcgcgcatgg | ggacttcact | gccgacgacc | tggaggagct | tgacaccctc | gcgtcacagg | 240 |
| ccctgagcca | atgtccggcc | gcggctcggg | acgtgtccag | tgatcataag | gtccacagat | 300 |
| tattagatgg | catgtcaaaa | aatccttcag | ggaaaaacag | agaaactgtt | ccaattaaag | 360 |
| ataatttcga | attagaggta | cttcaggcac | aatacaaaga | acttaaagaa | aagatgaaag | 420 |
| taatggaaga | agaagttctc | attaagaatg | gagaaattaa | aattttgcga | gactcactac | 480 |
| atcagacgga | atccgttcta | gaggaacaga | gaagatcaca | ttttcttctt | gagcaagaga | 540 |
| aaacccaagc | actcagtgac | aaggaaaagg | aattctccaa | aaagctccaa | tcattgcagt | 600 |
| ctgaactcca | gtttaaagat | gcagagatga | atgaattaag | gacaaagctc | cagaccagtg | 660 |
| aacgagcaaa | taaactggct | gctccctctg | tttcccatgt | cagtcctagg | aaaaacccctt | 720 |
| ctgtggttat | aaagccagaa | gcatgttctc | cacaatttgg | aaaaacatct | tttcctacaa | 780 |
| aggagtcttt | tagtgctaac | atgtcccttc | cccaccctg | ccagacggag | tcaggataca | 840 |
| agcctctggt | gggcagagag | gatagtaagc | cccacagtct | gagaggtgac | tccataaaac | 900 |
| aagaagaggc | ccagaaaagc | tttgttgaca | gctggagaca | gagatcaaac | actcaaggtt | 960 |
| ccattttgat | aaacctgctc | ctgaagcagc | ctttgatccc | agggtcatcc | ctaagccttt | 1020 |
| gccacctcct | gagtagtagt | tctgagtctc | ctgctggcac | cccctgcag | ccaccagggt | 1080 |
| ttggcagtac | cttggctgga | atgtcaggcc | tcaggaccac | aggttcttat | gatgggtcat | 1140 |
| tttccctctc | agccctgaga | gaagcacaga | acctggcatt | cactggactg | aatctggttg | 1200 |
| cccggaatga | gtgctcacgt | gatggagacc | cagcagaggg | aggcagaagg | gccttcccac | 1260 |
| tctgccagct | tcctggagcc | gtgcatttcc | tcccccttgt | acagttcttc | atcggcttac | 1320 |
| actgccaggc | cctgcaggac | ttggcagctg | ctaagagaag | cggagcacct | ggggactcac | 1380 |
| cgacacattc | ctcctgcgtg | agctctgggg | tagagaccaa | ccctgaggac | tcagtgtgca | 1440 |
| tcctggaagg | cttctctgtg | actgcactta | gcattcttca | gcacctggtg | tgccacagcg | 1500 |
| gagcagtcgt | ctccctatta | ctgtcaggag | tggggcaga | ttctgctgct | ggggaaggaa | 1560 |
| acaggagcct | ggttcacagg | cttagtgatg | gagatatgac | ctcagcccta | aggggggttg | 1620 |
| ctgatgacca | aggacagcac | ccactgttga | agatgcttct | tcacctgttg | gctttctctt | 1680 |
| ctgcagcaac | aggtcacctt | caagccagtg | tcctgaccca | gtgccttaag | gttttggtga | 1740 |
| aattagccga | aaacacttcc | tgtgatttct | gcccaggtt | ccagtgtgtg | ttccaagtgc | 1800 |
| tgccaaagtg | cctcagccca | gagacacccc | tgcctagcgt | gctgctggct | gttgagctcc | 1860 |
| tctccctgct | ggcggaccac | gaccagctgg | cacctcagct | ctgttcccac | tcagaaggct | 1920 |
| gcctcctgct | gctgctgtac | atgtacatca | catcacggcc | tgacagagtg | gccttggaga | 1980 |
| cacaatggct | ccagctggaa | caagaggtgg | tgtggctcct | ggctaagctt | ggtgtgcaga | 2040 |

-continued

```
gccccttgcc cccagtcact ggctccaact gccagtgtaa tgtggaggtg gtcagagcgc      2100
tcacggtgat gttgcacaga cagtggctga cagtgcggag ggcagggga ccccaagga       2160 ccgaccagca gaggcggaca gtgcgctgtc tgcgggacac ggtgctgctg ctgcacggcc      2220
tatcgcagaa ggacaagctc ttcatgatgc actgcgtgga ggtcctgcat cagtttgacc      2280
aggtgatgcc gggggtcagc atgctcatcc gagggcttcc tgatgtgacg gactgtgaag      2340
aggcagccct ggatgacctc tgtgccgcgg aaaccgatgt ggaagacccc gaggtggagt      2400
gtggctgagg ccctgagtgt ccagccacat ggtggcacca gcaccactcc tttccttacc      2460
acatcaactg attaaagcag tgaccagcag gaactgccca gagaactgg                 2509
```

<210> SEQ ID NO 2
<211> LENGTH: 791
<212> TYPE: PRT
<213> ORGANISM: Homo sapiens

<400> SEQUENCE: 2

```
Met Ala Gly Thr Ser Ala Pro Gly Ser Lys Arg Arg Ser Glu Pro Pro
 1               5                  10                  15

Ala Pro Arg Pro Gly Pro Pro Gly Thr Gly His Pro Pro Ser Lys
            20                  25                  30

Arg Ala Arg Gly Phe Ser Ala Ala Ala Pro Asp Pro Asp Asp Pro
        35                  40                  45

Phe Gly Ala His Gly Asp Phe Thr Ala Asp Asp Leu Glu Glu Leu Asp
    50                  55                  60

Thr Leu Ala Ser Gln Ala Leu Ser Gln Cys Pro Ala Ala Arg Asp
65                  70                  75                  80

Val Ser Ser Asp His Lys Val His Arg Leu Asp Gly Met Ser Lys
                85                  90                  95

Asn Pro Ser Gly Lys Asn Arg Glu Thr Val Pro Ile Lys Asp Asn Phe
            100                 105                 110

Glu Leu Glu Val Leu Gln Ala Gln Tyr Lys Glu Leu Lys Glu Lys Met
        115                 120                 125

Lys Val Met Glu Glu Val Leu Ile Lys Asn Gly Glu Ile Lys Ile
    130                 135                 140

Leu Arg Asp Ser Leu His Gln Thr Glu Ser Val Leu Glu Glu Gln Arg
145                 150                 155                 160

Arg Ser His Phe Leu Leu Glu Gln Glu Lys Thr Gln Ala Leu Ser Asp
                165                 170                 175

Lys Glu Lys Glu Phe Ser Lys Lys Leu Gln Ser Leu Gln Ser Glu Leu
            180                 185                 190

Gln Phe Lys Asp Ala Glu Met Asn Glu Leu Arg Thr Lys Leu Gln Thr
        195                 200                 205

Ser Glu Arg Ala Asn Lys Leu Ala Ala Pro Ser Val Ser His Val Ser
    210                 215                 220

Pro Arg Lys Asn Pro Ser Val Val Ile Lys Pro Glu Ala Cys Ser Pro
225                 230                 235                 240

Gln Phe Gly Lys Thr Ser Phe Pro Thr Lys Glu Ser Phe Ser Ala Asn
                245                 250                 255

Met Ser Leu Pro His Pro Cys Gln Thr Glu Ser Gly Tyr Lys Pro Leu
            260                 265                 270

Val Gly Arg Glu Asp Ser Lys Pro His Ser Leu Arg Gly Asp Ser Ile
        275                 280                 285
```

```
Lys Gln Glu Ala Gln Lys Ser Phe Val Asp Ser Trp Arg Gln Arg
    290                 295                 300
Ser Asn Thr Gln Gly Ser Ile Leu Ile Asn Leu Leu Leu Lys Gln Pro
305                 310                 315                 320
Leu Ile Pro Gly Ser Ser Leu Ser Leu Cys His Leu Leu Ser Ser Ser
                325                 330                 335
Ser Glu Ser Pro Ala Gly Thr Pro Leu Gln Pro Pro Gly Phe Gly Ser
            340                 345                 350
Thr Leu Ala Gly Met Ser Gly Leu Arg Thr Thr Gly Ser Tyr Asp Gly
        355                 360                 365
Ser Phe Ser Leu Ser Ala Leu Arg Glu Ala Gln Asn Leu Ala Phe Thr
    370                 375                 380
Gly Leu Asn Leu Val Ala Arg Asn Glu Cys Ser Arg Asp Gly Asp Pro
385                 390                 395                 400
Ala Glu Gly Gly Arg Arg Ala Phe Pro Leu Cys Gln Leu Pro Gly Ala
                405                 410                 415
Val His Phe Leu Pro Leu Val Gln Phe Phe Ile Gly Leu His Cys Gln
            420                 425                 430
Ala Leu Gln Asp Leu Ala Ala Lys Arg Ser Gly Ala Pro Gly Asp
    435                 440                 445
Ser Pro Thr His Ser Ser Cys Val Ser Ser Gly Val Glu Thr Asn Pro
    450                 455                 460
Glu Asp Ser Val Cys Ile Leu Glu Gly Phe Ser Val Thr Ala Leu Ser
465                 470                 475                 480
Ile Leu Gln His Leu Val Cys His Ser Gly Ala Val Val Ser Leu Leu
                485                 490                 495
Leu Ser Gly Val Gly Ala Asp Ser Ala Ala Gly Glu Gly Asn Arg Ser
            500                 505                 510
Leu Val His Arg Leu Ser Asp Gly Asp Met Thr Ser Ala Leu Arg Gly
        515                 520                 525
Val Ala Asp Asp Gln Gly Gln His Pro Leu Leu Lys Met Leu Leu His
    530                 535                 540
Leu Leu Ala Phe Ser Ser Ala Ala Thr Gly His Leu Gln Ala Ser Val
545                 550                 555                 560
Leu Thr Gln Cys Leu Lys Val Leu Val Lys Leu Ala Glu Asn Thr Ser
                565                 570                 575
Cys Asp Phe Leu Pro Arg Phe Gln Cys Val Phe Gln Val Leu Pro Lys
            580                 585                 590
Cys Leu Ser Pro Glu Thr Pro Leu Pro Ser Val Leu Leu Ala Val Glu
        595                 600                 605
Leu Leu Ser Leu Leu Ala Asp His Asp Gln Leu Ala Pro Gln Leu Cys
    610                 615                 620
Ser His Ser Glu Gly Cys Leu Leu Leu Leu Tyr Met Tyr Ile Thr
625                 630                 635                 640
Ser Arg Pro Asp Arg Val Ala Leu Glu Thr Gln Trp Leu Gln Leu Glu
                645                 650                 655
Gln Glu Val Val Trp Leu Leu Ala Lys Leu Gly Val Gln Ser Pro Leu
            660                 665                 670
Pro Pro Val Thr Gly Ser Asn Cys Gln Cys Asn Val Glu Val Val Arg
        675                 680                 685
Ala Leu Thr Val Met Leu His Arg Gln Trp Leu Thr Val Arg Arg Ala
    690                 695                 700
Gly Gly Pro Pro Arg Thr Asp Gln Gln Arg Arg Thr Val Arg Cys Leu
```

```
                  705                 710                 715                 720
              Arg Asp Thr Val Leu Leu His Gly Leu Ser Gln Lys Asp Lys Leu
                              725                 730                 735

Phe Met Met His Cys Val Glu Val Leu His Gln Phe Asp Gln Val Met
                          740                 745                 750

Pro Gly Val Ser Met Leu Ile Arg Gly Leu Pro Asp Val Thr Asp Cys
                      755                 760                 765

Glu Glu Ala Ala Leu Asp Asp Leu Cys Ala Ala Glu Thr Asp Val Glu
                  770                 775                 780

Asp Pro Glu Val Glu Cys Gly
              785                 790

<210> SEQ ID NO 3
              <211> LENGTH: 3584
              <212> TYPE: DNA
              <213> ORGANISM: Homo sapiens

<400> SEQUENCE: 3
tgcagtctga actccagttt aaagatgcag agatgaatga attaaggaca aagctccaga      60
ccagtgaacg agcaaataaa ctggctgctc cctctgtttc ccatgtcagt cctaggaaaa     120
acccttctgt ggttataaag ccagaagcat gttctccaca atttggaaaa acatcttttc     180
ctacaaagga gtcttttagt gctaacatgt cccttcccca ccctgccag acggagtcag      240 gatacaagcc tctggtgggc agagaggata gtaagcccca cagtctgaga ggtgactcca     300
taaaacaaga gaggcccag aaaagctttg ttgacagctg agacagaga tcaaacactc        360 aaggttccat tttgataaac ctgctcctga agcagccttt gatcccaggg tcatccctaa     420
gcctttgcca cctcctgagt agtagttctg agtctcctgc tggcaccccc ctgcagccac     480
cagggtttgg cagtaccttg gctggaatgt caggcctcag gaccacaggt tcttatgatg     540
ggtcattttc cctctcagcc ctgagagaag cacagaacct gcattcact ggactgaatc       600 tggttgcccg gaatgagtgc tcacgtgatg agacccagc agagggaggc agaagggcct       660
tcccactctg ccagcttcct ggagccgtgc atttcctccc ccttgtacag ttcttcatcg     720
gcttacactg ccaggccctg caggacttgg cagctgctaa gagaagcgga gcacctgggg     780
actcaccgac acattcctcc tgcgtgagct ctggggtaga gaccaaccct gaggactcag     840
tgtgcatcct ggaaggcttc tctgtgactg cacttagcat tcttcagcac ctggtgtgcc     900
acagcggagc agtcgtctcc ctattactgt caggagtggg ggcagattct gctgctgggg     960
aaggaaacag gagcctggtt cacaggctta gtgatggaga tatgacctca gccctaaggg    1020
gggttgctga tgaccaagga cagcacccac tgttgaagat gcttcttcac ctgttggctt    1080
tctcttctgc agcaacaggt caccttcaag ccagtgtcct gacccagtgc cttaaggttt    1140
tggtgaaatt agccgaaaac acttcctgtg atttcttgcc caggttccag tgtgtgttcc    1200
aagtgctgcc aaagtgcctc agcccagaga caccctgcc tagcgtgctg ctggctgttg     1260
agctcctctc cctgctggcg gaccacgacc agctggcacc tcagtctgt tcccactcag       1320 aaggctgcct cctgctgctg ctgtacatgt acatcacatc acggcctgac agagtggcct    1380
tggagacaca atggctccag ctggaacaag aggtggtgtg ctcctggct aagcttggtg      1440 tgcagagccc cttgccccca gtcactggct ccaactgcca gtgtaatgtg aggtggtca       1500 gagcgctcac ggtgatgttg cacagacagt ggctgacagt gcggagggca ggggacccc       1560 caaggaccga ccagcagagg cggacagtgc gctgtctgcg ggacacggtg ctgctgctgc    1620
```

-continued

```
acggcctatc gcagaaggac aagctcttca tgatgcactg cgtggaggtc ctgcatcagt    1680
ttgaccaggt gatgccgggg gtcagcatgc tcatccgagg gcttcctgat gtgacggact    1740
gtgaagaggc agccctggat gacctctgtg ccgcggaaac cgatgtggaa gaccccgagg    1800
tggagtgtgg ctgaggccct gagtgtccag ccacatggtg gcaccagcac cactcctttc    1860
cttaccacat caactgatta aagcagtgac cagcaggaac tgcccagaga actggctggc    1920
cttgtttcct gagtctgatc tgtttggcgg agtgggaggg gtggagcagg acccggaccc    1980
tgagtggctg ggatccttct tcctgtccct ggctgttgct gagcccgtcc ccatggtaac    2040
tgatctgcct tgaggaagga gccctgccct gcctgtggaa ttgtcctgag tcattgcttt    2100
gggctggggc catgggaaga aaccattgtg tggcagggaa ggaggtggct cttggcccag    2160
gcctaaacca ggaaagcctg ggaaactggg acccacaggt gggcatgaaa gggccgcagc    2220
aggggctccc agcagtgtgt aagaccggga gctggtctgg caccactgcc ctggtccttc    2280
cagctgcctg tcactggtat gatggccccg gtgcattgtg ccaccagcag gccacagctg    2340
tggatcttgg aaggcctctg ggtcccccg ggagcagggg agtgggtgtg gggggaacg    2400
gatggtggtg agagggacag accaggcagg ctgacgagca gggcgggcct ggctcacgtg    2460
ggcctgtagg cgggcccacg ccaagtttca cttaccgcca ctgctgccag cgagagccgc    2520
gggagagtgt gcagccgagt cactactgcc tgcctgcctg cctgctacgg ctcagcagca    2580
ggtacgtacc caaccatggg ctcgcaggcc ctgcccccgg ggcccatgca gaccctcatc    2640
tttttcgaca tggaggccac tggcttgccc ttctcccagc ccaaggtcac ggagctgtgc    2700
ctgctggctg tccacagatg tgccctggag agcccccca cctctcaggg gccacctccc    2760
acagttcctc caccaccgcg tgtggtagac aagctctccc tgtgtgtggc tccggggaag    2820
gcctgcagcc ctgcagccag cgagatcaca ggtctgagca cagctgtgct ggcagcgcat    2880
gggcgtcaat gttttgatga caacctggcc aacctgctcc tagccttcct gcggcgccag    2940
ccacagccct ggtgcctggt ggcacacaat ggtgaccgct acgacttccc cctgctccaa    3000
gcagagctgg ctatgctggg cctcaccagt gctctggatg gtgccttctg tgtggatagc    3060
atcactgcgc tgaaggccct ggagcgagca agcagcccct cagaacacgg cccaaggaag    3120
agctacagcc taggcagcat ctacactcgc ctgtatgggc agtcccctcc agactcgcac    3180
acggctgagg gtgatgtcct ggccctgctc agcatctgtc agtggagacc acaggccctg    3240
ctgcggtggg tggatgctca cgccaggcct ttcggcacca tcaggcccat gtatgggtc    3300
acagcctctg ctaggaccaa gccaagacca tctgctgtca caaccactgc acacctggcc    3360
acaaccagga acactagtcc cagccttgga gagagcaggg gtaccaagga tcttcctcca    3420
gtgaaggacc ctggagccct atccaggag gggctgctgg ccccactggg tctgctggcc    3480
atcctgacct tggcagtagc cacactgtat ggactatccc tggccacacc tggggagtag    3540
gccaagaagg aaaatctgac gaataaagac ccccgctgcc ccat                     3584
```

<210> SEQ ID NO 4
<211> LENGTH: 3623
<212> TYPE: DNA
<213> ORGANISM: Homo sapiens

<400> SEQUENCE: 4

```
tgcagtctga actccagttt aaagatgcag agatgaatga attaaggaca aagctccaga      60
ccagtgaacg agcaaataaa ctggctgctc cctctgtttc ccatgtcagt cctaggaaaa     120
acccttctgt ggttataaag ccagaagcat gttctccaca atttggaaaa acatctttc     180
```

-continued

```
ctacaaagga gtcttttagt gctaacatgt cccttcccca ccctgccag acggagtcag      240 gatacaagcc tctggtgggc agagaggata gtaagcccca cagtctgaga ggtgactcca     300
taaaacaaga agaggcccag aaaagctttg ttgacagctg gagacagaga tcaaacactc     360
aaggttccat tttgataaac ctgctcctga agcagcctca gttgatccgg tcatccctaa     420
gcctttgcca cctcctgagt agtagttctg agtctcctgc tggcaccccc ctgcagccac     480
cagggtttgg cagtaccttg gctggaatgt caggcctcag gaccacaggt tcttatgatg     540
ggtcattttc cctctcagcc ctgagagaag cacagaacct ggcattcact ggactgaatc     600
tggttgcccg gaatgagtgc tcacgtgatg gagacccagc agagggaggc agaagggcct     660
tcccactctg ccagcttcct ggagccgtgc atttcctccc ccttgtacag ttcttcatcg     720
gcttacactg ccaggccctg caggacttgg cagctgctaa gagaagcgga gcacctgggg     780
actcaccgac acattcctcc tgcgtgagct ctggggtaga gaccaaccct gaggactcag     840
tgtgcatcct ggaaggcttc tctgtgactg cacttagcat tcttcagcac ctggtgtgcc     900
acagcggagc agtcgtctcc ctattactgt caggagtggg ggcagattct gctgctgggg     960
aaggaaacag gagcctggtt cacaggctta gtgatggaga tatgacctca gccctaaggg    1020
gggttgctga tgaccaagga cagcacccac tgttgaagat gcttcttcac ctgttggctt    1080
tctcttctgc agcaacaggt caccttcaag ccagtgtcct gacccagtgc cttaaggttt    1140
tggtgaaatt agccgaaaac acttcctgtg atttcttgcc caggttccag tgtgtgttcc    1200
aagtgctgcc aaagtgcctc agcccagaga caccctgcc tagcgtgctg ctggctgttg    1260
agctcctctc cctgctggcg gaccacgacc agctggcacc tcagctctgt tcccactcag    1320
aaggctgcct cctgctgctg ctgtacatgt acatcacatc acggcctgac agagtggcct    1380
tggagacaca atggctccag ctggaacaag aggtggtgtg gctcctggct aagcttggtg    1440
tgcagagccc cttgccccca gtcactggct ccaactgcca gtgtaatgtg gaggtggtca    1500
gagcgctcac ggtgatgttg cacagacagt ggctgacagt gcggagggca gggggacccc    1560
caaggaccga ccagcagagg cggacagtgc gctgtctgcg gacacggtg ctgctgctgc    1620 acggcctatc gcagaaggac aagctcttca tgatgcactg cgtggaggtc ctgcatcagt    1680
ttgaccaggt gatgccgggg gtcagcatgc tcatccgagg gcttcctgat gtgacggact    1740
gtgaagaggc agccctggat gacctctgtg ccgcggaaac cgatgtggaa gaccccgagg    1800
tggagtgtgg ctgaggccct gagtgtccag ccacatggtg gcaccagcac cactcctttc    1860
cttaccacat caactgatta aagcagtgac cagcaggaac tgcccagaga actggctggc    1920
cttgtttcct gagtctgatc tgtttggcgg agtgggaggg gtggagcagg acccggaccc    1980
tgagtggctg ggatccttct tcctgtccct ggctgttgct gagcccgtcc ccatggtaac    2040
tgatctgcct tgaggaagga gccctgccct gcctgtggaa ttgtcctgag tcattgcttt    2100
gggctggggc catgggaaga aaccattgtg tggcagggaa ggaggtggct cttggcccag    2160 gcctaaaacca ggaaagcctg ggaaactggg acccacaggt gggcatgaaa gggccgcagc    2220
aggggctccc agcagtgtgt aagaccggga gctggtctgg caccactgcc ctggtccttc    2280
cagctgcctg tcactggtat gatggccccg gtgcattgtg ccaccagcag gccacagctg    2340
tggatcttgg aaggcctctg gggtccccg ggagcagggg agtgggtgtg gggggaacg    2400 gatggtggtg agagggacag accaggcagg ctgacgagca gggcgggcct ggctcacgtg    2460
ggcctgtagg cgggcccacg ccaagtttca cttaccgcca ctgctgccag cgagagccgc    2520
```

-continued

```
gggagagtgt gcagccgagt cactactgcc tgcctgcctg cctgctacgg ctcagcagca    2580
ggtacgtacc caaccatggg ctcgcaggcc ctgcccccgg ggcccatgca gaccctcatc    2640
tttttcgaca tggaggccac tggcttgccc ttctcccagc ccaaggtcac ggagctgtgc    2700
ctgctggctg tccacagatg tgccctggag agccccccca cctctcaggg gccacctccc    2760
acagttcctc caccaccgcg tgtggtagac aagctctccc tgtgtgtggc tccggggaag    2820
gcctgcagcc ctgcagccag cgagatcaca ggtctgagca cagctgtgct ggcagcgcat    2880
gggcgtcaat gttttgatga caacctggcc aacctgctcc tagccttcct gcggcgccag    2940
ccacagccct ggtgcctggt ggcacacaat ggtgaccgct acgacttccc cctgctccaa    3000
gcagagctgg ctatgctggg cctcaccagt gctctggatg gtgccttctg tgtggatagc    3060
atcactgcgc tgaaggccct ggagcgagca agcagcccct cagaacacgg cccaaggaag    3120
agctacagcc taggcagcat ctacactcgc ctgtatgggc agtcccctcc agactcgcac    3180
acggctgagg tgatgtcct ggccctgctc agcatctgtc agtggagacc acaggccctg    3240
ctgcggtggg tggatgctca cgccaggcct ttcggcacca tcaggcccat gtatggggtc    3300
acagcctctg ctaggaccaa gccaagacca tctgctgtca caaccactgc acacctggcc    3360
acaaccagga acactagtcc cagccttgga gagagcaggg gtaccaagga tcttcctcca    3420
gtgaaggacc ctggagccct atccaggag gggctgctgg ccccactggg tctgctggcc     3480
atcctgacct tggcagtagc cacactgtat ggactatccc tggccacacc tggggagtag    3540
gccaagaagg aaaatctgac gaataaagac ccccgctgcc ccataaaaaa aaaaaaaaa    3600
aaaaaaaaaa aaaaaaaaaa aaa                                            3623
```

<210> SEQ ID NO 5
<211> LENGTH: 2497
<212> TYPE: DNA
<213> ORGANISM: Homo sapiens

<400> SEQUENCE: 5

```
ggcacgaggg gcaggcaagt ctagctcggc gctgtcggat acttggggtg agcggaaagc      60
atggcgggga cctccgcgcc aggcagcaag aggcggagcg agccccggc gcctcgcccc     120
ggcccgccgc cggcaccgg gcacccccg agcaagcggg cccggggctt ctccgcagcc      180
gctgccccgg accctgacga cccgttcggc gcgcatgggg acttcactgc cgacgacctg     240
gaggagcttg acaccctcgc gtcacaggcc ctgagccaat gtccggccgc ggctcgggac     300
gtgtccagtg atcataaggt ccacagatta ttagatggca tgtcaaaaaa tccttcaggg     360
aaaaacagag aaactgttcc aattaaagat aatttcgaat tagaggtact tcaggcacaa     420
tacaaagaac ttaagaaaaa gatgaaagta atggaagaag aagttctcat taagaatgga     480
gaaattaaaa ttttgcgaga ctcactacat cagacggaat ccgttctaga ggaacagaga     540
agatcacatt ttcttcttga gcaagagaaa acccaagcac tcagtgacaa ggaaaaggaa     600
ttctccaaaa agctccaatc attgcagtct gaactccagt ttaaagatgc agagatgaat     660
gaattaagga caaagctcca gaccagtgaa cgagcaaata actggctgc tccctctgtt     720
tcccatgtca gtcctaggaa aaaccccttct gtggttataa agccagaagc atgttctcca     780
caatttggaa aaacatcttt tcctacaaag gagtctttta gtgctaacat gtcccttccc     840
caccccctgcc agacggagtc aggatacaag cctctggtgg gcagagagga tagtaagctc     900
cacagtctga gaggtgactc cataaaacaa gaagaggccc agaaaagctt tgttgacagc     960
tggagacaga gatcaaacac tcaaggttcc attttgataa acctgctcct gaagcagcct    1020
```

-continued

```
ttgatcccag ggtcatccct aagcctttgc cacctcctga gtagtagttc tgagtctcct      1080
gctggcaccc ccctgcagcc accagggttt ggcagtacct tggctggaat gtcaggcctc      1140
aggaccacag gttcttatga tgggtcattt tccctctcag ccctgagaga agcacagaac      1200
ctggcattca ctggactgaa tctggttgcc cggaatgagt gctcacgtga tggagaccca      1260
gcagagggag gcagaagggc cttcccactc tgccagcttc tggagccgt gcatttcctc       1320 ccccttgtac agttcttcat cggcttacac tgccaggccc tgcaggactt ggcagctgct      1380
aagagaagcg gagcacctgg ggactcaccg acacattcct cctgcgtgag ctctggggta      1440
gagaccaacc ctgaggactc agtgtgcatc ctggaaggct tctctgtgac tgcacttagc      1500
attcttcagc acctggtgtg ccacagcgga gcagtcgtct ccctattact gtcaggagtg      1560
ggggcagatt ctgctgctgg ggaaggaaac aggagcctgg ttcacaggct tagtgatgga      1620
gatatgacct cagccctaag gggggttgct gatgaccaag acagcaccc actgttgaag       1680 atgcttcttc acctgttggc tttctcttct gcagcaacag gtcaccttca agccagtgtc      1740
ctgacccagt gccttaaggt tttggtgaaa ttagccgaaa acacttcctg tgatttcttg      1800
cccaggttcc agtgtgtgtt ccaagtgctg ccaaagtgcc tcagcccaga gacacccctg      1860
cctagcgtgc tgctggctgt tgagctcctc tccctgctgg cggaccacga ccagctggca      1920
cctcagctct gttcccactc agaaggctgc ctcctgctgc tgctgtacat gtacatcaca      1980
tcacggcctg acagagtggc cttggagaca caatggctcc agctggaaca agaggtggtc      2040
agagcgctca cggtgatgtt gcacagacag tggctgacag tgcggagggc aggggaccc      2100 ccaaggaccg accagcagag gcggacagtg cgctgtctgc gggacacggt gctgctgctg      2160
cacggcctat cgcagaagga caagctcttc atgatgcact cgcgtggagt cctgcatcag      2220
tttgaccagg tgatgccggg ggtcagcatg ctcatccgag ggcttcctga tgtgacggac      2280
tgtgaagagg cagccctgga tgacctctgt gccgcgaaa ccgatgtgga agaccccgag       2340
gtggagtgtg gctgaggccc tgagtgtcca gccacatggt ggcaccagca ccactccttt      2400
ccttaccaca tcaactgatt aaagcagtga ccagcaggaa ctgcccagag aactggaaaa      2460
aaaaaaaaaa aaaaaaaaaa aaaaaaaaaa aaaaaaa                               2497
```

<210> SEQ ID NO 6
<211> LENGTH: 2066
<212> TYPE: DNA
<213> ORGANISM: Macaca fascicularis

<400> SEQUENCE: 6

```
ttctcattaa gaatggagaa attaaaattt tgcgagactc actacatcag acggaatccg       60
ttctagagga acagagaaga tcacattttc ttcttgagca agagaaaacc caagcactca      120
gtgacaaaga aaaggaattc tccaaaaagc tccaatcatt gcagtctgaa ctccagttta      180
aagatgcaga gatgaatgaa ttaaggacaa agctccagac cagtgaacgc gcaaataaac      240
tggctgctcc ctctgtttcc catgtcagtc ctaggaaaaa cccttctgtg gttataaagc      300
cagaagcatg ttctccacaa tttggaaaaa catcttttcc tacaaaggag tcttttagtg      360
ctaacatgtc ccttcccac ccctgccaga cagagtcagg atacaagccg ctggtgggca       420
gagaggatag taagacccac agtctgagag gtgactccat aaaacaagaa gaggcccaga      480
aaagctttgt tgacagctgg agacagagat caaacactca aggttccatt ttgataaacc      540
tgctcctgaa gcagcctttg atcccagggt catccctaag cctgtgccac ctcctgagta      600
```

```
gtagttctga gtctcctgct ggcacccccc tgcagccacc agggtttggc agtaccttgg    660
ctggaatgtc aggcctcagg accacaggtt ctcaggatgg gtcattttcc ctctcagccc    720
tgagagaagc acagaacctg gcattcactg gactgaatct ggttgccagg aatgagtgct    780
cacgtgatgg agacccagca gagggaggca gaagggcctt cccactctgc cagcttcctg    840
gagccgtgca tttcctcccc cttgtacagt tcttcatcgg cttacactgc caggccctgc    900
aggacttggc agctgctaag agaagtggag cacctgggga ctcaccgaca cattcctccc    960
gcgtgagctc tggggtagag accaaccctg aggactcagt gcgcatcctg gaaggcttct   1020
ctgtgactgc acttagcatt cttcagcacc tggtgtgcca gcggagca gtggtctccc    1080 tattactgtc acgagttggg gcagattctg ctgctgggga aggaaatggg agcctggttc   1140
acaggtttag tgatggagat atgacctcag ccccaagggg ggttgctgat gaccaaggac   1200
agcacccact gttgaagatg cttcttcacc tgttggcttt ctcttctgca gcaacaggtc   1260
accttcaagc cagtgtcctg acccagtgcc ttaaggtttt ggtgaaatta gccgaaaaca   1320
cttcctctga tttcttgccc aggttccagt gtgtgttcca agtgctgcca aagtgcctca   1380
gcccagagac accctgcct ggcatggtgc tggctgttga gctcctctcc ctccttgcgg    1440
accacgacca gttggcacct cagctctgtt cccactcgga ctgcctcctg ctgctgctgt   1500
acatgtacat cacatcacgg cctgacagag tggcctcaga gacacaatgg ctccagctgg   1560
aacaagaggt ggtgtggctc ctgtctaagc ttggtgtgca gagcccttg ccctagtca    1620 ctggctccaa ctgccagtgt aatgtagagg tggtcagagc gctcacgtg atgttgcata    1680 gacagtggct gacagtgcgg agggcaggtg ggcccccaag gactgaccag cagaggcgga   1740
cagtgcgctg tctgcgggac acggtgctgc tgctgcacgg cctgtcccag aaggacaagc   1800
tcttcataat gcactgcgtg gaggtcctgc atcagtatga ccaggtgatg ccggggggtca   1860 gcatgctcat ccgcgggctt cctgacgtga ccgactgtga agaggcagcc ctggatgacc   1920
tctgtgccgc ggaaaccgat gtggacgacc ccgagttgga gtgtggctga ggccctgagt   1980
gtccagccac atggtggcac cagcaccatt cctttcctta ccacatcaac tgattaaagc   2040
agtgaccagc aggaactgcc cagaaa                                         2066

<210> SEQ ID NO 7
<211> LENGTH: 2126
<212> TYPE: DNA
<213> ORGANISM: Homo sapiens

<400> SEQUENCE: 7
attagatggc atgtcaaaaa atccttcagg gaaaaacaga gaaactgttc caattaaaga     60
taatttcgaa ttagaggtac ttcaggcaca atacaaagaa cttaaagaaa agatgaaagt    120
aatggaagaa gaagttctca ttaagaatgg agaaattaaa attttgcgag actcactaca    180
tcagacggaa tccgttctag aggaacagag aagatcacat tttcttcttg agcaagagaa    240
aacccaagca ctcagtgaca aggaaaagga attctccaaa aagctccaat cattgcagtc    300
tgaactccag tttaaagatg cagagatgaa tgaattaagg acaaagctcc agaccagtga    360
acgagcaaat aaactggctg ctccctctgt ttcccatgtc agtcctagga aaaacccttc    420
tgtggttata aagccagaag catgttctcc acaatttgga aaaacatctt ttcctacaaa    480
ggagtctttt agtgctaaca tgtcccttcc ccacccctgc agacggagt caggatacaa    540 gcctctggtg gcagagagg atagtaagcc ccacagtctg agaggtgact ccataaaaca    600
agaagaggcc cagaaaagct tgttgacag ctggagacag agatcaaaca ctcaaggttc    660
```

-continued

```
cattttgata aacctgctcc tgaagcagcc tttgatccca gggtcatccc taagcctttg      720
ccacctcctg agtagtagtt ctgagtctcc tgctggcacc cccctgcagc caccagggtt      780
tggcagtacc ttggctggaa tgtcaggcct caggaccaca ggttcttatg atgggtcatt      840
ttccctctca gccctgagag aagcacagaa cctggcattc actggactga atctggttgc      900
ccggaatgag tgctcacgtg atggagaccc agcagaggga ggcagaaggg ccttcccact      960
ctgccagctt cctggagccg tgcatttcct cccccttgta cagttcttca tcggcttaca     1020
ctgccaggcc ctgcaggact tggcagctgc taagagaagc ggagcacctg ggactcacc      1080 gacacattcc tcctgcgtga gctctgggt agagaccaac cctgaggact cagtgtgcat     1140
cctggaaggc ttctctgtga ctgcacttag cattcttcag cacctggtgt gccacagcgg     1200
agcagtcgtc tccctattac tgtcaggagt gggggcagat tctgctgctg gggaaggaaa     1260
caggagcctg gttcacaggc ttagtgatgg agatatgacc tcagccctaa gggggggttgc     1320 tgatgaccaa ggacagcacc cactgttgaa gatgcttctt cacctgttgg ctttctcttc     1380
tgcagcaaca ggtcaccttc aagccagtgt cctgacccag tgccttaagg ttttggtgaa     1440
attagccgaa aacacttcct gtgatttctt gcccaggttc cagtgtgtgt tccaagtgct     1500
gccaaagtgc ctcagcccag agacacccct gcctagcgtg ctgctggctg ttgagctcct     1560
ctccctgctg gcggaccacg accagctggc acctcagctc tgttcccact cagaaggctg     1620
cctcctgctg ctgctgtaca tgtacatcac atcacggcct gacagagtgg ccttggagaa     1680
caatggctcc agctggaaca gaggtggtc agagcgctca cggtgatgtt gcacagacag     1740
tggctgacag tgcggagggc aggggaccc ccaaggaccg accagcagag gcggacagtg     1800
cgctgtctgc gggacacggt gctgctgctg cacggcctat cgcagaagga caagctcttc     1860
atgatgcact gcgtggaggt cctgcatcag tttgaccagg tgatgccggg ggtcagcatg     1920
ctcatccgag ggcttcctga tgtgacggac tgtgaagagg cagccctgga tgacctctgt     1980
gccgcggaaa ccgatgtgga agaccccgag gtggagtgtg ctgaggccc tgagtgtcca     2040 gccacatggt ggcaccagca ccactccttt ccttaccaca tcaactgatt aaagcagtga     2100
ccagcaggaa ctgcccagag aactgg                                         2126
```

<210> SEQ ID NO 8
<211> LENGTH: 2126
<212> TYPE: DNA
<213> ORGANISM: Homo sapiens

<400> SEQUENCE: 8

```
attagatggc atgtcaaaaa atccttcagg gaaaaacaga gaaactgttc caattaaaga      60
taatttcgaa ttagaggtac ttcaggcaca atacaaagaa cttaaagaaa agatgaaagt     120 aatgaagaa gaagttctca ttaagaatgg agaaattaaa attttgcgag actcactaca     180
tcagacggaa tccgttctag aggaacagag aagatcacat tttcttcttg agcaagagaa     240
aacccaagca ctcagtgaca aggaaaagga attctccaaa aagctccaat cattgcagtc     300
tgaactccag tttaaagatg cagagatgaa tgaattaagg acaaagctcc agaccagtga     360
acgagcaaat aaactggctg ctccctctgt ttcccatgtc agtcctagga aaaacccttc     420
tgtggttata aagccagaag catgttctcc acaatttgga aaaacatctt ttcctacaaa     480
ggagtctttt agtgctaaca tgtcccttcc ccacccctgc cagacggagt caggatacaa     540
gcctctggtg ggcagagagg atagtaagcc ccacagtctg agaggtgact ccataaaaca     600
```

```
agaagaggcc cagaaaagct tgttgacag  ctggagacag  agatcaaaca  ctcaaggttc     660
cattttgata  aacctgctcc  tgaagcagcc  tttgatccca  gggtcatccc  taagcctttg    720
ccacctcctg  agtagtagtt  ctgagtctcc  tgctggcacc  ccctgcagc   caccagggtt    780 tggcagtacc  ttggctggaa  tgtcaggcct  caggaccaca  ggttcttatg  atgggtcatt    840
ttccctctca  gccctgagag  aagcacagaa  cctggcattc  actggactga  atctggttgc    900
ccggaatgag  tgctcacgtg  atggagaccc  agcagaggga  ggcagaaggg  ccttcccact    960
ctgccagctt  cctggagccg  tgcatttcct  ccccttgta   cagttcttca  tcggcttaca   1020
ctgccaggcc  ctgcaggact  tggcagctgc  taagagaagc  ggagcacctg  ggactcacc    1080 gacacattcc  tcctgcgtga  gctctgggt   agagaccaac  cctgaggact  cagtgtgcat   1140 cctgaaggc   ttctctgtga  ctgcacttag  cattcttcag  cacctggtgt  gccacagcgg   1200
agcagtcgtc  tccctattac  tgtcaggagt  gggggcagat  tctgctgctg  ggaaggaaa    1260 caggagcctg  gttcacaggc  ttagtgatgg  agatatgacc  tcagccctaa  gggggttgc    1320 tgatgaccaa  ggacagcacc  cactgttgaa  gatgcttctt  cacctgttgg  ctttctcttc   1380
tgcagcaaca  ggtcaccttc  aagccagtgt  cctgacccag  tgccttaagg  ttttggtgaa   1440
attagccgaa  aacacttcct  gtgatttctt  gcccaggttc  cagtgtgtgt  tccaagtgct   1500
gccaaagtgc  ctcagcccag  agacacccct  gcctagcgtg  ctgctggctg  ttgagctcct   1560
ctccctgctg  gcggaccacg  accagctggc  acctcagctc  tgttcccact  cagaaggctg   1620
cctcctgctg  ctgctgtaca  tgtacatcac  atcacgcct   gacagagtgg  ccttggagaa   1680
caatggctcc  agctggaaca  agaggtggtc  agagcgctca  cggtgatgtt  gcacagacag   1740
tggctgacag  tgcggagggc  agggggaccc  ccaaggaccg  accagcagag  gcggacagtg   1800
cgctgtctgc  gggacacggt  gctgctgctg  cacggcctat  cgcagaagga  caagctcttc   1860
atgatgcact  gcgtggaggt  cctgcatcag  tttgaccagg  tgatgccggg  ggtcagcatg   1920
ctcatccgag  ggcttcctga  tgtgacggac  tgtgaagagg  cagccctgga  tgacctctgt   1980
gccgcggaaa  ccgatgtgga  agaccccgag  gtggagtgtg  gctgaggccc  tgagtgtcca   2040
gccacatggt  ggcaccagca  ccactccttt  ccttaccaca  tcaactgatt  aaagcagtga   2100
ccagcaggaa  ctgcccagag  aactgg                                          2126
```

<210> SEQ ID NO 9
<211> LENGTH: 2447
<212> TYPE: DNA
<213> ORGANISM: Homo sapiens
<220> FEATURE:
<221> NAME/KEY: modified_base
<222> LOCATION: (433)..(603)
<223> OTHER INFORMATION: N = A, C, G or T/U

<400> SEQUENCE: 9

```
ggcaggcaag  tctagctcgg  cgctgtcgga  tacttggggt  gagcggaaag  catggcgggg     60
acctccgcgc  caggcagcaa  gaggcggagc  gagccccgg   cgcctcgccc  cggcccgccg    120
ccgggcaccg  gcaccccccc  gagcaagcgg  gcccggggct  tctccgcagc  cgctgccccg    180
gaccctgacg  acccgttcgg  cgcgcatggg  gacttcactg  ccgacgacct  ggaggagctt    240 gacacccctcg  cgtcacaggc  cctgagccaa  tgtccggccg  cggctcggga  cgtgtccagt    300
gatcataagg  tccacagatt  attagatggc  atgtcaaaaa  atccttcagg  gaaaaacaga    360
gaaactgttc  caattaaaga  taatttcgaa  ttagaggtac  ttcaggcaca  atacaaagaa    420
cttaaagaaa  agnnnnnnnn  nnnnnnnnnn  nnnnnnnnnn  nnnnnnnnnn  nnnnnnnnnn    480
```

```
nnnnnnnnnn nnnnnnnnnn nnnnnnnnnn nnnnnnnnnn nnnnnnnnnn nnnnnnnnnn    540
nnnnnnnnnn nnnnnnnnnn nnnnnnnnnn nnnnnnnnnn nnnnnnnnnn nnnnnnnnnn    600
nnnctccaat cattgcagtc tgaactccag tttaaagatg cagagatgaa tgaattaagg    660
acaaagctcc agaccagtga acgagcaaat aaactggctg ctccctctgt ttcccatgtc    720
agtcctagga aaaacccttc tgtggttata agccagaag catgttctcc acaatttgga     780
aaaacatctt ttcctacaaa ggagtctttt agtgctaaca tgtcccttcc ccacccctgc    840
cagacggagt caggatacaa gcctctggtg ggcagagagg atagtaagcc ccacagtctg    900
agaggtgact ccataaaaca agaagaggcc cagaaaagct tgttgacag ctggagacag     960 agatcaaaca ctcaaggttc cattttgata aacctgctcc tgaagcagcc tttgatccca   1020
gggtcatccc taagcctttg ccacctcctg agtagtagtt ctgagtctcc tgctggcacc   1080
cccctgcagc caccagggtt tggcagtacc ttggctggaa tgtcaggcct caggaccaca   1140
ggttcttatg atgggtcatt ttccctctca gccctgagag aagcacagaa cctggcattc   1200
actggactga atctggttgc ccggaatgag tgctcacgtg atggagaccc agcagggga    1260 ggcagaaggg ccttcccact ctgccagctt cctggagccg tgcatttcct cccccttgta   1320
cagttcttca tcggcttaca ctgccaggcc ctgcaggact tggcagctgc taagagaagc   1380
ggagcacctg gggactcacc gacacattcc tcctgcgtga gctctggggt agagaccaac   1440
cctgaggact cagtgtgcat cctggaaggc ttctctgtga ctgcacttag cattcttcag   1500
cacctggtgt gccacagcgg agcagtcgtc tccctattac tgtcaggagt gggggcagat   1560
tctgctgctg gggaaggaaa caggagcctg gttcacaggc ttagtgatgg agatatgacc   1620
tcagccctaa ggggggttgc tgatgaccaa ggacagcacc cactgttgaa gatgcttctt   1680
cacctgttgg ctttctcttc tgcagcaaca ggtcaccttc aagccagtgt cctgacccag   1740
tgccttaagg ttttggtgaa attagccgaa aacacttcct gtgatttctt gcccaggttc   1800
cagtgtgtgt tccaagtgct gccaaagtgc ctcagcccag agacacccct gcctagcgtg   1860
ctgctggctg ttgagctcct ctccctgctg gcggaccacg accagctggc acctcagctc   1920
tgttcccact cagaaggctg cctcctgctg ctgctgtaca tgtacatcac atcacggcct   1980
gacagagtgg ccttggagac acaatggctc cagctggaac aagaggtggt cagagcgctc   2040
acggtgatgt tgcacagaca gtggctgaca gtgcggaggg cagggggacc cccaaggacc   2100
gaccagcaga ggcggacagt gcgctgtctg cgggacacgg tgctgctgct gcacggccta   2160
tcgcagaagg acaagctctt catgatgcac tgcgtggagg tcctgcatca gtttgaccag   2220
gtgatgccgg gggtcagcat gctcatccga gggcttcctg atgtgacgga ctgtgaagag   2280
gcagccctgg atgacctctg tgccgcggaa accgatgtgg aagacccga ggtggagtgt    2340 ggctgaggcc ctgagtgtcc agccacatgg tggcaccagc accactcctt tccttaccac   2400
atcaactgat taaagcagtg accagcagga actgcccaga gaactgg                 2447
```

<210> SEQ ID NO 10
<211> LENGTH: 2127
<212> TYPE: DNA
<213> ORGANISM: Homo sapiens
<220> FEATURE:
<221> NAME/KEY: modified_base
<222> LOCATION: (113)..(283)
<223> OTHER INFORMATION: N = A, C, G or T/U

<400> SEQUENCE: 10

| | |
|---|---|
| attagatggc atgtcaaaaa atccttcagg gaaaaacaga gaaactgttc caattaaaga | 60 |
| taatttcgaa ttagaggtac ttcaggcaca atacaaagaa cttaaagaaa agnnnnnnnn | 120 |
| nnnnnnnnnn nnnnnnnnnn nnnnnnnnnn nnnnnnnnnn nnnnnnnnnn nnnnnnnnnn | 180 |
| nnnnnnnnnn nnnnnnnnnn nnnnnnnnnn nnnnnnnnnn nnnnnnnnnn nnnnnnnnnn | 240 |
| nnnnnnnnnn nnnnnnnnnn nnnnnnnnnn nnnnnnnnnn nnnctccaat cattgcagtc | 300 |
| tgaactccag tttaaagatg cagagatgaa tgaattaagg acaaagctcc agaccagtga | 360 |
| acgagcaaat aaactggctg ctccctctgt ttcccatgtc agtcctagga aaaacccttc | 420 |
| tgtggttata aagccagaag catgttctcc acaatttgga aaaacatctt ttcctacaaa | 480 |
| ggagtctttt agtgctaaca tgtcccttcc caccoctgc cagacggagt caggatacaa | 540 |
| gcctctggtg ggcagagagg atagtaagcc ccacagtctg agaggtgact ccataaaaca | 600 |
| agaagaggcc cagaaaagct tgttgacag ctggagacag agatcaaaca ctcaaggttc | 660 |
| cattttgata aacctgctcc tgaagcagcc tttgatccca gggtcatccc taagcctttg | 720 |
| ccacctcctg agtagtagtt ctgagtctcc tgctggcacc ccctgcagc caccagggtt | 780 |
| tggcagtacc ttggctggaa tgtcaggcct caggaccaca ggttcttatg atgggtcatt | 840 |
| ttccctctca gccctgagag aagcacagaa cctggcattc actggactga atctggttgc | 900 |
| ccggaatgag tgctcacgtg atggagaccc agcagaggga ggcagaaggg ccttcccact | 960 |
| ctgccagctt cctggagccg tgcatttcct cccccttgta cagttcttca tcggcttaca | 1020 |
| ctgccaggcc ctgcaggact tggcagctgc taagagaagc ggagcacctg ggagactcacc | 1080 |
| gacacattcc tcctgcgtga gctctgggt agagaccaac cctgaggact cagtgtgcat | 1140 |
| cctggaaggc ttctctgtga ctgcacttag cattcttcag cacctggtgt gccacagcgg | 1200 |
| agcagtcgtc tccctattac tgtcaggagt gggggcagat tctgctgctg gggaaggaaa | 1260 |
| caggagcctg gttcacaggc ttagtgatgg agatatgacc tcagccctaa gggggttgc | 1320 |
| tgatgaccaa ggacagcacc cactgttgaa gatgcttctt cacctgttgg ctttctcttc | 1380 |
| tgcagcaaca ggtcaccttc aagccagtgt cctgacccag tgccttaagg ttttggtgaa | 1440 |
| attagccgaa aacacttcct gtgatttctt gcccaggttc cagtgtgtgt tccaagtgct | 1500 |
| gccaaagtgc ctcagcccag agacacccct gcctagcgtg ctgctggctg ttgagctcct | 1560 |
| ctccctgctg gcggaccacg accagctggc acctcagctc tgttcccact cagaaggctg | 1620 |
| cctcctgctg ctgctgtaca tgtacatcac atcacggcct gacagagtgg ccttggagac | 1680 |
| acaatggctc cagctggaac aagaggtggt cagagcgctc acggtgatgt tgcacagaca | 1740 |
| gtggctgaca gtgcggaggg caggggacc cccaaggacc gaccagcaga ggcggacagt | 1800 |
| gcgctgtctg cgggacacgg tgctgctgct gcacggccta tcgcagaagg acaagctctt | 1860 |
| catgatgcac tgcgtggagg tcctgcatca gtttgaccag gtgatgccgg gggtcagcat | 1920 |
| gctcatccga gggcttcctg atgtgacgga ctgtgaagag gcagccctgg atgacctctg | 1980 |
| tgccgcggaa accgatgtgg aagacccga ggtggagtgt ggctgaggcc ctgagtgtcc | 2040 |
| agccacatgg tggcaccagc accactcctt tccttaccac atcaactgat taaagcagtg | 2100 |
| accagcagga actgcccaga gaactgg | 2127 |

<210> SEQ ID NO 11
<211> LENGTH: 3981
<212> TYPE: DNA
<213> ORGANISM: Homo sapiens

<400> SEQUENCE: 11

-continued

```
atggcgggga cctccgcgcc aggcagcaag aggcggagcg agccccggc gcctcgcccc      60
ggcccgccgc cgggcaccgg gcaccccccg agcaagcggg cccggggctt ctccgcagcc    120
gctgccccgg accctgacga cccgttcggc gcgcatgggg acttcactgc cgacgacctg    180
gaggagcttg acaccctcgc gtcacaggcc ctgagccaat gtccggccgc ggctcgggac    240
gtgtccagtg atcataaggt ccacagatta ttagatggca tgtcaaaaaa tccttcaggg    300
aaaaacagag aaactgttcc aattaaagat aatttcgaat tagaggtact tcaggcacaa    360
tacaaagaac ttaaagaaaa gatgaaagta atggaagaag aagttctcat taagaatgga    420
gaaattaaaa ttttgcgaga ctcactacat cagacggaat ccgttctaga ggaacagaga    480
agatcacatt ttcttcttga gcaagagaaa acccaacact cagtgacaag gaaaaggaat    540
tctccaaaaa agctccaatc attgcagtct gaactccagt ttaaagatgc agagatgaat    600
gaattaagga caaagctcca gaccagtgaa cgagcaaata actggctgc tccctctgtt    660
tcccatgtca gtcctaggaa aaaccttct gtggttataa agccagaagc atgttctcca    720
caatttggaa aaacatcttt tcctacaaag gagtctttta gtgctaacat gtcccttccc    780
caccctgcc agacggagtc aggatacaag cctctggtgg gcagagagga tagtaagccc    840
cacagtctga gaggtgactc cataaaaca gaagaggccc agaaaagctt tgttgacagc    900
tggagacaga gatcaaacac tcaaggttcc attttgataa acctgctcct gaagcagcct    960
cagttgatcc ggtcatccct aagcctttgc cacctcctga gtagtagttc tgagtctcct   1020
gctggcaccc cctgcagcc accagggttt ggcagtacct ggctggaat gtcaggcctc   1080
aggaccacag gttcttatga tgggtcattt tccctctcag ccctgagaga agcacagaac   1140
ctggcattca ctggactgaa tctggttgcc cggaatgagt gctcacgtga tggagaccca   1200
gcagagggag gcagaagggc cttcccactc tgccagcttc ctggagccgt gcatttcctc   1260
cccttgtac agttcttcat cggcttacac tgccaggccc tgcaggactt ggcagctgct   1320
aagagaagcg gagcacctgg ggactcaccg acacattcct cctgccaaca ggtcaccttc   1380
aagccagtgt cctgacccag tgccttaagg ttttggtgaa attagccgaa aacacttcct   1440
gtgatttctt gcccagagcc gcaagattgg ggagaactgt gaacacaacc agcccacccc   1500
ctcatccagt aatccagtct ccctcagcac tctaccaaag ggttccagtg tgtgttccaa   1560
gtgctgccaa agtgcctcag cccagagaca cccctgccta gcgtgctgct ggctgttgag   1620
ctcctctccc tgctggcgga ccacgaccag ctggcacctc agctctgttc ccactcagaa   1680
ggctgcctcc tgctgctgct gtacatgtac atcacatcac ggcctgacag agtggccttg   1740
gagacacaat ggctccagct ggaacaagag gtggtgtggc tcctggctaa gcttggtgtg   1800
cagagccct tgcccccagt cactggctcc aactgccagt gtaatgtgga ggtggtcaga   1860
gcgctcacgg tgatgttgca cagacagtgg ctgacagtgc ggagggcagg gggacccca   1920
aggaccgacc agcagaggcg gacagtgcgc tgtctgcggg acacggtgct gctgctgcac   1980
ggcctatcgc agaaggacaa gctcttcatg atgcactgcg tggaggtcct gcatcagttt   2040
gaccaggtga tgccgggggt cagcatgctc atccgagggc ttcctgatgt gacggactgt   2100
gaagaggcag ccctggatga cctctgtgcc gcggaaaccg atgtggaaga ccccgaggtg   2160
gagtgtggct gaggccctga gtgtccagcc acatggtggc accagcacca ctcctttcct   2220
taccacatca actgattaaa gcagtgacca gcaggaactg cccagagaac tggctggcct   2280
tgtttcctga gtctgatctg tttggcggag tgggaggggt ggagcaggac ccggacccctg   2340
```

-continued

```
agtggctggg atccttcttc ctgtccctgg ctgttgctga gcccgtcccc atggtaactg    2400
atctgccttg aggaaggagc cctgcccgc ctgtggaatt gtcctgagtc attgctttgg    2460
gctggggcca tgggaagaaa ccattgtgtg gcagggaagg aggtggctct tggcccaggc    2520
ctaaaccagg aaagcctggg aaactgggac ccacaggtgg gcatgaaagg gccgcagcag    2580
gggctcccag cagtgtgtaa gaccgggagc tggtctggca ccactgccct ggtccttcca    2640
gctgcctgtc actggtatga tggccccggt gcattgtgcc accagcaggc cacagctgtg    2700
gatcttggaa ggcctctggg gtcccccggg agcaggggag tgggtgtggg ggggaacgga    2760
tggtggtgag agggacagac caggcaggct gacgagcagg gcgggcctgg ctcacgtggg    2820
cctgtaggcg ggcccacgcc aagtttcact taccgccact gctgccagcg agagccgcgg    2880
gagagtgtgc agccgagtca ctactgcctg cctgcctgcc tgctacggct cagcagcagg    2940
tacgtaccca accatgggct cgcaggccct gcccccgggg cccatgcaga ccctcatctt    3000
tttcgacatg gaggccactg gcttgccctt ctcccagccc aaggtcacgg agctgtgcct    3060
gctggctgtc cacagatgtg ccctggagag ccccccacc tctcaggggc acctcccac    3120 agttcctcca ccaccgcgtg tggtagacaa gctctccctg tgtgtggctc cggggaaggc    3180
ctgcagccct gcagccagcg agatcacagg tctgagcaca gctgtgctgg cagcgcatgg    3240
gcgtcaatgt tttgatgaca acctggccaa cctgctccta gccttcctgc ggcgccagcc    3300
acagccctgg tgcctggtgg cacacaatgg tgaccgctac gacttccccc tgctccaagc    3360
agagctggct atgctgggcc tcaccagtgc tctggatggt gccttctgtg tggatagcat    3420
cactgcgctg aaggccctgg agcgagcaag cagcccctca gaacacggcc caaggaagag    3480
ctacagccta ggcagcatct acactcgcct gtatgggcag tcccctccag actcgcacac    3540
ggctgagggt gatgtcctgg ccctgctcag catctgtcag tggagaccac aggccctgct    3600
gcggtgggtg gatgctcacg ccaggccttt cggcaccatc aggcccatgt atggggtcac    3660
agcctctgct aggaccaagc caagaccatc tgctgtcaca accactgcac acctggccac    3720
aaccaggaac actagtccca gccttggaga gagcaggggt accaaggatc ttcctccagt    3780
gaaggaccct ggagccctat ccagggaggg gctgctggcc ccactgggtc tgctggccat    3840
cctgaccttg gcagtagcca cactgtatgg actatccctg gccacacctg gggagtaggc    3900
caagaaggaa aatctgacga ataaagaccc ccgctgcccc ataaaaaaaa aaaaaaaaa    3960 aaaaaaaaaa aaaaaaaaaa a                                              3981
```

<210> SEQ ID NO 12
<211> LENGTH: 3942
<212> TYPE: DNA
<213> ORGANISM: Homo sapiens
<220> FEATURE:
<221> NAME/KEY: modified_base
<222> LOCATION: (382)..(552)
<223> OTHER INFORMATION: N = A, C, G or T/U

<400> SEQUENCE: 12

```
atggcgggga cctccgcgcc aggcagcaag aggcggagcg agccccggc gcctcgcccc     60 ggcccgccgc cgggcaccgg gcaccccccg agcaagcggg cccggggctt ctccgcagcc    120
gctgccccgg accctgacga cccgttcggc gcgcatgggg acttcactgc cgacgacctg    180
gaggagcttg acaccctcgc gtcacaggcc ctgagccaat gtccggccgc ggctcgggac    240
gtgtccagtg atcataaggt ccacagatta ttagatggca tgtcaaaaaa tccttcaggg    300
aaaaacagag aaactgttcc aattaaagat aatttcgaat tagaggtact tcaggcacaa    360
```

```
tacaaagaac ttaaagaaaa gnnnnnnnnn nnnnnnnnnn nnnnnnnnnn nnnnnnnnnn    420
nnnnnnnnnn nnnnnnnnnn nnnnnnnnnn nnnnnnnnnn nnnnnnnnnn nnnnnnnnnn    480
nnnnnnnnnn nnnnnnnnnn nnnnnnnnnn nnnnnnnnnn nnnnnnnnnn nnnnnnnnnn    540
nnnnnnnnnn nnctccaatc attgcagtct gaactccagt ttaaagatgc agagatgaat    600
gaattaagga caaagctcca gaccagtgaa cgagcaaata aactggctgc tccctctgtt    660
tcccatgtca gtcctaggaa aaacccttct gtggttataa agccagaagc atgttctcca    720
caatttggaa aaacatcttt tcctacaaag gagtctttta gtgctaacat gtcccttccc    780 caccccctgcc agacggagtc aggatacaag cctctggtgg gcagagagga tagtaagccc    840
cacagtctga gaggtgactc cataaaacaa gaagaggccc agaaaagctt tgttgacagc    900
tggagacaga gatcaaacac tcaaggttcc attttgataa acctgctcct gaagcagcct    960
ttgatcccag ggtcatccct aagcctttgc cacctcctga gtagtagttc tgagtctcct   1020
gctggcaccc ccctgcagcc accagggttt ggcagtacct tggctggaat gtcaggcctc   1080
aggaccacag gttcttatga tgggtcattt tccctctcag ccctgagaga agcacagaac   1140
ctggcattca ctggactgaa tctggttgcc cggaatgagt gctcacgtga tggagaccca   1200
gcagagggag gcagaaggc cttcccactc tgccagcttc ctggagccgt gcatttcctc    1260 cccccttgtac agttcttcat cggcttacac tgccaggccc tgcaggactt ggcagctgct   1320
aagagaagcg gagcacctgg ggactcaccg acacattcct cctgccaaca ggtcaccttc   1380
aagccagtgt cctgacccag tgccttaagg ttttggtgaa attagccgaa aacacttcct   1440
gtgatttctt gcccagagcc gcaagattgg ggagaactgt gaacacaacc agcccacccc   1500
ctcatccagt aatccagtct ccctcagcac tctaccaaag ggttccagtg tgtgttccaa   1560
gtgctgccaa agtgcctcag cccagagaca cccctgccta gcgtgctgct ggctgttgag   1620
ctcctctccc tgctggcgga ccacgaccag ctggcacctc agctctgttc ccactcagaa   1680
ggctgcctcc tgctgctgct gtacatgtac atcacatcac ggcctgacag agtggccttg   1740
gagacacaat ggctccagct ggaacaagag gtggtgtggc tcctggctaa gcttggtgtg   1800
cagagcccct gcccccagt cactggctcc aactgccagt gtaatgtgga ggtggtcaga    1860
gcgctcacgg tgatgttgca cagacagtgg ctgacagtgc ggagggcagg gggaccccca   1920
aggaccgacc agcagaggcg gacagtgcgc tgtctgcggg acacggtgct gctgctgcac   1980
ggcctatcgc agaaggacaa gctcttcatg atgcactgcg tggaggtcct gcatcagttt   2040
gaccaggtga tgccggggt cagcatgctc atccgagggc ttcctgatgt gacggactgt    2100
gaagaggcag ccctggatga cctctgtgcc gcggaaaccg atgtggaaga ccccgaggtg   2160
gagtgtggct gaggccctga gtgtccagcc acatggtggc accagcacca ctccttttcct   2220 taccacatca actgattaaa gcagtgacca gcaggaactg cccagagaac tggctggcct   2280
tgtttcctga gtctgatctg tttggcggag tgggagggt ggagcaggac ccggaccctg    2340
agtggctggg atccttcttc ctgtccctgg ctgttgctga gcccgtcccc atggtaactg   2400
atctgccttg aggaaggagc cctgccctgc ctgtggaatt gtcctgagtc attgctttgg   2460
gctgggccca tggaagaaa ccattgtgtg cagggaagg aggtggctct tggcccaggc     2520
ctaaaccagg aaagcctggg aaactgggac ccacaggtgg gcatgaaagg gccgcagcag   2580
gggctcccag cagtgtgtaa gaccgggagc tggtctggca ccactgccct ggtccttcca   2640
gctgcctgtc actggtatga tggccccggt gcattgtgcc accagcaggc cacagctgtg   2700
```

| | |
|---|---|
| gatcttggaa ggcctctggg gtcccccggg agcaggggag tgggtgtggg ggggaacgga | 2760 |
| tggtggtgag agggacagac caggcaggct gacgagcagg gcgggcctgg ctcacgtggg | 2820 |
| cctgtaggcg ggcccacgcc aagtttcact taccgccact gctgccagcg agagccgcgg | 2880 |
| gagagtgtgc agccgagtca ctactgcctg cctgcctgcc tgctacggct cagcagcagg | 2940 |
| tacgtaccca accatgggct cgcaggccct gccccgggg cccatgcaga ccctcatctt | 3000 |
| tttcgacatg gaggccactg gcttgccctt ctcccagccc aaggtcacgg agctgtgcct | 3060 |
| gctggctgtc cacagatgtg ccctggagag cccccccacc tctcaggggc cacctcccac | 3120 |
| agttcctcca ccaccgcgtg tggtagacaa gctctccctg tgtgtggctc cggggaaggc | 3180 |
| ctgcagccct gcagcagcg agatcacagg tctgagcaca gctgtgctgg cagcgcatgg | 3240 |
| gcgtcaatgt tttgatgaca acctggccaa cctgctccta gccttcctgc ggcgccagcc | 3300 |
| acagccctgg tgcctggtgg cacacaatgg tgaccgctac gacttccccc tgctccaagc | 3360 |
| agagctggct atgctgggcc tcaccagtgc tctggatggt gccttctgtg tggatagcat | 3420 |
| cactgcgctg aaggccctgg agcgagcaag cagcccctca gaacacggcc aaggaagag | 3480 |
| ctacagccta ggcagcatct acactcgcct gtatgggcag tccctccag actcgcacac | 3540 |
| ggctgagggt gatgtcctgg ccctgctcag catctgtcag tggagaccac aggccctgct | 3600 |
| gcggtgggtg gatgctcacg ccaggccttt cggcaccatc aggcccatgt atgggtcac | 3660 |
| agcctctgct aggaccaagc caagaccatc tgctgtcaca accactgcac acctggccac | 3720 |
| aaccaggaac actagtccca gccttggaga gagcaggggt accaaggatc ttcctccagt | 3780 |
| gaaggaccct ggagccctat ccagggaggg gctgctggcc ccactgggtc tgctggccat | 3840 |
| cctgaccttg gcagtagcca cactgtatgg actatccctg gccacacctg gggagtaggc | 3900 |
| caagaaggaa aatctgacga ataaagaccc ccgctgcccc at | 3942 |

<210> SEQ ID NO 13
<211> LENGTH: 1680
<212> TYPE: DNA
<213> ORGANISM: Homo sapiens

<400> SEQUENCE: 13

| | |
|---|---|
| cctccttccc tgccacacaa tggtttcttc ccatggcccc agcccaaagc aatgactcag | 60 |
| gacaattcca caggcagggc agggctcctt cctcaaggca gatcagttac catggggacg | 120 |
| ggctcagcaa cagccaggga caggaagaag gatcccagcc actcagggtc cgggtcctgc | 180 |
| tccaccctc ccactccgcc aaacagatca gactcaggaa acaaggccag ccagttctct | 240 |
| gggcagttcc tgctggtcac tgctttaatc agttgatgtg gtaaggaaag gagtggtgct | 300 |
| ggtgccacca tgtggctgga cactcaggc ctcagccaca ctccacctcg ggtcttcca | 360 |
| catcggtttc cgcggcacag aggtcatcca gggctgcctc tgagacaaaa aggagaggtt | 420 |
| cctggtgagg gcccaaaggt gccagggcct agggcaggtc ccacctctcc tccccaacg | 480 |
| tccgcaggaa ctaaccagtc ccttccacac ccaggccctg ctccctcagc tactgcaaac | 540 |
| aaagtgatac aaaggcaatt cagacacggc tatttctgga aaaccgtgg ctctgccagg | 600 |
| cacactcaac agatagatgc aaaaggcatc caatatgct tggagaagaa ctgaggcagg | 660 |
| aagataaaag aaaatggccc cagtgctgga acaggctgca gtgggcgggg gcctgctgag | 720 |
| gggacaccca ggaatctgac ttgttgggga acctctggaa gaagccatgg gggctgggca | 780 |
| ggatggcctc tggcaggctt accttcacag tccgtcacat caggaagccc tcggatgagc | 840 |
| atgctgaccc ccggcatcac ctggtcaaac tgatgcagga cctccacgca gtgcatcatg | 900 |

```
aagagcttgt ccttctgcga taggccgtgc agcagcagca ccgtgtcccg cagacagcgc     960
actgtccgcc tctgctggtc ggtccttggg ggtcccsctg ccctccgcac tgtcagccac    1020
```
(Note: reproducing as closely as possible)

```
aagagcttgt ccttctgcga taggccgtgc agcagcagca ccgtgtcccg cagacagcgc     960
actgtccgcc tctgctggtc ggtccttggg ggtccccctg ccctccgcac tgtcagccac    1020
tgtctgtgca acatcaccgt gagcgctctg accacctgag agagggggg tgcagactga    1080 ggcctggtgc caccatggcc tgcaccctaa caatccgctc agcctagcca cctcacgtga    1140
gggggtttgc agtggggcct acagtccttg cacggggccc ccttaccacc agagctgcca    1200
gctgttggcc cctacccact cacctccaca ttacactggc agttggagcc agtgactggg    1260
ggcaaggggc tctgcacacc aagcttagcc aggagccaca ccacctagaa caagaacaga    1320
gtggttccat cctgggcaga aggagaccag tccctgcgag ggttttctta agcttctata    1380
agagttcact tgcttcagca actgtttgtc tgcacaaatg gggtccaaga agtggtgtgg    1440
gaccttccca gggaagaccc aggacaagca ctcatgtgtc accagcaacc cacctgcctc    1500
cagcccccta ttctgccccc acgtcccaaa gccaagacag gatcagtcat caggcaactc    1560
tgccaagtcc tgtctgcatt gcatctgtgt ggtgcacagc ccccaaactg agtttacctc    1620
tttagttgct ttatcaactc ttgttactaa aatgaattaa agctccgttt ctcctcagcg    1680
```

<210> SEQ ID NO 14
<211> LENGTH: 764
<212> TYPE: PRT
<213> ORGANISM: Homo sapiens
<220> FEATURE:
<221> NAME/KEY: MOD_RES
<222> LOCATION: (128)..(184)
<223> OTHER INFORMATION: Xaa = anything

<400> SEQUENCE: 14

Met Ala Gly Thr Ser Ala Pro Gly Ser Lys Arg Arg Ser Glu Pro Pro
1               5                   10                  15

Ala Pro Arg Pro Gly Pro Pro Gly Thr Gly His Pro Pro Ser Lys
            20                  25                  30

Arg Ala Arg Gly Phe Ser Ala Ala Ala Pro Asp Pro Asp Asp Pro
        35                  40                  45

Phe Gly Ala His Gly Asp Phe Thr Ala Asp Asp Leu Glu Glu Leu Asp
    50                  55                  60

Thr Leu Ala Ser Gln Ala Leu Ser Gln Cys Pro Ala Ala Arg Asp
65                  70                  75                  80

Val Ser Ser Asp His Lys Val His Arg Leu Leu Asp Gly Met Ser Lys
                85                  90                  95

Asn Pro Ser Gly Lys Asn Arg Glu Thr Val Pro Ile Lys Asp Asn Phe
            100                 105                 110

Glu Leu Glu Val Leu Gln Ala Gln Tyr Lys Glu Leu Lys Glu Lys Xaa
        115                 120                 125

Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Leu Gln Ser Leu Gln Ser Glu Leu
            180                 185                 190

Gln Phe Lys Asp Ala Glu Met Asn Glu Leu Arg Thr Lys Leu Gln Thr
        195                 200                 205

Ser Glu Arg Ala Asn Lys Leu Ala Ala Pro Ser Val Ser His Val Ser

-continued

```
                210                 215                 220
Pro Arg Lys Asn Pro Ser Val Val Ile Lys Pro Glu Ala Cys Ser Pro
225                 230                 235                 240

Gln Phe Gly Lys Thr Ser Phe Pro Thr Lys Glu Ser Phe Ser Ala Asn
            245                 250                 255

Met Ser Leu Pro His Pro Cys Gln Thr Glu Ser Gly Tyr Lys Pro Leu
        260                 265                 270

Val Gly Arg Glu Asp Ser Lys Pro His Ser Leu Arg Gly Asp Ser Ile
    275                 280                 285

Lys Gln Glu Glu Ala Gln Lys Ser Phe Val Asp Ser Trp Arg Gln Arg
290                 295                 300

Ser Asn Thr Gln Gly Ser Ile Leu Ile Asn Leu Leu Leu Lys Gln Pro
305                 310                 315                 320

Leu Ile Pro Gly Ser Ser Leu Ser Leu Cys His Leu Leu Ser Ser Ser
            325                 330                 335

Ser Glu Ser Pro Ala Gly Thr Pro Leu Gln Pro Pro Gly Phe Gly Ser
        340                 345                 350

Thr Leu Ala Gly Met Ser Gly Leu Arg Thr Thr Gly Ser Tyr Asp Gly
    355                 360                 365

Ser Phe Ser Leu Ser Ala Leu Arg Glu Ala Gln Asn Leu Ala Phe Thr
370                 375                 380

Gly Leu Asn Leu Val Ala Arg Asn Glu Cys Ser Arg Asp Gly Asp Pro
385                 390                 395                 400

Ala Glu Gly Gly Arg Arg Ala Phe Pro Leu Cys Gln Leu Pro Gly Ala
            405                 410                 415

Val His Phe Leu Pro Leu Val Gln Phe Phe Ile Gly Leu His Cys Gln
        420                 425                 430

Ala Leu Gln Asp Leu Ala Ala Lys Arg Ser Gly Ala Pro Gly Asp
    435                 440                 445

Ser Pro Thr His Ser Ser Cys Val Ser Ser Gly Val Glu Thr Asn Pro
450                 455                 460

Glu Asp Ser Val Cys Ile Leu Glu Gly Phe Ser Val Thr Ala Leu Ser
465                 470                 475                 480

Ile Leu Gln His Leu Val Cys His Ser Gly Ala Val Ser Leu Leu
            485                 490                 495

Leu Ser Gly Val Gly Ala Asp Ser Ala Ala Gly Glu Gly Asn Arg Ser
        500                 505                 510

Leu Val His Arg Leu Ser Asp Gly Asp Met Thr Ser Ala Leu Arg Gly
    515                 520                 525

Val Ala Asp Asp Gln Gly Gln His Pro Leu Leu Lys Met Leu Leu His
530                 535                 540

Leu Leu Ala Phe Ser Ser Ala Ala Thr Gly His Leu Gln Ala Ser Val
545                 550                 555                 560

Leu Thr Gln Cys Leu Lys Val Leu Val Lys Leu Ala Glu Asn Thr Ser
            565                 570                 575

Cys Asp Phe Leu Pro Arg Phe Gln Cys Val Phe Gln Val Leu Pro Lys
        580                 585                 590

Cys Leu Ser Pro Glu Thr Pro Leu Pro Ser Val Leu Leu Ala Val Glu
    595                 600                 605

Leu Leu Ser Leu Leu Ala Asp His Asp Gln Leu Ala Pro Gln Leu Cys
610                 615                 620

Ser His Ser Glu Gly Cys Leu Leu Leu Leu Tyr Met Tyr Ile Thr
625                 630                 635                 640
```

-continued

Ser Arg Pro Asp Arg Val Ala Leu Glu Thr Gln Trp Leu Gln Leu Glu
            645                 650                 655

Gln Glu Val Val Arg Ala Leu Thr Val Met Leu His Arg Gln Trp Leu
        660                 665                 670

Thr Val Arg Arg Ala Gly Gly Pro Arg Thr Asp Gln Gln Arg Arg
        675                 680                 685

Thr Val Arg Cys Leu Arg Asp Thr Val Leu Leu His Gly Leu Ser
        690                 695                 700

Gln Lys Asp Lys Leu Phe Met Met His Cys Val Glu Val Leu His Gln
705                 710                 715                 720

Phe Asp Gln Val Met Pro Gly Val Ser Met Leu Ile Arg Gly Leu Pro
                725                 730                 735

Asp Val Thr Asp Cys Glu Glu Ala Ala Leu Asp Asp Leu Cys Ala Ala
            740                 745                 750

Glu Thr Asp Val Glu Asp Pro Glu Val Glu Cys Gly
            755                 760

<210> SEQ ID NO 15
<211> LENGTH: 671
<212> TYPE: PRT
<213> ORGANISM: Homo sapiens
<220> FEATURE:
<221> NAME/KEY: MOD_RES
<222> LOCATION: (35)..(91)
<223> OTHER INFORMATION: Xaa = anything

<400> SEQUENCE: 15

Met Ser Lys Asn Pro Ser Gly Lys Asn Arg Glu Thr Val Pro Ile Lys
1               5                   10                  15

Asp Asn Phe Glu Leu Glu Val Leu Gln Ala Gln Tyr Lys Glu Leu Lys
            20                  25                  30

Glu Lys Met Lys Val Met Glu Glu Val Leu Ile Lys Asn Gly Glu
        35                  40                  45

Ile Lys Ile Leu Arg Asp Ser Leu His Gln Thr Glu Ser Val Leu Glu
    50                  55                  60

Glu Gln Arg Arg Ser His Phe Leu Leu Glu Gln Glu Lys Thr Gln Ala
65                  70                  75                  80

Leu Ser Asp Lys Glu Lys Glu Phe Ser Lys Lys Leu Gln Ser Leu Gln
                85                  90                  95

Ser Glu Leu Gln Phe Lys Asp Ala Glu Met Asn Glu Leu Arg Thr Lys
            100                 105                 110

Leu Gln Thr Ser Glu Arg Ala Asn Lys Leu Ala Ala Pro Ser Val Ser
        115                 120                 125

His Val Ser Pro Arg Lys Asn Pro Ser Val Val Ile Lys Pro Glu Ala
    130                 135                 140

Cys Ser Pro Gln Phe Gly Lys Thr Ser Phe Pro Thr Lys Glu Ser Phe
145                 150                 155                 160

Ser Ala Asn Met Ser Leu Pro His Pro Cys Gln Thr Glu Ser Gly Tyr
                165                 170                 175

Lys Pro Leu Val Gly Arg Glu Asp Ser Lys Leu His Ser Leu Arg Gly
            180                 185                 190

Asp Ser Ile Lys Gln Glu Glu Ala Gln Lys Ser Phe Val Asp Ser Trp
        195                 200                 205

Arg Gln Arg Ser Asn Thr Gln Gly Ser Ile Leu Ile Asn Leu Leu Leu
    210                 215                 220

-continued

```
Lys Gln Pro Leu Ile Pro Gly Ser Ser Leu Ser Leu Cys His Leu Leu
225                 230                 235                 240

Ser Ser Ser Ser Glu Ser Pro Ala Gly Thr Pro Leu Gln Pro Pro Gly
                245                 250                 255

Phe Gly Ser Thr Leu Ala Gly Met Ser Gly Leu Arg Thr Thr Gly Ser
            260                 265                 270

Tyr Asp Gly Ser Phe Ser Leu Ser Ala Leu Arg Glu Ala Gln Asn Leu
        275                 280                 285

Ala Phe Thr Gly Leu Asn Leu Val Ala Arg Asn Glu Cys Ser Arg Asp
    290                 295                 300

Gly Asp Pro Ala Glu Gly Arg Arg Ala Phe Pro Leu Cys Gln Leu
305                 310                 315                 320

Pro Gly Ala Val His Phe Leu Pro Leu Val Gln Phe Phe Ile Gly Leu
                325                 330                 335

His Cys Gln Ala Leu Gln Asp Leu Ala Ala Lys Arg Ser Gly Ala
            340                 345                 350

Pro Gly Asp Ser Pro Thr His Ser Ser Cys Val Ser Ser Gly Val Glu
        355                 360                 365

Thr Asn Pro Glu Asp Ser Val Cys Ile Leu Gly Phe Ser Val Thr
370                 375                 380

Ala Leu Ser Ile Leu Gln His Leu Val Cys His Ser Ala Val Val
385                 390                 395                 400

Ser Leu Leu Leu Ser Gly Val Gly Ala Asp Ser Ala Ala Gly Glu Gly
                405                 410                 415

Asn Arg Ser Leu Val His Arg Leu Ser Asp Gly Asp Met Thr Ser Ala
            420                 425                 430

Leu Arg Gly Val Ala Asp Asp Gln Gly Gln His Pro Leu Leu Lys Met
        435                 440                 445

Leu Leu His Leu Leu Ala Phe Ser Ser Ala Thr Gly His Leu Gln
450                 455                 460

Ala Ser Val Leu Thr Gln Cys Leu Lys Val Leu Val Lys Leu Ala Glu
465                 470                 475                 480

Asn Thr Ser Cys Asp Phe Leu Pro Arg Phe Gln Cys Val Phe Gln Val
                485                 490                 495

Leu Pro Lys Cys Leu Ser Pro Glu Thr Pro Leu Pro Ser Val Leu Leu
            500                 505                 510

Ala Val Glu Leu Leu Ser Leu Leu Ala Asp His Asp Gln Leu Ala Pro
        515                 520                 525

Gln Leu Cys Ser His Ser Glu Gly Cys Leu Leu Leu Leu Tyr Met
530                 535                 540

Tyr Ile Thr Ser Arg Pro Asp Arg Val Ala Leu Glu Thr Gln Trp Leu
545                 550                 555                 560

Gln Leu Glu Gln Glu Val Val Arg Ala Leu Thr Val Met Leu His Arg
                565                 570                 575

Gln Trp Leu Thr Val Arg Arg Ala Gly Gly Pro Pro Arg Thr Asp Gln
            580                 585                 590

Gln Arg Arg Thr Val Arg Cys Leu Arg Asp Thr Val Leu Leu Leu His
        595                 600                 605

Gly Leu Ser Gln Lys Asp Lys Leu Phe Met Met His Cys Val Glu Val
    610                 615                 620

Leu His Gln Phe Asp Gln Val Met Pro Gly Val Ser Met Leu Ile Arg
625                 630                 635                 640

Gly Leu Pro Asp Val Thr Asp Cys Glu Glu Ala Ala Leu Asp Asp Leu
```

Cys Ala Ala Glu Thr Asp Val Glu Asp Pro Glu Val Glu Cys Gly
                645                 650                 655
        660                 665                 670

<210> SEQ ID NO 16
<211> LENGTH: 671
<212> TYPE: PRT
<213> ORGANISM: Homo sapiens
<220> FEATURE:
<221> NAME/KEY: MOD_RES
<222> LOCATION: (35)..(91)
<223> OTHER INFORMATION: Xaa = anything

<400> SEQUENCE: 16

Met Ser Lys Asn Pro Ser Gly Lys Asn Arg Glu Thr Val Pro Ile Lys
 1               5                  10                  15

Asp Asn Phe Glu Leu Glu Val Leu Gln Ala Gln Tyr Lys Glu Leu Lys
            20                  25                  30

Glu Lys Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa
 50                  55                  60

Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Leu Gln Ser Leu Gln
                    85                  90                  95

Ser Glu Leu Gln Phe Lys Asp Ala Glu Met Asn Glu Leu Arg Thr Lys
                100                 105                 110

Leu Gln Thr Ser Glu Arg Ala Asn Lys Leu Ala Ala Pro Ser Val Ser
            115                 120                 125

His Val Ser Pro Arg Lys Asn Pro Ser Val Val Ile Lys Pro Glu Ala
        130                 135                 140

Cys Ser Pro Gln Phe Gly Lys Thr Ser Phe Pro Thr Lys Glu Ser Phe
145                 150                 155                 160

Ser Ala Asn Met Ser Leu Pro His Pro Cys Gln Thr Glu Ser Gly Tyr
                165                 170                 175

Lys Pro Leu Val Gly Arg Glu Asp Ser Lys Pro His Ser Leu Arg Gly
            180                 185                 190

Asp Ser Ile Lys Gln Glu Glu Ala Gln Lys Ser Phe Val Asp Ser Trp
        195                 200                 205

Arg Gln Arg Ser Asn Thr Gln Gly Ser Ile Leu Ile Asn Leu Leu Leu
    210                 215                 220

Lys Gln Pro Leu Ile Pro Gly Ser Ser Leu Ser Leu Cys His Leu Leu
225                 230                 235                 240

Ser Ser Ser Ser Glu Ser Pro Ala Gly Thr Pro Leu Gln Pro Pro Gly
                245                 250                 255

Phe Gly Ser Thr Leu Ala Gly Met Ser Gly Leu Arg Thr Thr Gly Ser
            260                 265                 270

Tyr Asp Gly Ser Phe Ser Leu Ser Ala Leu Arg Glu Ala Gln Asn Leu
        275                 280                 285

Ala Phe Thr Gly Leu Asn Leu Val Ala Arg Asn Glu Cys Ser Arg Asp
    290                 295                 300

Gly Asp Pro Ala Glu Gly Arg Arg Ala Phe Pro Leu Cys Gln Leu
305                 310                 315                 320

Pro Gly Ala Val His Phe Leu Pro Leu Val Gln Phe Phe Ile Gly Leu
                325                 330                 335

-continued

```
His Cys Gln Ala Leu Gln Asp Leu Ala Ala Lys Arg Ser Gly Ala
            340                 345                 350

Pro Gly Asp Ser Pro Thr His Ser Ser Cys Val Ser Ser Gly Val Glu
            355                 360                 365

Thr Asn Pro Glu Asp Ser Val Cys Ile Leu Glu Gly Phe Ser Val Thr
            370                 375                 380

Ala Leu Ser Ile Leu Gln His Leu Val Cys His Ser Gly Ala Val Val
385                 390                 395                 400

Ser Leu Leu Leu Ser Gly Val Gly Ala Asp Ser Ala Ala Gly Glu Gly
            405                 410                 415

Asn Arg Ser Leu Val His Arg Leu Ser Asp Gly Asp Met Thr Ser Ala
            420                 425                 430

Leu Arg Gly Val Ala Asp Asp Gln Gly Gln His Pro Leu Leu Lys Met
            435                 440                 445

Leu Leu His Leu Leu Ala Phe Ser Ser Ala Ala Thr Gly His Leu Gln
            450                 455                 460

Ala Ser Val Leu Thr Gln Cys Leu Lys Val Leu Val Lys Leu Ala Glu
465                 470                 475                 480

Asn Thr Ser Cys Asp Phe Leu Pro Arg Phe Gln Cys Val Phe Gln Val
                485                 490                 495

Leu Pro Lys Cys Leu Ser Pro Glu Thr Pro Leu Pro Ser Val Leu Leu
            500                 505                 510

Ala Val Glu Leu Leu Ser Leu Leu Ala Asp His Asp Gln Leu Ala Pro
            515                 520                 525

Gln Leu Cys Ser His Ser Glu Gly Cys Leu Leu Leu Leu Tyr Met
            530                 535                 540

Tyr Ile Thr Ser Arg Pro Asp Arg Val Ala Leu Glu Thr Gln Trp Leu
545                 550                 555                 560

Gln Leu Glu Gln Glu Val Val Arg Ala Leu Thr Val Met Leu His Arg
            565                 570                 575

Gln Trp Leu Thr Val Arg Arg Ala Gly Gly Pro Pro Arg Thr Asp Gln
            580                 585                 590

Gln Arg Arg Thr Val Arg Cys Leu Arg Asp Thr Val Leu Leu Leu His
            595                 600                 605

Gly Leu Ser Gln Lys Asp Lys Leu Phe Met Met His Cys Val Glu Val
            610                 615                 620

Leu His Gln Phe Asp Gln Val Met Pro Gly Val Ser Met Leu Ile Arg
625                 630                 635                 640

Gly Leu Pro Asp Val Thr Asp Cys Glu Glu Ala Ala Leu Asp Asp Leu
                645                 650                 655

Cys Ala Ala Glu Thr Asp Val Glu Asp Pro Glu Val Glu Cys Gly
            660                 665                 670

<210> SEQ ID NO 17
<211> LENGTH: 592
<212> TYPE: PRT
<213> ORGANISM: Homo sapiens

<400> SEQUENCE: 17

Met Asn Glu Leu Arg Thr Lys Leu Gln Thr Ser Glu Arg Ala Asn Lys
  1               5                  10                  15

Leu Ala Ala Pro Ser Val Ser His Val Ser Pro Arg Lys Asn Pro Ser
                 20                  25                  30

Val Val Ile Lys Pro Glu Ala Cys Ser Pro Gln Phe Gly Lys Thr Ser
```

```
                35                  40                  45
Phe Pro Thr Lys Glu Ser Phe Ser Ala Asn Met Ser Leu Pro His Pro
 50                  55                  60

Cys Gln Thr Glu Ser Gly Tyr Lys Pro Leu Val Gly Arg Glu Asp Ser
 65                  70                  75                  80

Lys Thr His Ser Leu Arg Gly Asp Ser Ile Lys Gln Glu Ala Gln
                 85                  90                  95

Lys Ser Phe Val Asp Ser Trp Arg Gln Arg Ser Asn Thr Gln Gly Ser
                100                 105                 110

Ile Leu Ile Asn Leu Leu Lys Gln Pro Leu Ile Pro Gly Ser Ser
                115                 120                 125

Leu Ser Leu Cys His Leu Leu Ser Ser Ser Glu Ser Pro Ala Gly
    130                 135                 140

Thr Pro Leu Gln Pro Pro Gly Phe Gly Ser Thr Leu Ala Gly Met Ser
145                 150                 155                 160

Gly Leu Arg Thr Thr Gly Ser Gln Asp Gly Ser Phe Ser Leu Ser Ala
                165                 170                 175

Leu Arg Glu Ala Gln Asn Leu Ala Phe Thr Gly Leu Asn Leu Val Ala
                180                 185                 190

Arg Asn Glu Cys Ser Arg Asp Gly Asp Pro Ala Glu Gly Gly Arg Arg
                195                 200                 205

Ala Phe Pro Leu Cys Gln Leu Pro Gly Ala Val His Phe Leu Pro Leu
    210                 215                 220

Val Gln Phe Phe Ile Gly Leu His Cys Gln Ala Leu Gln Asp Leu Ala
225                 230                 235                 240

Ala Ala Lys Arg Ser Gly Ala Pro Gly Asp Ser Pro Thr His Ser Ser
                245                 250                 255

Arg Val Ser Ser Gly Val Glu Thr Asn Pro Glu Asp Ser Val Arg Ile
                260                 265                 270

Leu Glu Gly Phe Ser Val Thr Ala Leu Ser Ile Leu Gln His Leu Val
                275                 280                 285

Cys His Ser Gly Ala Val Val Ser Leu Leu Ser Arg Val Gly Ala
    290                 295                 300

Asp Ser Ala Ala Gly Glu Gly Asn Gly Ser Leu Val His Arg Phe Ser
305                 310                 315                 320

Asp Gly Asp Met Thr Ser Ala Pro Arg Gly Val Ala Asp Gln Gly
                325                 330                 335

Gln His Pro Leu Leu Lys Met Leu Leu His Leu Leu Ala Phe Ser Ser
                340                 345                 350

Ala Ala Thr Gly His Leu Gln Ala Ser Val Leu Thr Gln Cys Leu Lys
                355                 360                 365

Val Leu Val Lys Leu Ala Glu Asn Thr Ser Ser Asp Phe Leu Pro Arg
    370                 375                 380

Phe Gln Cys Val Phe Gln Val Leu Pro Lys Cys Leu Ser Pro Glu Thr
385                 390                 395                 400

Pro Leu Pro Gly Met Val Leu Ala Val Glu Leu Leu Ser Leu Leu Ala
                405                 410                 415

Asp His Asp Gln Leu Ala Pro Gln Leu Cys Ser His Ser Asp Cys Leu
                420                 425                 430

Leu Leu Leu Leu Tyr Met Tyr Ile Thr Ser Arg Pro Asp Arg Val Ala
                435                 440                 445

Ser Glu Thr Gln Trp Leu Gln Leu Glu Gln Glu Val Val Trp Leu Leu
450                 455                 460
```

```
Ser Lys Leu Gly Val Gln Ser Pro Leu Pro Leu Val Thr Gly Ser Asn
465                 470                 475                 480

Cys Gln Cys Asn Val Glu Val Val Arg Ala Leu Thr Val Met Leu His
            485                 490                 495

Arg Gln Trp Leu Thr Val Arg Arg Ala Gly Pro Pro Arg Thr Asp
        500                 505                 510

Gln Gln Arg Arg Thr Val Arg Cys Leu Arg Asp Thr Val Leu Leu Leu
        515                 520                 525

His Gly Leu Ser Gln Lys Asp Lys Leu Phe Ile Met His Cys Val Glu
530                 535                 540

Val Leu His Gln Tyr Asp Gln Val Met Pro Gly Val Ser Met Leu Ile
545                 550                 555                 560

Arg Gly Leu Pro Asp Val Thr Asp Cys Glu Glu Ala Ala Leu Asp Asp
                565                 570                 575

Leu Cys Ala Ala Glu Thr Asp Val Asp Asp Pro Glu Leu Glu Cys Gly
                580                 585                 590

<210> SEQ ID NO 18
<211> LENGTH: 571
<212> TYPE: PRT
<213> ORGANISM: Homo sapiens

<400> SEQUENCE: 18

Met Ser Lys Asn Pro Ser Gly Lys Asn Arg Glu Thr Val Pro Ile Lys
1               5                   10                  15

Asp Asn Phe Glu Leu Glu Val Leu Gln Ala Gln Tyr Lys Glu Leu Lys
            20                  25                  30

Glu Lys Met Lys Val Met Glu Glu Glu Val Leu Ile Lys Asn Gly Glu
        35                  40                  45

Ile Lys Ile Leu Arg Asp Ser Leu His Gln Thr Glu Ser Val Leu Glu
    50                  55                  60

Glu Gln Arg Arg Ser His Phe Leu Leu Glu Gln Glu Lys Thr Gln Ala
65                  70                  75                  80

Leu Ser Asp Lys Glu Lys Glu Phe Ser Lys Lys Leu Gln Ser Leu Gln
                85                  90                  95

Ser Glu Leu Gln Phe Lys Asp Ala Glu Met Asn Glu Leu Arg Thr Lys
            100                 105                 110

Leu Gln Thr Ser Glu Arg Ala Asn Lys Leu Ala Ala Pro Ser Val Ser
        115                 120                 125

His Val Ser Pro Arg Lys Asn Pro Ser Val Val Ile Lys Pro Glu Ala
    130                 135                 140

Cys Ser Pro Gln Phe Gly Lys Thr Ser Phe Pro Thr Lys Glu Ser Phe
145                 150                 155                 160

Ser Ala Asn Met Ser Leu Pro His Pro Cys Gln Thr Glu Ser Gly Tyr
                165                 170                 175

Lys Pro Leu Val Gly Arg Glu Asp Ser Lys Pro His Ser Leu Arg Gly
            180                 185                 190

Asp Ser Ile Lys Gln Glu Glu Ala Gln Lys Ser Phe Val Asp Ser Trp
        195                 200                 205

Arg Gln Arg Ser Asn Thr Gln Gly Ser Ile Leu Ile Asn Leu Leu Leu
    210                 215                 220

Lys Gln Pro Leu Ile Pro Gly Ser Ser Leu Ser Leu Cys His Leu Leu
225                 230                 235                 240

Ser Ser Ser Ser Glu Ser Pro Ala Gly Thr Pro Leu Gln Pro Pro Gly
```

```
                    245                 250                 255
Phe Gly Ser Thr Leu Ala Gly Met Ser Gly Leu Arg Thr Thr Gly Ser
                260                 265                 270
Tyr Asp Gly Ser Phe Ser Leu Ser Ala Leu Arg Glu Ala Gln Asn Leu
            275                 280                 285
Ala Phe Thr Gly Leu Asn Leu Val Ala Arg Asn Glu Cys Ser Arg Asp
        290                 295                 300
Gly Asp Pro Ala Glu Gly Arg Arg Ala Phe Pro Leu Cys Gln Leu
305                 310                 315                 320
Pro Gly Ala Val His Phe Leu Pro Leu Val Gln Phe Ile Gly Leu
                325                 330                 335
His Cys Gln Ala Leu Gln Asp Leu Ala Ala Lys Arg Ser Gly Ala
                340                 345                 350
Pro Gly Asp Ser Pro Thr His Ser Ser Cys Val Ser Ser Gly Val Glu
            355                 360                 365
Thr Asn Pro Glu Asp Ser Val Cys Ile Leu Gly Phe Ser Val Thr
        370                 375                 380
Ala Leu Ser Ile Leu Gln His Leu Val Cys His Ser Gly Ala Val Val
385                 390                 395                 400
Ser Leu Leu Ser Gly Val Gly Ala Asp Ser Ala Ala Gly Glu Gly
                405                 410                 415
Asn Arg Ser Leu Val His Arg Leu Ser Asp Gly Asp Met Thr Ser Ala
            420                 425                 430
Leu Arg Gly Val Ala Asp Asp Gln Gly Gln His Pro Leu Leu Lys Met
            435                 440                 445
Leu Leu His Leu Leu Ala Phe Ser Ser Ala Ala Thr Gly His Leu Gln
        450                 455                 460
Ala Ser Val Leu Thr Gln Cys Leu Lys Val Leu Val Lys Leu Ala Glu
465                 470                 475                 480
Asn Thr Ser Cys Asp Phe Leu Pro Arg Phe Gln Cys Val Phe Gln Val
                485                 490                 495
Leu Pro Lys Cys Leu Ser Pro Glu Thr Pro Leu Pro Ser Val Leu Leu
            500                 505                 510
Ala Val Glu Leu Leu Ser Leu Leu Ala Asp His Asp Gln Leu Ala Pro
        515                 520                 525
Gln Leu Cys Ser His Ser Glu Gly Cys Leu Leu Leu Leu Tyr Met
        530                 535                 540
Tyr Ile Thr Ser Arg Pro Asp Arg Val Ala Leu Glu Asn Asn Gly Ser
545                 550                 555                 560
Ser Trp Asn Lys Arg Trp Ser Glu Arg Ser Arg
                565                 570

<210> SEQ ID NO 19
<211> LENGTH: 14
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 19

Asp Ser Leu His Gln Thr Glu Ser Val Leu Glu Glu Gln Arg
  1               5                  10

<210> SEQ ID NO 20
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 20

Asp Thr Val Leu Leu Leu His Gly Leu Ser Gln Lys
 1               5                   10

<210> SEQ ID NO 21
<211> LENGTH: 19
<212> TYPE: RNA
<213> ORGANISM: Artificial Sequence
<220> FEATURE:
<223> OTHER INFORMATION: Description of Artificial Sequence: Synthetic
      Primer

<400> SEQUENCE: 21
gguccacaga uuauuagau                                              19

<210> SEQ ID NO 22
<211> LENGTH: 21
<212> TYPE: RNA
<213> ORGANISM: Artificial Sequence
<220> FEATURE:
<223> OTHER INFORMATION: Description of Artificial Sequence: Synthetic
      Primer

<400> SEQUENCE: 22
agaggaacag agaagaucac a                                           21

<210> SEQ ID NO 23
<211> LENGTH: 19
<212> TYPE: RNA
<213> ORGANISM: Artificial Sequence
<220> FEATURE:
<223> OTHER INFORMATION: Description of Artificial Sequence: Synthetic
      Primer

<400> SEQUENCE: 23
gaagaggccc agaaaagcu                                              19

<210> SEQ ID NO 24
<211> LENGTH: 21
<212> TYPE: RNA
<213> ORGANISM: Artificial Sequence
<220> FEATURE:
<223> OTHER INFORMATION: Description of Artificial Sequence: Synthetic
      Primer

<400> SEQUENCE: 24
gacccgcgcc gaggugaagu u                                           21

<210> SEQ ID NO 25
<211> LENGTH: 21
<212> TYPE: RNA
<213> ORGANISM: Artificial Sequence
<220> FEATURE:
<223> OTHER INFORMATION: Description of Artificial Sequence: Synthetic
      Primer

<400> SEQUENCE: 25
uggcuuucug uagaggacau c                                           21

<210> SEQ ID NO 26
<211> LENGTH: 12430
```

<212> TYPE: DNA
<213> ORGANISM: Homo sapiens

<400> SEQUENCE: 26

| | | | | | |
|---|---|---|---|---|---|
| gatcttcaaa | tgaactgttt | actacagaag | cacaaaataa | gtcattaatt | ataacttttc | 60 |
| cttaatcata | tctcttttaa | ataaaaataa | agacatttga | aatactatca | taatgatcat | 120 |
| tggataagca | gaaattctta | acacagagat | ctataaacga | tggtctgagg | tctgtgaacc | 180 |
| caaagaaatt | aaatgtgact | ttataaaaac | atgttatcta | tgcctgtttt | aaagaagaat | 240 |
| cacggcattc | ctcaaactcc | caaattaaaa | aactttgaag | ttataaataa | tttctattga | 300 |
| ctaaagaatc | aaaatattat | gcacataaat | tggcaactca | gaacttctat | tattgacaaa | 360 |
| tttaatagaa | ctgaaatcag | gaaaaaactt | ctgagtattc | caaacacgca | cttaggcttc | 420 |
| aggcaaaaaa | gaaagcatat | ttctatactg | attatcttta | aaggtattct | gatctgttgc | 480 |
| taatttgtct | caccttgcat | ataaatcaaa | gcatcataaa | ttttcaccac | cttatcaatg | 540 |
| gttgcctcca | ggtccagttt | ctgaacagat | tctaacaaac | ttctacagct | cttaagcact | 600 |
| tttgtgtaaa | aatccaatga | catccaagtt | atcactacag | aaggtttctt | cttggattta | 660 |
| tgttgacagt | ccttgaaagt | acggctgcag | taagtacatt | ttgttaaaaa | cattggaatt | 720 |
| aagatgaatt | ttgttatagt | caaacataaa | attgtagtaa | agccaaaaga | aattgtgagt | 780 |
| acgaaattta | tctataacaa | tttaaagtaa | acatgcaaat | caagtaatat | gttattacta | 840 |
| ttttaagttg | aatctattta | tgtcagctta | aatcaccctt | aggatttggg | aaccaaatga | 900 |
| ctttgggagc | ctgaggtggg | aggatcactt | gagcccagga | gtttgagacc | agccgggcca | 960 |
| atatagggaa | acccatctct | acaaaaaaaa | ttttttctaa | attagggtgt | ggcggcacat | 1020 |
| gcctatagtt | ccagctacat | gggaggctca | cttgagcccc | ggatagagat | caaggctgta | 1080 |
| gtgagccatg | atcatgccac | tgtgcaccag | cctgggagac | aaagcgagac | cctgtcttca | 1140 |
| acagccaaac | actgggtttt | gagttgtaca | caaatgtgtt | ctggtacttt | ctaatcatgt | 1200 |
| gtccccagga | aagtcagttt | tggcttcaga | caaaaagag | cctcagtttc | tctgagtgtc | 1260 |
| agtttctaat | ttttaaaata | ggcataatag | cctttacctt | acaggactat | tgtaaatatt | 1320 |
| aactaagata | tatacagtgc | ttagcaccgt | acctagcatt | tgactcaata | gaaaataaat | 1380 |
| ttattaacta | cttcagtgaa | aagtttgtgt | tctaaggtta | catgagtcaa | gtgaataatg | 1440 |
| agtaaacagt | aaatccaagt | tcattacagg | aaacccaacc | ccaagaaaca | agaagtttgt | 1500 |
| tttaccagtt | catgttttga | tgagaacaat | gaacagtaca | cagagcagtc | agttgtaaga | 1560 |
| caacagcaat | tccttctaac | atctcaataa | caggattctt | taggccactg | tattcaaggg | 1620 |
| aaatctgaag | ggattcagct | ttctgtttca | gtgcactcca | taatatgctc | ttttgggtca | 1680 |
| tgtccacatg | tttaattcta | taattatgaa | tatagtagag | agatattcat | atgccatata | 1740 |
| aatttggtta | aaacatgaaa | catatttaga | ataaaacata | ctatgtaata | tcaactattc | 1800 |
| aaaaaattt | ttttttttg | tgagacagag | tctcactctg | tctcccaggc | tggagtgcag | 1860 |
| tggcgccatc | tcggctcact | gcaagctccg | cctcccgggt | tcacgccatt | ctcctgcctc | 1920 |
| agcctcccga | gtagctggga | ctacaggcgc | caaccaccac | gcttggctaa | ttttttgtat | 1980 |
| ttttagtaga | gacagggttt | caccgtgtta | gccaggatga | tctcgatctt | ctgacctcgt | 2040 |
| gatctgcccg | cctcggcctc | ccaaagtgct | gggattacag | gcgtgagcca | ccgcgcccag | 2100 |
| cctgaaattt | atactaagat | ttaaaacaat | taaaacaatg | ttcagaagta | actgaaatat | 2160 |
| ggcaacttag | ccactttata | aaaatagtt | ggttaatgtt | ttaaaaattg | ctaatagatg | 2220 |

```
cacagtctca aagattttc acatattaaa aagttaaatt agataagcat ataaaaacat    2280
gcaaagtaac tatatttaac catgaaatgt tttatactac taaccgtcta caataattat    2340
aaaaatattt taagcactcc cttggctaca tttagaaaga tggtctttgg atttaaatca    2400
aagcacttaa ctaaagctga ttttaaaag tgaacaaagt tttatttaat ggctaaatac     2460
aaactgaatg aaggcatcat acttcctcag tctgttttgg tgctctttta gaagggttta    2520
gagacgagct gagacgacgc cttttgggtg atattccatc actattactg ctgaggtttt    2580
cctgttgagt ttggcattga atctcctcaa tgatttccat actttccatt ttcaaagctg    2640
cataaagtgg gcccaacaag tactgagaaa ataaaaaata atttccagaa atattcctta    2700
gaaaatatat ttatattatt cataggcagc aagaatgtat tagatgttag gtgttttcta    2760
gtgaaactac ttttagagtc tcataaagca aaataaacat ctaaattgat ctatattatt    2820
taagtctata tatagactat ggttctatag tcttagaagg tttaaacaaa tccttctctc    2880
tacatcctgt ttttcctctt accaaaatgc tataaatttt aattcccta taaaaaattc     2940 tgtaagggaa ttaccaactt tcttcatgta actttaatcc agcaagatta ataaactaaa    3000
atatttaatc aagttactgc atctctgatg attttattgt attacctgac tcccacagtc    3060
caaatagaaa aaagcgcata atttggcatg attaatcatt cataggtttt ctaaaagtga    3120
ttgattataa cttgtcagac acataatctg attgaccaaa gcttctgcaa ttaagttggt    3180
aactgccccc ttttaattaa taatgcaaca atacattta cacttcacag attctactta     3240
gaaacattct actccattgg cagttcatta ccaacttaat gaacaaatcc ttctgaaatc    3300
aaagtaaaag tccataatag tgagccagac tacactatga aaatcattat gttccaaata    3360
taaattacta ttaaagatat tctatttct tattattaca ttttgcacat atgtatacaa     3420
ttaaatgatg aacaaaatac atacttaact agtaacctga aaaattactt acctctgcat    3480
ctacctcaat tccaagcaca tccaaaagag ctttacaaat attctctcaca tagaccttcc   3540 tgacttgtaa agcagattca tacccagctg gcacaaattt aaggaaatac tgcagtaaat    3600
ggcacaaagc tgcttttagc aaatcagact taagccgcat gagcacaccg tcttcaaaca    3660
tgacacagag ttttccagc agcatattta aatagacagg ttcaatattt ctataagctt     3720
ctgcttcaaa gggaaatagt gtctttatca gctttgataa tggctcttca tagagtttca    3780
attggtcagt atccatttct acaaggtgtt ttaataattc caaaaatgag ctgaaaaaag    3840
tgctagctgg ttgtgctggt agtcctccaa gctgaaaaaa gtctgttaaa agctaattgc    3900
tagggattta attttggac taccatactc tagcagaaca caacctatct gccaaagtaa     3960
gagttcttgc cttctaaaaa acacaattgc aataatacga gtaagaacca ttaataaagt    4020
gacttcaata aattctaaat tttgcatact catcaactgc aaaggagctg attgtaaata    4080
tcccatgtgt tcatctaatt gacttaaaaa tcggctcatg accactggcc attccacagc    4140
atgacccatc acatttcttc tatggaggta accaagtct tcaaaagtt gtaataattc       4200 ttttgtgagt accccaaaaa tagcaggact cttgctttta aaagaaata ataatgaaca     4260 gatgacttca cagattttct tgtgtaacaa atgacaggag ggagttgctg caatccgcag    4320
aagtctcgtt atgatccaat tactgaattc tttgaaataa acaaaaaga tattaaataa     4380 acaagtatat ccgaagtgct aattcatttg ctaaatcctt gacgattgac ttttaaagaa    4440
taaacttcac taacaagagt gtaaaacatt ctcttcacaa tggaaacata atagtttaaa    4500
cacaggcata cccagtttta ttgcacgttg cagatactgc atttgtcaca aattgaaggt    4560
tgtggtaact ctgcatcaag caagtgtatc agtgccattt ttccaatagc atgtggtcac    4620
```

```
ttcatgtctc tgtatcacat tttggtaatt ctcaaaatat ttcaaacatt ttcattatta    4680
tcgtatctgt tatggtgatc tgtgatcagt gacgtttgat gttactattg taattgtttg    4740
gagctgtcat gaaccacacc gatataaggt ggcaaactta atggataaat gtatgtgttc    4800
tgacccaccg accagcagtt ccccatctct ctccctctcc ttgtgtctcc ctattccctg    4860
agacacagta ttgaaattag gttaattaat aacccttaca atggcctcta tgtgttcaaa    4920
tgaaaggaag agtcacacat ctctcacttc aaatcaaaag ctagaaatga ttaagcctac    4980
tgaggaaggc atgttgaaag ccaagacaag ttgaaagcta ggcctctttc accaaacaac    5040
caacttgtta aaacaaagaa aaagttttgg aggaaattaa agtactact ccactgaacg      5100 caccattgat gagaaagtga acagccttat tgctggtat ggagaaagtt tttgtactct      5160
gaatagaaga tcaaatcgtt aaaagatgag gaaatttcca gtaggaaaaa aagaagatca    5220
aaccagccac aacattccct taagccaaag cctaatccag agaaaggccc tcaacatcaa    5280
ggcaagacac tccaccagca caaatattac aacttgttga aggatgatat aatcgttagc    5340
attttttagt aataaagtat ttttaattag ggtacataca ttgtttttta gacataatgc    5400
tattccacac ttaagttaca acgtaaacat aactttata tgcactggga aaccaaaaaa     5460
ttcatgtgac ttactttatt gcaatattca ctttattgta gtggtctgga actgaaccca    5520
caatatttct gaggtatgcc tgtaacaact ttggagtcag acaggcaagg tcctagcttt    5580
ccacttacta gttgtataaa cttttcattt ctctgaacct ctgtaatttc atgtataagg    5640
agaataatgc tatctatgtt atgggttact gtgaggacca aataagaaaa tgcacatgaa    5700
atactcagca cagttccaaa gtaaaataaa tgttcaataa agggtagcta ttgtcattct    5760
ttcaactaaa atttgagtgg tgactctgtc tcaggtacac aagaataaat cagtcatagt    5820
cctgtcctca tgaatctcac agtacagttt cttgagcttt ttgactgcaa caaagaaata    5880
acattttata tcatgaccca gtacatatac atgcatttta tttaaatatt taaaacaaaa    5940
ggttcattaa atagtactta ctcttattac atacaatgta ctataatatt ttctttttt     6000 ttttcttgag acaggttctc actctgttac ccaggctgga gtgcaacggc atggtcttag    6060
ctcactgcaa tctctgcctc ccaggctaaa gcaattagtg tgcctcagcc ttccaagtag    6120
cttgtaccac aggcatgtgc caccatgttc agctaatgtt tttctgtttt gttttggttt    6180
ggtttggttt gttttggtag agacaggatt ttgccatgtt gcctaggctg gtctcgaact    6240
cccaaagtgc tgggattaca ggcgtgagac atcgtgccca gcctatgata ttttctagtt    6300
tatttcatct tgttttaaat gctgataatt gcctaatttc ataaccact agtgggttat       6360 gacctgtagt ttaaaaacta ctgtaggaaa gaatatagac aaaccaatga ttagagcaca    6420
gtttaatagc ctctatgata gatgaaatgc agaacactta gtactaagag agaataaagg    6480
aataaccaag ccagttctaa gcagttagaa gtagtgctca gaaaaaaact tcttggagga    6540
catgctatca aagttgagtt aaagtttgaa caaaaatttt taaaatactt tatccattat    6600
acaaaaaaaa tgtttatttt gcatctcttt atgaagacac caatgaaggg acaaaagtag    6660
taggtgcaat aaagaataag cctagagaaa agcttcaata tatagaatag cggtcagcaa    6720
acttttttta aaggaccaga tagtaatatt tttggcttga gtgcccaagt tgcctttgta    6780
gtagtcacag acaataagta aaagaatgag catggctgtg ttctaataaa actttgttta    6840
caaaaactga agccaggcac agtagcatgt gcctatggtc ccaggtatgc aggaggctga    6900
ggcaggagga tcccttgagt ctaccagttc aagaccagcc tgggcaacat agcgagaccc    6960
```

-continued

```
tgtcttattt aaaaaaaaaa aaaaaaaaaa aaaagggaac caaacaaaac accaaaactt      7020
tgttcacaaa aacaggcagc caccctgtgg actacagctt gccaagctct gatctagaag      7080
aaagagatta ccaaaacaga aaaagaaaa ccatgcccaa gtgttcaatg caaataaac       7140 aaatttgatt atttctaagt acctagtata caatactaaa aagaaaacaa taaggatatg     7200
tgaaggaaaa ataaccatta ccattttgct ccttcaattt atagcaaagc tgacccaaaa     7260
aagtataatc ctgtacatgt aatatttcag aagagcagta aaaggaggat tttatagaac     7320
agatggcaag tgaatgcatg aataacagca cttaccaata caactgcctt tggcctcatg    7380
gcttccactc acatttacaa acataagtgg ggaggatttc atgatatgct ggatgaaatc    7440
aagcaacatc acggaggttg gctgagagtc agttttcttt acaagttcta cagcaactaa    7500
aacaataaga ttcattttaa agagtcatga caaattaaac aatggtcctt ttgttaagaa    7560
accagactgt gggccaggca aggtgcctca ctcctgtaac ccctgtactt gggaggctg     7620 aagtgggcgg atcacctgag cccaggaact caagaccagc ctggataaga tgtcaagatc    7680
ccgtctctac aaaaaaaatt tttcttaaaa ttagctggga gtggtagtgt gcctatagtc    7740
ccagctactc aggggggctga ggctggagga ttcccttgag cccagaagtt caaggcagta   7800
gtgagctacg atcacactat tgcactccag cctggaacaa agcaagactc tgtctcttaa    7860
aattaaaaaa aaaaaatcaa aaaagtgggg tgggggtggg gaaccagact ttggtgacca    7920
gaattatatc cagcacagca ctcaacaaca ttcaagttaa attgatgggg ctaaacacta    7980
cagttttttt tttttttgaga cacagtctca ctgtgttgcc caggctggag tgtagtggtg    8040
tgatcttggc tcactgcaac ctgtgcctcc ggggtacaag tgattcttct gcctcagcct    8100
cctgagtagc taggactaca ggtgtgtgcc accacccca gctaattttg gtattttag       8160 tagagacagg gtttcgtcat gttggccagg ctggtctcaa actcctgacc tcaggtgatc    8220
cacccacctc ggcctcccaa agtgttggga ttacaggcgt gagccaccgt gcccagccaa    8280
cactacagtc ttatctaatt ttaaatgttt aaaaatcaca tgcattcctc taccatacat    8340
ctatttatca aacatgtact tcaggaataa atgccaggc aatgctaaaa tctaaggatt      8400
aaaaaaaagt tctcacaatc cagtggggcg ccaaacaaac caactaataa ttataataca    8460
atatggtaac agcactaatc cagaataagg agaaacaggt atctgggagg acactgtgaa    8520
ggaaatgatt cctagatgag gagttggtca gagaggggaa gggcaagtag tctaaacgga    8580
gggaatatga atacgataca aaacacatc ttgtaagtat tcagtagtcc tttgttattt      8640
ttcagcaacc catcatttta ctgattgaaa agaaaggat taatggctag tctaagtcat     8700
aaaatctgcg ccaaatttgg aatccaaatt ataaaccctg agcctaatgc cattttatat    8760
tatccctccc atgtaatttc aacagatatg acaaatgtga caccatcttg ccaggttggt    8820
aatattctgt ctagcagatt ggcacaaaca ggcaataatt gattcagtaa ctcacataat    8880
cctataattc tcctataggc caggcatgac ctacttaaag agtaacttac ttaaagaggt    8940
ttttttgggg gcatttgcta ttagtctacc actggcataa cagctaacca aaatagggtc   9000
cacatgattg gtactggaca aatatttta catataatat ccaatattaa agaactcata    9060
gcaagcagta gaaaatctag ataacaaaca ggaaaagaga attatttaa agcctaatt     9120 caaatttgt aacaagcaat aagcaatact gattaacaaa taacttgctt gaaaatagta   9180
actatcataa atactccata tctaaaacta catggagaaa atgctactat aatttataca   9240
tggaaaagaa aagtctaatt tataaagttt atataagaaa taattggttt cttaccaaca   9300
tttacatctg taagtatccg gtcaatgaat tgacacagaa tttgtcttgg cttctgtaca   9360
```

-continued

```
actgtattat attcctctgg tgtggcacta aaatacaaat taaaagcttt taatccttaa    9420
agtgactcag tttcatttgc aaaaaaaatt tctctaaagt agaactcatc aaatgtgttc    9480
agtgtcaatg ttgatattca cagtattctt ctgtttaaaa attgaaaaga aaatctgaat    9540
atgttaccaa cttacaagaa aaaaagaat  atgctaagta atactaaaga gatccaatca    9600
gcaaagccta gacctgaact tctcaatatg gtggccacta gctacaagta actagggaga    9660
acttgaaatg tgattagtac aaattgaaat gtgctattga tggcagtggc agcccagttg    9720
gagcggtgag gaaggtggtg ctagggctgc tctctccagg gcgctagtgg gcagaagccc    9780
cgccccttc  tgaggtgcaa gacaggtgga agccccgccc ccttccgagt tgcaggtcgg    9840
gagcccacca tcctgggtgc agctgcagcc cgcccaacca cggctgcaaa cccagcattc    9900
ctgctctttt caggccggg  aaggccccct gccctcacag acttggaaat gcctgctccc    9960
gctgcctggc ctctcccgc  tcccggcacc cacaccaatt tcggagcaaa gttgtggggg   10020
agcccaggtg ttgtcaggac caggccgcgt gtgcatgtgc tcaggacggc actgacacac   10080
cagcccctg  ctgcctcatc tccctctgga ctttgggcag gccaagcggt aggctgaggg   10140
cagctcaata tgggcctgca ggcgcccctc ggcacgaaca gcctcggtgt agtgggtggc   10200
aggttgatgg cagcaggaag taggctcctg ggaggaaagg ggtgggtccc cagtgaagac   10260
ccaccttcaa gccaggaaca gcttgaagcc tggaagcctg gctgccagtt acacggacca   10320
cagcgagaac ttagggtgct ttttccaggc ccacccatga ctgcctatgg accaattagc   10380
attcacttcc tcccttctga agcacataaa aactaaattt ttggtggaac gctaatccc    10440
ttttccacag tggctgtacc attgtacact cccacctgca gtggacaagg gttccaattt   10500
ctccacatct tcaccaacac acgttatttt ctgggtgttt ttttattatt atttattttt   10560
cccctttgg  cgacagggtc taaccctgtt gcccaggtta ctgtgcagtg gtgcacccat   10620
aactcactgc agcctcaacc tcccagcctc aggagatcct cccacctcag cctcctgagt   10680
agctggcacc acaggtgcat gtcaccacac ccagctaatt ttttgtattt tttgtagaga   10740
cagggtttca ccacgttgcc caggctggtc tcaatctcct gggctcaagc gatctgcctg   10800
ctttgacctc ccaaagtgct gggattgtag gcatgagtca ccatgcccaa ctgtgttttt   10860
tttttgtggg attttttttg tttttttggtt tttttgaga cagagtcttg ctctgtcacc   10920
aggctggagt gcagggcatg atctcaactc actgcaacct ctgtctcccg ggttcaagca   10980
attctcctgc ctcagcctct caagtagctg gtactacagg catgcaccac catgcctggc   11040
taatttttg  tattttagta gagatggggt tttaccatgt tggccaggat ggtctcaatc   11100
tcctgacctc gtgatccgcc tgcctcagcc tcccaaagtg ctgggattac aggcatcagc   11160
caacatgccc agccccaact gttttttttat taatagctat cataatgggt gtgaaacagt   11220
atcctgtggt tttgatttgc atctccctaa tgattagtaa ttgtgagcat cttctcatgt   11280
gcttatttgt ccatttgtat atcttctttg gagaaatgtc tattcaagtt cttttttctgt   11340
ttttcatcag gttatatttg ttgttaagct gtaggagttc ttaatatatt ctagatatta   11400
aactccttat cagacatatg atttgcaaat attttctcca gttccatggg ttgccttttc   11460
actctattga tactgccctt tgatgcacaa agttttttaat tttgatgaat tccaatttat   11520
ctgtttattt tgctgcctgt gctttgtgtc atatcaaaga aatcattgcc aaatccagtg   11580
tcataatgtt ttccctctat gttccctat  ttttatttat ttatttactt tttgagacag   11640
agtttcactc ttgttgccca ggctggagtg caatggcgcg atctcagctc accgcaacct   11700
```

-continued

| | |
|---|---|
| ccgcctcctg ggttcaagcg attctcctgc ctcagcctcc tgagtagctg cgattacaag | 11760 |
| catgtaccac cacgcctggc taattttgta tattttagt agagacaggg tttctccatg | 11820 |
| ttggtcaggc tagtctggaa ctcctgacct caggtgatcc acccatcttg gcctcccaaa | 11880 |
| gtgctgggat tataggtgtg agccaccatg cccggccccc tctatgttca cttctaagag | 11940 |
| tttcatagtt ttagttctta tgtttaggta tttgtatgcc ttttggactt ttaaaatttt | 12000 |
| cctgtagcag taaagagaga agccagattg caaggggctg aaaatctaat gaaatgtgaa | 12060 |
| tactgagaat agcgggttct ttccaaagct tgatcatgaa atgaagagaa gtagagttgg | 12120 |
| tgataactaa agaactgtat gagatcaaga gggctttgtt ttgtttctcc cttataatgg | 12180 |
| aaagacctaa gcaaccaatt cttgagatgt gactcctctt cttggaacca gatataagta | 12240 |
| aaaagacaat ccttggacag gagggtaact ctttcataaa catagaaaga atggatgggt | 12300 |
| acagacgcaa ataatttaat aaattcaaaa ggcaagtaaa acaagatcct ctgcttcaaa | 12360 |
| gaactcagaa tagttgctgg ggagaggaga ggaatgcact taaataatca aaagccgccg | 12420 |
| ggcctggtgg | 12430 |

<210> SEQ ID NO 27
<211> LENGTH: 14405
<212> TYPE: DNA
<213> ORGANISM: Artificial Sequence
<220> FEATURE:
<223> OTHER INFORMATION: Description of Artificial Sequence: Synthetic Knockout Construct

<400> SEQUENCE: 27

| | |
|---|---|
| gatcttcaaa tgaactgttt actacagaag cacaaaataa gtcattaatt ataacttttc | 60 |
| cttaatcata tctcttttaa ataaaaataa agacatttga aatactatca taatgatcat | 120 |
| tggataagca gaaattctta acacagagat ctataaacga tggtctgagg tctgtgaacc | 180 |
| caaagaaatt aaatgtgact ttataaaaac atgttatcta tgcctgtttt aaagaagaat | 240 |
| cacggcattc ctcaaactcc caaattaaaa aactttgaag ttataaataa tttctattga | 300 |
| ctaaagaatc aaaatattat gcacataaat tggcaactca gaacttctat tattgacaaa | 360 |
| tttaatagaa ctgaaatcag gaaaaaactt ctgagtattc caaacacgca cttaggcttc | 420 |
| aggcaaaaaa gaaagcatat ttctatactg attatcttta aaggtattct gatctgttgc | 480 |
| taatttgtct caccttgcat ataaatcaaa gcatcataaa ttttcaccac cttatcaatg | 540 |
| gttgcctcca ggtccagttt ctgaacagat tctaacaaac ttctacagct cttaagcact | 600 |
| tttgtgtaaa atccaatga catccaagtt atcactacag aaggtttctt cttggattta | 660 |
| tgttgacagt ccttgaaagt acggctgcag taagtacatt ttgttaaaaa cattggaatt | 720 |
| aagatgaatt ttgttatagt caaacataaa attgtagtaa agccaaaaga aattgtgagt | 780 |
| acgaaattta tctataacaa tttaaagtaa acatgcaaat caagtaatat gttattacta | 840 |
| ttttaagttg aatctatta tgtcagctta aatcacccctt aggatttggg aaccaaatga | 900 |
| ctttgggagc tgaggtggg aggatcactt gagcccagga gtttgagacc agccgggcca | 960 |
| atataggga acccatctct acaaaaaaaa ttttttctaa attagggtgt ggcggcacat | 1020 |
| gcctatagtt ccagctacat gggaggctca cttgagcccc ggatagagat caaggctgta | 1080 |
| gtgagccatg atcatgccac tgtgcaccag cctgggagac aaagcgagac cctgtcttca | 1140 |
| acagccaaac actgggtttt gagttgtaca caaatgtgtt ctggtacttt ctaatcatgt | 1200 |
| gtccccagga aagtcagttt tggcttcaga caaaaaagag cctcagtttc tctgagtgtc | 1260 |

-continued

```
agtttctaat ttttaaaata ggcataatag cctttacctt acaggactat tgtaaatatt    1320
aactaagata tatacagtgc ttagcaccgt acctagcatt tgactcaata gaaaataaat    1380
ttattaacta cttcagtgaa aagtttgtgt tctaaggtta catgagtcaa gtgaataatg    1440
agtaaacagt aaatccaagt tcattacagg aaacccaacc ccaagaaaca agaagtttgt    1500
tttaccagtt catgttttga tgagaacaat gaacagtaca cagagcagtc agttgtaaga    1560
caacagcaat tccttctaac atctcaataa caggattctt taggccactg tattcaaggg    1620
aaatctgaag ggattcagct ttctgtttca gtgcactcca taatatgctc ttttgggtca    1680
tgtccacatg tttaattcta taattatgaa tatagtagag agatattcat atgccatata    1740
aatttggtta aaacatgaaa catatttaga ataaaacata ctatgtaata tcaactattc    1800 aaaaaattt ttttttttg tgagacagag tctcactctg tctcccaggc tggagtgcag    1860
tggcgccatc tcggctcact gcaagctccg cctcccgggt tcacgccatt ctcctgcctc    1920
agcctcccga gtagctggga ctacaggcgc caaccaccac gcttggctaa ttttttgtat    1980
ttttagtaga gacagggttt caccgtgtta gccaggatga tctcgatctt ctgacctcgt    2040
gatctgcccg cctcggcctc ccaaagtgct gggattacag gcgtgagcca ccgcgcccag    2100
cctgaaattt atactaagat ttaaaacaat taaaacaatg ttcagaagta actgaaatat    2160
ggcaacttag ccactttata aaaaatagtt ggttaatgtt ttaaaaattg ctaatagatg    2220
cacagtctca aagattttc acatattaaa aagttaaatt agataagcat ataaaaacat    2280
gcaaagtaac tatatttaac catgaaatgt tttatactac taaccgtcta caataattat    2340 aaaaatatt taagcactcc cttggctaca tttagaaaga tggtctttgg atttaaatca    2400
aagcacttaa ctaaagctga tttttaaaag tgaacaaagt tttatttaat ggctaaatac    2460
aaactgaatg aaggcatcat acttcctcag tctgttttgg tgctctttta gaagggttta    2520
gagacgagct gagacgacgc cttttgggtg atattccatc actattactg ctgaggtttt    2580
cctgttgagt ttggcattga atctcctcaa tgatttccat actttccatt ttcaaagctg    2640
cataaagtgg gcccaacaag tactgagaaa ataaaaaata atttccagaa atattcctta    2700
gaaaatatat ttatattatt cataggcagc aagaatgtat tagatgttag gtgttttcta    2760
gtgaaactac ttttagagtc tcataaagca aaataaacat ctaaattgat ctatattatt    2820
taagtctata tatagactat ggttctatag tcttagaagg tttaaacaaa tccttctctc    2880
tacatcctgt ttttcctctt accaaaatgc tataaatttt aattcccta taaaaaattc    2940 tgtaagggaa ttaccaactt tcttcatgta actttaatcc agcaagatta ataaactaaa    3000
atatttaatc aagttactgc atctctgatg attttattgt attacctgac tcccacagtc    3060
caaatagaaa aaagcgcata atttggcatg attaatcatt cataggtttt ctaaaagtga    3120
ttgattataa cttgtcagac acataatctg attgaccaaa gcttctgcaa ttaagttggt    3180 aactgcccc ttttaattaa taatgcaaca aatacattta cacttcacag attctactta    3240
gaaacattct actccattgg cagttcatta ccaacttaat gaacaaatcc ttctgaaatc    3300
aaagtaaaag tccataatag tgagccagac tacactatga aaatcattat gttccaaata    3360
taaattacta ttaaagatat tctattttct tattattaca ttttgcacat atgtatacaa    3420
ttaaatgatg aacaaaatac atacttaact agtaacctga aaaattactt acctctgcat    3480
ctacctcaat tccaagcaca tccaaaagag ctttacaaat atttctcaca tagaccttcc    3540
tgacttgtaa agcagattca tacccagctg gcacaaattt aaggaaatac tgcagtaaat    3600
ggcacaaagc tgcttttagc aaatcagact taagccgcat gagcacaccg tcttcaaaca    3660
```

```
tgacacagag ttttttccagc agcatattta aatagacagg ttcaatatttt ctataagctt    3720 ctgcttcaaa gggaaatagt gtctttatca gctttgataa tggctcttca tagagtttca    3780
attggtcagt atccatttct acaaggtgtt ttaataattc caaaaatgag ctgaaaaaag    3840
tgctagctgg ttgtgctggt agtcctccaa gctgaaaaaa gtctgttaaa agctaattgc    3900 tagggatttta atttttggac taccatactc tagcagaaca caacctatct gccaaagtaa    3960
gagttcttgc cttctaaaaa acacaattgc aataatacga gtaagaacca ttaataaagt    4020
gacttcaata aattctaaat tttgcatact catcaactgc aaaggagctg attgtaaata    4080
tcccatgtgt tcatctaatt gacttaaaaa tcggctcatg accactggcc attccacagc    4140
atgacccatc acatttcttc tatggaggta accaagtct tcaaaaagtt gtaataattc    4200
ttttgtgagt accccaaaaa tagcaggact cttgctttta aaagaaata ataatgaaca    4260 gatgacttca cagatttttct tgtgtaacaa atgacaggag ggagttgctg caatccgcag    4320
aagtctcgtt atgatccaat tactgaattc tttgaaataa acaaaaaga tattaaataa    4380 acaagtatat ccgaagtgct aattcatttg ctaaatcctt gacgattgac ttttaaagaa    4440
taaacttcac taacaagagt gtaaaacatt ctcttcacaa tggaaacata atagtttaaa    4500
cacaggcata cccagtttta ttgcacgttg cagatactgc atttgtcaca aattgaaggt    4560
tgtggtaact ctgcatcaag caagtgtatc agtgccattt ttccaatagc atgtggtcac    4620
ttcatgtctc tgtatcacat tttggtaatt ctcaaaatat ttcaaacatt tcattatta    4680 tcgtatctgt tatggtgatc tgtgatcagt gacgtttgat gttactattg taattgtttg    4740
gagctgtcat gaaccacacc gatataaggt ggcaaactta atggataaat gtatgtgttc    4800
tgacccaccg accagcagtt ccccatctct ctccctctcc ttgtgtctcc ctattccctg    4860
agacacagta ttgaaattag gttaattaat aacccttaca atggcctcta tgtgttcaaa    4920
tgaaaggaag agtcacacat ctctcacttc aaatcaaaag ctagaaatga ttaagcctac    4980
tgaggaaggc atgttgaaag ccaagacaag ttgaaagcta ggcctctttc accaaacaac    5040
caacttgtta aaacaaagaa aaagttttgg aggaaattaa aagtactact ccactgaacg    5100
caccattgat gagaaagtga aacagcctta ttgctggtat ggagaaagtt tttgtactct    5160
gaatagaaga tcaaatcgtt aaaagatgag gaaatttcca gtaggaaaaa aagaagatca    5220
aaccagccac aacattccct taagccaaag cctaatccag agaaaggccc tcaacatcaa    5280
ggcaagacac tccaccagca caaatattac aacttgttga aggatgatat aatcgttagc    5340 atttttttagt aataaagtat tttttaattag ggtacataca ttgttttttta gacataatgc    5400 tattccacac ttaagttaca acgtaaacat aacttttata tgcactggga aaccaaaaaa    5460
ttcatgtgac ttactttatt gcaatattca ctttattgta gtggtctgga actgaaccca    5520
caatatttct gaggtatgcc tgtaacaact ttggagtcag acaggcaagg tcctagcttt    5580
ccacttacta gttgtataaa cttttcattt ctctgaacct ctgtaatttc atgtataagg    5640
agaataatgc tatctatgtt atgggttact gtgaggacca aataagaaaa tgcacatgaa    5700
atactcagca cagttccaaa gtaaaataaa tgttcaataa agggtagcta ttgtcattct    5760
ttcaactaaa atttgagtgg tgactctgtc tcaggtacac aagaataaat cagtcatagt    5820
cctgtcctca tgaatctcac agtacagttt cttgagcttt ttgactgcaa caaagaaata    5880
acattttata tcatgaccca gtacatatac atgcatttta tttaaatatt taaacaaaa    5940 ggttcattaa atagtactta ctcttattac atacaatgta ctataatatt ttctttttttt    6000
```

-continued

```
ttttcttgag acaggttctc actctgttac ccaggctgga gtgcaacggc atggtcttag      6060
ctcactgcaa tctctgcctc ccaggctaaa gcaattagtg tgcctcagcc ttccaagtag      6120
cttgtaccac aggcatgtgc caccatgttc agctaatgtt tttctgtttt gttttggttt      6180
ggtttggttt gttttggtag agacaggatt ttgccatgtt gcctaggctg gtctcgaact      6240
cccaaagtgc tgggattaca ggcgtgagac atcgtgccca gcctatgata ttttctagtt      6300
tatttcatct tgttttaaat gctgataatt gcctaatttc ataacccact agtgggttat      6360
gacctgtagt ttaaaaacta ctgtaggaaa gaatatagac aaaccaatga ttagagcaca      6420
gtttaatagc ctctatgata gatgaaatgc agaacactta gtactaagag agaataaagg      6480
aataaccaag ccagttctaa gcagttagaa gtagtgctca gaaaaaaact tcttggagga      6540
catgctatca aagttgagtt aaagtttgaa caaaaatttt aaaatactt tatccattat       6600 acaaaaaaaa tgtttatttt gcatctcttt atgaagacac caatgaaggg acaaaagtag      6660
taggtgcaat aaagaataag cctagagaaa agcttcaata tatagaatag cggtcagcaa      6720
acttttttta aaggaccaga tagtaatatt tttggcttga gtgcccaagt tgcctttgta      6780
gtagtcacag acaataagta aaagaatgag catggctgtg ttctaataaa actttgttta      6840
caaaaactga agccaggcac agtagcatgt gcctatggtc ccaggtatgc aggaggctga      6900
ggcaggagga tccctggagt ctaccagttc aagaccagcc tgggcaacat agcgagaccc      6960
tgtcttattt aaaaaaaaaa aaaaaaaaa aaagggaac caaacaaaac accaaaactt        7020
tgttcacaaa aacaggcagc caccctgtgg actacagctt gccaagctct gatctagaag      7080
aaagagatta ccaaaacaga aaaagaaaa ccatgcccaa gtgttcaatg gcaaataaac       7140
aaatttgatt atttctaagt acctagtata caatactaaa agaaaacaa taaggatatg       7200 tgaaggaaaa ataaccatta ccattttgct ccttcaattt atagcaaagc tgacccaaaa      7260
aagtataatc ctgtacatgt aatatttcag aagagcagta aaaggaggat tttatagaac      7320
agatggcaag tgaatgcatg aataacagca cttaccaata caactgcctt tggcctcatg      7380
gcttccactc acatttacaa acataagtgg ggaggatttc atgatatgct ggatgaaatc      7440
aagcaacatc acggaggttg gctgagagtc agttttcttt acaagttcta cagcaactaa      7500
aacaataaga ttcattttaa agagtcatga caaattaaac aatggtcctt ttgttaagaa      7560
accagactgt gggccaggca aggtgcctca ctcctgtaac ccctgtactt tgggaggctg      7620
aagtgggcgg atcacctgag cccaggaact caagaccagc ctggataaga tgtcaagatc      7680
ccgtctctac aaaaaaaatt tttcttaaaa ttagctggga gtggtagtgt gcctatagtc      7740
ccagctactc agggggctga ggctggagga ttcccttgag cccagaagtt caaggcagta      7800
gtgagctacg atcacactat tgcactccag cctggaacaa agcaagactc tgtctcttaa      7860
aattaaaaaa aaaaaatcaa aaagtgggg tggggtggg gaaccagact ttggtgacca       7920
gaattatatc cagcacagca ctcaacaaca ttcaagttaa attgatgggg ctaaacacta      7980
cagttttttt tttttgaga cacagtctca ctgtgttgcc caggctggag tgtagtggtg      8040
tgatcttggc tcactgcaac ctgtgcctcc ggggtacaag tgattcttct gcctcagcct      8100
cctgagtagc taggactaca ggtgtgtgcc accacaccca gctaattttg gtatttttag      8160
tagagacagg gtttcgtcat gttggccagg ctggtctcaa actcctgacc tcaggtgatc      8220
cacccacctc ggcctcccaa agtgttggga ttacaggcgt gagccaccgt gcccagccaa      8280
cactacagtc ttatctaatt ttaaatgttt aaaaatcaca tgcattcctc taccatacat      8340
ctatttatca aacatgtact tcaggaataa tatgccaggc aatgctaaaa tctaaggatt      8400
```

-continued

```
aaaaaaaagt tctcacaatc cagtggggcg ccaaacaaac caactaataa ttataataca      8460
atatggtaac agcactaatc cagaataagg agaaacaggt atctgggagg acactgtgaa      8520
ggaaatgatt cctagatgag gagttggtca gagaggggaa gggcaagtag tctaaacgga      8580
gggaatatga atacgataca aaaacacatc ttgtaagtat tcagtagtcc tttgttattt      8640
ttcagcaacc catcatttta ctgattgaaa agaaaggat taatggctag tctaagtcat      8700
aaaatctgcg ccaaatttgg aatccaaatt ataaaccctg agcctaatgc cattttatat      8760
tatccctccc atgtaatttc aacagatatg acaaatgtga caccatcttg ccaggttggt      8820
aatattctgt ctagcagatt ggcacaaaca ggcaataatt gattcagtaa ctcacataat      8880
cctataattc tcctataggc caggcatgac ctacttaaag agtaacttac ttaaagaggt      8940 tttttttgggg gcatttgcta ttagtctacc actggcataa cagctaacca aaatagggtc      9000
cacatgattg gtactggaca atatttttta catataatat ccaatattaa agaactcata      9060
gcaagcagta gaaaaagaat aacttcgtat agcatacatt atacgaagtt atgagctcag      9120
ataacaaaca ggaaaagaga attattttaa agcctaatt caaattttgt aacaagcaat      9180
aagcaatact gattaacaaa taacttgctt gaaaatagta actatcataa atactccata      9240
tctaaaacta catggagaaa atgctactat aatttataca tggaaaagaa aagtctaatt      9300
tataaagttt atataagaaa taattggttt cttaccaaca tttacatctg taagtatccg      9360
gtcaatgaat tgacacagaa tttgtcttgg cttctgtaca actgtattat attcctctgg      9420
tgtggcacta aaatacaaat taaaagcttt taatccttaa agtgactcag tttcatttgc      9480
aaaaaaaatt tctctaaagt agaactcatc aaatgtgttc agtgtcaatg ttgatattca      9540
cagtattctt ctgtttaaaa attgaaaaga aaatctgaat atgttaccaa cttcaagaa      9600 aaaaagaat atgctaagta atactaaaga gatccaatca gcaaagccta gacctgaact      9660
tctcaatatg gtggccacta gctacaagta actaggagga acttgaaatg tgattagtac      9720
aaattgaaat gtgctattga tggcagtggc agcccagttg gagcggtgag gaaggtggtg      9780
ctagggctgc tctctccagg gcgctagtgg gcagaagccc cgccccttc tgaggtgcaa      9840 gacaggtgga agccccgccc ccttccgagt tgcaggtcgg gagcccacca tcctgggtgc      9900
agctgcagcc gcccaaccac ggctgcaaac ccaggcatcc ctgctctttt cagggccggc      9960
cgctctagta aacttcgta tagcatacat tatacgaagt tatactagat aacaaacagg      10020
aaaagagaat tattttaaaa gcctaattca aattttgtaa caagcaataa gcaatactga      10080
ttaacaaata acttgcttga aaatagtaac tatcataaat actccatatc taaaactaca      10140
tggagaaaat gctactataa tttatacatg gaaaagaaaa gtctaattta taagtttat      10200 ataagaaata attggtttct taccaacatt tacatctgta agtatccggt ccatggtggg      10260
ccccctagaa aaaccctccc acacctcccc ctgaacctga acataaaat gaatgcaatt      10320 gttgttgtta acttgtttat tgcagcttat aatggttaca aataaagcaa tagcatcaca      10380
aatttcacaa ataaagcatt tttttcactg cattctagtt gtggtttgtc caaactcatc      10440
aatgtatctt atcatgtctg gatcctagaa gaactcgtca agaaggcgat agaaggcgat      10500
gcgctgcgaa tcgggagcgg cgataccgta agcacgagg aagcggtcag cccattcgcc      10560
gccaagctct tcagcaatat cacgggtagc caacgctatg tcctgatagc ggtccgccac      10620
acccagccgg ccacagtcga tgaatccaga aaagcggcca ttttccacca tgatattcgg      10680
caagcaggca tcgccgtggg tcacgacgag atcctcgccg tcgggcatgc gcgccttgag      10740
```

```
cctggcgaac agttcggctg gcgcgagccc ctgatgctct tcgtccagat catcctgatc   10800
gacaagaccg gcttccatcc gagtacgtgc tcgctcgatg cgatgtttcg cttggtggtc   10860
gaatgggcag gtagccggat caagcgtatg cagccgccgc attgcatcag ccatgatgga   10920
tactttctcg gcaggagcaa ggtgagatga caggagatcc tgccccggca cttcgcccaa   10980
tagcagccag tcccttcccg cttcagtgac aacgtcgagc acagctgcgc aaggaacgcc   11040
cgtcgtggcc agccacgata gccgcgctgc ctcgtcctgc agttcattca gggcaccgga   11100
caggtcggtc ttgacaaaaa gaaccgggcg ccctgcgct  gacagccgga acacggcggc   11160
atcagagcag ccgattgtct gttgtgccca gtcatagccg aatagcctct ccacccaagc   11220
ggccggagaa cctgcgtgca atccatcttg ttcagccatg gattgacaca gaatttgtct   11280
tggcttctgt acaactgtat tatattcctc tggtgtggca ctaaaataca aattaaaagc   11340
ttttaatcct taaagtgact cagtttcatt tgcaaaaaaa atttctctaa gtagaactc    11400 atcaaatgtg ttcagtgtca atgttgatat tcacagtatt cttctgttta aaaattgaaa   11460
agaaaatctg aatatgttac caacttacaa gaaaaaaag  aatatgctaa gtaatactaa   11520
agagatccaa tcagcaaagc ctagacctga acttctcaat atggtggcca ctagctacaa   11580
gtaactaggg agaacttgaa atgtgattag tacaaattga aatgtgctat tgatggcagt   11640
ggcagcccag ttggagcggt gaggaaggtg gtgctagggc tgctctctcc agggcgctag   11700
tgggcagaag ccccgccccc ttctgaggtg caagacaggt ggaagcccg ccccttccg    11760 agttgcaggt cgggagccca ccatcctggg tgcagctgca gcccgcccaa ccacggctgc   11820
aaacccagca ttcctgctct tttcagggcc gggaataact tcgtatagca tacattatac   11880
gaagttatgg aaggcccct  gccctcacag acttggaaat gcctgctccc gctgcctggc   11940
ctctccccgc tcccggcacc cacaccaatt tcggagcaaa gttgtggggg agcccaggtg   12000
ttgtcaggac caggccgcgt gtgcatgtgc tcaggacggc actgacacac cagcccctg    12060 ctgcctcatc tccctctgga cttttgggcag gccaagcggt aggctgaggg cagctcaata   12120
tgggcctgca ggcgcccctc ggcacgaaca gcctcggtgt agtgggtggc aggttgatgg   12180
cagcaggaag taggctcctg ggaggaaagg ggtgggtccc cagtgaagac ccaccttcaa   12240
gccaggaaca gcttgaagcc tggaagcctg gctgccagtt acacggacca cagcgagaac   12300
ttagggtgct tttccaggc  ccacccatga ctgcctatgg accaattagc attcacttcc   12360
tcccttctga agcacataaa aactaaattt ttggtggaac gctaataccc ttttccacag   12420
tggctgtacc attgtacact cccacctgca gtggacaagg gttccaattt ctccacatct   12480
tcaccaacac acgttatttt ctgggtgttt ttttattatt attttatttt cccttttgg    12540 cgacagggtc taaccctgtt gcccaggtta ctgtgcagtg gtgcactgca cccataactc   12600
actgcagcct caacctccca gcctcaggag atcctcccac ctcagcctcc tgagtagctg   12660
gcaccacagg tgcatgtcac cacacccagc taatttttg  tatttttgt  agagacaggg   12720 tttcaccacg ttgcccaggc tggtctcaat ctcctgggct caagcgatct gcctgctttg   12780
acctcccaaa gtgctgggat tgtaggcatg agtcaccatg cccaactgtg tttttttttt   12840
gtgggatttt ttttgttttt tggttttttt tgagacagag tcttgctctg tcaccaggct   12900
ggagtgcagg gcatgatctc aactcactgc aacctctgtc tcccgggttc aagcaattct   12960
cctgcctcag cctctcaagt agctggtact acaggcatgc accaccatgc ctggctaatt   13020
ttttgtattt tagtagagat ggggttttac catgttggcc aggatggtct caatctcctg   13080
acctcgtgat ccgcctgcct cagcctccca aagtgctggg attacaggca tcagccaaca   13140
```

-continued

```
tgcccagccc caactgtttt tttattaata gctatcataa tgggtgtgaa acagtatcct   13200
gtggttttga tttgcatctc cctaatgatt agtaattgtg agcatcttct catgtgctta   13260
tttgtccatt tgtatatctt ctttggagaa atgtctattc aagttctttt tctgtttttc   13320
atcaggttat atttgttgtt aagctgtagg agttcttaat atattctaga tattaaactc   13380
cttatcagac atatgatttg caaatatttt ctccagttcc atgggttgcc ttttcactct   13440
attgatactg ccctttgatg cacaaagttt ttaattttga tgaattccaa tttatctgtt   13500
tattttgctg cctgtgcttt gtgtcatatc aaagaaatca ttgccaaatc cagtgtcata   13560
atgttttccc tctatgttcc cttatttta tttatttatt tactttttga gacagagttt   13620
cactcttgtt gcccaggctg gagtgcaatg gcgcgatctc agctcaccgc aacctccgcc   13680
tcctgggttc aagcgattct cctgcctcag cctcctgagt agctgcgatt acaagcatgt   13740
accaccacgc ctggctaatt ttgtatattt ttagtagaga cagggtttct ccatgttggt   13800
caggctagtc tggaactcct gacctcaggt gatccaccca tcttggcctc ccaaagtgct   13860
gggattatag gtgtgagcca ccatgcccgg cccctctat gttcacttct aagagtttca   13920
tagttttagt tcttatgttt aggtatttgt atgccttttg gacttttaaa attttcctgt   13980
agcagtaaag agagaagcca gattgcaagg ggctgaaaat ctaatgaaat gtgaatactg   14040
agaatagcgg gttctttcca aagcttgatc atgaaatgaa gagaagtaga gttggtgata   14100
actaaagaac tgtatgagat caagagggct ttgttttgtt tctcccttat aatggaaaga   14160
cctaagcaac caattcttga gatgtgactc ctcttcttgg aaccagatat aagtaaaaag   14220
acaatccttg gacaggaggg taactctttc ataaacatag aaagaatgga tgggtacaga   14280
cgcaaataat ttaataaatt caaaaggcaa gtaaaacaag atcctctgct tcaaagaact   14340
cagaatagtt gctggggaga ggagaggaat gcacttaaat aatcaaaagc cgccgggcct   14400
ggtgg                                                                14405
```

<210> SEQ ID NO 28
<211> LENGTH: 6
<212> TYPE: DNA
<213> ORGANISM: Homo sapiens

<400> SEQUENCE: 28 aataaa                                                                6

<210> SEQ ID NO 29
<211> LENGTH: 791
<212> TYPE: PRT
<213> ORGANISM: Homo sapiens

<400> SEQUENCE: 29

Met Ala Gly Thr Ser Ala Pro Gly Ser Lys Arg Arg Ser Glu Pro Pro
 1               5                  10                  15

Ala Pro Arg Pro Gly Pro Pro Gly Thr Gly His Pro Pro Ser Lys
                20                  25                  30

Arg Ala Arg Gly Phe Ser Ala Ala Ala Pro Asp Pro Asp Pro
            35                  40                  45

Phe Gly Ala His Gly Asp Phe Thr Ala Asp Leu Glu Glu Leu Asp
        50                  55                  60

Thr Leu Ala Ser Gln Ala Leu Ser Gln Cys Pro Ala Ala Ala Arg Asp
65                  70                  75                  80

Val Ser Ser Asp His Lys Val His Arg Leu Leu Asp Gly Met Ser Lys

-continued

```
                85                  90                  95
Asn Pro Ser Gly Lys Asn Arg Glu Thr Val Pro Ile Lys Asp Asn Phe
            100                 105                 110
Glu Leu Glu Val Leu Gln Ala Gln Tyr Lys Glu Leu Lys Glu Lys Met
            115                 120                 125
Lys Val Met Glu Glu Val Leu Ile Lys Asn Gly Glu Ile Lys Ile
            130                 135                 140
Leu Arg Asp Ser Leu His Gln Thr Glu Ser Val Leu Glu Glu Gln Arg
145                 150                 155                 160
Arg Ser His Phe Leu Leu Glu Gln Glu Lys Thr Gln Ala Leu Ser Asp
                165                 170                 175
Lys Glu Lys Glu Phe Ser Lys Lys Leu Gln Ser Leu Gln Ser Glu Leu
            180                 185                 190
Gln Phe Lys Asp Ala Glu Met Asn Glu Leu Arg Thr Lys Leu Gln Thr
            195                 200                 205
Ser Glu Arg Ala Asn Lys Leu Ala Ala Pro Ser Val Ser His Val Ser
            210                 215                 220
Pro Arg Lys Asn Pro Ser Val Val Ile Lys Pro Glu Ala Cys Ser Pro
225                 230                 235                 240
Gln Phe Gly Lys Thr Ser Phe Pro Thr Lys Glu Ser Phe Ser Ala Asn
                245                 250                 255
Met Ser Leu Pro His Pro Cys Gln Thr Glu Ser Gly Tyr Lys Pro Leu
                260                 265                 270
Val Gly Arg Glu Asp Ser Lys Pro His Ser Leu Arg Gly Asp Ser Ile
            275                 280                 285
Lys Gln Glu Glu Ala Gln Lys Ser Phe Val Asp Ser Trp Arg Gln Arg
            290                 295                 300
Ser Asn Thr Gln Gly Ser Ile Leu Ile Asn Leu Leu Leu Lys Gln Pro
305                 310                 315                 320
Leu Ile Pro Gly Ser Ser Leu Ser Leu Cys His Leu Leu Ser Ser Ser
                325                 330                 335
Ser Glu Ser Pro Ala Gly Thr Pro Leu Gln Pro Pro Gly Phe Gly Ser
            340                 345                 350
Thr Leu Ala Gly Met Ser Gly Leu Arg Thr Thr Gly Ser Tyr Asp Gly
            355                 360                 365
Ser Phe Ser Leu Ser Ala Leu Arg Glu Ala Gln Asn Leu Ala Phe Thr
            370                 375                 380
Gly Leu Asn Leu Val Ala Arg Asn Glu Cys Ser Arg Asp Gly Asp Pro
385                 390                 395                 400
Ala Glu Gly Gly Arg Arg Ala Phe Pro Leu Cys Gln Leu Pro Gly Ala
                405                 410                 415
Val His Phe Leu Pro Leu Val Gln Phe Phe Ile Gly Leu His Cys Gln
            420                 425                 430
Ala Leu Gln Asp Leu Ala Ala Lys Arg Ser Gly Ala Pro Gly Asp
            435                 440                 445
Ser Pro Thr His Ser Ser Cys Val Ser Ser Gly Val Glu Thr Asn Pro
            450                 455                 460
Glu Asp Ser Val Cys Ile Leu Glu Gly Phe Ser Val Thr Ala Leu Ser
465                 470                 475                 480
Ile Leu Gln His Leu Val Cys His Ser Gly Ala Val Val Ser Leu Leu
                485                 490                 495
Leu Ser Gly Val Gly Ala Asp Ser Ala Ala Gly Glu Gly Asn Arg Ser
            500                 505                 510
```

-continued

```
Leu Val His Arg Leu Ser Asp Gly Asp Met Thr Ser Ala Leu Arg Gly
            515                 520                 525
Val Ala Asp Asp Gln Gly Gln His Pro Leu Leu Lys Met Leu Leu His
        530                 535                 540
Leu Leu Ala Phe Ser Ala Ala Thr Gly His Leu Gln Ala Ser Val
545                 550                 555                 560
Leu Thr Gln Cys Leu Lys Val Leu Val Lys Leu Ala Glu Asn Thr Ser
                565                 570                 575
Cys Asp Phe Leu Pro Arg Phe Gln Cys Val Phe Gln Val Leu Pro Lys
            580                 585                 590
Cys Leu Ser Pro Glu Thr Pro Leu Pro Ser Val Leu Leu Ala Val Glu
        595                 600                 605
Leu Leu Ser Leu Leu Ala Asp His Asp Gln Leu Ala Pro Gln Leu Cys
            610                 615                 620
Ser His Ser Glu Gly Cys Leu Leu Leu Leu Tyr Met Tyr Ile Thr
625                 630                 635                 640
Ser Arg Pro Asp Arg Val Ala Leu Glu Thr Gln Trp Leu Gln Leu Glu
                645                 650                 655
Gln Glu Val Val Trp Leu Leu Ala Lys Leu Gly Val Gln Ser Pro Leu
            660                 665                 670
Pro Pro Val Thr Gly Ser Asn Cys Gln Cys Asn Val Glu Val Val Arg
            675                 680                 685
Ala Leu Thr Val Met Leu His Arg Gln Trp Leu Thr Val Arg Arg Ala
        690                 695                 700
Gly Gly Pro Pro Arg Thr Asp Gln Gln Arg Arg Thr Val Arg Cys Leu
705                 710                 715                 720
Arg Asp Thr Val Leu Leu Leu His Gly Leu Ser Gln Lys Asp Lys Leu
                725                 730                 735
Phe Met Met His Cys Val Glu Val Leu His Gln Phe Asp Gln Val Met
            740                 745                 750
Pro Gly Val Ser Met Leu Ile Arg Gly Leu Pro Asp Val Thr Asp Cys
        755                 760                 765
Glu Glu Ala Ala Leu Asp Asp Leu Cys Ala Ala Glu Thr Asp Val Glu
    770                 775                 780
Asp Pro Glu Val Glu Cys Gly
785                 790

<210> SEQ ID NO 30
<211> LENGTH: 698
<212> TYPE: PRT
<213> ORGANISM: Homo sapiens

<400> SEQUENCE: 30

Met Ser Lys Asn Pro Ser Gly Lys Asn Arg Glu Thr Val Pro Ile Lys
1               5                   10                  15
Asp Asn Phe Glu Leu Glu Val Leu Gln Ala Gln Tyr Lys Glu Leu Lys
            20                  25                  30
Glu Lys Met Lys Val Met Glu Glu Val Leu Ile Lys Asn Gly Glu
        35                  40                  45
Ile Lys Ile Leu Arg Asp Ser Leu His Gln Thr Glu Ser Val Leu Glu
    50                  55                  60
Glu Gln Arg Arg Ser His Phe Leu Leu Glu Gln Glu Lys Thr Gln Ala
65                  70                  75                  80
Leu Ser Asp Lys Glu Lys Glu Phe Ser Lys Lys Leu Gln Ser Leu Gln
```

-continued

```
              85                  90                  95
Ser Glu Leu Gln Phe Lys Asp Ala Glu Met Asn Glu Leu Arg Thr Lys
            100                 105                 110
Leu Gln Thr Ser Glu Arg Ala Asn Lys Leu Ala Ala Pro Ser Val Ser
        115                 120                 125
His Val Ser Pro Arg Lys Asn Pro Ser Val Val Ile Lys Pro Glu Ala
    130                 135                 140
Cys Ser Pro Gln Phe Gly Lys Thr Ser Phe Pro Thr Lys Glu Ser Phe
145                 150                 155                 160
Ser Ala Asn Met Ser Leu Pro His Pro Cys Gln Thr Glu Ser Gly Tyr
                165                 170                 175
Lys Pro Leu Val Gly Arg Glu Asp Ser Lys Pro His Ser Leu Arg Gly
            180                 185                 190
Asp Ser Ile Lys Gln Glu Ala Gln Lys Ser Phe Val Asp Ser Trp
        195                 200                 205
Arg Gln Arg Ser Asn Thr Gln Gly Ser Ile Leu Ile Asn Leu Leu Leu
    210                 215                 220
Lys Gln Pro Leu Ile Pro Gly Ser Ser Leu Ser Leu Cys His Leu Leu
225                 230                 235                 240
Ser Ser Ser Ser Glu Ser Pro Ala Gly Thr Pro Leu Gln Pro Pro Gly
                245                 250                 255
Phe Gly Ser Thr Leu Ala Gly Met Ser Gly Leu Arg Thr Thr Gly Ser
            260                 265                 270
Tyr Asp Gly Ser Phe Ser Leu Ser Ala Leu Arg Glu Ala Gln Asn Leu
        275                 280                 285
Ala Phe Thr Gly Leu Asn Leu Val Ala Arg Asn Glu Cys Ser Arg Asp
    290                 295                 300
Gly Asp Pro Ala Glu Gly Arg Arg Ala Phe Pro Leu Cys Gln Leu
305                 310                 315                 320
Pro Gly Ala Val His Phe Leu Pro Leu Val Gln Phe Phe Ile Gly Leu
                325                 330                 335
His Cys Gln Ala Leu Gln Asp Leu Ala Ala Ala Lys Arg Ser Gly Ala
            340                 345                 350
Pro Gly Asp Ser Pro Thr His Ser Ser Cys Val Ser Ser Gly Val Glu
        355                 360                 365
Thr Asn Pro Glu Asp Ser Val Cys Ile Leu Glu Gly Phe Ser Val Thr
    370                 375                 380
Ala Leu Ser Ile Leu Gln His Leu Val Cys His Ser Gly Ala Val Val
385                 390                 395                 400
Ser Leu Leu Leu Ser Gly Val Gly Ala Asp Ser Ala Ala Gly Glu Gly
                405                 410                 415
Asn Arg Ser Leu Val His Arg Leu Ser Asp Gly Asp Met Thr Ser Ala
            420                 425                 430
Leu Arg Gly Val Ala Asp Asp Gln Gly Gln His Pro Leu Leu Lys Met
        435                 440                 445
Leu Leu His Leu Leu Ala Phe Ser Ser Ala Thr Gly His Leu Gln
    450                 455                 460
Ala Ser Val Leu Thr Gln Cys Leu Lys Val Leu Val Lys Leu Ala Glu
465                 470                 475                 480
Asn Thr Ser Cys Asp Phe Leu Pro Arg Phe Gln Cys Val Phe Gln Val
                485                 490                 495
Leu Pro Lys Cys Leu Ser Pro Glu Thr Pro Leu Pro Ser Val Leu Leu
            500                 505                 510
```

```
Ala Val Glu Leu Leu Ser Leu Leu Ala Asp His Asp Gln Leu Ala Pro
        515                 520                 525

Gln Leu Cys Ser His Ser Glu Gly Cys Leu Leu Leu Leu Tyr Met
        530                 535                 540

Tyr Ile Thr Ser Arg Pro Asp Arg Val Ala Leu Glu Thr Gln Trp Leu
545                 550                 555                 560

Gln Leu Glu Gln Glu Val Val Trp Leu Leu Ala Lys Leu Gly Val Gln
                565                 570                 575

Ser Pro Leu Pro Pro Val Thr Gly Ser Asn Cys Gln Cys Asn Val Glu
            580                 585                 590

Val Ile Arg Ala Leu Thr Val Met Leu His Arg Gln Trp Leu Thr Val
        595                 600                 605

Arg Arg Ala Gly Gly Pro Pro Arg Thr Asp Gln Gln Arg Arg Thr Val
        610                 615                 620

Arg Cys Leu Arg Asp Thr Val Leu Leu Leu His Gly Leu Ser Gln Lys
625                 630                 635                 640

Asp Lys Leu Phe Met Met His Cys Val Glu Val Leu His Gln Phe Asp
                645                 650                 655

Gln Val Met Pro Gly Val Ser Met Leu Ile Arg Gly Leu Pro Asp Val
            660                 665                 670

Thr Asp Cys Glu Glu Ala Ala Leu Asp Asp Leu Cys Ala Ala Glu Thr
        675                 680                 685

Asp Val Glu Asp Pro Glu Val Glu Cys Gly
        690                 695

<210> SEQ ID NO 31
<211> LENGTH: 671
<212> TYPE: PRT
<213> ORGANISM: Homo sapiens

<400> SEQUENCE: 31

Met Ser Lys Asn Pro Ser Gly Lys Asn Arg Glu Thr Val Pro Ile Lys
1               5                   10                  15

Asp Asn Phe Glu Leu Glu Val Leu Gln Ala Gln Tyr Lys Glu Leu Lys
                20                  25                  30

Glu Lys Met Lys Val Met Glu Glu Val Leu Ile Lys Asn Gly Glu
            35                  40                  45

Ile Lys Ile Leu Arg Asp Ser Leu His Gln Thr Glu Ser Val Leu Glu
    50                  55                  60

Glu Gln Arg Arg Ser His Phe Leu Leu Glu Gln Glu Lys Thr Gln Ala
65                  70                  75                  80

Leu Ser Asp Lys Glu Lys Glu Phe Ser Lys Lys Leu Gln Ser Leu Gln
                85                  90                  95

Ser Glu Leu Gln Phe Lys Asp Ala Glu Met Asn Glu Leu Arg Thr Lys
            100                 105                 110

Leu Gln Thr Ser Glu Arg Ala Asn Lys Leu Ala Ala Pro Ser Val Ser
        115                 120                 125

His Val Ser Pro Arg Lys Asn Pro Ser Val Val Ile Lys Pro Glu Ala
    130                 135                 140

Cys Ser Pro Gln Phe Gly Lys Thr Ser Phe Pro Thr Lys Glu Ser Phe
145                 150                 155                 160

Ser Ala Asn Met Ser Leu Pro His Pro Cys Gln Thr Glu Ser Gly Tyr
                165                 170                 175

Lys Pro Leu Val Gly Arg Glu Asp Ser Lys Leu His Ser Leu Arg Gly
```

```
            180                 185                 190
Asp Ser Ile Lys Gln Glu Glu Ala Gln Lys Ser Phe Val Asp Ser Trp
            195                 200                 205
Arg Gln Arg Ser Asn Thr Gln Gly Ser Ile Leu Ile Asn Leu Leu Leu
            210                 215                 220
Lys Gln Pro Leu Ile Pro Gly Ser Ser Leu Ser Cys His Leu Leu
225                 230                 235                 240
Ser Ser Ser Ser Glu Ser Pro Ala Gly Thr Pro Leu Gln Pro Pro Gly
                245                 250                 255
Phe Gly Ser Thr Leu Ala Gly Met Ser Gly Leu Arg Thr Thr Gly Ser
            260                 265                 270
Tyr Asp Gly Ser Phe Ser Leu Ser Ala Leu Arg Glu Ala Gln Asn Leu
            275                 280                 285
Ala Phe Thr Gly Leu Asn Leu Val Ala Arg Asn Glu Cys Ser Arg Asp
            290                 295                 300
Gly Asp Pro Ala Glu Gly Arg Arg Ala Phe Pro Leu Cys Gln Leu
305                 310                 315                 320
Pro Gly Ala Val His Phe Leu Pro Leu Val Gln Phe Ile Gly Leu
                325                 330                 335
His Cys Gln Ala Leu Gln Asp Leu Ala Ala Lys Arg Ser Gly Ala
                340                 345                 350
Pro Gly Asp Ser Pro Thr His Ser Ser Cys Val Ser Ser Gly Val Glu
            355                 360                 365
Thr Asn Pro Glu Asp Ser Val Cys Ile Leu Gly Phe Ser Val Thr
            370                 375                 380
Ala Leu Ser Ile Leu Gln His Leu Val Cys His Ser Gly Ala Val Val
385                 390                 395                 400
Ser Leu Leu Leu Ser Gly Val Gly Ala Asp Ser Ala Ala Gly Glu Gly
                405                 410                 415
Asn Arg Ser Leu Val His Arg Leu Ser Asp Gly Asp Met Thr Ser Ala
                420                 425                 430
Leu Arg Gly Val Ala Asp Asp Gln Gly Gln His Pro Leu Leu Lys Met
            435                 440                 445
Leu Leu His Leu Leu Ala Phe Ser Ser Ala Thr Gly His Leu Gln
            450                 455                 460
Ala Ser Val Leu Thr Gln Cys Leu Lys Val Leu Val Lys Leu Ala Glu
465                 470                 475                 480
Asn Thr Ser Cys Asp Phe Leu Pro Arg Phe Gln Cys Val Phe Gln Val
                485                 490                 495
Leu Pro Lys Cys Leu Ser Pro Glu Thr Pro Leu Pro Ser Val Leu Leu
                500                 505                 510
Ala Val Glu Leu Leu Ser Leu Leu Ala Asp His Asp Gln Leu Ala Pro
            515                 520                 525
Gln Leu Cys Ser His Ser Glu Gly Cys Leu Leu Leu Leu Tyr Met
            530                 535                 540
Tyr Ile Thr Ser Arg Pro Asp Arg Val Ala Leu Glu Thr Gln Trp Leu
545                 550                 555                 560
Gln Leu Glu Gln Glu Val Val Arg Ala Leu Thr Val Met Leu His Arg
                565                 570                 575
Gln Trp Leu Thr Val Arg Arg Ala Gly Gly Pro Pro Arg Thr Asp Gln
                580                 585                 590
Gln Arg Arg Thr Val Arg Cys Leu Arg Asp Thr Val Leu Leu Leu His
            595                 600                 605
```

```
Gly Leu Ser Gln Lys Asp Lys Leu Phe Met Met His Cys Val Glu Val
    610                 615                 620

Leu His Gln Phe Asp Gln Val Met Pro Gly Val Ser Met Leu Ile Arg
625                 630                 635                 640

Gly Leu Pro Asp Val Thr Asp Cys Glu Glu Ala Ala Leu Asp Asp Leu
                645                 650                 655

Cys Ala Ala Glu Thr Asp Val Glu Asp Pro Glu Val Glu Cys Gly
                660                 665                 670

<210> SEQ ID NO 32
<211> LENGTH: 571
<212> TYPE: PRT
<213> ORGANISM: Homo sapiens

<400> SEQUENCE: 32

Met Ser Lys Asn Pro Ser Gly Lys Asn Arg Glu Thr Val Pro Ile Lys
  1               5                  10                  15

Asp Asn Phe Glu Leu Glu Val Leu Gln Ala Gln Tyr Lys Glu Leu Lys
                 20                  25                  30

Glu Lys Met Lys Val Met Glu Glu Val Leu Ile Lys Asn Gly Glu
             35                  40                  45

Ile Lys Ile Leu Arg Asp Ser Leu His Gln Thr Glu Ser Val Leu Glu
 50                  55                  60

Glu Gln Arg Arg Ser His Phe Leu Leu Glu Gln Glu Lys Thr Gln Ala
 65                  70                  75                  80

Leu Ser Asp Lys Glu Lys Glu Phe Ser Lys Lys Leu Gln Ser Leu Gln
                 85                  90                  95

Ser Glu Leu Gln Phe Lys Asp Ala Glu Met Asn Glu Leu Arg Thr Lys
                100                 105                 110

Leu Gln Thr Ser Glu Arg Ala Asn Lys Leu Ala Ala Pro Ser Val Ser
             115                 120                 125

His Val Ser Pro Arg Lys Asn Pro Ser Val Val Ile Lys Pro Glu Ala
     130                 135                 140

Cys Ser Pro Gln Phe Gly Lys Thr Ser Phe Pro Thr Lys Glu Ser Phe
145                 150                 155                 160

Ser Ala Asn Met Ser Leu Pro His Pro Cys Gln Thr Glu Ser Gly Tyr
                165                 170                 175

Lys Pro Leu Val Gly Arg Glu Asp Ser Lys Pro His Ser Leu Arg Gly
             180                 185                 190

Asp Ser Ile Lys Gln Glu Glu Ala Gln Lys Ser Phe Val Asp Ser Trp
     195                 200                 205

Arg Gln Arg Ser Asn Thr Gln Gly Ser Ile Leu Ile Asn Leu Leu Leu
210                 215                 220

Lys Gln Pro Leu Ile Pro Gly Ser Ser Leu Ser Leu Cys His Leu Leu
225                 230                 235                 240

Ser Ser Ser Ser Glu Ser Pro Ala Gly Thr Pro Leu Gln Pro Pro Gly
                245                 250                 255

Phe Gly Ser Thr Leu Ala Gly Met Ser Gly Leu Arg Thr Thr Gly Ser
             260                 265                 270

Tyr Asp Gly Ser Phe Ser Leu Ser Ala Leu Arg Glu Ala Gln Asn Leu
     275                 280                 285

Ala Phe Thr Gly Leu Asn Leu Val Ala Arg Asn Glu Cys Ser Arg Asp
290                 295                 300

Gly Asp Pro Ala Glu Gly Gly Arg Arg Ala Phe Pro Leu Cys Gln Leu
```

```
                305                 310                 315                 320
        Pro Gly Ala Val His Phe Leu Pro Leu Val Gln Phe Phe Ile Gly Leu
                        325                 330                 335

His Cys Gln Ala Leu Gln Asp Leu Ala Ala Ala Lys Arg Ser Gly Ala
                    340                 345                 350

Pro Gly Asp Ser Pro Thr His Ser Ser Cys Val Ser Ser Gly Val Glu
                    355                 360                 365

Thr Asn Pro Glu Asp Ser Val Cys Ile Leu Glu Gly Phe Ser Val Thr
                370                 375                 380

Ala Leu Ser Ile Leu Gln His Leu Val Cys His Ser Gly Ala Val Val
        385                 390                 395                 400

Ser Leu Leu Leu Ser Gly Val Gly Ala Asp Ser Ala Ala Gly Glu Gly
                        405                 410                 415

Asn Arg Ser Leu Val His Arg Leu Ser Asp Gly Asp Met Thr Ser Ala
                    420                 425                 430

Leu Arg Gly Val Ala Asp Asp Gln Gly Gln His Pro Leu Leu Lys Met
                435                 440                 445

Leu Leu His Leu Ala Phe Ser Ser Ala Ala Thr Gly His Leu Gln
        450                 455                 460

Ala Ser Val Leu Thr Gln Cys Leu Lys Val Leu Val Lys Leu Ala Glu
        465                 470                 475                 480

Asn Thr Ser Cys Asp Phe Leu Pro Arg Phe Gln Cys Val Phe Gln Val
                        485                 490                 495

Leu Pro Lys Cys Leu Ser Pro Glu Thr Pro Leu Pro Ser Val Leu Leu
                    500                 505                 510

Ala Val Glu Leu Leu Ser Leu Leu Ala Asp His Asp Gln Leu Ala Pro
                515                 520                 525

Gln Leu Cys Ser His Ser Glu Gly Cys Leu Leu Leu Leu Tyr Met
                530                 535                 540

Tyr Ile Thr Ser Arg Pro Asp Arg Val Ala Leu Glu Asn Asn Gly Ser
        545                 550                 555                 560

Ser Trp Asn Lys Arg Trp Ser Glu Arg Ser Arg
                        565                 570

<210> SEQ ID NO 33
<211> LENGTH: 2509
<212> TYPE: DNA
<213> ORGANISM: Homo sapiens

<400> SEQUENCE: 33
gcgctgtcgg atacttgggg tgagcggaaa gcatggcggg gacctccgcg ccaggcagca      60
agaggcggag cgagcccccg gcgcctcgcc ccggcccgcc gccgggcacc gggcaccccc     120
cgagcaagcg ggcccggggc ttctccgcag ccgctgcccc ggaccctgac gacccgttcg     180
gcgcgcatgg ggacttcact gccgacgacc tggaggagct tgacaccctc gcgtcacagg     240
ccctgagcca atgtccggcc gcggctcggg acgtgtccag tgatcataag gtccacagat     300
tattagatgg catgtcaaaa aatccttcag ggaaaaacag agaaactgtt ccaattaaag     360
ataatttcga attagaggta cttcaggcac aatacaaaga acttaaagaa aagatgaaag     420
taatggaaga agaagttctc attaagaatg gagaaattaa aattttgcga gactcactac     480
atcagacgga atccgttcta gaggaacaga gaagatcaca ttttcttctt gagcaagaga     540
aaacccaagc actcagtgac aaggaaaagg aattctccaa aaagctccaa tcattgcagt     600
ctgaactcca gtttaaagat gcagagatga atgaattaag gacaaagctc cagaccagtg     660
```

-continued

```
aacgagcaaa taaactggct gctccctctg tttcccatgt cagtcctagg aaaaacccctt    720 ctgtggttat aaagccagaa gcatgttctc cacaatttgg aaaaacatct tttcctacaa    780
aggagtcttt tagtgctaac atgtcccttc cccaccccctg ccagacggag tcaggataca    840
agcctctggt gggcagagag gatagtaagc cccacagtct gagaggtgac tccataaaac    900
aagaagaggc ccagaaaagc tttgttgaca gctggagaca gagatcaaac actcaaggtt    960
ccattttgat aaacctgctc ctgaagcagc ctttgatccc agggtcatcc ctaagccttt   1020
gccacctcct gagtagtagt tctgagtctc ctgctggcac cccctgcag ccaccagggt   1080 ttggcagtac cttggctgga atgtcaggcc tcaggaccac aggttcttat gatgggtcat   1140
tttccctctc agccctgaga gaagcacaga acctggcatt cactggactg aatctggttg   1200
cccggaatga gtgctcacgt gatggagacc cagcagaggg aggcagaagg gccttcccac   1260
tctgccagct tcctggagcc gtgcatttcc tcccccttgt acagttcttc atcggcttac   1320
actgccaggc cctgcaggac ttggcagctg ctaagagaag cggagcacct ggggactcac   1380
cgacacattc ctcctgcgtg agctctgggg tagagaccaa ccctgaggac tcagtgtgca   1440
tcctggaagg cttctctgtg actgcactta gcattcttca gcacctggtg tgccacagcg   1500
gagcagtcgt ctccctatta ctgtcaggag tgggggcaga ttctgctgct ggggaaggaa   1560
acaggagcct ggttcacagg cttagtgatg gagatatgac ctcagcccta agggggggttg   1620 ctgatgacca aggacagcac ccactgttga agatgcttct tcacctgttg gctttctctt   1680
ctgcagcaac aggtcacctt caagccagtg tcctgaccca gtgccttaag gttttggtga   1740
aattagccga aaacacttcc tgtgatttct gcccaggtt ccagtgtgtg ttccaagtgc   1800
tgccaaagtg cctcagccca gagacacccc tgcctagcgt gctgctggct gttgagctcc   1860
tctccctgct ggcggaccac gaccagctgg cacctcagct ctgttcccac tcagaaggct   1920
gcctcctgct gctgctgtac atgtacatca catcacggcc tgacagagtg gccttggaga   1980
cacaatggct ccagctggaa caagaggtgg tgtggctcct ggctaagctt ggtgtgcaga   2040
gccccttgcc cccagtcact ggctccaact gccagtgtaa tgtggaggtg gtcagagcgc   2100
tcacggtgat gttgcacaga cagtggctga cagtgcggag ggcaggggga cccccaagga   2160
ccgaccagca gaggcggaca gtgcgctgtc tgcgggacac ggtgctgctg ctgcacggcc   2220
tatcgcagaa ggacaagctc ttcatgatgc actgcgtgga ggtcctgcat cagtttgacc   2280
aggtgatgcc gggggtcagc atgctcatcc gagggcttcc tgatgtgacg gactgtgaag   2340
aggcagccct ggatgacctc tgtgccgcgg aaaccgatgt ggaagacccc gaggtggagt   2400
gtggctgagg ccctgagtgt ccagccacat ggtggcacca gcaccactcc tttccttacc   2460
acatcaactg attaaagcag tgaccagcag gaactgccca gagaactgg              2509
```

<210> SEQ ID NO 34
<211> LENGTH: 2509
<212> TYPE: DNA
<213> ORGANISM: Homo sapiens

<400> SEQUENCE: 34

```
gcgctgtcgg atacttgggg tgagcggaaa gcatggcggg gacctccgcg ccaggcagca     60
agaggcggag cgagccccccg gcgcctcgcc ccggcccgcc gccgggcacc gggcaccccc    120
cgagcaagcg ggcccgggc ttctccgcag ccgctgcccc ggaccctgac gacccgttcg    180
gcgcgcatgg ggacttcact gccgacgacc tggaggagct tgacaccctc gcgtcacagg    240
```

-continued

```
ccctgagcca atgtccggcc gcggctcggg acgtgtccag tgatcataag gtccacagat    300
tattagatgg catgtcaaaa aatccttcag ggaaaaacag agaaactgtt ccaattaaag    360
ataatttcga attagaggta cttcaggcac aatacaaaga acttaaagaa agatgaaag    420
taatggaaga agaagttctc attaagaatg gagaaattaa aattttgcga gactcactac    480
atcagacgga atccgttcta gaggaacaga aagatcaca tttcttctt gagcaagaga    540
aaacccaagc actcagtgac aaggaaaagg aattctccaa aaagctccaa tcattgcagt    600
ctgaactcca gtttaaagat gcagagatga atgaattaag gacaaagctc cagaccagtg    660
aacgagcaaa taaactggct gctccctctg tttcccatgt cagtcctagg aaaaacccctt    720
ctgtggttat aaagccagaa gcatgttctc cacaatttgg aaaaacatct tttcctacaa    780
aggagtcttt tagtgctaac atgtcccttc cccaccctg ccagacggag tcaggataca    840
agcctctggt gggcagagag gatagtaagc ccacagtct gagaggtgac tccataaaac    900
aagaagaggc ccagaaaagc tttgttgaca gctggagaca gagatcaaac actcaaggtt    960
ccattttgat aaacctgctc ctgaagcagc ctttgatccc agggtcatcc ctaagccttt   1020
gccacctcct gagtagtagt tctgagtctc ctgctggcac cccctgcag ccaccagggt   1080
ttggcagtac cttggctgga atgtcaggcc tcaggaccac aggttcttat gatgggtcat   1140
tttccctctc agccctgaga gaagcacaga acctggcatt cactggactg aatctggttg   1200
cccggaatga gtgctcacgt gatggagacc cagcagaggg aggcagaagg gccttcccac   1260
tctgccagct tcctggagcc gtgcatttcc tcccccttgt acagttcttc atcggcttac   1320
actgccaggc cctgcaggac ttggcagctg ctaagagaag cggagcacct ggggactcac   1380
cgacacattc ctcctgcgtg agctctgggg tagagaccaa ccctgaggac tcagtgtgca   1440
tcctggaagg cttctctgtg actgcactta gcattcttca gcacctggtg tgccacagcg   1500
gagcagtcgt ctccctatta ctgtcaggag tggggggcaga ttctgctgct ggggaaggaa   1560
acaggagcct ggttcacagg cttagtgatg gagatatgac ctcagcccta agggggttg   1620
ctgatgacca aggacagcac ccactgttga agatgcttct tcacctgttg gctttctctt   1680
ctgcagcaac aggtcacctt caagccagtg tcctgaccca gtgccttaag gttttggtga   1740
aattagccga aaacacttcc tgtgatttct gcccaggtt ccagtgtgtg ttccaagtgc   1800
tgccaaagtg cctcagccca gagacacccc tgcctagcgt gctgctggct gttgagctcc   1860
tctccctgct ggcggaccac gaccagctgg cacctcagct ctgttccac tcagaaggct   1920
gcctcctgct gctgctgtac atgtacatca catcacggcc tgacagagtg gccttggaga   1980
cacaatggct ccagctggaa caagaggtgg tgtggctcct ggctaagctt ggtgtgcaga   2040
gcccccttgcc cccagtcact ggctccaact gccagtgtaa tgtggaggtg gtcagagcgc   2100
tcacggtgat gttgcacaga cagtggctga cagtgcggag ggcagggggga cccccaagga   2160
ccgaccagca gaggcggaca gtgcgctgtc tgcgggacac ggtgctgctg ctgcacggcc   2220
tatcgcagaa ggacaagctc ttcatgatgc actgcgtgga ggtcctgcat cagtttgacc   2280
aggtgatgcc ggggggtcagc atgctcatcc gagggcttcc tgatgtgacg gactgtgaag   2340
aggcagccct ggatgacctc tgtgccgcgg aaaccgatgt ggaagacccc gaggtggagt   2400
gtggctgagg ccctgagtgt ccagccacat ggtggcacca gcaccactcc tttccttacc   2460
acatcaactg attaaagcag tgaccagcag gaactgccca gagaactgg             2509
```

<210> SEQ ID NO 35
<211> LENGTH: 2681

<212> TYPE: DNA
<213> ORGANISM: Homo sapiens

<400> SEQUENCE: 35

| | | | | | |
|---|---|---|---|---|---|
| agcgggtgag | tgctcctcgc | ggccttttgc | tcggagggag | ttgtcaaccg | cgccagatcc | 60 |
| ccttgatggc | tgtggcttcg | gaacctcgcg | gccagcactg | cctttcgcc | ttttaaaat | 120 |
| atgggaacac | cctgatttaa | gcagcggttg | tcttccagaa | ggtcctttga | ttttaggggg | 180 |
| aaatgcatta | gccaggtcaa | acagccgatt | tgaaacacag | aaggctaagt | tgacatttta | 240 |
| cgttattttc | taaagtttag | gccacttggt | tcttggttct | aagcagagat | ccttggaaca | 300 |
| cacctaccac | caccatcaga | accatcacta | cccatgcatg | gggacccatt | cttgtgacaa | 360 |
| gtttgagcgg | ctttagatct | tatgaagccc | actgtctccc | ttgggcagtg | tgagcatggg | 420 |
| aggagccaga | cacaggtgat | cataaggtcc | acagattatt | agatggcatg | tcaaaaaatc | 480 |
| cttcagggaa | aaacagagaa | actgttccaa | ttaaagataa | tttcgaatta | gaggtacttc | 540 |
| aggcacaata | caaagaactt | aaagaaaaga | tgaaagtaat | ggaagaagaa | gttctcatta | 600 |
| agaatggaga | aattaaaatt | ttgcgagact | cactacatca | gacggaatcc | gttctagagg | 660 |
| aacagagaag | atcacatttt | cttcttgagc | aagagaaaac | ccaagcactc | agtgacaagg | 720 |
| aaaaggaatt | ctccaaaaag | ctccaatcat | tgcagtctga | actccagttt | aaagatgcag | 780 |
| agatgaatga | attaaggaca | aagctccaga | ccagtgaacg | agcaaataaa | ctggctgctc | 840 |
| cctctgtttc | ccatgtcagt | cctaggaaaa | acccttctgt | ggttataaag | ccagaagcat | 900 |
| gttctccaca | atttggaaaa | acatcttttc | ctacaaagga | gtcttttagt | gctaacatgt | 960 |
| cccttcccca | cccctgccag | acggagtcag | gatacaagcc | tctggtgggc | agagaggata | 1020 |
| gtaagcccca | cagtctgaga | ggtgactcca | taaacaaga | agaggcccag | aaaagctttg | 1080 |
| ttgacagctg | gagacagaga | tcaaacactc | aaggttccat | tttgataaac | ctgctcctga | 1140 |
| agcagccttt | gatcccaggg | tcatccctaa | gcctttgcca | cctcctgagt | agtagttctg | 1200 |
| agtctcctgc | tggcaccccc | ctgcagccac | cagggtttgg | cagtaccttg | gctggaatgt | 1260 |
| caggcctcag | gaccacaggt | tcttatgatg | ggtcattttc | cctctcagcc | ctgagagaag | 1320 |
| cacagaacct | ggcattcact | ggactgaatc | tggttgcccg | gaatgagtgc | tcacgtgatg | 1380 |
| gagacccagc | agagggaggc | agaagggcct | tcccactctg | ccagcttcct | ggagccgtgc | 1440 |
| atttcctccc | ccttgtacag | ttcttcatcg | gcttacactg | ccaggccctg | caggacttgg | 1500 |
| cagctgctaa | gagaagcgga | gcacctgggg | actcaccgac | acattcctcc | tgcgtgagct | 1560 |
| ctggggtaga | gaccaacccct | gaggactcag | tgtgcatcct | ggaaggcttc | tctgtgactg | 1620 |
| cacttagcat | tcttcagcac | ctggtgtgcc | acagcggagc | agtcgtctcc | ctattactgt | 1680 |
| caggagtggg | ggcagattct | gctgctgggg | aaggaaacag | gagcctggtt | cacaggctta | 1740 |
| gtgatggaga | tatgacctca | gccctaaggg | gggttgctga | tgaccaagga | cagcacccac | 1800 |
| tgttgaagat | gcttcttcac | ctgttggctt | tctcttctgc | agcaacaggt | caccttcaag | 1860 |
| ccagtgtcct | gacccagtgc | cttaaggttt | tggtgaaatt | agccgaaaac | acttcctgtg | 1920 |
| atttcttgcc | caggttccag | tgtgtgttcc | aagtgctgcc | aaagtgcctc | agcccagaga | 1980 |
| caccctgcc | tagcgtgctg | ctggctgttg | agctcctctc | cctgctggcg | gaccacgacc | 2040 |
| agctggcacc | tcagctctgt | tcccactcag | aaggctgcct | cctgctgctg | ctgtacatgt | 2100 |
| acatcacatc | acggcctgac | agagtggcct | tggagacaca | atggctccag | ctggaacaag | 2160 |
| aggtggtgtg | gctcctggct | aagcttggtg | tgcagagccc | cttgccccca | gtcactggct | 2220 |

| | |
|---|---|
| ccaactgcca gtgtaatgtg gaggtaatca gagcgctcac ggtgatgttg cacagacagt | 2280 |
| ggctgacagt gcggagggca gggggacccc caaggaccga ccagcagagg cggacagtgc | 2340 |
| gctgtctgcg ggacacggtg ctgctgctgc acggcctatc gcagaaggac aagctcttca | 2400 |
| tgatgcactg cgtggaggtc ctgcatcagt ttgaccaggt gatgccgggg gtcagcatgc | 2460 |
| tcatccgagg gcttcctgat gtgacggact gtgaagaggc agccctggat gacctctgtg | 2520 |
| ccgcggaaac cgatgtggaa gaccccgagg tggagtgtgg ctgaggccct gagtgtccag | 2580 |
| ccacatggtg gcaccagcac cactcctttc cttaccacat caactgatta aagcagtgac | 2640 |
| cagcaggaac tgcccagaga actggaaaaa aaaaaaaaa a | 2681 |

<210> SEQ ID NO 36
<211> LENGTH: 2095
<212> TYPE: DNA
<213> ORGANISM: Homo sapiens

<400> SEQUENCE: 36

| | |
|---|---|
| gaagttctca ttaagaatgg agaaattaaa attttgcgag actcactaca tcagacggaa | 60 |
| tccgttctag aggaacagag aagatcacat tttcttcttg agcaagagaa acccaagca | 120 |
| ctcagtgaca aggaaaagga attctccaaa aagctccaat cattgcagtc tgaactccag | 180 |
| tttaaagatg cagagatgaa tgaattaagg acaaagctcc agaccagtga acgagcaaat | 240 |
| aaactggctg ctccctctgt tcccatgtc agtcctagga aaaacccttc tgtggttata | 300 |
| aagccagaag catgttctcc acaatttgga aaaacatctt ttcctacaaa ggagtctttt | 360 |
| agtgctaaca tgtcccttcc ccaccctgc cagacggagt caggatacaa gcctctggtg | 420 |
| ggcagagagg atagtaagcc ccacagtctg agaggtgact ccataaaaca agaagaggcc | 480 |
| cagaaaagct tgttgacag ctggagacag agatcaaaca ctcaaggttc cattttgata | 540 |
| aacctgctcc tgaagcagcc tttgatccca gggtcatccc taagcctttg ccacctcctg | 600 |
| agtagtagtt ctgagtctcc tgctggcacc ccctgcagc caccagggtt tggcagtacc | 660 |
| ttggctggaa tgtcaggcct caggaccaca ggttcttatg atgggtcatt ttccctctca | 720 |
| gccctgagag aagcacagaa cctggcattc actggactga atctggttgc ccggaatgag | 780 |
| tgctcacgtg atggagaccc agcagaggga ggcagaaggg ccttcccact ctgccagctt | 840 |
| cctggagccg tgcatttcct cccccttgta cagttcttca tcggcttaca ctgccaggcc | 900 |
| ctgcaggact tggcagctgc taagagaagc ggagcacctg ggactcacc gacacattcc | 960 |
| tcctgcgtga gctctggggt agagaccaac cctgaggact cagtgtgcat cctggaaggc | 1020 |
| ttctctgtga ctgcacttag cattcttcag cacctggtgt gccacagcgg agcagtcgtc | 1080 |
| tccctattac tgtcaggagt gggggcagat tctgctgctg gggaaggaaa caggagcctg | 1140 |
| gttcacaggc ttagtgatgg agatatgacc tcagccctaa gggggttgc tgatgaccaa | 1200 |
| ggacagcacc cactgttgaa gatgcttctt cacctgttgg cttttctcttc tgcagcaaca | 1260 |
| ggtcaccttc aagccagtgt cctgacccag tgccttaagg ttttggtgaa attagccgaa | 1320 |
| aacacttcct gtgatttctt gcccaggttc cagtgtgtgt tccaagtgct gccaaagtgc | 1380 |
| ctcagcccag agacacccct gcctagcgtg ctgctggctg ttgagctcct ctccctgctg | 1440 |
| gcggaccacg accagctggc acctcagctc tgttcccact cagaaggctg cctcctgctg | 1500 |
| ctgctgtaca tgtacatcac atcacggcct gacagagtgg ccttggagac acaatggctc | 1560 |
| cagctggaac aagaggtggt gtggcttctg gctaagcttg tgtgtcagag ccccttgccc | 1620 |
| ccagtcactg gctccaactg ccagtgtaat gtggaggtgg tcagagcgct cacggtgatg | 1680 |

```
ttgcacagac agtggctgac agtgcggagg gcaggggggac ccccaaggac cgaccagcag    1740
aggcggacag tgcgctgtct gcgggacacg gtgctgctgc tgcacggcct atcgcagaag    1800
gacaagctct tcatgatgca ctgcgtggag gtcctgcatc agtttgacca ggtgatgccg    1860
ggggtcagca tgctcatccg agggcttcct gatgtgacgg actgtgaaga ggcagccctg    1920
gatgacctct gtgccgcgga aaccgatgtg aagacccccg aggtggagtg tggctgaggc    1980
cctgagtgtc cagccacatg gtggcaccag caccactcct ttccttacca catcaactga    2040
ttaaagcagt gaccagcagg aactgcccag agaactggaa aaaaaaaaaa aaaaa         2095
```

<210> SEQ ID NO 37
<211> LENGTH: 3623
<212> TYPE: DNA
<213> ORGANISM: Homo sapiens

<400> SEQUENCE: 37

```
tgcagtctga actccagttt aaagatgcag agatgaatga attaaggaca aagctccaga     60
ccagtgaacg agcaaataaa ctggctgctc cctctgtttc ccatgtcagt cctaggaaaa    120
acccttctgt ggttataaag ccagaagcat gttctccaca atttggaaaa acatctttc    180 ctacaaagga gtcttttagt gctaacatgt cccttcccca ccctgccag acggagtcag    240 gatacaagcc tctggtgggc agagaggata gtaagcccca cagtctgaga ggtgactcca    300
taaaacaaga agaggcccag aaaagctttg ttgacagctg gagacagaga tcaaacactc    360
aaggttccat tttgataaac ctgctcctga agcagcctca gttgatccgg tcatccctaa    420 gccttttgcca cctcctgagt agtagttctg agtctcctgc tggcacccc ctgcagccac    480 cagggttttgg cagtaccttg gctggaatgt caggcctcag gaccacaggt tcttatgatg    540
ggtcattttc cctctcagcc ctgagagaag cacagaacct ggcattcact ggactgaatc    600
tggttgcccg gaatgagtgc tcacgtgatg gagacccagc agagggaggc agaagggcct    660
tcccactctg ccagcttcct ggagccgtgc atttcctccc ccttgtacag ttcttcatcg    720
gcttacactg ccaggccctg caggacttgg cagctgctaa gagaagcgga gcacctgggg    780
actcaccgac acattcctcc tgcgtgagct ctggggtaga gaccaaccct gaggactcag    840
tgtgcatcct ggaaggcttc tctgtgactg cacttagcat tcttcagcac ctggtgtgcc    900
acagcggagc agtcgtctcc ctattactgt caggagtggg ggcagattct gctgctgggg    960
aaggaaacag gagcctggtt cacaggctta gtgatggaga tatgacctca gccctaaggg   1020
gggttgctga tgaccaagga cagcacccac tgttgaagat gcttcttcac ctgttggctt   1080
tctcttctgc agcaacaggt caccttcaag ccagtgtcct gacccagtgc cttaaggttt   1140
tggtgaaatt agccgaaaac acttcctgtg atttcttgcc caggttccag tgtgtgttcc   1200
aagtgctgcc aaaagtgcctc agcccagaga caccctgcc tagcgtgctg ctggctgttg   1260
agctcctctc cctgctggcg gaccacgacc agctggcacc tcagctctgt tcccactcag   1320
aaggctgcct cctgctgctg ctgtacatgt acatcacatc acggcctgac agagtggcct   1380
tggagacaca atggctccag ctggaacaag aggtggtgtg gctcctggct aagcttggtg   1440
tgcagagccc cttgccccca gtcactggct ccaactgcca gtgtaatgtg gaggtggtca   1500
gagcgctcac ggtgatgttg cacagacagt ggctgacagt gcgagggca gggggacccc   1560 caaggaccga ccagcagagg cggacagtgc gctgtctgcg ggacacgtgt ctgctgctgc   1620
acggcctatc gcagaaggac aagctcttca tgatgcactg cgtggaggtc ctgcatcagt   1680
```

| | |
|---|---:|
| ttgaccaggt gatgccgggg gtcagcatgc tcatccgagg gcttcctgat gtgacggact | 1740 |
| gtgaagaggc agccctggat gacctctgtg ccgcggaaac cgatgtggaa gaccccgagg | 1800 |
| tggagtgtgg ctgaggccct gagtgtccag ccacatggtg gcaccagcac cactcctttc | 1860 |
| cttaccacat caactgatta aagcagtgac cagcaggaac tgcccagaga actggctggc | 1920 |
| cttgtttcct gagtctgatc tgtttggcgg agtgggaggg gtggagcagg acccggaccc | 1980 |
| tgagtggctg ggatccttct tcctgtccct ggctgttgct gagcccgtcc ccatggtaac | 2040 |
| tgatctgcct tgaggaagga gccctgccct gcctgtggaa ttgtcctgag tcattgcttt | 2100 |
| gggctggggc catgggaaga aaccattgtg tggcagggaa ggaggtggct cttggcccag | 2160 |
| gcctaaaacca ggaaagcctg ggaaactggg acccacaggt gggcatgaaa gggccgcagc | 2220 |
| aggggctccc agcagtgtgt aagaccggga gctggtctgg caccactgcc ctggtccttc | 2280 |
| cagctgcctg tcactggtat gatggccccg gtgcattgtg ccaccagcag gccacagctg | 2340 |
| tggatcttgg aaggcctctg ggtcccccg ggagcagggg agtgggtgtg gggggaacg | 2400 |
| gatggtggtg agagggacag accaggcagg ctgacgagca gggcgggcct ggctcacgtg | 2460 |
| ggcctgtagg cgggcccacg ccaagtttca cttaccgcca ctgctgccag cgagagccgc | 2520 |
| gggagagtgt gcagccgagt cactactgcc tgcctgcctg cctgctacgg ctcagcagca | 2580 |
| ggtacgtacc caaccatggg ctcgcaggcc ctgcccccgg ggcccatgca gaccctcatc | 2640 |
| tttttcgaca tggaggccac tggcttgccc ttctcccagc ccaaggtcac ggagctgtgc | 2700 |
| ctgctggctg tccacagatg tgccctggag agcccccca cctctcaggg gccacctccc | 2760 |
| acagttcctc caccaccgcg tgtggtagac aagctctccc tgtgtgtggc tccggggaag | 2820 |
| gcctgcagcc ctgcagccag cgagatcaca gtctgagca cagctgtgct ggcagcgcat | 2880 |
| gggcgtcaat gttttgatga caacctggcc aacctgctcc tagccttcct gcggcgccag | 2940 |
| ccacagccct ggtgcctggt ggcacacaat ggtgaccgct acgacttccc cctgctccaa | 3000 |
| gcagagctgg ctatgctggg cctcaccagt gctctggatg gtgccttctg tgtggatagc | 3060 |
| atcactgcgc tgaaggccct ggagcgagca agcagcccct cagaacacgg cccaaggaag | 3120 |
| agctacagcc taggcagcat ctacactcgc ctgtatgggc agtcccctcc agactcgcac | 3180 |
| acggctgagg gtgatgtcct ggccctgctc agcatctgtc agtggagacc acaggccctg | 3240 |
| ctgcggtggg tggatgctca cgccaggcct ttcggcacca tcaggcccat gtatggggtc | 3300 |
| acagcctctg ctaggaccaa gccaagacca tctgctgtca caaccactgc acacctggcc | 3360 |
| acaaccagga acactagtcc cagccttgga gagagcaggg gtaccaagga tcttcctcca | 3420 |
| gtgaaggacc ctggagccct atccaggag gggctgctgg ccccactggg tctgctggcc | 3480 |
| atcctgacct tggcagtagc cacactgtat ggactatccc tggccacacc tggggagtag | 3540 |
| gccaagaagg aaaatctgac gaataaagac ccccgctgcc ccataaaaaa aaaaaaaaa | 3600 |
| aaaaaaaaaa aaaaaaaaaa aaa | 3623 |

<210> SEQ ID NO 38
<211> LENGTH: 8265
<212> TYPE: DNA
<213> ORGANISM: Homo sapiens

<400> SEQUENCE: 38

| | |
|---|---:|
| gcctccacac ggctccgtcg ggcgccgcgc tcttccggca gcggtacgtt tggagacgcc | 60 |
| gggaacccgc gttggcgtgg ttgactagtg cctcgcagcc tcagcatggg ggaacatggc | 120 |
| ctggagctgg cttccatgat ccccgccctg cgggagctgg gcagtgccac accagaggaa | 180 |

-continued

| | | | |
|---|---|---|---|
| tataatacag ttgtacagaa gccaagacaa attctgtgtc aattcattga ccggatactt | 240 |
| acagatgtaa atgttgttgc tgtagaactt gtaaagaaaa ctgactctca gccaacctcc | 300 |
| gtgatgttgc ttgatttcat ccagcatatc atgaaatcct ccccacttat gtttgtaaat | 360 |
| gtgagtggaa gccatgagcg caaaggcagt tgtattgaat tcagtaattg gatcataacg | 420 |
| agacttctgc ggattgcagc aactccctcc tgtcatttgt tacacaagaa aatctgtgaa | 480 |
| gtcatctgtt cattattatt tcttttaaa agcaagagtc ctgctatttt tggggtactc | 540 |
| acaaaagaat tattcaaact ttttgaagac ttggtttacc tccatagaag aaatgtgatg | 600 |
| ggtcatgctg tggaatggcc agtggtcatg agccgatttt aagtcaatt agatgaacac | 660 |
| atgggatatt tacaatcagc tcctttgcag ttgatgagta tgcaaaattt agaatttatt | 720 |
| gaagtcactt tattaatggt tcttactcgt attattgcaa ttgtgttttt tagaaggcaa | 780 |
| gaactcttac tttggcagat aggttgtgtt ctgctagagt atggtagtcc aaaaattaaa | 840 |
| tccctagcaa ttagcttttt aacagaactt tttcagcttg gaggactacc agcacaacca | 900 |
| gctagcactt ttttcagctc atttttggaa ttattaaaac accttgtaga aatggatact | 960 |
| gaccaattga aactctatga agagccatta tcaaagctga taaagacact atttcccttt | 1020 |
| gaagcagaag cttatagaaa tattgaacct gtctatttaa atatgctgct ggaaaaactc | 1080 |
| tgtgtcatgt ttgaagacgg tgtgctcatg cggcttaagt ctgatttgct aaaagcagct | 1140 |
| ttgtgccatt tactgcagta tttccttaaa tttgtgccag ctgggtatga atctgcttta | 1200 |
| caagtcagga aggtctatgt gagaaatatt tgtaaagctc ttttggatgt gcttggaatt | 1260 |
| gaggtagatg cagagtactt gttgggccca ctttatgcag ctttgaaaat ggaaagtatg | 1320 |
| gaaatcattg aggagattca atgccaaact caacaggaaa acctcagcag taatagtgat | 1380 |
| ggaatatcac ccaaaaggcg tcgtctcagc tcgtctctaa acccttctaa aagagcacca | 1440 |
| aaacagactg aggaaattaa acatgtggac atgaaccaaa agagcatatt atggagtgca | 1500 |
| ctgaaacaga aagctgaatc ccttcagatt tcccttgaat acagtggcct aaagaatcct | 1560 |
| gttattgaga tgttagaagg aattgctgtt gtccttacaac tgactgctct gtgtactgtt | 1620 |
| cattgttctc atcaaaacat gaactgccgt actttcaagg actgtcaaca taaatccaag | 1680 |
| aagaaaccctt ctgtagtgat aacttggatg tcattggatt tttacacaaa agtgcttaag | 1740 |
| agctgtagaa gtttgttaga atctgttcag aaactggacc tggaggcaac cattgataag | 1800 |
| gtggtgaaaa tttatgatgc tttgatttat atgcaagtaa acagttcatt tgaagatcat | 1860 |
| atcctggaag atttatgtgg tatgctctca cttccatgga tttattccca ttctgatgat | 1920 |
| ggctgtttaa agttgaccac atttgccgct aatcttctaa cattaagctg taggatttca | 1980 |
| gatagctatt caccacaggc acaatcacga tgtgtgtttc ttctgactct gtttccaaga | 2040 |
| agaatattcc ttgagtggag aacagcagtt tacaactggg ccctgcagag ctcccatgaa | 2100 |
| gtaatccggg ctagttgtgt tagtggattt tttatcttat tgcagcagca gaattcttgt | 2160 |
| aacagagttc ccaagattct tatagataaa gtcaaagatg attctgacat tgtcaagaaa | 2220 |
| gaatttgctt ctatacttgg tcaacttgtc tgtactcttc acggcatgtt ttatctgaca | 2280 |
| agttctttaa cagaaccttt ctctgaacac ggacatgtgg acctcttctg taggaacttg | 2340 |
| aaagccactt ctcaacatga atgttcatct tctcaactaa agcttctgt ctgcaagcca | 2400 |
| ttccttttcc tactgaaaaa aaaaatacct agtccagtaa aacttgcttt catagataat | 2460 |
| ctacatcatc tttgtaagca tcttgatttt agagaagatg aaacagatgt aaaagcagtt | 2520 |

-continued

```
cttggaactt tattaaattt aatggaagat ccagacaaag atgttagagt ggcttttagt      2580
ggaaatatca agcacatatt ggaatccttg gactctgaag atggatttat aaaggagctt      2640
tttgtcttaa gaatgaagga agcatataca catgcccaaa tatcaagaaa taatgagctg      2700
aaggatacct tgattcttac aacagggat attggaaggg ccgcaaaagg agatttggta       2760
ccatttgcac tcttacactt attgcattgt ttgttatcca agtcagcatc tgtctctgga      2820
gcagcataca cagaaattag agctctggtt gcagctaaaa gtgttaaact gcaaagtttt      2880
ttcagccagt ataagaaacc catctgtcag ttttttggtag aatcccttca ctctagtcag     2940
atgacagcac ttccgaatac tccatgccag aatgctgacg tgcgaaaaca agatgtggct     3000
caccagagag aaatggcttt aaatacgttg tctgaaattg ccaacgtttt cgactttcct     3060
gatcttaatc gttttcttac taggacatta caagttctac tacctgatct tgctgccaaa    3120
gcaagccctg cagcttctgc tctcattcga actttaggaa acaattaaa tgtcaatcgt      3180 agagagattt taataaacaa cttcaaatat attttttctc atttggtctg ttcttgttcc     3240
aaagatgaat tagaacgtgc ccttcattat ctgaagaatg aaacagaaat tgaactgggg     3300
agcctgttga gacaagattt ccaaggattg cataatgaat tattgctgcg tattggagaa    3360
cactatcaac aggtttttaa tggtttgtca atacttgcct catttgcatc cagtgatgat    3420
ccatatcagg gcccgagaga tatcatatca cctgaactga tggctgatta tttacaaccc     3480
aaattgttgg gcattttggc ttttttttaac atgcagttac tgagctctag tgttggcatt   3540
gaagataaga aaatggcctt gaacagtttg atgtctttga tgaagttaat gggacccaaa    3600
catgtcagtt ctgtgagggt gaagatgatg accacactga gaactggcct tcgattcaag    3660
gatgattttc ctgaattgtg ttgcagagct tgggactgct tgttcgctg cctggatcat      3720 gcttgtctgg gctcccttct cagtcatgta atagtagctt tgttacctct tatacacatc    3780
cagcctaaag aaactgcagc tatcttccac tacctcataa ttgaaaacag ggatgctgtg    3840
caagattttc ttcatgaaat atattttttta cctgatcatc cagaattaaa aaagataaaa    3900
gccgttctcc aggaatacag aaaggagacc tctgagagca ctgatcttca gacaactctt    3960
cagctctcta tgaaggccat tcaacatgaa aatgtcgatg ttcgtattca tgctcttaca    4020
agcttgaagg aaaccttgta taaaaatcag gaaaaactga taaagtatgc aacagacagt    4080
gaaacagtag aacctattat ctcacagttg gtgacagtgc ttttgaaagg ttgccaagat    4140
gcaaactctc aagctcggtt gctctgtggg gaatgtttag gggaattggg ggcgatagat    4200
ccaggtcgat tagatttctc aacaactgaa actcaaggaa aagatttac atttgtgact    4260 ggagtagaag attcaagctt tgcctatgga ttattgatgg agctaacaag agcttacctt   4320
gcgtatgctg ataatagccg agctcaagat tcagctgcct atgccattca ggagttgctt    4380
tctatttatg actgtagaga gatggagacc aacggcccag gtcaccaatt gtggaggaga    4440
tttcctgagc atgttcggga aatactagaa cctcatctaa ataccagata caagagttct     4500
cagaagtcaa ccgattggtc tggagtaaag aagccaattt acttaagtaa attgggtagt    4560
aactttgcag aatggtcagc atcttgggca ggttatctta ttacaaaggt tcgacatgat   4620
cttgccagta aaattttcac ctgctgtagc attatgatga agcatgattt caaagtgacc    4680
atctatcttc ttccacatat tctggtgtat gtcttactgg gttgtaatca agaagatcag    4740
caggaggttt atgcagaaat tatggcagtt ctaaagcatg acgatcagca taccataaat    4800
acccaagaca ttgcatctga tctgtgtcaa ctcagtacac agactgtgtt ctccatgctt    4860
gaccatctca cacagtgggc aaggcacaaa tttcaggcac tgaaagctga gaaatgtcca    4920
```

```
cacagcaaat caaacagaaa taaggtagac tcaatggtat ctactgtgga ttatgaagac    4980
tatcagagtg taacccgttt tctagacctc ataccccagg atactctggc agtagcttcc    5040
tttcgctcca aagcatacac acgagctgta atgcactttg aatcatttat tacagaaaag    5100
aagcaaaata ttcaggaaca tcttggattt ttacagaaat tgtatgctgc tatgcatgaa    5160
cctgatggag tggccggagt cagtgcaatt agaaaggcag aaccatctct aaaagaacag    5220
atccttgaac atgaaagcct tggcttgctg agggatgcca ctgcttgtta tgacagggct    5280
attcagctag aaccagacca gatcattcat tatcatggtg tagtaaagtc catgttaggt    5340
cttggtcagc tgtctactgt tatcactcag gtgaatggag tgcatgctaa caggtccgag    5400
tggacagatg aattaaacac gtacagagtg aagcagctt ggaaattgtc acagtgggat    5460
ttggtggaaa actatttggc agcagatgga aaatctacaa catggagtgt cagactggga    5520
cagctattat tatcagccaa aaaaagagat atcacagctt tttatgactc actgaaaacta   5580 gtgagagcag aacaaattgt acctctttca gctgcaagct ttgaaagagg ctcctaccaa    5640
cgaggatatg aatatattgt gagattgcac atgttatgtg agttggagca tagcatcaaa    5700
ccacttttcc agcattctcc aggtgacagt tctcaagaag attctctaaa ctgggtagct    5760
cgactagaaa tgacccagaa ttcctacaga gccaaggagc ctatcctggc tctccggagg    5820
gctttactaa gcctcaacaa aagaccagat tacaatgaaa tggttggaga atgctggctg    5880
cagagtgcca gggtagctag aaaggctggt caccaccaga cagcctacaa tgctctcctt    5940
aatgcagggg aatcacgact cgctgaactg tacgtgaaaa gggcaaagtg gctctggtcc    6000
aagggtgatg ttcaccaggc actaattgtt cttcaaaaag gtgttgaatt atgttttcct    6060
gaaaatgaaa ccccacctga gggtaagaac atgttaatcc atggtcgagc tatgctacta    6120
gtgggccgat ttatggaaga aacagctaac tttgaaagca atgcaattat gaaaaaatat    6180
aaggatgtga ccgcgtgcct gccagaatgg gaggatgggc attttttacct tgccaagtac    6240 tatgacaaat tgatgcccat ggtcacagac aacaaaatgg aaaagcaagg tgatctcatc    6300
cggtatatag ttcttcattt tggcagatct ctacaatatg gaaatcagtt catatatcag    6360
tcaatgccac gaatgttaac tctatggctt gattatggta caaaggcata tgaatgggaa    6420
aaagctggcc gctccgatcg tgtacaaatg aggaatgatt tgggtaaaat aaacaaggtt    6480
atcacagagc atacaaacta tttagctcca tatcaatttt tgactgcttt ttcacaattg    6540
atctctcgaa tttgtcattc tcacgatgaa gtttttgttg tcttgatgga ataatagcc    6600 aaagtatttc tagcctatcc tcaacaagca atgtggatga tgacagctgt gtcaaagtca    6660
tcttatccca tgcgtgtgaa cagatgcaag gaaatcctca ataaagctat tcatatgaaa    6720
aaatccttag agaagtttgt tggagatgca actcgcctaa cagataagct tctagaattg    6780
tgcaataaac cggttgatgg aagtagttcc acattaagca tgagcactca ttttaaaatg    6840
cttaaaaagc tggtagaaga agcaacattt agtgaaatcc tcattcctct acaatcagtc    6900
atgataccta cacttccatc aattctgggt acccatgcta accatgctag ccatgaacca    6960
tttcctggac attgggccta tattgcaggg tttgatgata tggtggaaat tcttgcttct    7020
cttcagaaac caaagaagat ttcttttaaa ggctcagatg gaaagttcta catcatgatg    7080
tgtaagccaa aagatgacct gagaaaggat tgtagactaa tggaattcaa ttccttgatt    7140
aataagtgct taagaaaaga tgcagagtct cgtagaagag aacttcatat tcgaacatat    7200
gcagttattc cactaaatga tgaatgtggg attattgaat gggtgaacaa cactgctggt    7260
```

-continued

```
ttgagaccta ttctgaccaa actatataaa gaaaagggag tgtatatgac aggaaaagaa    7320
cttcgccagt gtatgctacc aaagtcagca gctttatctg aaaaactcaa agtattccga    7380
gaatttctcc tgcccaggca tcctcctatt tttcatgagt ggtttctgag aacattccct    7440
gatcctacat catggtacag tagtagatca gcttactgcc gttccactgc agtaatgtca    7500
atggttggtt atattctggg gcttggagac cgtcatggtg aaaatattct ctttgattct    7560
ttgactggtg aatgcgtaca tgtagatttc aattgtcttt tcaataaggg agaaaccttt    7620
gaagttccag aaattgtgcc atttcgcctg actcataata tggttaatgg aatgggtcct    7680
atgggaacag agggtctttt tcgaagagca tgtgaagtta caatgaggct gatgcgtgat    7740
cagcgagagc ctttaatgag tgtcttaaag acttttctac atgatcctct tgtggaatgg    7800
agtaaaccag tgaaagggca ttccaaagcg ccactgaatg aaactggaga agttgtcaat    7860
gaaaaggcca agaccccatgt tcttgacatt gagcagcgac tacaaggtgt aatcaagact    7920
cgaaatagag tgcacaggact gccgttatct attgaaggac atgtgcatta ccttatacaa    7980
gaagctactg atgaaaactt actatgccag atgtatcttg gttggactcc atatatgtga    8040
aatgaaatta tgtaaaagaa tatgttaata atctaaaagt aatgcatttg gtatgaatct    8100
gtggttgtat ctgttcaatt ctaaagtaca acataaattt acgttctcag caactgttat    8160
ttctctctga tcattaatta tatgtaaaat aatatacatt cagttattaa gaaataaact    8220
gctttcttaa taaaaaaaaa aaaaaaaaaa aaaaaaaaaa aaaaa                    8265
```

<210> SEQ ID NO 39
<211> LENGTH: 2644
<212> TYPE: PRT
<213> ORGANISM: Homo sapiens

<400> SEQUENCE: 39

```
Met Gly Glu His Gly Leu Glu Leu Ala Ser Met Ile Pro Ala Leu Arg
  1               5                  10                  15

Glu Leu Gly Ser Ala Thr Pro Glu Glu Tyr Asn Thr Val Val Gln Lys
                 20                  25                  30

Pro Arg Gln Ile Leu Cys Gln Phe Ile Asp Arg Ile Leu Thr Asp Val
             35                  40                  45

Asn Val Val Ala Val Glu Leu Val Lys Lys Thr Asp Ser Gln Pro Thr
         50                  55                  60

Ser Val Met Leu Leu Asp Phe Ile Gln His Ile Met Lys Ser Ser Pro
 65                  70                  75                  80

Leu Met Phe Val Asn Val Ser Gly Ser His Glu Arg Lys Gly Ser Cys
                 85                  90                  95

Ile Glu Phe Ser Asn Trp Ile Ile Thr Arg Leu Leu Arg Ile Ala Ala
                100                 105                 110

Thr Pro Ser Cys His Leu Leu His Lys Lys Ile Cys Glu Val Ile Cys
            115                 120                 125

Ser Leu Leu Phe Leu Phe Lys Ser Lys Ser Pro Ala Ile Phe Gly Val
        130                 135                 140

Leu Thr Lys Glu Leu Leu Gln Leu Phe Glu Asp Leu Val Tyr Leu His
145                 150                 155                 160

Arg Arg Asn Val Met Gly His Ala Val Glu Trp Pro Val Met Ser
                165                 170                 175

Arg Phe Leu Ser Gln Leu Asp Glu His Met Gly Tyr Leu Gln Ser Ala
            180                 185                 190

Pro Leu Gln Leu Met Ser Met Gln Asn Leu Glu Phe Ile Glu Val Thr
```

-continued

```
                195                 200                 205
Leu Leu Met Val Leu Thr Arg Ile Ile Ala Ile Val Phe Phe Arg Arg
210                 215                 220

Gln Glu Leu Leu Leu Trp Gln Ile Gly Cys Val Leu Leu Glu Tyr Gly
225                 230                 235                 240

Ser Pro Lys Ile Lys Ser Leu Ala Ile Ser Phe Leu Thr Glu Leu Phe
                245                 250                 255

Gln Leu Gly Gly Leu Pro Ala Gln Pro Ala Ser Thr Phe Phe Ser Ser
                260                 265                 270

Phe Leu Glu Leu Lys His Leu Val Glu Met Asp Thr Asp Gln Leu
        275                 280                 285

Lys Leu Tyr Glu Glu Pro Leu Ser Lys Leu Ile Lys Thr Leu Phe Pro
290                 295                 300

Phe Glu Ala Glu Ala Tyr Arg Asn Ile Glu Pro Val Tyr Leu Asn Met
305                 310                 315                 320

Leu Leu Glu Lys Leu Cys Val Met Phe Glu Asp Gly Val Leu Met Arg
                325                 330                 335

Leu Lys Ser Asp Leu Leu Lys Ala Ala Leu Cys His Leu Leu Gln Tyr
                340                 345                 350

Phe Leu Lys Phe Val Pro Ala Gly Tyr Glu Ser Ala Leu Gln Val Arg
                355                 360                 365

Lys Val Tyr Val Arg Asn Ile Cys Lys Ala Leu Leu Asp Val Leu Gly
            370                 375                 380

Ile Glu Val Asp Ala Glu Tyr Leu Leu Gly Pro Leu Tyr Ala Ala Leu
385                 390                 395                 400

Lys Met Glu Ser Met Glu Ile Ile Glu Glu Ile Gln Cys Gln Thr Gln
                405                 410                 415

Gln Glu Asn Leu Ser Ser Asn Ser Asp Gly Ile Ser Pro Lys Arg Arg
                420                 425                 430

Arg Leu Ser Ser Ser Leu Asn Pro Ser Lys Arg Ala Pro Lys Gln Thr
            435                 440                 445

Glu Glu Ile Lys His Val Asp Met Asn Gln Lys Ser Ile Leu Trp Ser
450                 455                 460

Ala Leu Lys Gln Lys Ala Glu Ser Leu Gln Ile Ser Leu Glu Tyr Ser
465                 470                 475                 480

Gly Leu Lys Asn Pro Val Ile Glu Met Leu Glu Gly Ile Ala Val Val
                485                 490                 495

Leu Gln Leu Thr Ala Leu Cys Thr Val His Cys Ser His Gln Asn Met
            500                 505                 510

Asn Cys Arg Thr Phe Lys Asp Cys Gln His Lys Ser Lys Lys Pro
            515                 520                 525

Ser Val Val Ile Thr Trp Met Ser Leu Asp Phe Tyr Thr Lys Val Leu
530                 535                 540

Lys Ser Cys Arg Ser Leu Leu Glu Ser Val Gln Lys Leu Asp Leu Glu
545                 550                 555                 560

Ala Thr Ile Asp Lys Val Val Lys Ile Tyr Asp Ala Leu Ile Tyr Met
                565                 570                 575

Gln Val Asn Ser Ser Phe Glu Asp His Ile Leu Glu Asp Leu Cys Gly
                580                 585                 590

Met Leu Ser Leu Pro Trp Ile Tyr Ser His Ser Asp Asp Gly Cys Leu
            595                 600                 605

Lys Leu Thr Thr Phe Ala Ala Asn Leu Leu Thr Leu Ser Cys Arg Ile
610                 615                 620
```

-continued

```
Ser Asp Ser Tyr Ser Pro Gln Ala Gln Ser Arg Cys Val Phe Leu Leu
625                 630                 635                 640

Thr Leu Phe Pro Arg Arg Ile Phe Leu Glu Trp Arg Thr Ala Val Tyr
                645                 650                 655

Asn Trp Ala Leu Gln Ser Ser His Glu Val Ile Arg Ala Ser Cys Val
                660                 665                 670

Ser Gly Phe Phe Ile Leu Leu Gln Gln Gln Asn Ser Cys Asn Arg Val
            675                 680                 685

Pro Lys Ile Leu Ile Asp Lys Val Lys Asp Asp Ser Asp Ile Val Lys
        690                 695                 700

Lys Glu Phe Ala Ser Ile Leu Gly Gln Leu Val Cys Thr Leu His Gly
705                 710                 715                 720

Met Phe Tyr Leu Thr Ser Ser Leu Thr Glu Pro Phe Ser Glu His Gly
                725                 730                 735

His Val Asp Leu Phe Cys Arg Asn Leu Lys Ala Thr Ser Gln His Glu
                740                 745                 750

Cys Ser Ser Ser Gln Leu Lys Ala Ser Val Cys Lys Pro Phe Leu Phe
        755                 760                 765

Leu Leu Lys Lys Lys Ile Pro Ser Pro Val Lys Leu Ala Phe Ile Asp
    770                 775                 780

Asn Leu His His Leu Cys Lys His Leu Asp Phe Arg Glu Asp Glu Thr
785                 790                 795                 800

Asp Val Lys Ala Val Leu Gly Thr Leu Leu Asn Leu Met Glu Asp Pro
                805                 810                 815

Asp Lys Asp Val Arg Val Ala Phe Ser Gly Asn Ile Lys His Ile Leu
                820                 825                 830

Glu Ser Leu Asp Ser Glu Asp Gly Phe Ile Lys Glu Leu Phe Val Leu
            835                 840                 845

Arg Met Lys Glu Ala Tyr Thr His Ala Gln Ile Ser Arg Asn Asn Glu
850                 855                 860

Leu Lys Asp Thr Leu Ile Leu Thr Thr Gly Asp Ile Gly Arg Ala Ala
865                 870                 875                 880

Lys Gly Asp Leu Val Pro Phe Ala Leu Leu His Leu His Cys Leu
                885                 890                 895

Leu Ser Lys Ser Ala Ser Val Ser Gly Ala Ala Tyr Thr Glu Ile Arg
            900                 905                 910

Ala Leu Val Ala Ala Lys Ser Val Lys Leu Gln Ser Phe Phe Ser Gln
        915                 920                 925

Tyr Lys Lys Pro Ile Cys Gln Phe Leu Val Glu Ser Leu His Ser Ser
    930                 935                 940

Gln Met Thr Ala Leu Pro Asn Thr Pro Cys Gln Asn Ala Asp Val Arg
945                 950                 955                 960

Lys Gln Asp Val Ala His Gln Arg Glu Met Ala Leu Asn Thr Leu Ser
                965                 970                 975

Glu Ile Ala Asn Val Phe Asp Phe Pro Asp Leu Asn Arg Phe Leu Thr
                980                 985                 990

Arg Thr Leu Gln Val Leu Leu Pro Asp Leu Ala Ala Lys Ala Ser Pro
            995                 1000                1005

Ala Ala Ser Ala Leu Ile Arg Thr Leu Gly Lys Gln Leu Asn Val Asn
    1010                1015                1020

Arg Arg Glu Ile Leu Ile Asn Asn Phe Lys Tyr Ile Phe Ser His Leu
1025                1030                1035                1040
```

-continued

```
Val Cys Ser Cys Ser Lys Asp Glu Leu Glu Arg Ala Leu His Tyr Leu
            1045                1050                1055

Lys Asn Glu Thr Glu Ile Glu Leu Gly Ser Leu Leu Arg Gln Asp Phe
        1060                1065                1070

Gln Gly Leu His Asn Glu Leu Leu Leu Arg Ile Gly Glu His Tyr Gln
    1075                1080                1085

Gln Val Phe Asn Gly Leu Ser Ile Leu Ala Ser Phe Ala Ser Ser Asp
    1090                1095                1100

Asp Pro Tyr Gln Gly Pro Arg Asp Ile Ile Ser Pro Glu Leu Met Ala
1105                1110                1115                1120

Asp Tyr Leu Gln Pro Lys Leu Leu Gly Ile Leu Ala Phe Phe Asn Met
        1125                1130                1135

Gln Leu Leu Ser Ser Ser Val Gly Ile Glu Asp Lys Lys Met Ala Leu
            1140                1145                1150

Asn Ser Leu Met Ser Leu Met Lys Leu Met Gly Pro Lys His Val Ser
            1155                1160                1165

Ser Val Arg Val Lys Met Met Thr Thr Leu Arg Thr Gly Leu Arg Phe
        1170                1175                1180

Lys Asp Asp Phe Pro Glu Leu Cys Cys Arg Ala Trp Asp Cys Phe Val
1185                1190                1195                1200

Arg Cys Leu Asp His Ala Cys Leu Gly Ser Leu Leu Ser His Val Ile
            1205                1210                1215

Val Ala Leu Leu Pro Leu Ile His Ile Gln Pro Lys Glu Thr Ala Ala
        1220                1225                1230

Ile Phe His Tyr Leu Ile Ile Glu Asn Arg Asp Ala Val Gln Asp Phe
        1235                1240                1245

Leu His Glu Ile Tyr Phe Leu Pro Asp His Pro Glu Leu Lys Lys Ile
    1250                1255                1260

Lys Ala Val Leu Gln Glu Tyr Arg Lys Glu Thr Ser Glu Ser Thr Asp
1265                1270                1275                1280

Leu Gln Thr Thr Leu Gln Leu Ser Met Lys Ala Ile Gln His Glu Asn
        1285                1290                1295

Val Asp Val Arg Ile His Ala Leu Thr Ser Leu Lys Glu Thr Leu Tyr
        1300                1305                1310

Lys Asn Gln Glu Lys Leu Ile Lys Tyr Ala Thr Asp Ser Glu Thr Val
    1315                1320                1325

Glu Pro Ile Ile Ser Gln Leu Val Thr Val Leu Leu Lys Gly Cys Gln
    1330                1335                1340

Asp Ala Asn Ser Gln Ala Arg Leu Leu Cys Gly Glu Cys Leu Gly Glu
1345                1350                1355                1360

Leu Gly Ala Ile Asp Pro Gly Arg Leu Asp Phe Ser Thr Thr Glu Thr
        1365                1370                1375

Gln Gly Lys Asp Phe Thr Phe Val Thr Gly Val Glu Asp Ser Ser Phe
    1380                1385                1390

Ala Tyr Gly Leu Leu Met Glu Leu Thr Arg Ala Tyr Leu Ala Tyr Ala
        1395                1400                1405

Asp Asn Ser Arg Ala Gln Asp Ser Ala Ala Tyr Ala Ile Gln Glu Leu
    1410                1415                1420

Leu Ser Ile Tyr Asp Cys Arg Glu Met Glu Thr Asn Gly Pro Gly His
1425                1430                1435                1440

Gln Leu Trp Arg Arg Phe Pro Glu His Val Arg Glu Ile Leu Glu Pro
        1445                1450                1455

His Leu Asn Thr Arg Tyr Lys Ser Ser Gln Lys Ser Thr Asp Trp Ser
```

```
                    1460              1465              1470
Gly Val Lys Lys Pro Ile Tyr Leu Ser Lys Leu Gly Ser Asn Phe Ala
         1475              1480              1485
Glu Trp Ser Ala Ser Trp Ala Gly Tyr Leu Ile Thr Lys Val Arg His
         1490              1495              1500
Asp Leu Ala Ser Lys Ile Phe Thr Cys Cys Ser Ile Met Met Lys His
1505              1510              1515              1520
Asp Phe Lys Val Thr Ile Tyr Leu Leu Pro His Ile Leu Val Tyr Val
                    1525              1530              1535
Leu Leu Gly Cys Asn Gln Glu Asp Gln Gln Glu Val Tyr Ala Glu Ile
         1540              1545              1550
Met Ala Val Leu Lys His Asp Asp Gln His Thr Ile Asn Thr Gln Asp
         1555              1560              1565
Ile Ala Ser Asp Leu Cys Gln Leu Ser Thr Gln Thr Val Phe Ser Met
         1570              1575              1580
Leu Asp His Leu Thr Gln Trp Ala Arg His Lys Phe Gln Ala Leu Lys
1585              1590              1595              1600
Ala Glu Lys Cys Pro His Ser Lys Ser Asn Arg Asn Lys Val Asp Ser
                    1605              1610              1615
Met Val Ser Thr Val Asp Tyr Glu Asp Tyr Gln Ser Val Thr Arg Phe
         1620              1625              1630
Leu Asp Leu Ile Pro Gln Asp Thr Leu Ala Val Ala Ser Phe Arg Ser
         1635              1640              1645
Lys Ala Tyr Thr Arg Ala Val Met His Phe Gly Ser Phe Ile Thr Glu
         1650              1655              1660
Lys Lys Gln Asn Ile Gln Glu His Leu Gly Phe Leu Gln Lys Leu Tyr
1665              1670              1675              1680
Ala Ala Met His Glu Pro Asp Gly Val Ala Gly Val Ser Ala Ile Arg
         1685              1690              1695
Lys Ala Glu Pro Ser Leu Lys Glu Gln Ile Leu Glu His Glu Ser Leu
              1700              1705              1710
Gly Leu Leu Arg Asp Ala Thr Ala Cys Tyr Asp Arg Ala Ile Gln Leu
         1715              1720              1725
Glu Pro Asp Gln Ile Ile His Tyr His Gly Val Val Lys Ser Met Leu
         1730              1735              1740
Gly Leu Gly Gln Leu Ser Thr Val Ile Thr Gln Val Asn Gly Val His
1745              1750              1755              1760
Ala Asn Arg Ser Glu Trp Thr Asp Glu Leu Asn Thr Tyr Arg Val Glu
              1765              1770              1775
Ala Ala Trp Lys Leu Ser Gln Trp Asp Leu Val Glu Asn Tyr Leu Ala
         1780              1785              1790
Ala Asp Gly Lys Ser Thr Thr Trp Ser Val Arg Leu Gly Gln Leu Leu
         1795              1800              1805
Leu Ser Ala Lys Lys Arg Asp Ile Thr Ala Phe Tyr Asp Ser Leu Lys
         1810              1815              1820
Leu Val Arg Ala Glu Gln Ile Val Pro Leu Ser Ala Ala Ser Phe Glu
1825              1830              1835              1840
Arg Gly Ser Tyr Gln Arg Gly Tyr Glu Tyr Ile Val Arg Leu His Met
                    1845              1850              1855
Leu Cys Glu Leu Glu His Ser Ile Lys Pro Leu Phe Gln His Ser Pro
         1860              1865              1870
Gly Asp Ser Ser Gln Glu Asp Ser Leu Asn Trp Val Ala Arg Leu Glu
         1875              1880              1885
```

```
Met Thr Gln Asn Ser Tyr Arg Ala Lys Glu Pro Ile Leu Ala Leu Arg
    1890                1895                1900

Arg Ala Leu Leu Ser Leu Asn Lys Arg Pro Asp Tyr Asn Glu Met Val
1905                1910                1915                1920

Gly Glu Cys Trp Leu Gln Ser Ala Arg Val Ala Arg Lys Ala Gly His
            1925                1930                1935

His Gln Thr Ala Tyr Asn Ala Leu Leu Asn Ala Gly Glu Ser Arg Leu
        1940                1945                1950

Ala Glu Leu Tyr Val Glu Arg Ala Lys Trp Leu Trp Ser Lys Gly Asp
    1955                1960                1965

Val His Gln Ala Leu Ile Val Leu Gln Lys Gly Val Glu Leu Cys Phe
    1970                1975                1980

Pro Glu Asn Glu Thr Pro Pro Glu Gly Lys Asn Met Leu Ile His Gly
1985                1990                1995                2000

Arg Ala Met Leu Leu Val Gly Arg Phe Met Glu Glu Thr Ala Asn Phe
            2005                2010                2015

Glu Ser Asn Ala Ile Met Lys Lys Tyr Lys Asp Val Thr Ala Cys Leu
        2020                2025                2030

Pro Glu Trp Glu Asp Gly His Phe Tyr Leu Ala Lys Tyr Tyr Asp Lys
        2035                2040                2045

Leu Met Pro Met Val Thr Asp Asn Lys Met Glu Lys Gln Gly Asp Leu
        2050                2055                2060

Ile Arg Tyr Ile Val Leu His Phe Gly Arg Ser Leu Gln Tyr Gly Asn
2065                2070                2075                2080

Gln Phe Ile Tyr Gln Ser Met Pro Arg Met Leu Thr Leu Trp Leu Asp
            2085                2090                2095

Tyr Gly Thr Lys Ala Tyr Glu Trp Glu Lys Ala Gly Arg Ser Asp Arg
        2100                2105                2110

Val Gln Met Arg Asn Asp Leu Gly Lys Ile Asn Lys Val Ile Thr Glu
        2115                2120                2125

His Thr Asn Tyr Leu Ala Pro Tyr Gln Phe Leu Thr Ala Phe Ser Gln
        2130                2135                2140

Leu Ile Ser Arg Ile Cys His Ser His Asp Glu Val Phe Val Val Leu
2145                2150                2155                2160

Met Glu Ile Ile Ala Lys Val Phe Leu Ala Tyr Pro Gln Gln Ala Met
            2165                2170                2175

Trp Met Met Thr Ala Val Ser Lys Ser Ser Tyr Pro Met Arg Val Asn
            2180                2185                2190

Arg Cys Lys Glu Ile Leu Asn Lys Ala Ile His Met Lys Lys Ser Leu
        2195                2200                2205

Glu Lys Phe Val Gly Asp Ala Thr Arg Leu Thr Asp Lys Leu Leu Glu
    2210                2215                2220

Leu Cys Asn Lys Pro Val Asp Gly Ser Ser Ser Thr Leu Ser Met Ser
2225                2230                2235                2240

Thr His Phe Lys Met Leu Lys Lys Leu Val Glu Glu Ala Thr Phe Ser
            2245                2250                2255

Glu Ile Leu Ile Pro Leu Gln Ser Val Met Ile Pro Thr Leu Pro Ser
        2260                2265                2270

Ile Leu Gly Thr His Ala Asn His Ala Ser His Glu Pro Phe Pro Gly
        2275                2280                2285

His Trp Ala Tyr Ile Ala Gly Phe Asp Asp Met Val Glu Ile Leu Ala
    2290                2295                2300
```

```
Ser Leu Gln Lys Pro Lys Lys Ile Ser Leu Lys Gly Ser Asp Gly Lys
    2305                2310                2315                2320

Phe Tyr Ile Met Met Cys Lys Pro Lys Asp Asp Leu Arg Lys Asp Cys
                2325                2330                2335

Arg Leu Met Glu Phe Asn Ser Leu Ile Asn Lys Cys Leu Arg Lys Asp
            2340                2345                2350

Ala Glu Ser Arg Arg Arg Glu Leu His Ile Arg Thr Tyr Ala Val Ile
        2355                2360                2365

Pro Leu Asn Asp Glu Cys Gly Ile Ile Glu Trp Val Asn Asn Thr Ala
    2370                2375                2380

Gly Leu Arg Pro Ile Leu Thr Lys Leu Tyr Lys Glu Lys Gly Val Tyr
2385                2390                2395                2400

Met Thr Gly Lys Glu Leu Arg Gln Cys Met Leu Pro Lys Ser Ala Ala
                2405                2410                2415

Leu Ser Glu Lys Leu Lys Val Phe Arg Glu Phe Leu Leu Pro Arg His
            2420                2425                2430

Pro Pro Ile Phe His Glu Trp Phe Leu Arg Thr Phe Pro Asp Pro Thr
        2435                2440                2445

Ser Trp Tyr Ser Ser Arg Ser Ala Tyr Cys Arg Ser Thr Ala Val Met
    2450                2455                2460

Ser Met Val Gly Tyr Ile Leu Gly Leu Gly Asp Arg His Gly Glu Asn
2465                2470                2475                2480

Ile Leu Phe Asp Ser Leu Thr Gly Glu Cys Val His Val Asp Phe Asn
                2485                2490                2495

Cys Leu Phe Asn Lys Gly Glu Thr Phe Glu Val Pro Glu Ile Val Pro
            2500                2505                2510

Phe Arg Leu Thr His Asn Met Val Asn Gly Met Gly Pro Met Gly Thr
        2515                2520                2525

Glu Gly Leu Phe Arg Arg Ala Cys Glu Val Thr Met Arg Leu Met Arg
    2530                2535                2540

Asp Gln Arg Glu Pro Leu Met Ser Val Leu Lys Thr Phe Leu His Asp
2545                2550                2555                2560

Pro Leu Val Glu Trp Ser Lys Pro Val Lys Gly His Ser Lys Ala Pro
                2565                2570                2575

Leu Asn Glu Thr Gly Glu Val Val Asn Glu Lys Ala Lys Thr His Val
            2580                2585                2590

Leu Asp Ile Glu Gln Arg Leu Gln Gly Val Ile Lys Thr Arg Asn Arg
        2595                2600                2605

Val Thr Gly Leu Pro Leu Ser Ile Glu Gly His Val His Tyr Leu Ile
    2610                2615                2620

Gln Glu Ala Thr Asp Glu Asn Leu Leu Cys Gln Met Tyr Leu Gly Trp
2625                2630                2635                2640

Thr Pro Tyr Met

<210> SEQ ID NO 40
<211> LENGTH: 2824
<212> TYPE: DNA
<213> ORGANISM: Homo sapiens

<400> SEQUENCE: 40
ggagctgttg cggggtccgc ggggaagtct tggcggtgga gccatggtcg gccaactgag    60
cgagggggcc attgcggcca tcatgcagaa gggggataca aacataaagc ccatcctcca   120
agtcatcaac atccgtccca ttactacggg gaatagtccg ccgcgttatc gactgctcat   180
```

-continued

```
gagtgatgga ttgaacactc tatcctctttt catgttggcg acacagttga accctctcgt    240
ggaggaagaa caattgtcca gcaactgtgt atgccagatt cacagattta ttgtgaacac    300
tctgaaagac ggaaggagag tagttatctt gatggaatta gaagttttga agtcagctga    360
agcagttgga gtgaagattg caatccagt gccctataat aaggactcg ggcagccgca      420
agtagctcct ccagcgccag cagccagccc agcagcaagc agcaggcccc agccgcagaa    480
tggaagctcg ggaatgggtt ctactgtttc taaggcttat ggtgcttcaa agacatttgg    540
aaaagctgca ggtcccagcc tgtcacacac ttctggggga acacagtcca aagtggtgcc    600
cattgccagc ctcactcctt accagtccaa gtggaccatt tgtgctcgtg ttaccaacaa    660
aagtcagatc cgtacctgga gcaactcccg aggggaaggg aagcttttct ccctagaact    720
ggttgacgaa agtggtgaaa tccgagctac agctttcaat gagcaagtgg acaagttctt    780
tcctcttatt gaagtgaaca aggtgtatta tttctcgaaa ggcaccctga agattgctaa    840
caagcagttc acagctgtta aaaatgacta cgagatgacc ttcaataacg agacttccgt    900
catgccctgt gaggacgacc atcatttacc tacggttcag tttgatttca cggggattga    960
tgacctcgag aacaagtcga aagactcact tgtagacatc atcgggatct gcaagagcta   1020
tgaagacgcc actaaaatca cagtgaggtc taacaacaga gaagttgcca gaggaatat    1080
ctacttgatg gacacatctg ggaaggtggt gactgctaca ctgtgggggg aagatgctga   1140
taaatttgat ggttctagac agcccgtgtt ggctatcaaa ggagcccgag tctctgattt   1200
cggtggacgg agcctctccg tgctgtcttc aagcactatc attgcgaatc ctgacatccc   1260
agaggcctat aagcttcgtg gatggtttga cgcagaagga caagccttag atggtgtttc   1320
catctctgat ctaaagagcg gcggagtcgg agggagtaac accaactgga aaaccttgta   1380
tgaggtcaaa tccgagaacc tgggccaagg cgacaagccg gactacttta gttctgtggc   1440
cacagtggtg tatcttcgca aagagaactg catgtaccaa gcctgcccga ctcaggactg   1500
caataagaaa gtgattgatc aacagaatgg attgtaccgc tgtgagaagt gcgacaccga   1560
atttcccaat ttcaagtacc gcatgatcct gtcagtaaat attgcagatt tcaagagaa   1620
tcagtgggtg acttgttttcc aggagtctgc tgaagctatc cttggacaaa atgctgctta   1680
tcttggggaa ttaaaagaca agaatgaaca ggcatttgaa gaagttttcc agaatgccaa   1740
cttccgatct ttcatattca gagtcagggt caaagtggag acctacaacg acgagtctcg   1800
aattaaggcc actgtgatgg acgtgaagcc cgtggactac agagagtatg ccgaaggct    1860
ggtcatgagc atcaggagaa gtgcattgat gtgagaggag cagtgccaat cgggcagaag   1920
tttgcaaata ggcagaatgg aatcgatttc ctcccacctc cgtgtgacga tcccatgtta   1980
gctacacagt gcagaggctc ttgatggtgg actaagcaat ttcctccctt gtgcgcatct   2040
cagaacccat cggtaggcaa aggaaaatac gctcaggtgg ttgtggtgta gactgtgtca   2100
ggcctacgga gtcagccagt ggctagcgca agaccagtca ctccctctgc cttcaggctt   2160
ctgtcaattt cattatcatc aagcaggaat tatgtcgtaa gtcactgacc ctaactgcag   2220
accatgaagt aaattatgta actaggtttt tgcttctcca gtggtgacca cccccccccc   2280
atccccgctc acaacttggg ttcttctcag cggggcgagc tgagaagcgg tcatgagcac   2340
ctggggattt tagtaagtgt gtcttcctag aattcgaagg ctctctcttt ctagaggtgc   2400
tacatagttg gtaatgcttg gaatggcaat agggtagaat gattaatcaa aggcatatct   2460
tctatatctg aagagtatcc ttccttcagg gtttaataga ctgagtcaga tgggtctgat   2520
attaatcaaa attgtctctt ctgaggaccg ctgataagca ttgacttgct gtcccctaag   2580
```

-continued

```
gaaatccgag cggctacaaa gcgtttcttt acttttcact tcaattaatg ctgcgcttcg   2640
cttggtgagt gcgtactttt tctacctgta cacattcctg cattcatgta ttttgttttt   2700
tttgactaaa gctatgttac atggaaagga ttttgaagcc ttttgtttcc cttgctttgt   2760
tttaataaac agtatattct tggttgtga atcctaaaaa aaaaaaaaaa aaaaaaaaa    2820 aaaa                                                                2824
```

<210> SEQ ID NO 41
<211> LENGTH: 616
<212> TYPE: PRT
<213> ORGANISM: Homo sapiens

<400> SEQUENCE: 41

```
Met Val Gly Gln Leu Ser Glu Gly Ala Ile Ala Ile Met Gln Lys
 1               5                  10                  15

Gly Asp Thr Asn Ile Lys Pro Ile Leu Gln Val Ile Asn Ile Arg Pro
                20                  25                  30

Ile Thr Thr Gly Asn Ser Pro Pro Arg Tyr Arg Leu Leu Met Ser Asp
            35                  40                  45

Gly Leu Asn Thr Leu Ser Ser Phe Met Leu Ala Thr Gln Leu Asn Pro
        50                  55                  60

Leu Val Glu Glu Gln Leu Ser Ser Asn Cys Val Cys Gln Ile His
 65                  70                  75                  80

Arg Phe Ile Val Asn Thr Leu Lys Asp Gly Arg Arg Val Val Ile Leu
                85                  90                  95

Met Glu Leu Glu Val Leu Lys Ser Ala Glu Ala Val Gly Val Lys Ile
            100                 105                 110

Gly Asn Pro Val Pro Tyr Asn Glu Gly Leu Gly Gln Pro Gln Val Ala
        115                 120                 125

Pro Pro Ala Pro Ala Ala Ser Pro Ala Ala Ser Ser Arg Pro Gln Pro
    130                 135                 140

Gln Asn Gly Ser Ser Gly Met Gly Ser Thr Val Ser Lys Ala Tyr Gly
145                 150                 155                 160

Ala Ser Lys Thr Phe Gly Lys Ala Ala Gly Pro Ser Leu Ser His Thr
                165                 170                 175

Ser Gly Gly Thr Gln Ser Lys Val Val Pro Ile Ala Ser Leu Thr Pro
            180                 185                 190

Tyr Gln Ser Lys Trp Thr Ile Cys Ala Arg Val Thr Asn Lys Ser Gln
        195                 200                 205

Ile Arg Thr Trp Ser Asn Ser Arg Gly Glu Gly Lys Leu Phe Ser Leu
    210                 215                 220

Glu Leu Val Asp Glu Ser Gly Glu Ile Arg Ala Thr Ala Phe Asn Glu
225                 230                 235                 240

Gln Val Asp Lys Phe Phe Pro Leu Ile Glu Val Asn Lys Val Tyr Tyr
                245                 250                 255

Phe Ser Lys Gly Thr Leu Lys Ile Ala Asn Lys Gln Phe Thr Ala Val
            260                 265                 270

Lys Asn Asp Tyr Glu Met Thr Phe Asn Asn Glu Thr Ser Val Met Pro
        275                 280                 285

Cys Glu Asp Asp His His Leu Pro Thr Val Gln Phe Asp Phe Thr Gly
    290                 295                 300

Ile Asp Asp Leu Glu Asn Lys Ser Lys Asp Ser Leu Val Asp Ile Ile
305                 310                 315                 320
```

-continued

```
Gly Ile Cys Lys Ser Tyr Glu Asp Ala Thr Lys Ile Thr Val Arg Ser
            325                 330                 335
Asn Asn Arg Glu Val Ala Lys Arg Asn Ile Tyr Leu Met Asp Thr Ser
        340                 345                 350
Gly Lys Val Val Thr Ala Thr Leu Trp Gly Glu Asp Ala Asp Lys Phe
    355                 360                 365
Asp Gly Ser Arg Gln Pro Val Leu Ala Ile Lys Gly Ala Arg Val Ser
370                 375                 380
Asp Phe Gly Gly Arg Ser Leu Ser Val Leu Ser Ser Ser Thr Ile Ile
385                 390                 395                 400
Ala Asn Pro Asp Ile Pro Glu Ala Tyr Lys Leu Arg Gly Trp Phe Asp
            405                 410                 415
Ala Glu Gly Gln Ala Leu Asp Gly Val Ser Ile Ser Asp Leu Lys Ser
        420                 425                 430
Gly Gly Val Gly Gly Ser Asn Thr Asn Trp Lys Thr Leu Tyr Glu Val
    435                 440                 445
Lys Ser Glu Asn Leu Gly Gln Gly Asp Lys Pro Asp Tyr Phe Ser Ser
450                 455                 460
Val Ala Thr Val Val Tyr Leu Arg Lys Glu Asn Cys Met Tyr Gln Ala
465                 470                 475                 480
Cys Pro Thr Gln Asp Cys Asn Lys Lys Val Ile Asp Gln Gln Asn Gly
            485                 490                 495
Leu Tyr Arg Cys Glu Lys Cys Asp Thr Glu Phe Pro Asn Phe Lys Tyr
        500                 505                 510
Arg Met Ile Leu Ser Val Asn Ile Ala Asp Phe Gln Glu Asn Gln Trp
    515                 520                 525
Val Thr Cys Phe Gln Glu Ser Ala Glu Ala Ile Leu Gly Gln Asn Ala
530                 535                 540
Ala Tyr Leu Gly Glu Leu Lys Asp Lys Asn Glu Gln Ala Phe Glu Glu
545                 550                 555                 560
Val Phe Gln Asn Ala Asn Phe Arg Ser Phe Ile Phe Arg Val Arg Val
            565                 570                 575
Lys Val Glu Thr Tyr Asn Asp Glu Ser Arg Ile Lys Ala Thr Val Met
        580                 585                 590
Asp Val Lys Pro Val Asp Tyr Arg Glu Tyr Gly Arg Arg Leu Val Met
    595                 600                 605
Ser Ile Arg Arg Ser Ala Leu Met
610                 615

<210> SEQ ID NO 42
<211> LENGTH: 1750
<212> TYPE: DNA
<213> ORGANISM: Homo sapiens

<400> SEQUENCE: 42
ggcacgaggc ttcgtaaaga tggccgcgga ggcttttgga gccaactggg agcgcagtac      60
gcgttttctg gagcatgggc agaggagaca ggaacaagcg tagcatccgt gagcaccgat     120
tggctgaagc gagcaccccg ggagctgact ggctccgcca ttcgcgggaa ggcgtttgtg     180
gtgccagaga aaagtagcca gagcggcgca gtggcggccg cgttctgtgg ttttccgcta     240
ttcccccaga cccgcacctt ctcggcctct tgcggagaa tcgtgaccaa gatgtggaac      300
agtggattcg aaagctatgg cagctcctca tacggggag ccggcggcta cacgcagtcc      360 ccgggggggct tggatcgcc cgcaccttct caagccgaaa agaaatcaag agcccgagcc     420
```

```
cagcacattg tgccctgtac tatatctcag ctgctttctg ccactttggt tgatgaagtg    480
ttcagaattg ggaatgttga gatttcacag gtcactattg tggggatcat cagacatgca    540
gagaaggctc caaccaacat tgtttacaaa atagatgaca tgacagctgc acccatggac    600
gttcgccagt gggttgacac agatgacacc agcagtgaaa acactgtggt tcctccagaa    660
acatatgtga agtggcagg ccacctgaga tcttttcaga acaaaaagag cctggtagcc    720
tttaagatca tgcccctgga ggatatgaat gagttcacca cacatattct ggaagtgatc    780
aatgcacaca tggtactaag caaagccaac agccagccct cagcagggag agcacctatc    840
agcaatccag gaatgagtga agcagggaac tttggtggga atagcttcat gccagcaaat    900
ggcctcactg tggcccaaaa ccaggtgttg aatttgatta aggcttgtcc aagacctgaa    960
gggttgaact tcaggatct caagaaccag ctgaaacaca tgtctgtatc ctcaatcaag   1020
caagctgtgg attttctgag caatgagggg cacatctatt ctactgtgga tgatgaccat   1080
tttaaatcca cagatgcaga ataactggat ctaactgggt acctgagata ttttacagct   1140
ggacctagtt tcacaatctg ttgtctccag ctctgcatat gtctggccag ggggcttcta   1200
ggaagtaggt ttcatctatc aaatgtctcc tctgacttcc ttttgaaact tactgctctt   1260 ctgtttttatt ttgttttgtt tgaagctcag agggagatgg gcaattgaca gggatgcaat   1320
ccagggtggg atttcttgag gaagttacaa ataagcttgt tacaacatca agatagatgg   1380
aattggaagg atgctaccag gagagtactt acatagtgct caggagtttc tcttcttaaa   1440
atgtttactg ctgaaagatg agcaggacca gggcgttata ggcagagccc tagccgagaa   1500
acctgctggc ctctgcctgt tttcatttcc cactttggtt gtgtggcatt actttcagaa   1560
ttgcactttc ctgcttgtca tgacttttg acacacttgc catgacgtgt gtttctgtga   1620
acatgaagtt ctgcggtagt gcctccaggg gcagaggaaa agaagaagtg ttactgcgtt   1680
ttgtacaaaa taaatacagt catatgttta ataaaacagt tctattgtaa aaaaaaaaa   1740 aaaaaaaaaa                                                         1750
```

<210> SEQ ID NO 43
<211> LENGTH: 270
<212> TYPE: PRT
<213> ORGANISM: Homo sapiens

<400> SEQUENCE: 43

```
Met Trp Asn Ser Gly Phe Glu Ser Tyr Gly Ser Ser Tyr Gly Gly
  1               5                  10                  15

Ala Gly Gly Tyr Thr Gln Ser Pro Gly Gly Phe Gly Ser Pro Ala Pro
             20                  25                  30

Ser Gln Ala Glu Lys Lys Ser Arg Ala Arg Ala Gln His Ile Val Pro
         35                  40                  45

Cys Thr Ile Ser Gln Leu Leu Ser Ala Thr Leu Val Asp Glu Val Phe
     50                  55                  60

Arg Ile Gly Asn Val Glu Ile Ser Gln Val Thr Ile Val Gly Ile Ile
 65                  70                  75                  80

Arg His Ala Glu Lys Ala Pro Thr Asn Ile Val Tyr Lys Ile Asp Asp
                 85                  90                  95

Met Thr Ala Ala Pro Met Asp Val Arg Gln Trp Val Asp Thr Asp Asp
                100                 105                 110

Thr Ser Ser Glu Asn Thr Val Val Pro Pro Glu Thr Tyr Val Lys Val
            115                 120                 125

Ala Gly His Leu Arg Ser Phe Gln Asn Lys Lys Ser Leu Val Ala Phe
```

```
                130             135             140
Lys Ile Met Pro Leu Glu Asp Met Asn Glu Phe Thr Thr His Ile Leu
145                 150                 155                 160

Glu Val Ile Asn Ala His Met Val Leu Ser Lys Ala Asn Ser Gln Pro
                165                 170                 175

Ser Ala Gly Arg Ala Pro Ile Ser Asn Pro Gly Met Ser Glu Ala Gly
            180                 185                 190

Asn Phe Gly Gly Asn Ser Phe Met Pro Ala Asn Gly Leu Thr Val Ala
        195                 200                 205

Gln Asn Gln Val Leu Asn Leu Ile Lys Ala Cys Pro Arg Pro Glu Gly
    210                 215                 220

Leu Asn Phe Gln Asp Leu Lys Asn Gln Leu Lys His Met Ser Val Ser
225                 230                 235                 240

Ser Ile Lys Gln Ala Val Asp Phe Leu Ser Asn Glu Gly His Ile Tyr
                245                 250                 255

Ser Thr Val Asp Asp Asp His Phe Lys Ser Thr Asp Ala Glu
                260                 265                 270

<210> SEQ ID NO 44
<211> LENGTH: 1622
<212> TYPE: DNA
<213> ORGANISM: Homo sapiens

<400> SEQUENCE: 44
ggcacgagga agctactcag ataagaggct ccaagaggac attttttggat gtgaaaaaca      60
atgagaagga ggacaacaca catttacaat cgtcttaatt ttgtactcag aaaaaggatg     120
tgaagacaat gcacagggaa tacaatagtt tcagatctgt gtacagtttc cttttgcttc     180
atctcctgca acaatgtaat gaagacacca tgatatcatt aacatttcac acaaaaggaa     240
aatgaggctg aaatggtgtg gcaaggccca aggaatctgg agcatcccta accaagcagc     300
agagcacctg ggatagagaa agtgctcaag aatgttcact tactgattac tacaatcaaa     360
aaaagatacg acactaattt accacattct tcttacttat tttatgagat actattcttc     420
caaggtggag aaagtggaga agtagagtg acgcagctaa gggagtaaat cgaccctcag     480
ccaacaagtg gcaaaagcct gaagaaagtg atcaagatca ctgatgaccc cgcggcccat     540
ctccaagggg gcgggtatca aaccccgac gccacaccac gtatcattcc gcaaaactcc     600
cgcgcctccc acgcagaact ggcaagaggg aaggcgagac agcagtgaac agctggtacg     660
cagcacccac agcaccgcgg cagcagctag tgccgactcc cgcctagctc ttttgactct     720
gttcgcggga agaatgggga aacagtaagg ttgcggcgcc tcccgcgaga cgaggtacct     780
gaggctggcc ccgcagtccc ccgccgcacc agcaccggga cttcacaccc cacttccggg     840
gtcaagtcac cgccgggaat cctgtgatcg cagaaaggta gtctcaggtt ccgcccctat     900
ccaagtcccg cctccactgc ctctcgccct gtatctgtca acttccggga cgccgcgcgt     960
cactaagcag ccaatctcca cttccggact catccagccc cttctccacc cctttcagag    1020
acagcgcgat tgcgatttag gtttccgcgc atttaattgg cgaagctgga gcgctagtct    1080
tcgctgattg gtgccgagaa atctgcccca tagacacccg cggggcgcac agtttcagtc    1140
gtccgtgggt ttcccgccag ccgcagtctt ggaccataat catggtggac atgatggact    1200
tgcccaggtc gcgcatcaac gccggcatgc tagctcaatt catcgacaag cctgtctgct    1260
tcgtagggag gctggaaaag attcatccca ccggaaaaat gtttattctt tcagatggag    1320
aaggaaaaaa tggaaccatc gagttgatgg aacccctga tgaagaaatc tctggaattg    1380
```

| | |
|---|---|
| tggaagtggt tggaagagta accgccaagg ccaccatctt gtgtacatct tatgtccagt | 1440 |
| ttaaagaaga tagccatcct tttgatcttg gactttacaa tgaagctgtg aaaattatcc | 1500 |
| atgacttccc tcagttttat cctttaggga ttgtgcaaca tgattgatct tgatggattt | 1560 |
| tcatacgatt gtaaatgagc tatattaaag tctattaaag gaaaaaaaaa aaaaaaaaa | 1620 |
| aa | 1622 |

<210> SEQ ID NO 45
<211> LENGTH: 121
<212> TYPE: PRT
<213> ORGANISM: Homo sapiens

<400> SEQUENCE: 45

```
Met Val Asp Met Met Asp Leu Pro Arg Ser Arg Ile Asn Ala Gly Met
  1               5                  10                  15
Leu Ala Gln Phe Ile Asp Lys Pro Val Cys Phe Val Gly Arg Leu Glu
                 20                  25                  30
Lys Ile His Pro Thr Gly Lys Met Phe Ile Leu Ser Asp Gly Glu Gly
             35                  40                  45
Lys Asn Gly Thr Ile Glu Leu Met Glu Pro Leu Asp Glu Glu Ile Ser
         50                  55                  60
Gly Ile Val Glu Val Val Gly Arg Val Thr Ala Lys Ala Thr Ile Leu
     65                  70                  75                  80
Cys Thr Ser Tyr Val Gln Phe Lys Glu Asp Ser His Pro Phe Asp Leu
                 85                  90                  95
Gly Leu Tyr Asn Glu Ala Val Lys Ile Ile His Asp Phe Pro Gln Phe
            100                 105                 110
Tyr Pro Leu Gly Ile Val Gln His Asp
            115                 120
```

<210> SEQ ID NO 46
<211> LENGTH: 2816
<212> TYPE: DNA
<213> ORGANISM: Homo sapiens

<400> SEQUENCE: 46

| | |
|---|---|
| atggtatttt acttttttgg gaaatacttg gaaatgaaga cctgcaactg taatttgaaa | 60 |
| taaggaaaac tttaattttc agtataaaaa ttgctcaaat agaattgcct gattttaatg | 120 |
| acaaagtat atgggagtcc acatttatgt aagaaatgaa actataaaat gtataaataa | 180 |
| tttgcaaatc agaattgctg tcgaaagttt tactataatg aaagatattt tcatactctc | 240 |
| aaaaatatag aggaaagggg ccaagattat agtaccagtc acaatctttt gatgaggacg | 300 |
| aaatgaatca ggtaacagac tgggttgacc catcatttga tgattttcta gagtgtagtg | 360 |
| gcgtctctac tattactgcc acatcattag gtgtgaataa ctcaagtcat agaagaaaaa | 420 |
| atgggccttc tacattagaa agcagcagat tccagcgag aaaaagagga aatctatctt | 480 |
| ccttagaaca gatttatggt ttagaaaatt caaaagaata tctgtctgaa atgaaccat | 540 |
| gggtggataa atataaacca gaaactcagc atgaacttgc tgtgcataaa aagaaaattg | 600 |
| aagaagtcga aacctggtta aaagctcaag ttttagaaag gcaaccaaaa cagggtggat | 660 |
| ctatttttatt aataacaggt cctcctggat gtggaaagac aacgacctta aaatactat | 720 |
| caaaggagca tggtattcaa gtacaagagt ggattaatcc agttttacca gacttccaaa | 780 |
| aagatgattt caagggggatg tttaatactg aatcaagctt ccatatgttt ccctatcagt | 840 |

-continued

```
ctcagatagc agttttcaaa gagtttctac taagagcgac aaagtataac aagttacaaa    900
tgcttggaga tgatctgaga actgataaga agataattct ggttgaagat ttacctaacc    960
agttttatcg ggattctcat actttacatg aagttctaag gaagtatgtg aggattggtc   1020
gatgtcctct tatatttata atctcggaca gtctcagtgg agataataat caaaggttat   1080
tgtttcccaa agaaattcag gaagagtgtt ctatctcaaa tattagtttc aaccctgtgg   1140
caccaacaat tatgatgaaa tttcttaatc gaatagtgac tatagaagct aacaagaatg   1200
gaggaaaaat tactgtccct gacaaaactt ctctagagtt gctctgtcag ggatgttctg   1260
gtgatatcag aagtgcaata aacagcctcc agttttcttc ttcaaaagga gaaacaact    1320
tacggccaag gaaaaaagga atgtctttaa aatcagatgc tgtgctgtca aaatcaaaac   1380
gaagaaaaaa acctgatagg gttttttgaaa atcaagaggt ccaagctatt ggtggcaaag   1440
atgtttctct gtttctcttc agagctttgg ggaaaattct atattgtaaa agagcatctt   1500
taacagaatt agactcacct cggttgccct ctcatttatc agaatatgaa cgggatacat   1560
tacttgttga acctgaggag gtagtagaaa tgtcacacat gcctggagac ttatttaatt   1620
tatatcttca ccaaaactac atagatttct tcatggaaat tgatgatatt gtgagagcca   1680
gtgaatttct gagttttgca gatatcctca gtggtgactg aatacacgc tctttactca    1740
gggaatatag cacatctata gctacgagag gtgtgatgca ttccaacaaa gcccgaggat   1800
atgctcattg ccaaggagga ggatcaagtt ttcgacccct gcacaaacct cagtggtttc   1860
taataaataa aaagtatcgg gaaaattgcc tggcagcaaa agcacttttt cctgacttct   1920
gcctaccagc tttatgcctc caaactcagc tattgccata ccttgctcta ctaaccattc   1980
caatgagaaa tcaagctcag atttcttttta tccaagatat tggaaggctc cctctgaagc   2040
gacactttgg aagattgaaa atggaagccc tgactgacag ggaacatgga atgatagacc   2100
ctgacagcgg agatgaagcc cagcttaatg gaggacattc tgcagaggaa tctctgggtg   2160
aacccactca agccactgtg ccggaaacct ggtctcttcc tttgagtcag aatagtgcca   2220
gtgaactgcc tgctagccag ccccagcccc tttcagccca aggagacatg gaagaaaaca   2280
taataataga agactacgag agtgatggga catagaagcc agcctgctaa tcagattgct   2340
acttcacagc ttcattttttg tttcattcag tggtacttca gcagagttaa tatgcttttc   2400
tgatgaatta cacaacagtt tgttaattct tcattcttgt agtatttcat cacaagaaac   2460
ctactcttct gtcatcttga agtaaataga agatcaagcc ttcaaatctc ttaattttt    2520
cggtatttat taaatctgtg agtggtttaa ggagcggtca gtgtgtataa agtgtgtttg   2580
aacattatgc caaatatcaa gatgtgaagg actaattcag gatgcaaaaa cgttattggg   2640
gggttgtaaa tatcaactat tcaacagttt aggatgcaat tacgagtgta aactgtgtgc   2700
cttatttaca ctttattgtc tcccgcttct cagatagttt tgatgtgttg tacagtggaa   2760
tatcttagat acttttttgga aagtatttac ataagttata tcacaattaa aatgtt      2816
```

<210> SEQ ID NO 47
<211> LENGTH: 670
<212> TYPE: PRT
<213> ORGANISM: Homo sapiens

<400> SEQUENCE: 47

```
Met Asn Gln Val Thr Asp Trp Val Asp Pro Ser Phe Asp Asp Phe Leu
  1               5                  10                  15

Glu Cys Ser Gly Val Ser Thr Ile Thr Ala Thr Ser Leu Gly Val Asn
             20                  25                  30
```

```
Asn Ser Ser His Arg Arg Lys Asn Gly Pro Ser Thr Leu Glu Ser Ser
         35                  40                  45

Arg Phe Pro Ala Arg Lys Arg Gly Asn Leu Ser Ser Leu Glu Gln Ile
         50                  55                  60

Tyr Gly Leu Glu Asn Ser Lys Glu Tyr Leu Ser Glu Asn Glu Pro Trp
 65                  70                  75                  80

Val Asp Lys Tyr Lys Pro Glu Thr Gln His Glu Leu Ala Val His Lys
                 85                  90                  95

Lys Lys Ile Glu Glu Val Glu Thr Trp Leu Lys Ala Gln Val Leu Glu
                100                 105                 110

Arg Gln Pro Lys Gln Gly Gly Ser Ile Leu Leu Ile Thr Gly Pro Pro
             115                 120                 125

Gly Cys Gly Lys Thr Thr Thr Leu Lys Ile Leu Ser Lys Glu His Gly
         130                 135                 140

Ile Gln Val Gln Glu Trp Ile Asn Pro Val Leu Pro Asp Phe Gln Lys
145                 150                 155                 160

Asp Asp Phe Lys Gly Met Phe Asn Thr Glu Ser Ser Phe His Met Phe
                 165                 170                 175

Pro Tyr Gln Ser Gln Ile Ala Val Phe Lys Glu Phe Leu Leu Arg Ala
             180                 185                 190

Thr Lys Tyr Asn Lys Leu Gln Met Leu Gly Asp Asp Leu Arg Thr Asp
         195                 200                 205

Lys Lys Ile Ile Leu Val Glu Asp Leu Pro Asn Gln Phe Tyr Arg Asp
         210                 215                 220

Ser His Thr Leu His Glu Val Leu Arg Lys Tyr Val Arg Ile Gly Arg
225                 230                 235                 240

Cys Pro Leu Ile Phe Ile Ile Ser Asp Ser Leu Ser Gly Asp Asn Asn
                 245                 250                 255

Gln Arg Leu Leu Phe Pro Lys Glu Ile Gln Glu Glu Cys Ser Ile Ser
             260                 265                 270

Asn Ile Ser Phe Asn Pro Val Ala Pro Thr Ile Met Met Lys Phe Leu
         275                 280                 285

Asn Arg Ile Val Thr Ile Glu Ala Asn Lys Asn Gly Gly Lys Ile Thr
         290                 295                 300

Val Pro Asp Lys Thr Ser Leu Glu Leu Leu Cys Gln Gly Cys Ser Gly
305                 310                 315                 320

Asp Ile Arg Ser Ala Ile Asn Ser Leu Gln Phe Ser Ser Ser Lys Gly
                 325                 330                 335

Glu Asn Asn Leu Arg Pro Arg Lys Lys Gly Met Ser Leu Lys Ser Asp
             340                 345                 350

Ala Val Leu Ser Lys Ser Lys Arg Arg Lys Lys Pro Asp Arg Val Phe
         355                 360                 365

Glu Asn Gln Glu Val Gln Ala Ile Gly Gly Lys Asp Val Ser Leu Phe
         370                 375                 380

Leu Phe Arg Ala Leu Gly Lys Ile Leu Tyr Cys Lys Arg Ala Ser Leu
385                 390                 395                 400

Thr Glu Leu Asp Ser Pro Arg Leu Pro Ser His Leu Ser Glu Tyr Glu
                 405                 410                 415

Arg Asp Thr Leu Leu Val Glu Pro Glu Val Val Glu Met Ser His
             420                 425                 430

Met Pro Gly Asp Leu Phe Asn Leu Tyr Leu His Gln Asn Tyr Ile Asp
         435                 440                 445
```

-continued

```
Phe Phe Met Glu Ile Asp Asp Ile Val Arg Ala Ser Glu Phe Leu Ser
    450             455             460
Phe Ala Asp Ile Leu Ser Gly Asp Trp Asn Thr Arg Ser Leu Leu Arg
465             470             475                     480
Glu Tyr Ser Thr Ser Ile Ala Thr Arg Gly Val Met His Ser Asn Lys
            485             490                 495
Ala Arg Gly Tyr Ala His Cys Gln Gly Gly Gly Ser Ser Phe Arg Pro
            500             505             510
Leu His Lys Pro Gln Trp Phe Leu Ile Asn Lys Lys Tyr Arg Glu Asn
        515             520             525
Cys Leu Ala Ala Lys Ala Leu Phe Pro Asp Phe Cys Leu Pro Ala Leu
        530             535             540
Cys Leu Gln Thr Gln Leu Leu Pro Tyr Leu Ala Leu Leu Thr Ile Pro
545             550             555             560
Met Arg Asn Gln Ala Gln Ile Ser Phe Ile Gln Asp Ile Gly Arg Leu
            565             570             575
Pro Leu Lys Arg His Phe Gly Arg Leu Lys Met Glu Ala Leu Thr Asp
            580             585             590
Arg Glu His Gly Met Ile Asp Pro Asp Ser Gly Asp Glu Ala Gln Leu
        595             600             605
Asn Gly Gly His Ser Ala Glu Glu Ser Leu Gly Glu Pro Thr Gln Ala
        610             615             620
Thr Val Pro Glu Thr Trp Ser Leu Pro Leu Ser Gln Asn Ser Ala Ser
625             630             635             640
Glu Leu Pro Ala Ser Gln Pro Gln Pro Phe Ser Ala Gln Gly Asp Met
            645             650             655
Glu Glu Asn Ile Ile Ile Glu Asp Tyr Glu Ser Asp Gly Thr
            660             665             670
```